US012227574B2

(12) United States Patent
Shang et al.

(10) Patent No.: US 12,227,574 B2
(45) Date of Patent: Feb. 18, 2025

(54) ANTI-CD3 CONSTRUCTS AND USES THEREOF

(71) Applicant: Amberstone Biosciences, Inc., Laguna Hills, CA (US)

(72) Inventors: Yonglei Shang, Irvine, CA (US); Aude I. Segaliny, Laguna Hills, CA (US); Xiaoya Ma, Laguna Hills, CA (US); Xianzhi Jiang, Laguna Hills, CA (US); George Wu, Irvine, CA (US)

(73) Assignee: AMBERSTONE BIOSCIENCES, INC., Irvine, CA (US)

( * ) Notice: Subject to any disclaimer, the term of this patent is extended or adjusted under 35 U.S.C. 154(b) by 0 days.

(21) Appl. No.: 18/570,578

(22) PCT Filed: Jun. 16, 2022

(86) PCT No.: PCT/US2022/072996
§ 371 (c)(1),
(2) Date: Dec. 14, 2023

(87) PCT Pub. No.: WO2022/266660
PCT Pub. Date: Dec. 22, 2022

(65) Prior Publication Data
US 2024/0279334 A1 Aug. 22, 2024

Related U.S. Application Data

(60) Provisional application No. 63/212,024, filed on Jun. 17, 2021, provisional application No. 63/305,588, filed on Feb. 1, 2022.

(51) Int. Cl.
*C07K 16/28* (2006.01)
*A61K 39/00* (2006.01)
*A61P 35/00* (2006.01)
*C07K 16/30* (2006.01)
*C07K 16/32* (2006.01)

(52) U.S. Cl.
CPC .......... *C07K 16/2809* (2013.01); *A61P 35/00* (2018.01); *C07K 16/30* (2013.01); *C07K 16/32* (2013.01); *A61K 2039/505* (2013.01); *C07K 2317/31* (2013.01); *C07K 2317/55* (2013.01); *C07K 2317/622* (2013.01); *C07K 2317/732* (2013.01)

(58) Field of Classification Search
None
See application file for complete search history.

(56) References Cited

U.S. PATENT DOCUMENTS

| 4,816,567 A | 3/1989 | Cabilly |
| 5,399,346 A | 3/1995 | Anderson |
| 5,500,362 A | 3/1996 | Robinson |
| 5,580,859 A | 12/1996 | Felgner |
| 5,589,466 A | 12/1996 | Felgner |
| 5,624,821 A | 4/1997 | Winter |
| 5,648,260 A | 7/1997 | Winter |
| 5,750,373 A | 5/1998 | Garrard |
| 5,770,429 A | 6/1998 | Lonberg et al. |
| 5,821,337 A | 10/1998 | Carter |
| 6,075,181 A | 6/2000 | Kucherlapati |
| 6,150,584 A | 11/2000 | Kucherlapati |
| 6,194,551 B1 | 2/2001 | Idusogie |
| 6,312,384 B1 | 11/2001 | Chiao |
| 6,326,193 B1 | 12/2001 | Liu |
| 6,602,684 B1 | 8/2003 | Umana |
| 6,737,056 B1 | 5/2004 | Presta |
| 6,982,321 B2 | 1/2006 | Winter |
| 7,041,870 B2 | 5/2006 | Tomizuka |
| 7,087,409 B2 | 8/2006 | Barbas, III |
| 7,189,826 B2 | 3/2007 | Rodman |
| 7,332,581 B2 | 2/2008 | Presta |
| 7,371,826 B2 | 5/2008 | Presta |
| 7,371,849 B2 | 5/2008 | Honda |
| 7,521,541 B2 | 4/2009 | Eigenbrot |
| 7,527,791 B2 | 5/2009 | Adams |
| 8,754,287 B2 | 6/2014 | Macdonald |
| 9,670,286 B2 | 6/2017 | Chang |
| 9,890,377 B2 | 2/2018 | Igawa |
| 2002/0164328 A1 | 11/2002 | Shinkawa |
| 2003/0115614 A1 | 6/2003 | Kanda |

(Continued)

FOREIGN PATENT DOCUMENTS

| JP | WO2002031140 A1 | 2/2004 |
| WO | 198704462 A1 | 7/1987 |

(Continued)

OTHER PUBLICATIONS

Gura (Science, 1997, 278:1041-1042) (Year: 1997).*
Kaiser (Science, 2006, 313: 1370) (Year: 2006).*
Chames et al (British J. of Pharmacology, 2009, 157, 220-233) (Year: 2009).*
Abhinandan, K.R. et al. (Aug. 2008, e-pub. Jul. 9, 2008). "Analysis and Improvements To Kabat and Structurally Correct Numbering Of Antibody Variable Domains," Molecular Immunology 45(14):3832-3839.
Adolf-Bryfogle, J. et al. (2015, e-pub. Nov. 11, 2014). "PylgClassify: A Database of Antibody CDR Structural Classifications," Nucleic Acids Res. 43:D432-D438.

(Continued)

*Primary Examiner* — Peter J Reddig
(74) *Attorney, Agent, or Firm* — MORRISON & FOERSTER LLP

(57) ABSTRACT

The present application provides tumor microenvironment acidity activated anti-CD3 constructs that bind to CD3 (e.g., anti-CD3 monoclonal and multispecific antibodies), nucleic acid molecules encoding an amino acid sequence of the anti-CD3, vectors comprising the nucleic acid molecules, host cells containing the vectors, methods of preparing the anti-CD3 construct, pharmaceutical compositions containing the anti-CD3 construct, and methods of using the anti-CD3 construct or compositions.

19 Claims, 57 Drawing Sheets
Specification includes a Sequence Listing.

(56) References Cited

U.S. PATENT DOCUMENTS

| | | |
|---|---|---|
| 2003/0157108 A1 | 8/2003 | Presta |
| 2004/0001825 A1 | 1/2004 | Govindan |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2004/0197328 A1* | 10/2004 | Young ............... A61K 51/1045 424/155.1 |
| 2004/0259150 A1 | 12/2004 | Nakamura |
| 2005/0014934 A1 | 1/2005 | Hinton |
| 2005/0031613 A1 | 2/2005 | Nakamura |
| 2005/0079574 A1 | 4/2005 | Bond |
| 2005/0119455 A1 | 6/2005 | Fuh |
| 2005/0123546 A1 | 6/2005 | Umana |
| 2005/0266000 A1 | 12/2005 | Bond |
| 2006/0270045 A1 | 11/2006 | Cregg |
| 2007/0061900 A1 | 3/2007 | Murphy |
| 2007/0117126 A1 | 5/2007 | Sidhu |
| 2007/0160598 A1 | 7/2007 | Dennis |
| 2007/0237764 A1 | 10/2007 | Birtalan |
| 2007/0292936 A1 | 12/2007 | Barthelemy |
| 2009/0002360 A1 | 1/2009 | Chen |
| 2009/0307787 A1 | 12/2009 | Grosveld |
| 2010/0122358 A1 | 5/2010 | Brueggemann |
| 2012/0052076 A1 | 3/2012 | Alberti |
| 2012/0237518 A1 | 9/2012 | Yamaguchi |
| 2013/0122020 A1 | 5/2013 | Liu |
| 2013/0336963 A1 | 12/2013 | Igawa |
| 2015/0166661 A1* | 6/2015 | Chen ..................... A61P 37/00 435/254.2 |
| 2015/0289489 A1 | 10/2015 | Macdonald |
| 2016/0053018 A1 | 2/2016 | Nakamura |
| 2016/0264678 A1 | 9/2016 | Chang |
| 2018/0002437 A1 | 1/2018 | Guerra |
| 2018/0321130 A1 | 11/2018 | Wu |

FOREIGN PATENT DOCUMENTS

| | | |
|---|---|---|
| WO | 199429351 A2 | 12/1994 |
| WO | 199634103 A1 | 10/1996 |
| WO | 199704801 A1 | 2/1997 |
| WO | 199730087 A1 | 8/1997 |
| WO | 199858964 A1 | 12/1998 |
| WO | 199922764 A1 | 5/1999 |
| WO | 199951642 A1 | 10/1999 |
| WO | 199954440 A1 | 10/1999 |
| WO | 200061739 A1 | 10/2000 |
| WO | 200129058 A1 | 4/2001 |
| WO | 200129246 A1 | 4/2001 |
| WO | 200196584 A2 | 12/2001 |
| WO | 2003011878 A2 | 2/2003 |
| WO | 2003048731 A2 | 6/2003 |
| WO | 2003084570 A1 | 10/2003 |
| WO | 2003085107 A1 | 10/2003 |
| WO | 2003085119 A1 | 10/2003 |
| WO | 2004049794 A2 | 6/2004 |
| WO | 2004056312 A2 | 7/2004 |
| WO | 2005035586 A1 | 4/2005 |
| WO | 2005035778 A1 | 4/2005 |
| WO | 2005053742 A1 | 6/2005 |
| WO | 2005100402 A1 | 10/2005 |
| WO | 2006029879 A2 | 3/2006 |
| WO | 2008077546 A1 | 7/2008 |
| WO | 2014047231 A1 | 3/2014 |
| WO | 2015143079 A1 | 9/2015 |
| WO | 2019241216 A1 | 12/2019 |
| WO | 2020076730 A1 | 4/2020 |
| WO | 2020243581 A1 | 12/2020 |
| WO | 2020247932 A1 | 12/2020 |
| WO | 2022266660 A1 | 12/2022 |

OTHER PUBLICATIONS

Al-Lazikani, B. et al. (1997). "Standard Conformations for the Canonical Structures of Immunoglobulins," J. Mol. Biol. 273:927-948.

Almagro, J.C. et al. (Jan. 1, 2008). "Humanization of Antibodies," Frontiers in Bioscience 13:1619-1633.

Baca, M. et al. (Apr. 18, 1997). "Antibody Humanization Using Monovalent Phage Display," J. Biol. Chem. 272(16):10678-10684.

Boder, E.T. et al. (Jun. 1997). "Yeast Surface Display for Screening Combinatorial Polypeptide Libraries," Nat. Biotechnol. 15:553-557.

Boedtkjer, E. et al. (2020). "The Acidic Tumor Microenvironment As A Driver Of Cancer," Annual Review Of Physiology 82(1):103-126.

Boerner, P. et al. (Jul. 1, 1991). "Production of Antigen-Specific Human Monoclonal Antibodies from In Vitro-Primed Human Splenocytes," J. Immunol. 147(1):86-95.

Bogen, J. P. et al. (Aug. 9, 2019). "Dual Function Ph Responsive Bispecific Antibodies For Tumor Targeting And Antigen Depletion In Plasma," Frontiers in Immunology 10(1892):1-13.

Brodeur, B.R. et al. (1987). "Mouse-Human Myeloma Partners for the Production Monoclonal Antibody Production of Heterohybridomas," Chapter 4 in Techniques and Applications, Marcel Dekker, Inc., New York, pp. 51-63.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Burton, D.R. (1985). "Immunoglobulin G: Functional Sites," Molec. Immunol. 22(3):161-206.

Capel, P.J.A. et al. (Feb. 1994). "Heterogeneity of Human IgG Fc Receptors," Immunomethods 4(1):25-34.

Carter, P. et al. (May 1992). "Humanization of an Anti-p185HER2 Antibody for Human Cancer Therapy," Proc. Natl. Acad. Sci. USA 89:4285-4289.

Cheadle, C. et al. (Jan. 1992). "Cloning And Expression Of The Variable Regions Of Mouse Myeloma Protein Mopc315 In *E. coli*: Recovery Of Active Fv Fragments," Molecular Immunology 29(1):21-30.

Chen, W. et al. (Jan. 2010). "A Large Human Domain Antibody Library Combining Heavy and Light Chain CDR3 Diversity," Mol. Immunol. 47(4):912-921, 23 pages.

Chothia, C. et al. (Aug. 20, 1987). "Canonical Structures for the Hypervariable Regions of Immunoglobulins," J. Mol. Biol. 196(4):901-917.

Chothia, C. et al. (Dec. 21/28, 1989). "Conformations of Immunoglobulin Hypervariable Regions," Nature 342(6252):877-883.

Chothia, C. et al. (Dec. 5, 1985). "Domain Association In Immunoglobulin Molecules. The Packing Of Variable Domains," J. Mol. Biol. 186(3):651-663.

Chowdhury, P.S. (2008). "Engineering Hot Spots for Affinity Enhancement of Antibodies," Methods Mol. Biol. 207:179-196.

Clackson, T. et al. (Aug. 15, 1991). "Making Antibody Fragments Using Phage Display Libraries," Nature 352:624-628.

Clynes, R. et al. (Jan. 1998). "Fc Receptors are Required in Passive and Active Immunity to Melanoma," Proc. Natl. Acad. Sci. U.S.A. 95:652-656.

Cole, S.P.C. et al. (1985). "The EBV-Hybridoma Technique And Its Application To Human Lung Cancer," Monolclonal Antibodies and Cancer Therapy 27:77-96.

Cragg, M.S. et al. (Apr. 1, 2004, e-pub. Oct. 9, 2003). "Antibody Specificity Controls In Vivo Effector Mechanisms Of Anti-CD20 Reagents," Blood 103(7):2738-2743, 7 pages.

Cragg, M.S. et al. (Feb. 1, 2003). "Complement-Mediated Lysis By Anti-CD20 Mab Correlates With Segregation Into Lipid Rafts," Blood 101(3):1045-1052.

Cunningham, B.C. et al. (Jun. 2, 1989). "High-Resolution Epitope Mapping of hGH-Receptor Interactions by Alanine-Scanning Mutagenesis," Science 244:1081-1085.

(56) References Cited

OTHER PUBLICATIONS

Dall'Acqua, W.F. et al. (2005). "Antibody Humanization by Framework Shuffling," Methods 36:43-60.
Dall'Acqua, W. et al. (1998). "Contribution of Domain Interface Residues to the Stability of Antibody CH3 Domain Homodimers," Biochemistry 37(26):9266-9273.
Daëron, M. (1997). "Fc Receptor Biology," Ann. Rev. Immunol. 15:203-234.
De Haas, M. et al. (Oct. 1995). "Fcγ Receptors of Phagocytes," J. Lab. Clin. Med. 126(4):330-341.
Dondelinger, M. et al. (Oct. 16, 2018). "Understanding the Significance and Implications of Antibody Numbering and Antigen-Binding Surface/Residue Definition," Frontiers in Immunology 9(2278):1-15.
Duncan, A.R. et al. (Apr. 21, 1988). "The Binding Site for C1q on IgG," Nature 322:738-740.
Edgar, R.C. (2004, e-pub. Mar. 19, 2004). "Muscle: Multiple Sequence Alignment With High Accuracy And High Throughput," Nucleic Acids Research 32(5):1792-1797.
Edgar, R.C. (Aug. 19, 2004). "Muscle: A Multiple Sequence Alignment Method With Reduced Time and Space Complexity," BMC Bioinformatics 5:113, pp. 1-19.
Ehrenmann, F. et al. (Jan. 2010, e-pub. Nov. 9, 2009). "IMGT/3Dstructure-DB and IMGT/DomainGapAlign: A Database and a Tool For Immunoglobulins or Antibodies, T Cell Receptors, MHC, IgSF and MhcSF," Nucleic Acids Res. 38:D301-D307.
Endo, Y. et al. (2003). "High-Throughput, Genome-Scale Protein Production Method Based On The Wheat Germ Cell-Free Expression System," Biotechnol. Adv. 21:695-713.
Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101(34):12467-12472.
Gazzano-Santoro, H. et al. (1997). "A Non-Radioactive Complement-Dependent Cytotoxicity Assay Anti-CD20 Monoclonal Antibody," J. Immunol. Methods 202:163-171.
Goding, J.W. (1986). "Production of Monoclonal Antibodies," Chapter 3 in Monoclonal Antibodies: Principles and Practice, Academic Press, New York, pp. 59-103.
Griffiths, A.D. et al. (1993). "Human Anti-Self Antibodies with High Specificity from Phage Display Libraries," EMBO J. 12(2):725-734.
Guyer, R.L. et al. (Aug. 1976). "Immunoglobulin Binding By Mouse Intestinal Epithelial Cell Receptors," J. Immunol. 117(2):587-593.
Hellstrom, I. et al. (Mar. 1985). "Strong Antitumor Activities of IgG3 Antibodies to a Human Melanoma-Associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Honegger, A. et al. (Jun. 8, 2001). "Yet Another Numbering Scheme For Immunoglobulin Variable Domains: An Automatic Modeling And Analysis Tool," J. Mol. Biol. 309:657-670.
Hoogenboom, H.R. et al. (Sep. 20, 1992). "By-Passing Immunisation. Human Antibodies From Synthetic Repertoires of Germline VH Gene Segments Rearranged in Vitro," J. Mol. Biol. 227:381-388.
Hoogenboom, H.R. (2001). "Overview of Antibody Phage-Display Technology and Its Applications," Methods in Molecular Biology 178:1-37.
Idusogie, E.E. et al. (2000). "Mapping of the C1q Binding Site on Rituxan, a Chimeric Antibody With a Human IgG1 Fc," J. Immunol. 164:4178-4184.
Igawa, T. et al. (Nov. 2010, e-pub. Oct. 17, 2010). "Antibody Recycling By Engineered Ph-Dependent Antigen Binding Improves The Duration Of Antigen Neutralization," Nature Biotechnology 28(11):1203-1207.
International Preliminary Report on Patentability issued on Dec. 14, 2023 for PCT Application No. PCT/US2022/072996, filed on Jun. 16, 2022, 8 pages.
International Search Report and Written Opinion, mailed Sep. 23, 2022, for PCT Application No. PCT/US2022/072996, filed Jun. 16, 2022, 18 pages.
Jansen, F.K. et al. (1982). "Immunotoxins: Hybrid Molecules Combining High Specificity and Potent Cytotoxicity," Immunol. Rev. 62:185-216.
Johnston, R. J. et al. (2019). "VISTA is an Acidic Ph-Selective Ligand for PSGL-1," Nature 574(7779):565-570.
Jones, P.T. et al. (May 29, 1986). "Replacing The Complementarity-Determining Regions In A Human Antibody With Those From A Mouse," Nature 321:522-525.
Kabat, E.A. et al. (Oct. 10, 1977). "Unusual Distributions Of Amino Acids In Complementarity-Determining (Hypervariable) Segments Of Heavy And Light Chains Of Immunoglobulins And Their Possible Roles In Specificity Of Antibody-Combining Sites," J. Biol. Chem. 252(19):6609-6616.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.
Kashmiri, S.V. et al. (2005). "SDR Grafting—A New Approach to Antibody Humanization," Methods 36:25-34.
Killen, J.A. et al. (Nov. 1, 1984). "Specific Killing Of Lymphocytes That Cause Experimental Autoimmune Myasthenia Gravis By Ricin Toxin-Acetylcholine Receptor Conjugates," J. Immunol. 133(5):2549-2553.
Kim, J-K. et al. (Apr. 1994). "Localization of the Site of the Murine IgG1 Molecule That is Involved in Binding to the Murine Intestinal Fc Receptor," Eur. J. Immunol. 24:2429-2434.
Klimka, A. et al. (2000). "Human Anti-CD30 Recombinant Antibodies by Guided Phage Antibody Selection Using Cell Panning," Br. J. Cancer 83(2):252-260.
Kozbor, D. (Dec. 1984). "A Human Hybrid Myeloma for Production of Human Monoclonal Antibodies," J. Immunol. 133(6):3001-3005.
Köhler, G. et al. (Aug. 7, 1975). "Continuous Cultures of Fused Cells Secreting Antibody of Predefined Specificity," Nature 256:495-497.
Lee, C.V. et al. (2004). "Bivalent Antibody Phage Display Mimics Natural Immunoglobulin," J. Immunol. Methods 284(1-2):119-132.
Lee, C.V. et al. (2004). "High-affinity Human Antibodies From Phage-displayed Synthetic Fab Libraries With a Single Framework Scaffold," J. Mol. Biol. 340(5):1073-1093.
Lefranc, M.P. et al. (Jan. 2003). "IMGT Unique Numbering For Immunoglobulin And T Cell Receptor Variable Domains And Ig Superfamily V-Like Domains," Dev. Comp. Immunol. 27(1):55-77.
Li, J. et al. (Mar. 7, 2006). "Human Antibodies for Immunotherapy Development Generated via a Human B Cell Hybridoma Technology," Proc. Natl. Acad. Sci. USA 103(10):3557-3562.
Lonberg, N. (2008, e-pub. Jul. 21, 2008). "Fully Human Antibodies From Transgenic Mouse and Phage Display Platforms," Curr. Opin. Immunol. 20:450-459.
Lonberg, N. (Sep. 2005). "Human Antibodies From Transgenic Animals," Nat. Biotech. 23(9):1117-1125.
MacCallum, R.M. et al. (1996). "Antibody-Antigen Interactions: Contact Analysis and Binding Site Topography," J. Mol. Biol. 262:732-745.
Marks, J.D. et al. (1991). "By-Passing Immunization Human Antibodies from V-gene Libraries Displayed on Phage," J. Mol. Biol. 222:581-597.
Marks, J.D. et al. (2004) "Selection of Human Antibodies from Phage Display Libraries," Chapter 8 in Methods in Molecular Biology, Lo, B.K.C. (ed.), Humana Press Inc., Totowa, NJ, 248:161-176, 29 pages.
Marks, J.D. et al. (Jul. 1992). "By-Passing Immunization: Building High Affinity Human Antibodies by Chain Shuffling," Bio/Technology 10:779-783.
McCafferty, J et al. (Dec. 6, 1990). "Phage Antibodies: Filamentous Phage Displaying Antibody Variable Domains," Nature 348:552-554.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.

(56) References Cited

OTHER PUBLICATIONS

Munson, P.J. et al. (1980). "Ligand: A Versatile Computerized Approach for Characterization of Ligand-Binding Systems," Analy. Biochem. 107:220-239.
Nair, A.B. et al. (2016). "A Simple Practice Guide for Dose Conversion Between Animals and Humans," Journal of Basic and Clinical Pharmacy 7:27-31.
Ni, J. (Oct. 23, 2006). "Research Progress and Future Perspectives in Antibodmics and Antibodomic Drugs," J. General Review 26(4):265-268, 3 pages.
Okazaki, A. et al. (Mar. 5, 2004). "Fucose Depletion From Human IgG1 Oligosaccharide Enhances Binding Enthalpy And Association Rate Between IgG1 and FcγRIIIa," J. Mol. Biol. 336(5):1239-1249.
Osbourn, J. et al. (2005). "From Rodent Reagents to Human Therapeutics Using Antibody Guided Selection," Methods 36:61-68.
Padlan, E.A. (1991). "A Possible Procedure for Reducing the Immunogenicity of Antibody Variable Domains While Preserving Their Ligand-Binding Properties," Mol. Immunol. 28(4/5):489-498.
Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.
Pillai, S. R. et al. (Jun. 2019). "Causes, Consequences, And Therapy Of Tumors Acidosis," Cancer and Metastasis Reviews 38(1-2):205-222, 25 pages.
Plückthun, A. (1992). "Mono- and Bivalent Antibody Fragments Produced in *Escherichia coli*: Engineering, Folding and Antigen Binding," Immunol. Revs. 130:151-188.
Plückthun, A. (1994). "Antibodies From *Escherichia coli*," Chapter 11 in The Pharmacology of Monoclonal Antibodies, Rosenburg and Moore eds., Springer-Verlag, New York, N.Y., pp. 269-315.
Presta, L.G. (1992). "Antibody Engineering," Current Opinion in Structural Biology 2:593-596.
Presta, L.G. et al. (Sep. 1, 1993). "Humanization of an Antibody Directed Against IgE," J. Immunol. 151(5):2623-2632.
Queen, C. et al. (Dec. 1989). "A Humanized Antibody That Binds to the Interleukin 2 Receptor," Proc. Natl Acad. Sci. USA 86:10029-10033.
Raag, R. et al. (Jan. 1995). "Single-chain Fvs," The FASEB Journal 9:73-80.
Ramakrishnan, S. et al. (Jan. 1984). "Comparison of the Selective Cytotoxic Effects of Immunotoxins Containing Ricin A Chain or Pokeweed Antiviral Protein and Anti-Thy 1.1 Monoclonal Antibodies," Cancer Res. 44:201-208.
Ravetch, J.V. et al. (1991). "Fc Receptors," Annu. Rev. Immunol. 9:457-492.
Riechmann, L. et al. (Mar. 24, 1988). "Reshaping Human Antibodies for Therapy," Nature 332:323-329.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Rosok, M.J. et al. (Sep. 13, 1996). "A Combinatorial Library Strategy for the Rapid Humanization of Anticarcinoma BR96 Fab," J. Biol. Chem. 271(37):22611-22618.
Running Deer, J. et al. (May-Jun. 2004, e-pub. Mar. 10, 2004). "High-Level Expression Of Proteins In Mammalian Cells Using Transcription Regulatory Sequences From The Chinese Hamster EF-1Alpha Gene," Biotechnol. Prog. 20(3):880-889.
Schröter, C. et al. (Jan. 2015). "A Generic Approach To Engineer Antibody Ph-Switches Using Combinatorial Histidine Scanning Libraries And Yeast Display," MAbs 7(1):138-151.
Shields, R.L. et al. (Mar. 2, 2001). "High Resolution Mapping of the Binding Site on Human IgG1 for FcγRI, FcγRII, FcγRIII, and FcRn and Design of IgG1 Variants With Improved Binding to the FcγR," J. Biol. Chem. 276(9):6591-6604.
Sidhu, S.S. et al. (2004). "Phage-Displayed Antibody Libraries of Synthetic Heavy Chain Complementarity Determining Regions," J. Mol. Biol. 338(2):299-310.
Sims, M.J. et al. (Aug. 15, 1993). "A Humanized CD18 Antibody Can Block Function Without Cell Destruction," J. Immunol. 151(4):2296-2308.
Sitaraman, K. et al. (2009). "High-Throughput Protein Expression Using Cell-Free System," Methods Mol. Biol. 498:229-244.
Skerra, A. (1993). "Bacterial Expression of Immunoglobulin Fragments," Current Opinion in Immunology 5:256-262.
Spirin, A.S. (Oct. 2004). "High-Throughput Cell-Free Systems For Synthesis Of Functionally Active Proteins," Trends Biotechnol. 22(10):538-545.
Stein, R. et al. (Feb. 15, 1990). "Murine Monoclonal Antibodies Raised Against Human Non-Small Cell Carcinoma Of The Lung: Specificity And Tumor Targeting," Cancer Research 50(4):1330-1336.
Sulea, T. et al. (Jan. 2020, e-pub. Nov. 28, 2019). "Structure-Based Engineering Of Ph-Dependent Antibody Binding For Selective Targeting Of Solid-Tumor Microenvironment," In MAbs 12(1):e1682866, 16 pages.
Traxlmayr, M. W. et al. (2014). "Construction Of Ph-Sensitive Her2-Binding Igg1-Fc By Directed Evolution," Biotechnology Journal 9(8):1013-1022.
Van Dijk, M.A. et al. (Aug. 2001). "Human Antibodies as Next Generation Therapeutics," Curr. Opin. Che. Biology 5(4):368-374.
Vitetta, E.S. et al. (Nov. 20, 1987). "Redesigning Nature's Poisons to Create Anti-Tumor Reagents," Science 238:1098-1104.
Vollmers, H.P. et al. (2005). "Death By Stress: Natural IgM-Induced Apoptosis," Methods and Findings in Experimental and Clinical Pharmacology 27(3):185-191.
Vollmers, H.P. et al. (2005). "The 'Early Birds': Natural IgM Antibodies and Immune Surveillance," Histology and Histopathology, 20(3):927-937.
Waterhouse, P. et al. (1993). "Combinatorial Infection and In Vivo Recombination: A Strategy For Making Large Phage Antibody Repertoires," Nucleic Acids Research 21(9):2265-2266.
Winter, G. et al. (1994). "Making Antibodies by Phage Display Technology," Ann. Rev. Immunol. 12:433-455.
Wright, A. et al. (Jan. 1997). "Effect of Glycosylation on Antibody Function: Implications for Genetics Engineering," Trends Biotechnol. 15:26-32.
Yamane-Ohnuki, N. et al. (Sep. 5, 2004, e-pub Aug. 6, 2004). "Establishment Of FUT8 Knockout Chinese Hamster Ovary Cells: An Ideal Host Cell Line For Producing Completely Defucosylated Antibodies With Enhanced Antibody-Dependent Cellular Cytotoxicity," Biotechnology and Bioengineering 87(5):614-622.

\* cited by examiner

Fig. 5
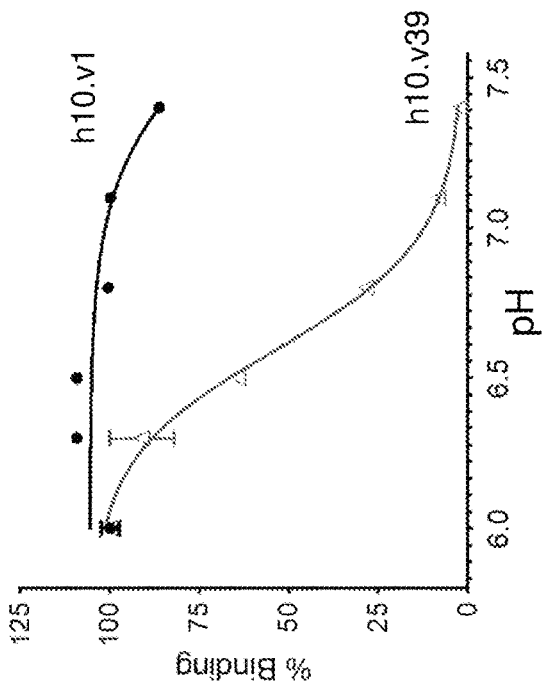
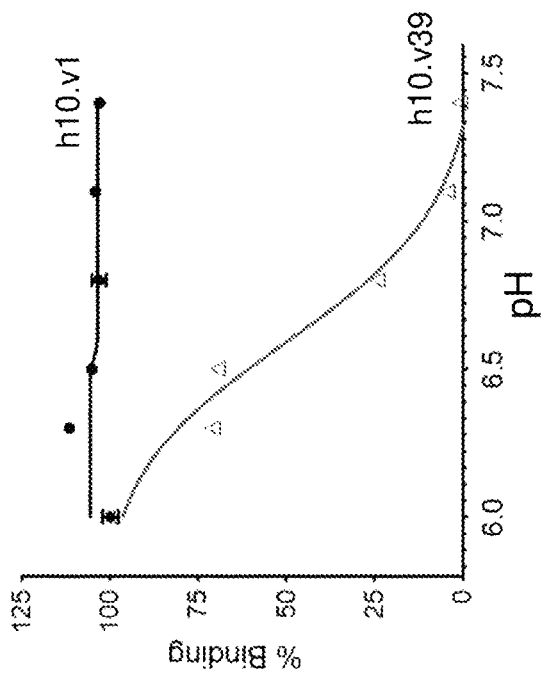

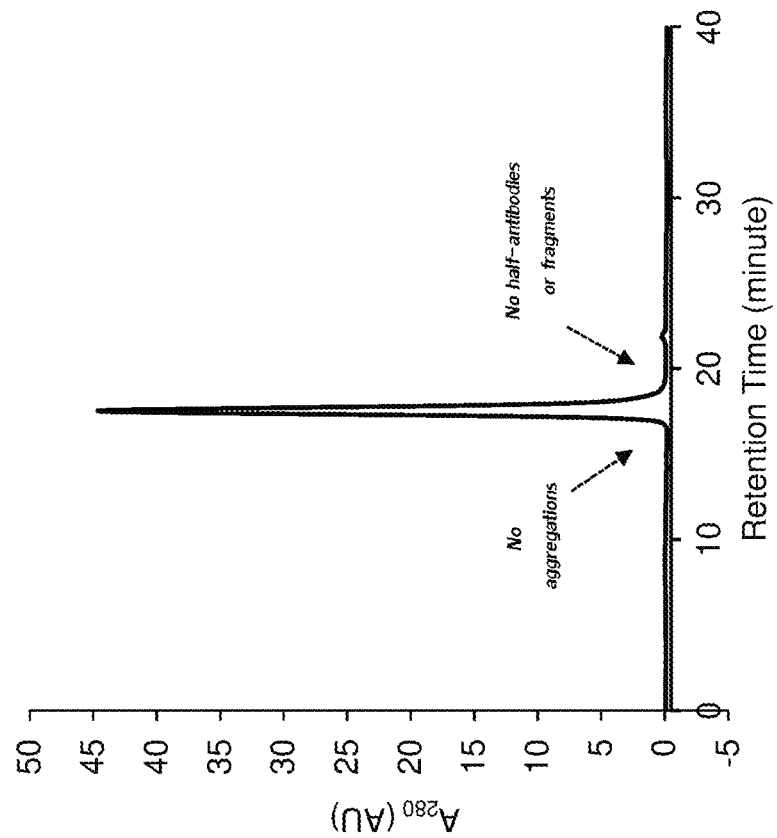
Fig. 9
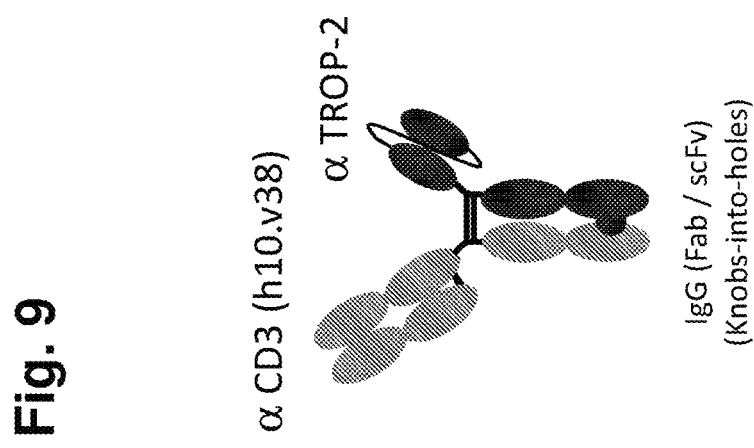

Fig. 11 T cell mediated killing (cytotoxicity) of BT474 (HER2high); Human donor #81

Fig. 13
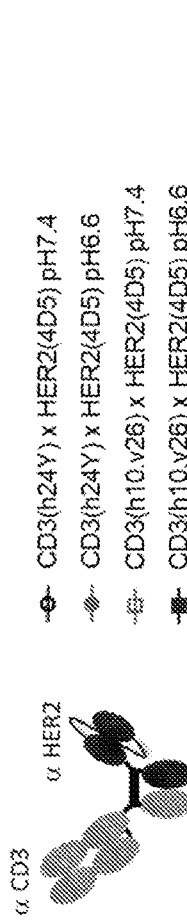
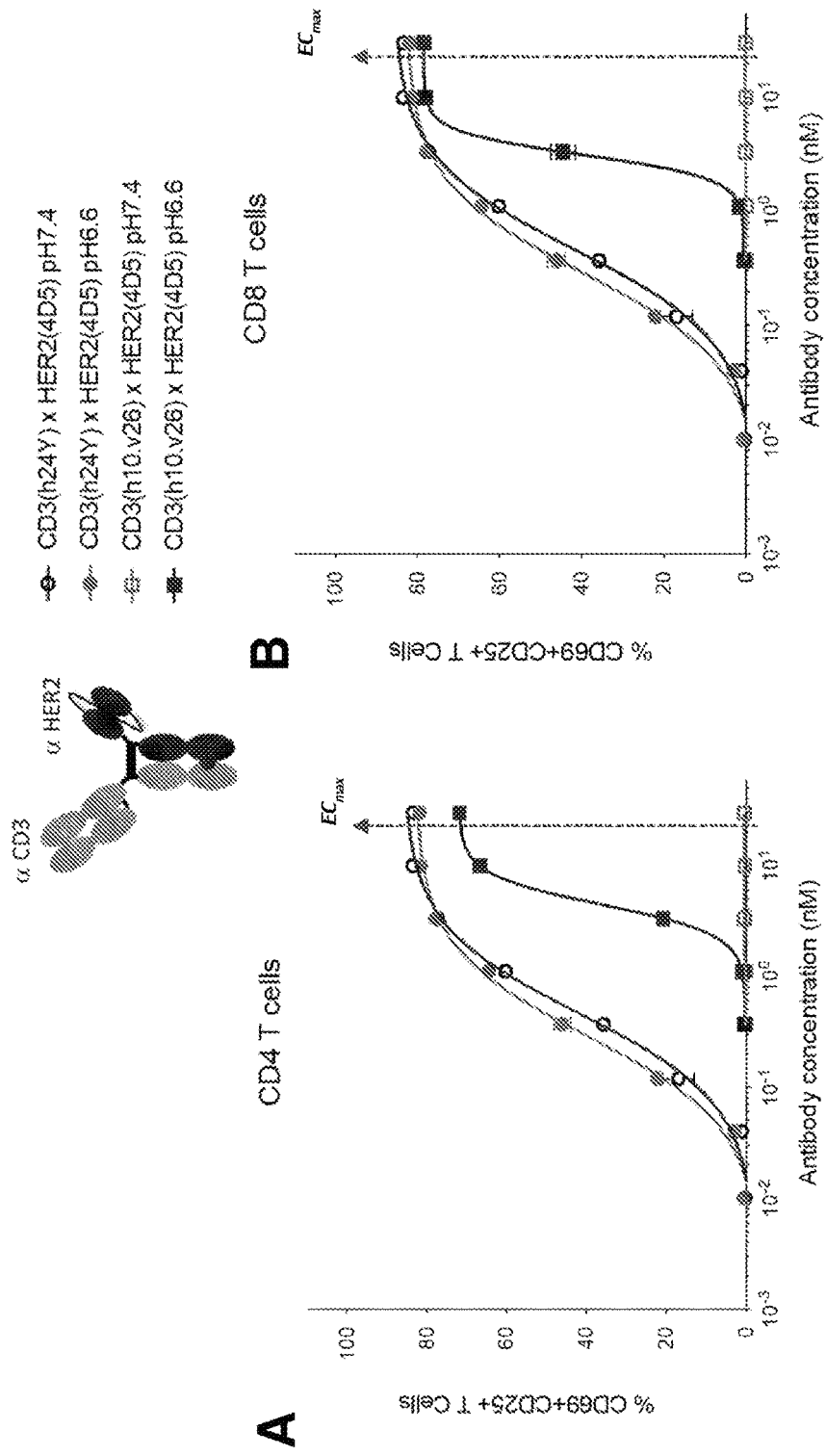
T cell activation assays with BT474 (HER2high); Donor #81

Summary of T cell mediated killing activity EC50s with BT474 (HER2^high); Various donors

Fig. 23 T cell mediated killing assays with MCF7 (HER2^low) and BT474 (HER2^high); Donor #24

Fig. 24 Cytokine secretion upon MCF7 (HER2^low) and BT474 (HER2^high) treatment; Donor #24

Summary of T cell cytotoxicity (shown as % of cell killing) on MCF7 (HER2$^{low}$) treated with 400 nM CD3(h10.v39) x HER2(4D5) TMATE under same conditions except various pHs

| | pH ≈ 6.6 or 6.7 | pH ≈ 7.1 or 7.2 | pH ≈ 7.4 or 7.5 |
|---|---|---|---|
| Donor #24 | No killing | No killing | No killing |
| Donor #78 | 20% | No killing | No killing |
| Donor #81 | 3% | No killing | No killing |
| Donor #94 | N.D. | No killing | No killing |
| Donor #97 | N.D. | No killing | No killing |

N.D. not determined (h10.v39)
α CD3

α HER2

Summary of T cell activation (% CD69+ CD25+ cells) profiles upon MCF7 (HER2 low) treatment with 400 nM CD3 (h10.v39) x HER2 (4D5) TMATE

|  | pH = 6.6–6.7 | pH = 7.1–7.2 | pH = 7.4–7.5 |
|---|---|---|---|
| Donor #24 | Near 0% (baseline) | Near 0% (baseline) | Near 0% (baseline) |
| Donor #28 | 20% | Near 0% (baseline) | Near 0% (baseline) |
| Donor #81 | 32% | Near 0% (baseline) | Near 0% (baseline) |
| Donor #94 | N.D. | Near 0% (baseline) | Near 0% (baseline) |
| Donor #97 | N.D. | Near 0% (baseline) | Near 0% (baseline) |

N.D., not determined (h10.v39)
α CD3

α HER2

Fig. 28 T cell activation assays with MCF7 (HER2^low); Various donors

Fig. 29

Cytokine release profile with MCF7 (HER2$^{low}$) and BT474 (HER2$^{high}$) treated with 400 nM of CD3 (h10.v39) x HER2 (4D5) TMATE; Various donors IL-2, IFN-γ and TNF-α

|  | pH = 6.6 to 6.7 | pH = 7.1 to 7.2 | pH = 7.4 to 7.5 |
|---|---|---|---|
| Donor #24 | Base line (no increase) | Base line (no increase) | Base line (no increase) |
| Donor #78 | N.D. | N.D. | Base line (no increase) |
| Donor #81 | N.D. | N.D. | Base line (no increase) |
| Donor #94 | N.D. | N.D. | N.D. |
| Donor #97 | N.D. | N.D. | N.D. |

N.D. not determined

Fig. 31

| Cell line/type | Cell surface TROP-2 copy # |
|---|---|
| MDA-MB-231 | 43,870 ± 399 |
| Keratinocytes | 62,112 ± 1,407 |
| BT-20 | 143,128 ± 2,871 |
| MDA-MB-468 | 174,549 ± 1,859 |

T cell mediated killing assays with MDA-MB-468 cells (TROP-2^high); three different donors Cytokine induction by CD3(h10.v38) x TROP-2 (RS.v1) with MDA-MB-468 (TROP-2^high); Donors #201538 and #201550

Cytokine induction by CD3(h10.v38) x TROP-2 (RS.v1) with MDA-MB-468 (TROP-2$^{high}$); Donors #201538 and #201550

Cytokine induction by CD3(h10.v38) x TROP-2(RS.v1) with MDA-MB-468 (TROP-2^high); Donors #201538 and #201550

Cytokine induction by CD3(h10.v38) x TROP-2(RS.v1) with MDA-MB-468 (TROP-2^high); Donors #201538 and #201550

T cell mediated killing of MDA-MB-468 (TROP-2 high) by CD3(h10.v38) x TROP-2(RS7.v1) TMATE; Donor #201538

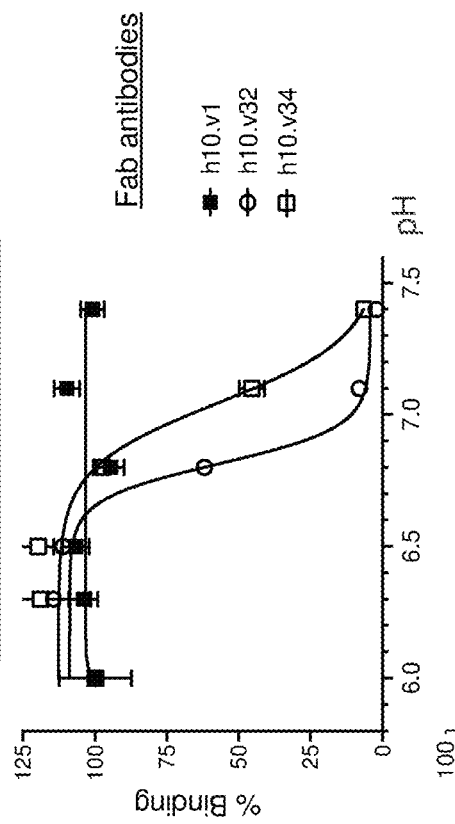
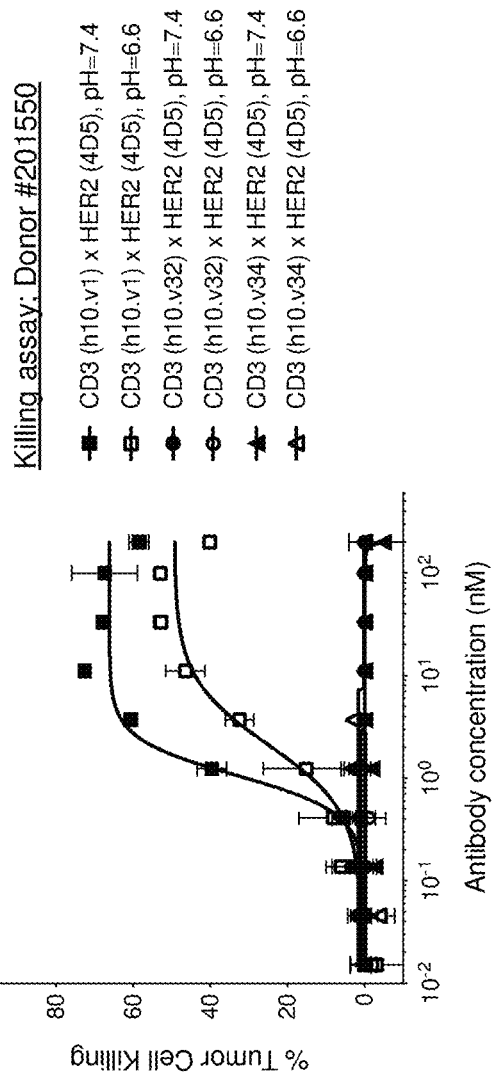
Fig. 50

ANTI-CD3 CONSTRUCTS AND USES THEREOF

CROSS-REFERENCE TO RELATED APPLICATION

This application is a national stage application under 35 U.S.C. § 371 of International Application No. PCT/US2022/072996, filed internationally on Jun. 16, 2022, which claims priority to U.S. provisional application 63/212,024, filed on Jun. 17, 2021, and U.S. provisional application 63/305,588, filed on Feb. 1, 2022, the contents of which are incorporated by reference in their entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 202222000100SEQLIST.TXT, date recorded: Dec. 14, 2023, size: 106,821 bytes).

TECHNICAL FIELD

The present disclosure relates to microenvironment acidity dependent anti-CD3 constructs such as antigen binding molecules thereof, which are specific for cluster of differentiation 3 (CD3), such as multispecific antigen-binding molecules that bind to CD3 and a tumor associated target molecule, and the uses thereof.

BACKGROUND OF THE APPLICATION

Immunotherapy has been a fast-arising approach that is increasingly shifting the treatment paradigm for a variety of human disease conditions including cell proliferative disorders, autoimmunity, allergy, graft versus host diseases, and transplant rejections. One important class of immunotherapeutics is multispecific molecules which are capable of engaging at least two molecular sites (i.e., epitopes) on a same target or on two distinct targets. Example multispecific molecules are CD3-targeting antibodies that can engage a T cell through a CD3-binding moiety, and a tumor cell through a tumor-specific moiety, to achieve effective tumor cell killing by activating the engaged T cell. These CD3-dependent T cell mediated multispecific antibodies (TMAs, aka T cell engagers or TCEs) hold great promises in disease intervention.

CD3 is a complex of transmembrane proteins that are expressed primarily on the surface of T cells, consisting of four distinct signaling molecules: CD3ζ, CD3γ, CD3δ, and CD3ε. One CD3εγ heterodimer, one CD3εδ heterodimer, and one CD3ζ homodimer, together with the T cell receptor (TCR) heavy and light chains, form a highly delicate octameric TCR complex that is responsible for recognizing fragments of antigen as peptides bound to major histocompatibility complex (MHC) molecules (pep-MHC). While the TCR heavy and light chains are primarily responsible for recognizing pep-MHC presented to a T cell by antigen presenting cell, CD3 has been exploited as a target to engage T cells for disease treatment, to bypass the restriction by the MHC. However, conventional TMAs are largely limited by their suboptimal safety profile which is widely considered as a major bottleneck that has been limiting the otherwise broader clinical usages of TMAs. Relevant to the suboptimal property features of conventional TMAs are two critical safety concerns: (1) on-target off-site killing of non-tumorous normal tissue cells, and (2) cytokine release related toxicity. Thus, there are significant unmet clinical needs for developing innovative TMAs that are potent yet safer than conventional TMAs for the treatment of human diseases such as abnormal cell proliferation disorders including cancer.

The disclosures of all publications, patents, patent applications and published patent applications referred to herein are hereby incorporated herein by reference in their entirety.

BRIEF SUMMARY OF THE APPLICATION

The following summary is illustrative only and is not intended to be limiting in any way. That is, the following summary is provided to introduce highlights, benefits and advantages of the novel molecules and the uses thereof. Thus, the following summary is not intended to identify essential features of the claimed subject matter, nor is it intended for use in determining the scope of the claimed subject matter.

Provided are the sequences of anti-CD3 antibodies (including but not limited to humanized pH-sensitive anti-CD3 antibodies). In this application, antibodies are broadly defined as antigen binding molecules. Provided are the variable regions of the heavy and light chains of these pH sensitive anti-CD3 antibodies, and the relevant Cluster Determination Regions (CDRs) thereof. Provided are the CDR consensus sequences of the provided CDRs among select anti-CD3 antibodies.

Provided are biophysical and cell-based binding activity characterizations of exemplary pH-sensitive CD3 antibodies. Provided are the molecular formats of exemplary multispecific anti-CD3 TMATEs (Tumor Microenvironment Acidity-activated T cell Engagers) including various CD3×HER2, CD3×TROP-2, and CD3×EpCAM TMATEs.

Provided are biophysical, biochemical, and functional characterizations of exemplary multispecific anti-CD3 TMATEs. Provided are exemplary characteristic profiles of pH-dependent T cell activation triggered by anti-CD3 TMATEs comprising one of the select pH sensitive anti-CD3 construct variants.

Provided are pH sensitive CD3×HER2 dual-binding multispecific molecules (or "CD3×HER2 TMATEs" or "anti-HER2 TMATEs") that comprise a Fragment antigen-binding (Fab) domain of one of the select pH sensitive anti-CD3 antibody moieties, and an anti-HER2 arm. Provided are biophysical and functional characterizations of these multispecific CD3×HER2 TMATEs.

Provided are exemplary uses of CD3×HER2 TMATEs for effective killing of HER2 positive cancer cells in a T cell mediated and pH-dependent manner. Provided are exemplary uses of these CD3×HER2 TMATEs, which upon engaging tumor and target cells show favorable profiles of triggering low cytokine-secretion under tumor microenvironment relevant low pH conditions or physiologically relevant pH conditions.

Provided are example uses of the CD3×HER2 TMATEs exhibiting virtually no or minimal killing activity towards normal-mimicry HER2-low cells under physiologically relevant pH conditions. Provided are examples of these CD3×HER2 TMATEs exhibiting a functional profile with virtually no or minimal cytokine release towards the normal-like HER2-low target cells under physiologically relevant pH conditions.

Provided are pH sensitive CD3×TROP-2 dual-binding multispecific molecules ("CD3×TROP-2 TMATEs" or "anti-TROP-2 TMATEs") that comprise one of the select pH-sensitive anti-CD3 arms, and an anti-TROP-2 arm.

Provided are exemplary uses of CD3×TROP-2 TMATEs for effective killing TROP-2-positive cancer cells in a T cell mediated and pH-dependent manner.

Provided are examples of these CD3×TROP-2 TMATEs exhibiting virtually no or minimal killing activity towards normal-like TROP-2-low target cells under physiologically relevant pH conditions. These CD3×TROP-2 TMATEs engaging tumor and target cells exhibit a preferred profile of triggering only a low level of cytokine secretion under tumor microenvironment relevant low pH conditions.

Provided are pH-sensitive CD3×EpCAM dual-binding multispecific molecules ("CD3×EpCAM TMATEs" or "anti-EpCAM TMATEs) that comprise one of the select pH-sensitive anti-CD3 antibody arms, and an anti-EpCAM antibody arm.

Provided are exemplary alternative therapeutic modalities or agents comprising an anti-CD3 TMATE that comprises a pH-sensitive anti-CD3 antibody moiety; such modalities or agents include without limitation to immunoconjugates, RNA based therapeutics, gene therapeutics, engineered cell therapies such as TCR-T cells, CAR-T cells, CAR-NK cells, NK cells, NKT cells, gene-edited T or NK cells, tissue progenitor cells, mesenchymal stem cells, stem and stem like cells, and artificially induced cells.

Provided are exemplary uses of anti-CD3 TMATEs in a combination therapy with a second agent or therapy. Such a second agent or therapy includes without limitation to immune checkpoint inhibitors, anti-angiogenesis inhibitors, tyrosine kinase inhibitors, DNA-damage-repair or DNA-recombination inhibitors, chemotherapeutic agents, oncolytic viruses, CDK4/CDK6 inhibitors, lactate transporter inhibitors, and vaccines.

BRIEF DESCRIPTION OF THE DRAWINGS

The accompanying drawings are included to provide a further understanding of the present disclosure and are incorporated in and constitute a part of this specification. The drawings illustrate embodiments of the present disclosure and, together with the description, serve to explain the principles of the present disclosure. The drawings may not necessarily be in scale so as to better present certain features of the illustrated subject matter. Like annotation symbols in the various drawings indicate like elements, unless otherwise stated.

FIG. 2 (bottom panel B) shows exemplary alternative TMATE configurations wherein the disease target molecule is a tumor associated antigen (TAA).

FIG. 3 (bottom panel B) illustrates alternative exemplary single polypeptide formats of TMATEs that generally bear an anti-CD3 domain, one or more anti-TAA domains recognizing a same TAA or two different TAAs, and optionally a half-life-elongating domain such as an anti-HSA moiety.

FIGS. 5A-B show the ELISA based binding of a pH sensitive anti-CD3 antibody h10.v39 (Fab) and the non-pH-selective control clone (h10.v1) to the extracellular domain of either human (FIG. 5A) or cynomolgus monkey (FIG. 5B) CD3E.

FIG. 9 shows the molecular configuration of a multispecific CD3 (h10.v38)×TROP-2 (RS7.v1) TMATE and an analytical HPLC chromatogram result indicating ≥98% high purity of the said TMATE that is recombinantly expressed in Expi293 cells and purified via chromatography.

FIG. 11 (bottom panel B) shows the molecular configuration of a multispecific TMATE, CD3 (h10.v26)×HER2(4D5) (Fab-scFv) and its tumor cell killing performance at different pH compared to the CD3(H24Y)× HER2(4D5).

FIGS. 13A-B shows the percentage of T cell activation, as measured by CD69 and CD25 double positive cell surface expression with flow cytometry, after 48 hours of co-incubation of donor-derived human primary T cells, including CD4 T cells (FIG. 13A) and CD8 T cells (FIG. 13B), and HER2-positive BT474 cells in the presence of one of the two multispecific antibodies (CD3(h10.v26)×HER2(4D5) and CD3(H24Y)×HER2(4D5)) under specific pH media, respectively. This activation assay is based on samples from one and the same T cell cytotoxicity assay described in FIG. 11.

FIG. 29 provides an ELISA result summary table indicating no cytokine release from the T cells beyond the baseline triggered by the TMATE comprising CD3 (h10.v39)×HER2 (4D5) provided at a high dose of 400 nM, in the presence of the HER2$^{low}$ target cell MCF7 and various donor T cells (E:T=11:1), under the same culture conditions of about 6.6 or 6.7, about 7.1 or 7.2 and about 7.4 or 7.5, respectively.

FIG. 31 provides a table showing the surface expression level of a tumor associated antigen TROP-2 in a panel of cell types, which are quantified by flow cytometry with a serial of standard fluorescent calibration microbeads and an anti-TROP-2 antibody (RS7).

FIG. 48 (middle and right, B and C) shows flow cytometry-based cell surface binding activity of h10.v23 (Fab) towards human primary T cells, shown as % of cells with surface binding (middle, B) and mean fluorescence intensity (right C) respectively. Here h10.v1 is a conventional anti-CD3 control antibody.

FIG. 50A shows an ELISA based binding profile of two pH-dependent anti-CD3 clones h10.v32 and h10.v34 (Fabs) to recombinant human CD3E (ECD). FIG. 50B shows T cell mediated tumor-cell killing assays for two multispecific antibodies, namely CD3 (h10.v32)×HER2 (4D5) and CD3 (h10.v34)×HER2 (4D5), each formatted as the same hIgG1-Fc (KiH) format, showing that the killing activity for both of these two bispecific antibodies is sub-optimal under either pH (about pH 6.6 or pH 7.4) and is not pH-dependent under all tested doses up to 200 nM.

DETAILED DESCRIPTION OF THE APPLICATION

Figure 1:
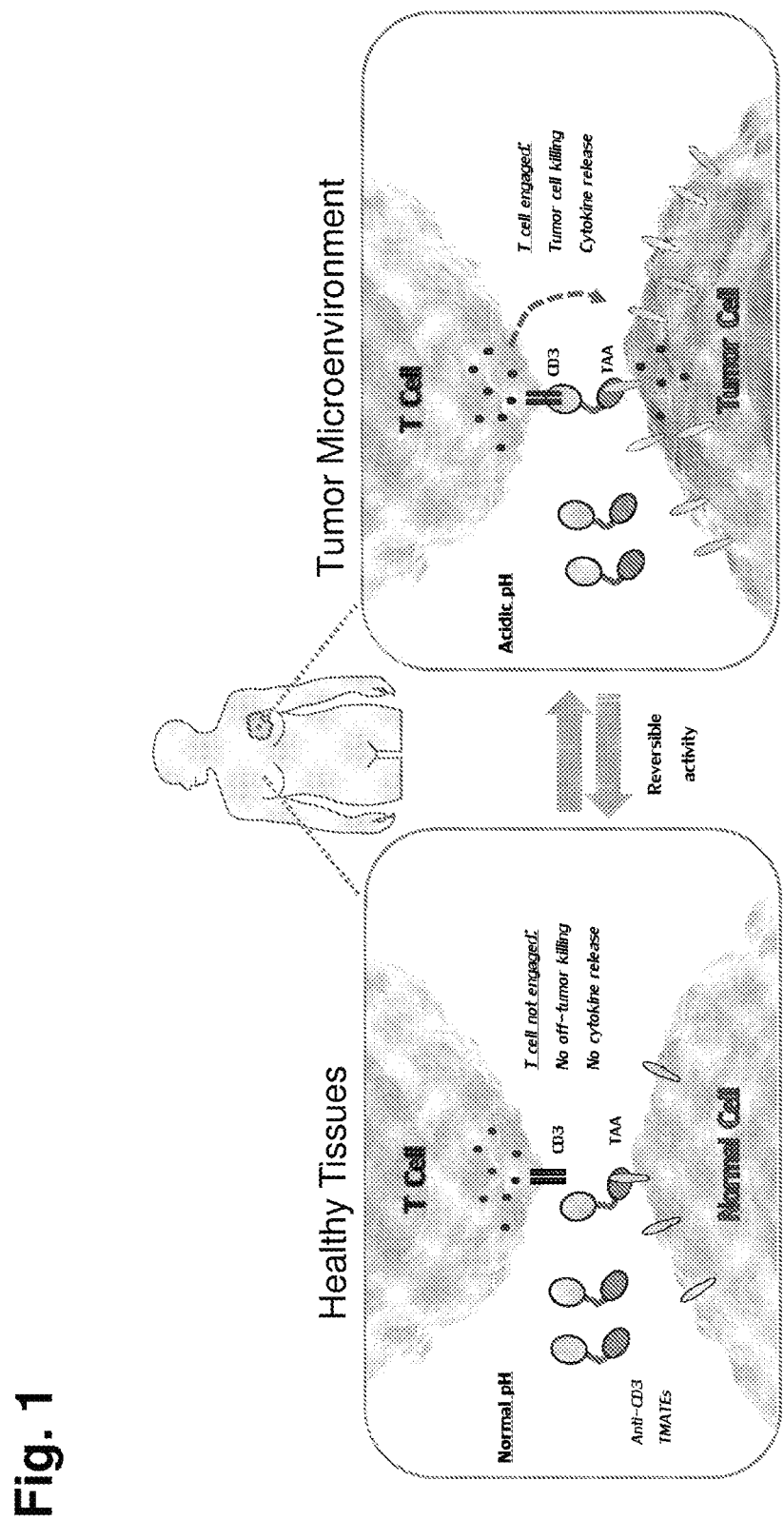
FIG. 1 is a schematic illustrating the concept that an anti-CD3 multispecific TMATE (Tumor Microenvironment Acidity-activated T-cell Engagers) will engage T cells in an acidity dependent manner to achieve direct tumor cell killing and cytokine secretion, wherein such killing activity is reversible upon pH changes in the tissue microenvironment. TMATE can also indirectly activate bystander immune cells in part through local cytokine signaling to enhance anti-tumor immunity.

The present application provides novel anti-CD3 constructs (such as agonist anti-CD3 constructs) that specifically bind to CD3, such as humanized anti-CD3 antibody moieties, anti-CD3 monoclonal antibodies, and multispecific antibodies that bind to a tumor-associated antigen (TAA), methods of preparing the anti-CD3 constructs, methods of using the constructs (e.g., methods of treating a disease or condition, methods of modulating an immune response, or methods of modulating a cell composition).

One hallmark feature of cancer is the aerobic glycolysis metabolism first reported by Otto Warburg in the 1920s and further supported by over 15,000 scientific publications based on PubMed search results. Aerobic glycolytic metabolism commonly leads to unique acidic tumor microenvironment with a typical pH range of about 5.8 to about 7.0 and an average pH of about 6.6 or 6.7, in comparison to the commonly known extracellular interstitial pH range of about 7.2 to about 7.5. Through complex effects on genetics, epigenetics, cell metabolism and signaling, the tumor acidity may promote cancer progression. There have been prior therapeutics research and development efforts to reverse tumor glycolytic metabolism through using H+/lactate transporter inhibitors such as small molecule compounds for MCT1, MCT4 and CA-IX, yet little progress has been achieved in this direction (reviewed in Cancer Metastasis Rev. (2019) 38: 205-222; Annu. Rev. Phyiol. (2020) 82: 21.1-21.24).

CD3 dependent T cell engaging immune-therapeutic antibodies ("T cell mediated antibodies", TMA) are conventionally known in the arts as monoclonal and bispecific antibodies such as those based on anti-CD3 clones OKT3, L2K-07, SP34, UCHT1, hu38E4, hu40G5c and SK7. These conventional TMAs are generally not selective for tumor acidic microenvironment versus normal extracellular interstitial conditions. Tumor microenvironment acidity-activated T-cell engagers ("TMATEs") can potentially improve the specificity of tumor targeting. While there are references for isolating antibodies with pH-biased binding activity, such pH-dependent binding activity does not readily translate into pH-dependent killing activity that could be otherwise critical for a TMATE, in part due to the exquisite biological nature of the T Cell Receptor signaling machinery that entails delicate molecular engineering of the said CD3 antibody to ultimately achieve its pH-dependent killing activity relevant to therapeutic uses. There is still lack of innovative anti-CD3 TMATEs with definitive acidity-dependent target tumor cell killing activity (e.g., potent tumor cell killing activity under pH 6.6 or 6.7) as well as a preferred profile with significantly reduced cytokine induction under normal tissue environment, as compared to that of conventional TMAs.

The present application provides anti-CD3 constructs that have unique and advantageous features of: a) having a pH sensitive binding to CD3, wherein the anti-CD3 exhibits medium-low to high affinity to CD3 under acidic conditions with a pH value of about 6.0 to about 6.9 or from about 6.4 to about 6.8 (e.g., having an affinity $K_D$ value ranging from about 0.1 nM to about 1000 nM, such as about 5 nM to about 300 nM, about 100 nM to about 500 nM, and about 400 nM to about 1000 nM), but having only minimal or low affinity to CD3 under weakly basic or neutral conditions with a pH value of about 7.4 or from about 7.2 to about 7.6 (e.g., having an affinity $K_D$ value range of about 100 nM, about 200 nM or 300 nM to about 1 μM, about 5000 μM or to a near undetectable level, such as about 150 nM to about 1.5 µM, about 500 nM to about 5 µM, about 2 µM to about 200 µM, about 100 µM to about 1000 µM, about 500 µM to 5000 µM or to a near undetectable level); b) preferentially triggering T-cell mediated killing of TAA-positive target cells in acidic conditions of about pH 6.4 to about pH 6.9, but with negligible or weak killing under physiologically relevant pH conditions of about 7.2 to about 7.6; c) only triggering relatively low cytokine (such as IL-2, IFNγ, TNFα, IL-6, IL-10, IL-8) secretion (such as only triggering relatively low cytokine secretion of at least two of these cytokines, upon engaging TAA-positive target cells in acidic or near-neutral conditions), and/or d) triggering minimal or virtually no killing of TAA-low cells (e.g., normal cells with low TAA expression) at physiologically relevant conditions of about pH 7.2 to about pH 7.6.

I. Definitions

The term "antibody" is used in its broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity. The term "antibody moiety" refers to a full-length antibody or an antigen-binding fragment thereof.

A full-length antibody comprises two heavy chains and two light chains. The variable regions of the light and heavy chains are responsible for antigen binding. The variable domains of the heavy chain and light chain may be referred to as "$V_H$" and "$V_L$", respectively. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and µ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Plückthun in *The Pharmacology of Monoclonal Antibodies*, vol. 113, Rosenburg and Moore eds., Springer-Verlag, New York, pp. 269-315 (1994).

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.*, 273: 927-948 (1997); MacCallum et al., J. Mol. Biol. 262:732-745 (1996); Abhinandan and Martin, *Mol. Immunol.*, 45: 3832-3839 (2008); Lefranc M. P. et al., *Dev. Comp. Immunol.*, 27: 55-77 (2003); and Honegger and Plückthun, *J. Mol. Biol.*, 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, *Mol. Immunol.*, 45: 3832-3839 (2008); Ehrenmann F. et al., *Nucleic Acids Res.*, 38: D301-D307 (2010); and Adolf-Bryfogle J. et al., *Nucleic Acids Res.*, 43: D432-D438 (2015). The contents of the references cited in this paragraph are incorporated herein by reference in their entireties for use in the present application and for possible inclusion in one or more claims herein.

TABLE 1

| CDR DEFINITIONS | | | | | |
|---|---|---|---|---|---|
| | Kabat[1] | Chothia[2] | MacCallum[3] | IMGT[4] | AHo[5] |
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |

TABLE 1-continued

CDR DEFINITIONS

|  | Kabat[1] | Chothia[2] | MacCallum[3] | IMGT[4] | AHo[5] |
|---|---|---|---|---|---|
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or hypervariable region (HVR) of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the CDR residues as herein defined.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227: 381 (1991), Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., Nucleic Acids Research 32(5):1792-1797, 2004; Edgar, R. C., BMC Bioinformatics 5(1):113, 2004).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, $C_H$) of the heavy chain and the CHL (or $C_L$) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

The "CH1 domain" (also referred to as "C1" of "H1" domain) usually extends from about amino acid 118 to about amino acid 215 (EU numbering system).

"Hinge region" is generally defined as a region in IgG corresponding to Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

The term "Fc region" or "fragment crystallizable region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See M. Dadron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody or fragment thereof "competes" for binding to a target antigen with a second antibody or fragment thereof when the first antibody or fragment thereof inhibits the target antigen binding of the second antibody of fragment thereof by at least about 50% (such as at least about any one of 55%, 60%, 65%, 70%, 75%, 80%, 85%, 90%, 95%, 98% or 99%) in the presence of an equimolar concentration of the first antibody or fragment thereof, or vice versa. A high throughput process for "binning" antibodies based upon their cross-competition is described in PCT Publication No. WO 03/48731.

As use herein, the terms "specifically binds," "specifically recognizing," and "is specific for" refer to measurable and reproducible interactions, such as binding between a target and an antibody or antibody moiety, which is determinative of the presence of the target in the presence of a heterogeneous population of molecules, including biological molecules. For example, an antibody or antibody moiety that specifically recognizes a target (which can be an epitope) is an antibody or antibody moiety that binds this target with greater affinity, avidity, more readily, and/or with greater duration than its bindings to other targets. In some embodiments, the extent of binding of an antibody to an unrelated target is less than about 10% of the binding of the antibody to the target as measured, e.g., by a radioimmunoassay (RIA). In some embodiments, an antibody that specifically binds a target has a dissociation constant (Kn) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, an antibody specifically binds an epitope on a protein that is conserved among the protein from different species. In some embodiments, specific binding can include, but does not require exclusive binding. Binding specificity of the antibody or antigen-binding domain can be determined experimentally by methods known in the art. Such methods comprise, but are not limited to Western blots, ELISA-, RIA-, ECL-, IRMA-, EIA-tests, biolayer interferometry, surface plasma resonance, and peptide scans.

The term "tumor microenvironment" or "TME" refers to the environment around a tumor, including the surrounding blood vessels, immune cells, fibroblasts, signaling molecules and the extracellular matrix. In some embodiments, tumor microenvironment comprises the microenvironment of a tumor draining lymph node.

The term "TAA positive" and "TAA-positive" can be used interchangeably, which refers to a cell-surface expression level of a tumor associated antigen ("TAA") at a pathologically relevant high level or at a commonly accepted high level defined in clinical or diagnostic practices. For instance, "HER2-positive" is generally defined as HER2 3+ based on immunohistology analysis of tumor specimen sections, or as HER2 2+ plus positive HER2 gene amplification status confirmed by FISH (fluorescent in situ hybridization). In comparison, "TAA low" or "TAA-low" refers to a cell-surface expression level of a tumor associated antigen at a low level commonly observed in normal tissues or in some tumor cells which are categorized as "TAA low" in clinical or diagnostic practices. For instance, heart cardiomyocytes are generally considered as HER2-low cells due to their low HER2 expression level. In some embodiments, a TAA positive cell means a target cell expressing a high or medium-high level of the said TAA on the said target cell's surface.

An "isolated" antibody (or construct) is one that has been identified, separated and/or recovered from a component of its production environment (e.g., natural or recombinant). Preferably, the isolated polypeptide is free of association with all other components from its production environment.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a pre-sequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, and may contain mutations. Mutant progeny that have the same function or biological activity as screened or selected for in the originally transformed cell are included herein.

As used herein, "treatment" or "treating" is an approach for obtaining beneficial or desired results, including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the application contemplate any one or more of these aspects of treatment.

In the context of cancer, the term "treating" includes any or all of: inhibiting growth of cancer cells, inhibiting replication of cancer cells, lessening of overall tumor burden and ameliorating one or more symptoms associated with the disease.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to that of a reference. In certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, 98% or greater.

The term "EC50" or "$EC_{50}$" refers to the dose of a therapeutic agent such as a TMATE that can reach the killing or growth inhibition of about 50% of target cells as compared to or normalized with the 0% killing or 0% growth inhibition by a negative control (or a mock control) under a defined experimental condition. EC50 may be determined using a software or informatics tool such as GraphPad Prism, Excel, MATLAB, and R.

The term "ECmax" or "$EC_{max}$" refers to the lowest dose of a therapeutic agent such as a TMATE that can reach the maximal plateau killing or growth inhibition of target cells, i.e., the increase of which will not further enhance the killing or growth inhibition effect. ECmax may be determined using a software or informatics tool such as GraphPad Prism, Excel, MATLAB, and R.

A "reference" as used herein, refers to any sample, standard, or level that is used for comparison purposes. A reference may be obtained from a healthy and/or non-diseased sample. In some examples, a reference may be obtained from an untreated sample. In some examples, a reference is obtained from a non-diseased or non-treated sample of an individual. In some examples, a reference is obtained from one or more healthy individuals who are not the individual or patient.

The term "benchmark" as in "benchmark clone" or "benchmark antibody" or "benchmark TMA" refers to well characterized or standard antibody clones that are used for comparison purpose. A commonly used benchmark antibody can be an antibody clone sequence that is comprised by a clinically approved antibody drug. For example, the well characterized anti-CD3 clones OKT3 and the related L2K-07 (aka L2K or de-immunized L2K) comprised by the FDA-approved Blinatumomab, and SP34 that is commonly adapted as a component of some conventional TMAs. In some embodiment, a benchmark is meant a reference.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late-stage cancer, such as development of metastasis, may be delayed.

"Preventing" as used herein, includes providing prophylaxis with respect to the occurrence or recurrence of a disease in an individual that may be predisposed to the disease but has not yet been diagnosed with the disease.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

The terms "subject," "individual," and "patient" are used interchangeably herein to refer to a mammal, including, but not limited to, human, bovine, horse, feline, canine, rodent, or primate. In some embodiments, the individual is a human.

An "effective amount" of an agent refers to an amount effective, at dosages and for periods of time necessary, to achieve the desired therapeutic or prophylactic result. The specific dose may vary depending on one or more of: the particular agent chosen, the dosing regimen to be followed, whether it is administered in combination with other compounds, timing of administration, the tissue to be imaged, and the physical delivery system in which it is carried.

A "therapeutically effective amount" of a substance/molecule of the application, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

The terms "pharmaceutical formulation" and "pharmaceutical composition" refer to a preparation which is in such form as to permit the biological activity of the active ingredient(s) to be effective, and which contains no additional components which are unacceptably toxic to an individual to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to an individual. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about 60 minutes, such as no more than about any of 30, 15, 10, 5, or 1 minutes.

The term "sequentially" is used herein to refer to administration of two or more therapeutic agents where the administration of one or more agent(s) continues after discontinuing the administration of one or more other agent(s). For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month, or longer.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

It is understood that embodiments of the application described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

The term "tissue environment" or "tumor microenvironment" refers to interstitial extracellular environment, which is explicitly distinct from intracellular environment.

The term "Fig." refers to its common meaning as an abbreviation for "Figure" and can be used interchangeably with "Fig.", such that FIG. 1 represents FIG. 1 and bears the same meaning as "FIG. 1", so on and so forth throughput this disclosure.

The term "CD3×TAA" refers to its common meaning as an abbreviation for a multispecific antibody that comprises an anti-CD3 moiety and an anti-TAA moiety. Herein and thereafter and throughout this disclosure, "CD3×TAA" and "TAA×CD3" shall bear the same meaning and can be used interchangeably. As such, CD3×HER2 shall mean the same as HER2×CD3, both referring to the same bispecific antibody that recognizes HER2 and CD3.

As used herein and in the appended claims, the singular forms "a," "or," and "the" include plural referents unless the context clearly indicates otherwise.

II. Anti-CD3 TMATE Constructs

Anti-CD3 constructs described herein comprise anti-CD3 moiety (such as any of the anti-CD3 moiety described herein). In some embodiments, the anti-CD3 constructs described herein comprise an multispecific anti-CD3 construct such as anti-CD3 based Tumor Microenvironment Acidity activated T cell Engagers (TMATEs) that are sensitive to pH changes. The current application provides the key features and moieties of such anti-CD3 TMATEs, the exemplary molecular formats of such TMATEs and the uses thereof for disease intervention.

In general, TMATEs are meant non-conventional T cell mediated multispecific antibodies that preferentially engage T cells via CD3 to achieve T cell activation for target cell killing under an acidic microenvironment (e.g., an environment of about pH 6.5 to pH 6.9). In comparison, currently available CD3-based T cell-mediated multispecific antibodies typically do not show acidity selectivity and in some cases rather exhibit weaker T cell mediated target cell killing activity under acidic conditions of about pH 6.5 to about pH 6.9 as compared to conditions of about pH 7.1 to about pH 7.4.

For clarity, the term "TMATE" used herein in the current disclosure can be used interchangeably with "anti-CD3 TMATE", or "anti-CD3 TMATE construct" or "multispecific anti-CD3 TMATE construct" or "multispecific anti-CD3 TMATE molecules".

As used herein, the term "T cell mediated multispecific antibody" ("TMA") refers to a biologic molecule that comprises at least a first and a second binding module, wherein the first binding module is capable of binding to a first antigen or target, and the second binding module is capable of binding to a second antigen or target, or to a second epitope of the same first antigen or target. In some embodiments, TMAs refer to a bispecific construct or molecule. In some embodiments, TMAs refer to a multi-specific binding molecule such as a trispecific binding molecule comprising three binding modules or a tetra-specific binding molecule comprising four unique binding modules. As used herein, the term "binding module" can be used interchangeably with "moiety" or "domain" or "region" or "fragment" or "subunit" or "arm". In some embodiments, TMAs comprise a single fusion polypeptide, a dimeric complex consisting of two polypeptides, a trimeric complex consisting of three polypeptides, or a multimeric complex consisting of four or more polypeptides. In some embodiments, the binding module is a polypeptide or a portion or fragment of it thereof. In some embodiments, the binding module comprises two or more portions from two or more polypeptides respectively. In the case that the TMA is a bispecific molecule, the term "TMA" is interchangeable with "TMB" (T cell mediated bispecific antibody). In some embodies, TMA can be interchangeably with "TCE" (T cell engagers). In some embodiments, conventional TMAs shows no significant pH preferences in terms of engaging T cells.

In one aspect, a TMA can engage a T cell from one side of the TMA molecule, and engage a target molecule on a target cell (e.g., a disease cell) from another side of the same TMA, wherein the target molecule on the disease cell is assumed to serve as a mechanical anchor and provide recognition specificity for the TMA. Upon forming a molecule bridge and an immune synapse between the said target cell and the said T cell, the T cell may become activated, and subsequently allow a molecular signaling cascade to occur, ultimately leading to intracellular transcriptional alterations, and phenotypic and functional changes of the T cell. Typical phenotypic and functional changes of the T cells include upregulation of activation markers (e.g., CD69, CD25, CD137), the immune-checkpoint molecules (e.g., PD-1, LAG3, TIM3), secretion of cytokines (e.g., IL-2, IFNγ, TNFα, IL-6, IL-10, IL-1, IL-8, IL-4, IL-12, MCP-1, CXCL10) and in some cases the upregulation or mobilization of the T cell's intrinsic "killing machinery" (i.e., the apoptotic perforins and granzymes, and death receptor ligands such as Fas ligands). In some embodiments, the activated T cells can kill the engaged target cell by locally delivering a payload of granzymes through cell-surface holes on the target cells. Such cell-surface holes are generated by perforins that are also locally and directionally delivered via a microtubule network from the engaged T cell to the target cells. Upon the target cell death, the molecule bridge may become disengaged, and the T cells may then move on to engage and kill another target cell bearing the same target antigen molecules.

In some embodiments, there is provided an anti-CD3 construct that comprises an anti-CD3 antibody moiety such as any of those described herein, optionally plus one other moiety that binds to a disease cell such as a tumor cell.

In general, as illustrated in FIG. 1, in an acidic tumor microenvironment TMATEs can now interact with CD3 to adequately link T cells to a cancer cell for direct killing. Moreover, TMATEs will induce cytokine secretion from the activated T cells, which can in turn activate, promote, or mobilize proximal bystander immune cells to achieve enhanced immune response against the tumor cells. In some embodiments the bystander cells can be T cells such as tumor infiltrating T cells and tissue resident T cells. In some embodiments, the bystander cells can be innate immune cells such as dendritic cells, NK cells, monocytes, neutrophils, basophils, eosinophils, and macrophages. In some embodiments, the bystander cells can be adaptive immune cells such as B cells. On the other hand, in a healthy tissue environment with near pH 7.4, TMATEs will not engage T cells and therefore will not or will barely trigger any killing of or any cytokine release towards normal cells that may express a target molecule at a physiological level.

Figure 2:
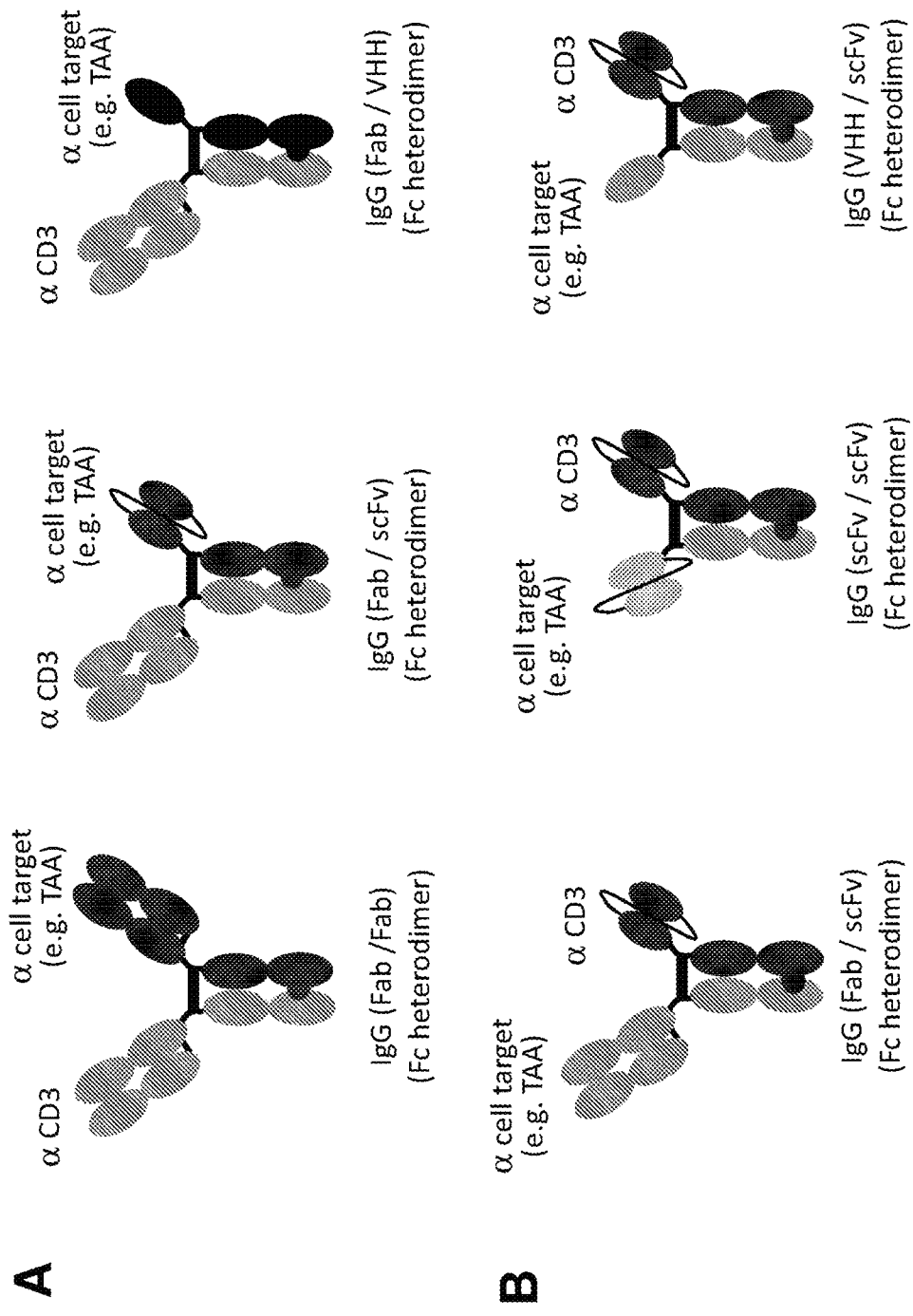
FIG. 2 (top panel A) illustrates exemplary configurations of multispecific TMATEs that generally bear an anti-"disease target" (e.g., a tumor associated antigen) arm such as a Fab, a scFv, and a VHH (i.e., $V_HH$) domain, and an anti-CD3 arm such as a Fab and scFv, wherein the anti-disease-target arm and the anti-CD3 arm form a complex molecule through a linker or an engineered fragment crystallizable (Fc) domain represented by a human IgG1 Fc with so-called "Knobs-into-Holes" variants.

As exemplified in FIG. 2, the anti-CD3 multispecific TMATEs can be a bispecific molecule comprising a pH-dependent anti-CD3 moiety and one anti-disease-target (i.e., anti target-cell-molecule) moiety. In some embodiments, the said anti-CD3 moiety is a Fab, a scFv, a single-domain antibody (sdAB), a nanobody, a VHH-only domain or an alternative antibody-mimicking scaffold. In some embodiments, the anti-disease-target moiety is anti-tumor associated antigen (TAA) moiety, which is a Fab, a scFv, a single-domain antibody, a nanobody, a VHH-only domain or an alternative antibody-mimicking scaffold. In some embodiments, the TMATE comprises a Fc or Fc-like domain that prolongs antibody half-life in circulations. In some embodiments, the Fc or Fc-like domain is derived from an IgG1, an IgG2, an IgG3, an IgG4 or an IgM of human.

In some embodiments, the target cells are tumor cells. In some embodiments, the target cells are cells with an abnormal proliferation property exemplified by a neoplasia or dysplasia pathological condition. In some embodiments, the target cells are general kinds of "disease associated cells", which are not tumoral per se but nonetheless directly contribute to a disease condition. Exemplary non-tumoral disease cells include but are not limited to the following: (a) myeloid derived immune suppress cells (MDSCs) and regulatory T cells (Treg), each type of which is known to contribute to an immune-suppressive tumor microenvironment, (b) virus-infected immune or non-immune cells, and (c) tumor promoting cells such as M2 macrophages, M2-like macrophages, and/or stromal cells represented by cancer associated fibroblasts (CAFs). Generally, a disease cell associated target molecule can be a marker that is preferentially upregulated or overexpressed in the said disease associated cell. Exemplary disease cell associated targets are various tumor associated antigens for a variety of types of tumors, CD33 for myeloid derived suppressive cells, and virus-derived peptides that are presented on the surface of infected human cells via an MHC-I or MHC-II complex. As used herein, the term "tumor associated antigen" or "TAA" shall generally include the so-called "tumor neoantigen" and "tumor specific antigen".

In some embodiments, anti-TAA moieties are one of the following: (1) antibodies and antibody-like molecules, and further derivative or fusion forms of these molecules thereof; (2) cytokine or cytokine-like molecules, including cytokines, growth factors, chemokines, extra-cellular domains of cell membrane associated proteins, and the further derivative or fusion forms of these said molecules thereof; (3) non-antibody alternative scaffolds; (4) any combination or pairing from (1), (2) and (3) in the foregoing sentence with exemplary examples of antibody-cytokine fusions or immunocytokines and their various forms of derivatives and modifications.

Figure 3:
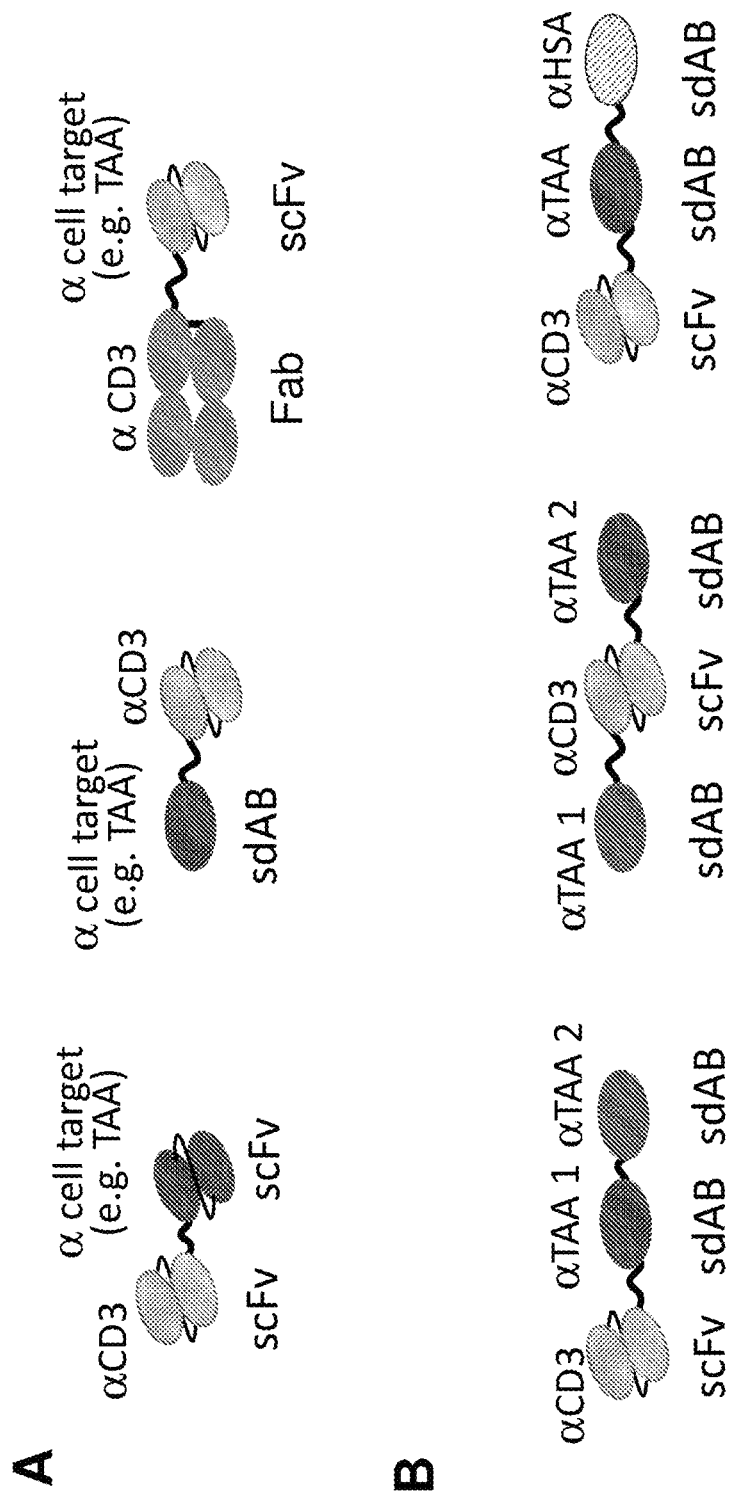
FIG. 3 (top panel A) illustrates exemplary single polypeptide or non-Fc multispecific formats of TMATEs that generally bear an anti-CD3 domain and one anti-TAA domain.

In some embodiments, as exemplified in FIG. 3 (top panel A), TMATE can comprise a single polypeptide chain (or "single chain") comprising one pH-sensitive anti-CD3 fragment and one anti disease-target molecule (e.g. anti-TAA) fragment; the two fragments are fused by a linker sequence. Optionally, the TMATE in the single polypeptide chain further comprises a domain that serves to extend the half-life (or pharmacokinetics) of the TMATE. Such "half-life extending" domains are exemplified by a single domain antibody recognizing human serum albumin (HSA) or transferrin.

In some embodiments, as exemplified in FIG. 3 (top panel A), the anti-CD3 multispecific TMATEs comprise a single polypeptide or a non-Fc format comprising a pH-dependent anti-CD3 antibody moiety and an anti-disease-target moiety such as an anti-TAA moiety. In some embodiments, as exemplified in FIG. 3 (bottom panel B), the TMATEs comprise a trispecific molecule comprising one pH dependent anti-CD3 moiety, one or two anti-TAA moieties, and optionally one half-life-prolonging moiety such as an anti-HSA (human serum albumin) moiety or an anti-human transferrin domain. In some embodiments, the two anti-disease-target moieties (e.g., anti-TAA moieties) bind to two epitopes of a same disease-target and two different disease-targets respectively. In some embodiments, the two anti-disease-target moieties bind to two target molecules of distinct types. In some embodiments, the two anti-disease-target moieties bind to one and the same target cell. In some embodiments, the two anti-disease-target moieties bind to two target cells of the same type. In some embodiments, the two anti-disease-target moieties bind to two or three cells of distinct types. In some embodiments, at least one of the anti-disease-target moieties are an anti-TAA moiety.

In one aspect, it is understood for a person skilled in the art that a moiety representing an antibody-derivative can be selected from a group consisting of a scFv (i.e., single-chain variable fragment), a Fab, a Fab', a F(ab')2, a single domain antibody (sdAB), a CrossMab, a VHH-only domain, a nanobody, an IgG heavy chain, an IgG light chain, and an engineered or a combination of these antibody-derivative molecules thereof. In some embodiments, antibody derivatives are a single chain (IgG heavy or light chain), a scFv, a Fab, a CrossMab, and a nanobody. In some embodiments, an antibody moiety is an antibody or antigen-binding fragment thereof selected from the group consisting of a full-length antibody, a bispecific antibody, a single-chain Fv (scFv) fragment, a Fab fragment, a Fab' fragment, a F(ab')2, an Fv fragment, a disulfide stabilized Fv fragment (dsFv), a (dsFv) 2, a Fv-Fc fusion, a scFv-Fc fusion, a scFv-Fv fusion, a diabody, a tribody, and a tetrabody. In another aspect, it is also understood by an artisan that a non-antibody alternative scaffold can be used as a building block of TMATE; such a scaffold can be selected from a group consisting of an Affibody, an Affilin, an Alphabody, a Knottin, a DARPin, an Anticalin, a Kunitz domain peptide, a FN3 scaffold, a Fynomer, a Cys-knots, a Monobody, an Affimer, a lectin or lectin-derived domain and a non-natural or semi-natural synthetic peptide or polypeptide.

In some embodiments, the two or more antibody moieties comprised by a TMATE are linked to form an integral molecule by a linker (such as any one of the linkers described herein). In some embodiments, the linker is a peptide linker or a chemical linker. Exemplary peptide linkers are: (1) a flexible peptide linker with a length of about 1 to about 49 amino acids, represented by a glycine/serine (G/S) rich linker such as $(GS)_n$ (SEQ ID NO: 128), $(GGS)_n$ (SEQ ID NO: 129), $(GGGS)_n$ (SEQ ID NO: 130), $(GGSG)_n$ (SEQ ID NO: 131), $(GGGGS)_n$ (SEQ ID NO: 132), $(GGSGG)_n$ (SEQ ID NO: 133), wherein n is an integer between 1 and 10; (2) a rigid peptide linker with a length of about 1 to about 50 amino acids, represented by a E/A/P rich linker such as $A(EAAAK)_n$ A (SEQ ID NO: 134) and $T(A4T)_n$ AAA (SEQ ID NO: 135), wherein n is an integer between 1 and 9; (3) a peptide linker derived from a natural protein, such protein represented by FNRGEC (SEQ ID NO: 136) and EPSGP (SEQ ID NO: 137, derived from an IgG upper hinge region), LGGC (SEQ ID NO: 138) and VEPKEC (SEQ ID NO: 139, derived from the C-terminus of the kappa light chain of an IgG molecule), and PSGQAGAAASESLFVSNHAY (SEQ ID NO: 140, derived from human muscle aldolase); (4) a combination of any of the foregoing described (1) and (2) peptide linkers of various compositions and biophysical properties. In some embodiments, the linkers are chemical linkers, such as polyethylene glycol (PEG), polylactic-co-glycolic acid (PLGA), polylactic acid (PLA), and poly(ε-caprolactone) (PCL). In some embodiments, the preferred linker is a peptide linker with a length of about 2 to about 50 amino acids. It is understood that the composition, length, stiffness, flexibility, orientation, and charge of the linker is often crucial for the proper assembling and functional activity of bispecific or multispecific molecules including TMATEs.

In some embodiments, the TMATE is a multispecific dimer, trimer or multimer that is joined by a dimerization domain such as an engineered Fc domain derived from an IgG, or by a trimerization domain such as a Dock-and-Lock (DNL) domain (e.g., a leucine zipper derived from cAMP-dependent protein kinase (PKA) and A kinase anchor proteins (AKAPs). In some embodiments, the preferred heterodimerizing Fc domain is achieved by introducing asymmetric mutations in each of CH2 and/or CH3 domain respectively, which favors the assembly of a heterodimeric Fc rather than a conventional homodimer one. These asymmetric mutations either form hydrophobic/steric complementarity (e.g. mutations in the so-called Knobs-into-Holes format), electrostatic complementarity (e.g., DD vs KK variations), complementarity from alternating sequences from IgG and IgA (e.g., mutations in the so-called SEED format) or stable complementarity through charge and hydrogen bonding (e.g. mutations in the so-called XmAb format). Other types of heterodimerizations are achieved through purification by introducing mutations that abolish protein binding (e.g. so-called Veloci-Bi or BEAM technologies).

To achieve correct pairing of light chains (LC) from two different antibodies, heterodimeric heavy chain bispecific antibodies have been developed in combination with a common LC approach or with two distinct LCs, using the CrossMab technology with only the VH and VL domains crossover, using FIT-IgG technology with Fab domains crossover, using engineered interface between CH/VL, using the so-called WuXiBody technology by replacing CK/CH1 with TCR alpha and beta constant regions, using EFab domain technology by replacing one of CK and CH1 with the CH2 of IgE.

In some embodiments, heterodimerization between TMATE moieties can be achieved using other variants of engineered human IgG1 Fc domain that favors heterodimerization, for instance, Alphamab's bispecific Fc platform "CRIB" (Charge Repulsion Induced Bispecific), Merus' bispecific Fc platform "Biclonics" that bears L351D/L368E changes in Fc chain 1 and L351K/T366K changes in Fc chain 2, Zymework's bispecific Fc domain that harbors T350V/T366L/K392L/T394W mutations in Fc chain 1 and T350V/L351Y/F405A/Y407V in Fc chain 2, Glenmark's "BEAT" bispecific Fc platform, and other variants of Knobs-into-Holes.

Anti-CD3 Antibody Moieties

The present application provides various anti-CD3 constructs that comprise an antibody moiety that specifically binds to CD3 ("anti-CD3 antibody moiety"), comprising a heavy variable region ($V_H$) and a light chain variable region ($V_L$).

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 3, or a variant thereof comprising up to 5, 4, 3, 2, or 1 amino acid substitutions in the HC-CDRs, and the $V_L$ comprises the LC-CDR1 comprising the amino acid sequence of SEQ ID NO: 23, the LC-CDR2 comprising the amino acid sequence of SEQ ID NO: 24, and the LC-CDR3 comprising the amino acid sequence of SEQ ID NO: 25, or a variant thereof comprising up to 5, 4, 3, 2, or 1 amino acid substitutions in the LC-CDRs. In some embodiments, the $V_H$ comprises an amino acid sequence of SEQ ID NO: 42, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 72, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 9, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 25, or a variant thereof comprising up to 5, 4, 3, 2, or 1 amino acid substitutions in the LC-CDRs. In some embodiments, the $V_H$ comprises an amino acid sequence of SEQ ID NO: 43, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 73, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 10, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 25, or a variant thereof comprising up to 5, 4, 3, 2, or 1 amino acid substitutions in the LC-CDRs. In some embodiments, the $V_H$ comprises an amino acid sequence of SEQ ID NO: 44, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 74, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 11, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 25, or a variant thereof comprising up to 5, 4, 3, 2, or 1 amino acid substitutions in the LC-CDRs. In some embodiments, the $V_H$ comprises an amino acid sequence of SEQ ID NO: 45, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 75, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 7, and the HC-CDR3 comprising the amino acid sequence of SEQ ID NO: 3, or a variant thereof comprising up to 5, 4, 3, 2, or 1 amino acid substitutions in the HC-CDRs, and the $V_L$ comprises the LC-CDR1 comprising the amino acid sequence of SEQ ID NO: 23, the LC-CDR2 comprising the amino acid sequence of SEQ ID NO: 24, and the LC-CDR3 comprising the amino acid sequence of SEQ ID NO: 25, or a variant thereof comprising up to 5, 4, 3, 2, or 1 amino acid substitutions in the LC-CDRs. In some embodiments, the $V_H$ comprises an amino acid sequence of SEQ ID NO: 46, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 76, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 7, and the HC-CDR3 comprising the amino acid sequence of SEQ ID NO: 3, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 25, or a variant thereof comprising up to 5, 4, 3, 2, or 1 amino acid substitutions in the LC-CDRs. In some embodiments, the $V_H$ comprises an amino acid sequence of SEQ ID NO: 47, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 77, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 12, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 48, or a variant comprising an amino acid sequence having at least about 80% (such as at least about any one of 80%, 85%, 90%, 95%, 96%, 97%, 98%, or 99%) sequence identity; and the V comprises an amino acid sequence of SEQ ID NO: 78, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 12, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 25, or a variant thereof comprising up to 5, 4, 3, 2, or 1 amino acid substitutions in the LC-CDRs. In some embodiments, the $V_H$ comprises an amino acid sequence of SEQ ID NO: 49, or a variant comprising an amino acid sequence having at least about 80% (such as at least about any one of 80%, 85%, 90%, 95%, 96%, 97%, 98%, or 99%) sequence identity; and the V comprises an amino acid sequence of SEQ ID NO: 79, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 9, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 50, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 80, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 12, or a variant thereof comprising up to 5, 4, 3, 2, or 1 amino acid substitutions in the HC-CDRs, and the $V_L$ comprises the LC-CDR1 comprising the amino acid sequence of SEQ ID NO: 27, the LC-CDR2 comprising the amino acid sequence of SEQ ID NO: 24, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 51, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 81, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 12, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 28, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 52, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 82, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 12, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 32, or a variant thereof comprising up to 5, 4, 3, 2, or 1 amino acid substitutions in the LC-CDRs. In some embodiments, the $V_H$ comprises an amino acid sequence of SEQ ID NO: 53, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 83, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 4, the HC-CDR2 comprising the amino acid sequence of SEQ ID NO: 2, and the HC-CDR3 comprising the amino acid sequence of SEQ ID NO: 12, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 54, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 84, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 5, the HC-CDR2 comprising the amino acid sequence of SEQ ID NO: 2, and the HC-CDR3 comprising the amino acid sequence of SEQ ID NO: 12, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 55, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 85, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 12, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 56, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 86, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 8, and the HC-CDR3 comprising the amino acid sequence of SEQ ID NO: 12, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 57, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 87, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 11, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 58, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 88, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 7, and the HC-CDR3 comprising the amino acid sequence of SEQ ID NO: 12, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 59, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 89, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 6, the HC-CDR2 comprising the amino acid sequence of SEQ ID NO: 7, and the HC-CDR3 comprising the amino acid sequence of SEQ ID NO: 12, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 60, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 90, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 11, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 61, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 91, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 1, the HC-CDR2 comprising the amino acid sequence of SEQ ID NO: 2, and the HC-CDR3 comprising the amino acid sequence of SEQ ID NO: 11, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 28, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 62, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 92, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 11, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 28, and the LC-CDR3 comprising the amino acid sequence of SEQ ID NO: 31, or a variant thereof comprising up to 5, 4, 3, 2, or 1 amino acid substitutions in the LC-CDRs. In some embodiments, the $V_H$ comprises an amino acid sequence of SEQ ID NO: 63, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 93, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 11, or a variant thereof comprising up to 5, 4, 3, 2, or 1 amino acid substitutions in the HC-CDRs, and the $V_L$ comprises the LC-CDR1 comprising the amino acid sequence of SEQ ID NO: 26, the LC-CDR2 comprising the amino acid sequence of SEQ ID NO: 29, and the LC-CDR3 comprising the amino acid sequence of SEQ ID NO: 33, or a variant thereof comprising up to 5, 4, 3, 2, or 1 amino acid substitutions in the LC-CDRs. In some embodiments, the V$_H$ comprises an amino acid sequence of SEQ ID NO: 64, or a variant comprising an amino acid sequence having at least about 80% (such as at least about any one of 80%, 85%, 90%, 95%, 96%, 97%, 98%, or 99%) sequence identity; and the V$_L$ comprises an amino acid sequence of SEQ ID NO: 94, or a variant comprising an amino acid sequence having at least about 80% (such as at least about any one of 80%, 85%, 90%, 95%, 96%, 97%, 98%, or 99%) sequence identity.

In some embodiments, the V$_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 11, or a variant thereof comprising up to 5, 4, 3, 2, or 1 amino acid substitutions in the HC-CDRs, and the V$_L$ comprises the LC-CDR1 comprising the amino acid sequence of SEQ ID NO: 26, the LC-CDR2 comprising the amino acid sequence of SEQ ID NO: 29, and the LC-CDR3 comprising the amino acid sequence of SEQ ID NO: 34, or a variant thereof comprising up to 5, 4, 3, 2, or 1 amino acid substitutions in the LC-CDRs. In some embodiments, the V$_H$ comprises an amino acid sequence of SEQ ID NO: 65, or a variant comprising an amino acid sequence having at least about 80% (such as at least about any one of 80%, 85%, 90%, 95%, 96%, 97%, 98%, or 99%) sequence identity; and the V$_L$ comprises an amino acid sequence of SEQ ID NO: 95, or a variant comprising an amino acid sequence having at least about 80% (such as at least about any one of 80%, 85%, 90%, 95%, 96%, 97%, 98%, or 99%) sequence identity.

In some embodiments, the V$_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 12, or a variant thereof comprising up to 5, 4, 3, 2, or 1 amino acid substitutions in the HC-CDRs, and the V$_L$ comprises the LC-CDR1 comprising the amino acid sequence of SEQ ID NO: 26, the LC-CDR2 comprising the amino acid sequence of SEQ ID NO: 28, and the LC-CDR3 comprising the amino acid sequence of SEQ ID NO: 31, or a variant thereof comprising up to 5, 4, 3, 2, or 1 amino acid substitutions in the LC-CDRs. In some embodiments, the V$_H$ comprises an amino acid sequence of SEQ ID NO: 66, or a variant comprising an amino acid sequence having at least about 80% (such as at least about any one of 80%, 85%, 90%, 95%, 96%, 97%, 98%, or 99%) sequence identity; and the V$_L$ comprises an amino acid sequence of SEQ ID NO: 96, or a variant comprising an amino acid sequence having at least about 80% (such as at least about any one of 80%, 85%, 90%, 95%, 96%, 97%, 98%, or 99%) sequence identity.

In some embodiments, the V$_H$ comprising the HC-CDR1 comprising the amino acid sequence of SEQ ID NO: 5, the HC-CDR2 comprising the amino acid sequence of SEQ ID NO: 2, and the HC-CDR3 comprising the amino acid sequence of SEQ ID NO: 12, or a variant thereof comprising up to 5, 4, 3, 2, or 1 amino acid substitutions in the HC-CDRs, and the V$_L$ comprises the LC-CDR1 comprising the amino acid sequence of SEQ ID NO: 26, the LC-CDR2 comprising the amino acid sequence of SEQ ID NO: 28, and the LC-CDR3 comprising the amino acid sequence of SEQ ID NO: 31, or a variant thereof comprising up to 5, 4, 3, 2, or 1 amino acid substitutions in the LC-CDRs. In some embodiments, the V$_H$ comprises an amino acid sequence of SEQ ID NO: 67, or a variant comprising an amino acid sequence having at least about 80% (such as at least about any one of 80%, 85%, 90%, 95%, 96%, 97%, 98%, or 99%) sequence identity; and the V comprises an amino acid sequence of SEQ ID NO: 97, or a variant comprising an amino acid sequence having at least about 80% (such as at least about any one of 80%, 85%, 90%, 95%, 96%, 97%, 98%, or 99%) sequence identity.

In some embodiments, the V$_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 13, or a variant thereof comprising up to 5, 4, 3, 2, or 1 amino acid substitutions in the HC-CDRs, and the V$_L$ comprises the LC-CDR1 comprising the amino acid sequence of SEQ ID NO: 26, the LC-CDR2 comprising the amino acid sequence of SEQ ID NO: 28, and the LC-CDR3 comprising the amino acid sequence of SEQ ID NO: 31, or a variant thereof comprising up to 5, 4, 3, 2, or 1 amino acid substitutions in the LC-CDRs. In some embodiments, the V$_H$ comprises an amino acid sequence of SEQ ID NO: 68, or a variant comprising an amino acid sequence having at least about 80% (such as at least about any one of 80%, 85%, 90%, 95%, 96%, 97%, 98%, or 99%) sequence identity; and the VW comprises an amino acid sequence of SEQ ID NO: 98, or a variant comprising an amino acid sequence having at least about 80% (such as at least about any one of 80%, 85%, 90%, 95%, 96%, 97%, 98%, or 99%) sequence identity.

In some embodiments, the V$_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 14, or a variant thereof comprising up to 5, 4, 3, 2, or 1 amino acid substitutions in the HC-CDRs, and the V$_L$ comprises the LC-CDR1 comprising the amino acid sequence of SEQ ID NO: 26, the LC-CDR2 comprising the amino acid sequence of SEQ ID NO: 28, and the LC-CDR3 comprising the amino acid sequence of SEQ ID NO: 31, or a variant thereof comprising up to 5, 4, 3, 2, or 1 amino acid substitutions in the LC-CDRs. In some embodiments, the V$_H$ comprises an amino acid sequence of SEQ ID NO: 69, or a variant comprising an amino acid sequence having at least about 80% (such as at least about any one of 80%, 85%, 90%, 95%, 96%, 97%, 98%, or 99%) sequence identity; and the V$_L$ comprises an amino acid sequence of SEQ ID NO: 99, or a variant comprising an amino acid sequence having at least about 80% (such as at least about any one of 80%, 85%, 90%, 95%, 96%, 97%, 98%, or 99%) sequence identity.

In some embodiments, the V$_H$ comprising the HC-CDR1 comprising the amino acid sequence of SEQ ID NO: 19, the HC-CDR2 comprising the amino acid sequence of SEQ ID NO: 20, and the HC-CDR3 comprising the amino acid sequence of SEQ ID NO: 21, or a variant thereof comprising up to 5, 4, 3, 2, or 1 amino acid substitutions in the HC-CDRs, and the V$_L$ comprises the LC-CDR1 comprising the amino acid sequence of SEQ ID NO: 23, the LC-CDR2 comprising the amino acid sequence of SEQ ID NO: 30, and the LC-CDR3 comprising the amino acid sequence of SEQ ID NO: 35, or a variant thereof comprising up to 5, 4, 3, 2, or 1 amino acid substitutions in the LC-CDRs. In some embodiments, the V$_H$ comprises an amino acid sequence of SEQ ID NO: 70, or a variant comprising an amino acid sequence having at least about 80% (such as at least about any one of 80%, 85%, 90%, 95%, 96%, 97%, 98%, or 99%) sequence identity; and the V$_L$ comprises an amino acid sequence of SEQ ID NO: 100, or a variant comprising an amino acid sequence having at least about 80% (such as at least about any one of 80%, 85%, 90%, 95%, 96%, 97%, 98%, or 99%) sequence identity.

In some embodiments, the $V_H$ comprising the HC-CDR1 comprising the amino acid sequence of SEQ ID NO: 19, the HC-CDR2 comprising the amino acid sequence of SEQ ID NO: 20, and the HC-CDR3 comprising the amino acid sequence of SEQ ID NO: 22, or a variant thereof comprising up to 5, 4, 3, 2, or 1 amino acid substitutions in the HC-CDRs, and the $V_L$ comprises the LC-CDR1 comprising the amino acid sequence of SEQ ID NO: 23, the LC-CDR2 comprising the amino acid sequence of SEQ ID NO: 30, and the LC-CDR3 comprising the amino acid sequence of SEQ ID NO: 35, or a variant thereof comprising up to 5, 4, 3, 2, or 1 amino acid substitutions in the LC-CDRs. In some embodiments, the $V_H$ comprises an amino acid sequence of SEQ ID NO: 71, or a variant comprising an amino acid sequence having at least about 80% (such as at least about any one of 80%, 85%, 90%, 95%, 96%, 97%, 98%, or 99%) sequence identity; and the $V_L$ comprises an amino acid sequence of SEQ ID NO: 101, or a variant comprising an amino acid sequence having at least about 80% (such as at least about any one of 80%, 85%, 90%, 95%, 96%, 97%, 98%, or 99%) sequence identity.

In some embodiments, the amino acid substitutions are limited to "exemplary substitutions" shown in Table 2 of this application. In some embodiments, the amino acid substitutions are limited to "preferred substitutions" shown in Table 2 of this application.

In some embodiments, the $V_H$ comprising the HC-CDR1 comprising the amino acid sequence of SEQ ID NO: 15, the HC-CDR2 comprising the amino acid sequence of SEQ ID NO: 16, and the HC-CDR3 comprising the amino acid sequence of SEQ ID NO: 17 or 18, and the $V_L$ comprises the LC-CDR1 comprising the amino acid sequence of SEQ ID NO: 36 or 37, the LC-CDR2 comprising the amino acid sequence of SEQ ID NO: 38, and the LC-CDR3 comprising the amino acid sequence of SEQ ID NO: 39.

In some embodiments, the $V_H$ comprising the HC-CDR1 comprising the amino acid sequence of SEQ ID NO: 15 or 19, the HC-CDR2 comprising the amino acid sequence of SEQ ID NO: 16 or 20, and the HC-CDR3 comprising the amino acid sequence of SEQ ID NO: 17, 18, 21, or 22, and the $V_L$ comprises the LC-CDR1 comprising the amino acid sequence of SEQ ID NO: 36 or 37, the LC-CDR2 comprising the amino acid sequence of SEQ ID NO: 40, and the LC-CDR3 comprising the amino acid sequence of SEQ ID NO: 41.

In some embodiments, the $V_H$ comprising the HC-CDR1 comprising the amino acid sequence of SEQ ID NO: 1, 4, 5, or 6, the HC-CDR2 comprising the amino acid sequence of SEQ ID NO: 2, 7, or 8, and the HC-CDR3 comprising the amino acid sequence of SEQ ID NO: 3, 9, 10, 11, 12, 13, or 14, and the $V_L$ comprises the LC-CDR1 comprising the amino acid sequence of SEQ ID NO: 23, 26 or 27, the LC-CDR2 comprising the amino acid sequence of SEQ ID NO: 24, 28, or 29, and the LC-CDR3 comprising the amino acid sequence of SEQ ID NO: 25, 31, 32, 33, or 34.

In some embodiments, the anti-CD3 antibody moiety is a pH-sensitive antibody moiety. In some embodiments, the $V_H$ comprising the HC-CDR1 comprising the amino acid sequence of SEQ ID NO: 1, 5, or 6, the HC-CDR2 comprising the amino acid sequence of SEQ ID NO: 2, and the HC-CDR3 comprising the amino acid sequence of SEQ ID NO: 11, 12, 13, or 14, and the $V_L$ comprises the LC-CDR1 comprising the amino acid sequence of SEQ ID NO: 26, the LC-CDR2 comprising the amino acid sequence of SEQ ID NO: 24 or 28, and the LC-CDR3 comprising the amino acid sequence of SEQ ID NO: 31.

In some embodiments, the anti-CD3 antibody moiety within a TMATE is a pH-sensitive antibody moiety that promotes a higher cytotoxicity of T cells at a pH of about 6.0-6.9 (e.g., 6.7) than at a pH of about 7.2-7.6 (e.g., 7.4) upon having the TMATE contact with T cells and tumor cells. In some embodiments, the $V_H$ comprising the HC-CDR1 comprising the amino acid sequence of SEQ ID NO: 5 or 6, the HC-CDR2 comprising the amino acid sequence of SEQ ID NO: 2, and the HC-CDR3 comprising the amino acid sequence of SEQ ID NO: 12, and the $V_L$ comprises the LC-CDR1 comprising the amino acid sequence of SEQ ID NO: 26, the LC-CDR2 comprising the amino acid sequence of SEQ ID NO: 24 or 28, and the LC-CDR3 comprising the amino acid sequence of SEQ ID NO: 31.

a) Antibody Affinity

Binding specificity of the antibody moieties can be determined experimentally by methods known in the art. Such methods comprise, but are not limited to Western blots, ELISA, RIA, ECL, IRMA, EIA, Flow Cytometry (FC), Bio-Layer Interferometry (e.g., Octet® and Gator®), Surface Plasma Resonance (e.g., BIACORE®) and peptide scans.

Figure 4:
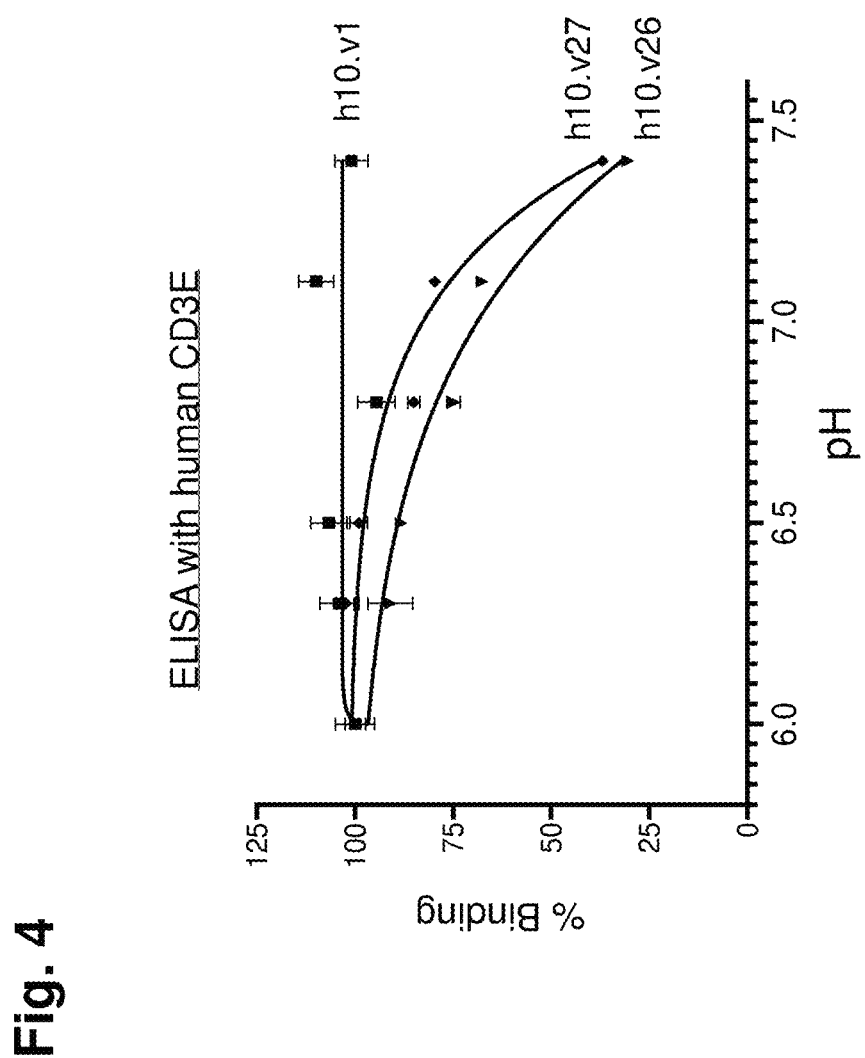
FIG. 4 shows the enzyme-linked immunosorbent assay (ELISA) based binding of select pH sensitive anti-CD3 Fab antibodies (h10.v26 and h10.v27) and a non-pH-selective conventional control clone (h10.v1), to the extracellular domain of human CD3E.
Figure 6:
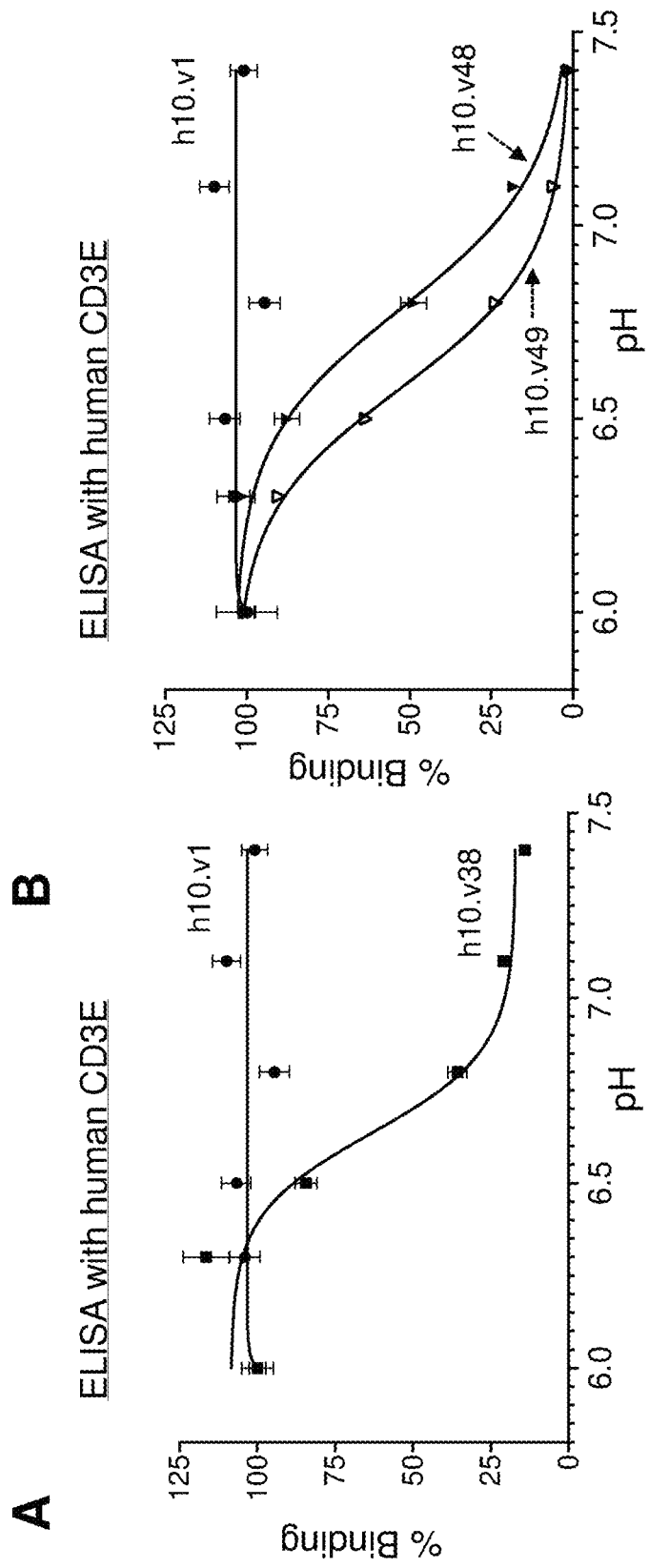
FIGS. 6A-B show ELISA-based pH-dependent binding of pH sensitive anti-CD3 h10.v38 (FIG. 6A) and h10.v48 and h10.v49 (FIG. 6B) Fab antibodies respectively.

As shown in ELISA assays (FIGS. 4 through 6), representative clones of pH sensitive anti-CD3 antibodies such as h10.v26, h10.v27, h10.v39, h10.v38, h10.v48 and h10.v49 (the same as disclosed in the Sequence Table) can bind to human CD3 and its homologue in cynomolgus monkey ("cyno") in a pH dependent manner, exhibiting much stronger binding under the acidic conditions (about pH 6.0 to 6.7), and significantly reduced binding under near physiological pH conditions (about pH 7.3 to pH 7.5). In contrast, the non-pH-sensitive clone h10.v1 that was established in house shows insignificant change of its binding activity towards either human or monkey CD3 under acidic or near physiological pH conditions.

In some embodiments, under conditions with a pH range of about pH 6.0 to pH 6.6 or of about pH 6.4 to pH 6.7, the $K_D$ value of the monovalent binding between TMATE (or the anti-CD3 antibody moiety) and CD3 is about 1 nM to about 1000 nM, about 5 nM to about 200 nM, about 50 nM to about 400 nM, or about 400 to about 1000 nM. In comparison, under weakly basic or neutral conditions with a pH value of about 7.2 to 7.6 or of about 7.4, the monovalent $K_D$ of the same TMATE or the anti-CD3 antibody moiety for CD3 is significantly reduced, e.g., ranging from about 150 nM to about 1.5 µM, about 500 nM to about 1000 µM or to a nearly undetectable level, about 600 nM to about 2 µM, about 1 µM to about 5 µM, about 5 µM to about 100 µM, or about 100 µM to about 1000 µM. In some embodiments, the anti-CD3 antibody moiety and CD3 have a $K_D$ value at a pH of about 7.4 at least about 5-fold or about 10-fold (e.g., at least 5-fold, at least 10-fold, 25-fold, 50-fold, 100-fold, 125-fold, 150-fold, 200-fold, 300-fold, 400-fold, or 500-fold) as great as the $K_D$ value at a pH of about 6.6. In some embodiments, the CD3 is human CD3E or a complex comprising human CD3E.

In some embodiments, the affinity between the anti-disease-target antibody moiety (e.g. anti-TAA) and the disease-target (e.g. a TAA) is stronger (i.e., having a smaller $K_D$ value) than the affinity between the anti-CD3 moiety and CD3, for instance, being at least 5 times stronger, at least 10 times stronger or at least 50 times stronger based on the measured KY value. In some embodiments, the affinity between the anti-disease-target antibody moiety (e.g. anti- TAA) and the disease-target (e.g. a TAA) is similar or comparable to the affinity between the anti-CD3 moiety and CD3.

In some embodiments, the $K_{on}$ of the kinetic binding between the antibody moiety and CD3 is about $10^3$ $M^{-1}s^{-1}$ to about $10^8$ $M^{-1}s^{-1}$, about $10^3$ $M^{-1}s^{-1}$ to about $10^4$ $M^{-1}s^{-1}$, about $10^4$ $M^{-1}s^{-1}$ to about $10^5$ $M^{-1}s^{-1}$, about $10^5$ $M^{-1}s^{-1}$ to about $10^6$ $M^{-1}s^{-1}$, about $10^6$ $M^{-1}s^{-1}$ to about $10^7$ $M^{-1}s^{-1}$, or about $10^7$ $M^{-1}s^{-1}$ to about $10^8$ $M^{-1}s^{-1}$. In some embodiments, the $K_{on}$ of the binding between the antibody moiety and CD3 is about $10^3$ $M^{-1}s^{-1}$ to about $10^5$ $M^{-1}s^{-1}$, about $10^4$ $M^{-1}s^{-1}$ to about $10^6$ $M^{-1}s^{-1}$, about $10^7$ $M^{-1}s^{-1}$ to about $10^7$ $M^{-1}s^{-1}$, about $10^6$ $M^{-1}s^{-1}$ to about 10 $M^{-1}s^{-1}$, about $10^4$ $M^{-1}s^{-1}$ to about $10^7$ $M^{-1}s^{-1}$, or about $10^5$ $M^{-1}s^{-1}$ to about $10^8$ $M^{-1}s^{-1}$. In some embodiments, the $K_{on}$ of the binding between the antibody moiety and CD3 is no more than about any one of 103 $M^{-1}s^{-1}$, $10^4$ $M^{-1}s^{-1}$, $10^5$ $M^{-1}s^{-1}$, $10^6$ $M^{-1}s^{-1}$, $10^7$ $M^{-1}s^{-1}$ or $10^8$ $M^{-1}s^{-1}$. In some embodiments, CD3 is human CD3.

In some embodiments, the $K_On$ of the binding between the antibody moiety and CD3 is about 1 $s^{-1}$ to about $10^{-6}$ $s^{-1}$, about $10^{-2}$ $s^{-1}$ to about $10^{-2}$ $s^{-1}$, about $10^{-2}$ $s^{-1}$ to about $10^{-3}$ $s^{-1}$, about $10^{-3}$ $s^{-1}$ to about $10^{-4}$ $s^{-1}$, about $10^{-4}$ $s^{-1}$ to about $10^{-5}$ $s^{-1}$, about $10^{-5}$ $s^{-1}$ to about $10^{-6}$ $s^{-1}$, about 1 $s^{-1}$ to about $10^{-5}$ $s^{-1}$, about $10^{-2}$ $s^{-1}$ to about $10^{-6}$ $s^{-1}$, about $10^{-3}$ $s^{-1}$ to about $10^{-6}$ $s^{-1}$, about $10^{-4}$ $s^{-1}$ to about $10^{-6}$ $s^{-1}$, about $10^{-2}$ $s^{-1}$ to about $10^{-5}$ $s^{-1}$, or about $10^{-3}$ $s^{-1}$ to about $10^{-5}$ $s^{-1}$. In some embodiments, the $K_{off}$ of the binding between the antibody moiety and CD3 is at least about any one of 1 $s^{-1}$, 10–2 $s^{-1}$, $10^{-3}$ $s^{-1}$, $10^{-4}$ $s^{-1}$, $10^{-5}$ $s^{-1}$ or $10^{-6}$ $s^{-1}$. In some embodiments, CD3 is human CD3.

Figure 7:
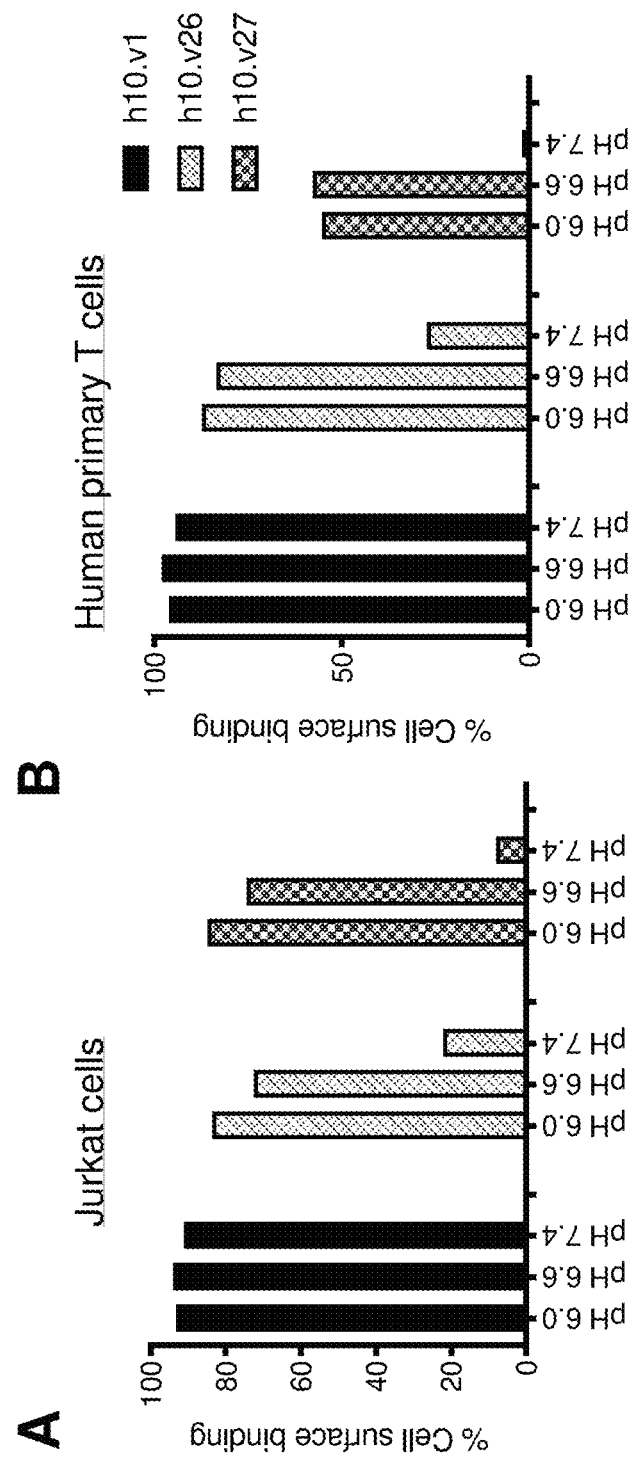
FIGS. 7A-B display the pH-dependent binding towards Jurkat reporter cells (FIG. 7A) and human primary T cells (FIG. 7B) for two pH sensitive anti-CD3 Fab antibodies (h10.v26 and h10.v27) and a conventional anti-CD3 Fab as a control (h10.v1), respectively, which is profiled using flow cytometry.

In some embodiments, as shown in flow cytometry based cell binding assays (FIG. 7), pH selective anti-CD3 antibody moieties (e.g. clones h10.v26 and h10.v27 in a Fab format) each bind to human T cells (Jurkat or human primary T cells) in a pH dependent manner, respectively, wherein the cell binding affinity is the strongest at about pH 6.0, is slightly reduced or barely changes at about pH6.6 and dramatically reduced at about pH 7.4. In comparison, the non-pH selective anti-CD3 clone h10.v1 shows little to no difference in its binding to the same T cells under the three different pH conditions. As described herein, flow cytometry is a commonly used cell analysis technology that can be readily performed by an average person using any one of the many available flow cytometer instruments (e.g. Accuri™ C6 plus, BD Biosciences, Franklin Lakes, NJ, USA; or NovoCyte™, Acea Biosciences, San Diego, CA, USA).

b) Chimeric or Humanized Antibodies

In some embodiments, the antibody moiety is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In some embodiments, a chimeric antibody comprises a non-human variable region (e.g., a variable region derived from mouse) and a human constant region. In some embodiments, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005)(describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); Framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

It is understood that the humanization of mouse derived antibodies is a common and routinely used art. It is therefore understood that a humanized format of any and all of the anti-CD3 antibodies disclosed in Sequence Table can be used in a preclinical or clinical setting. In cases where a humanized format of any of the referenced anti-CD3 antibodies or their antigen-binding regions thereof is used in such a preclinical or clinical setting, the then humanized format is expected to bear the same or similar biological activities and profiles as the original non-humanized format.

c) Human Antibodies

In some embodiments, the antibody moiety is a human antibody (known as human domain antibody, or human DAb). Human antibodies can be produced using various techniques known in the art. Human antibodies are described generally in van Dijk and van de Winkel, *Curr. Opin. Pharmacol.* 5: 368-74 (2001), Lonberg, *Curr. Opin. Immunol.* 20:450-459 (2008), and Chen, *Mol. Immunol.* 47(4):912-21 (2010). Transgenic mice or rats capable of producing fully human single-domain antibodies (or DAb) are known in the art. See, e.g., US20090307787A1, U.S. Pat. No. 8,754,287, US20150289489A1, US20100122358A1, and WO2004049794.

Human antibodies (e.g., human DAbs) may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated.

For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies (e.g., human DAbs) can also be made by hybridoma-based methods. Human myeloma and mouse-human heteromyeloma cell lines for the production of human monoclonal antibodies have been described (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991)). Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4): 265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies (e.g., human DAbs) may also be generated by isolating Fv clone variable domain sequences selected from human-derived phage display libraries. Such variable domain sequences may then be combined with a desired human constant domain. Techniques for selecting human antibodies from antibody libraries are described below.

d) Library-Derived Antibodies

The antibody moieties may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Method.* 284(1-2): 119-132(2004). Methods for constructing single-domain antibody libraries have been described, for example, see U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically displays antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

e) Substitution, Insertion, Deletion and Variants

In some embodiments, antibody variants having one or more amino acid substitutions are provided. Sites of interest for substitutional mutagenesis include the HVRs (or CDRs) and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

Amino acid substitutions

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg, (5) residues that influence chain orientation: Gly, Pro; and (6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_H H$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

f) Glycosylation Variants

In some embodiments, the antibody moiety is altered to increase or decrease the extent to which the construct is glycosylated. Addition or deletion of glycosylation sites to an antibody may be conveniently accomplished by altering the amino acid sequence such that one or more glycosylation sites is created or removed.

Where the antibody moiety comprises an Fc region (e.g., scFv-Fc), the carbohydrate attached thereto may be altered. Native antibodies produced by mammalian cells typically comprise a branched, biantennary oligosaccharide that is generally attached by an N-linkage to Asn297 of the $C_H2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the antibody moiety may be made in order to create antibody variants with certain improved properties.

In some embodiments, the antibody moiety has a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4): 680-688 (2006); and WO2003/085107).

In some embodiments, the antibody moiety has bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

g) Fc Region Variants

In some embodiments, one or more amino acid modifications may be introduced into the Fc region of the antibody moiety (e.g., scFv-Fc), thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the Fc fragment possesses some but not all effector functions, which make it a desirable candidate for applications in which the half-life of the antibody moiety in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 2 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Fp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and Cyto-Tox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, Blood 103: 2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). In some embodiments, the Fc fragment comprises a N297A mutation. In some embodiments, the Fc fragment comprises a N297G mutation.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, the Fc fragment is an IgG1 Fc fragment. In some embodiments, the IgG1 Fc fragment comprises a L234A mutation and/or a L235A mutation. In some embodiments, the Fc fragment is an IgG2 or IgG4 Fc fragment. In some embodiments, the Fc fragment is an IgG4 Fc fragment comprising a S228P, F234A, and/or a L235A mutation.

In some embodiments, the antibody moiety comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

In some embodiments, the antibody moiety (e.g., scFv-Fc) variant comprising a variant Fc region comprising one or more amino acid substitutions which alters half-life and/or changes binding to the neonatal Fc receptor (FcRn). Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which alters binding of the Fc region to FcRn. Such Fc variants include those with substitutions at one or more of Fc region residues, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

h) Cysteine Engineered Antibody Variants

In some embodiments, it may be desirable to create cysteine engineered antibody moieties, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered antibody moieties may be generated as described, e.g., in U.S. Pat. No. 7,521,541.

i) Antibody Derivatives

In some embodiments, the antibody moiety described herein may be further modified to comprise additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in diagnosis under defined conditions, etc.

In some embodiments, the antibody moiety may be further modified to comprise one or more biologically active protein, polypeptides or fragments thereof. "Bioactive" or "biologically active", as used herein interchangeably, means showing biological activity in the body to carry out a specific function. For example, it may mean the combination with a particular biomolecule such as protein, DNA, etc., and then promotion or inhibition of the activity of such biomolecule. In some embodiments, the bioactive protein or fragments thereof include proteins and polypeptides that are administered to patients as the active drug substance for prevention of or treatment of a disease or condition, as well as proteins and polypeptides that are used for diagnostic purposes, such as enzymes used in diagnostic tests or in vitro assays, as well as proteins and polypeptides that are administered to a patient to prevent a disease such as a vaccine.

Multispecific Anti-CD3 TMATE Constructs

The anti-CD3 TMATE constructs in some embodiments comprise a multi-specific (e.g., bispecific or trispecific or tetra-specific) anti-CD3 TMATE constructs comprising an anti-CD3 antibody moiety according to any one of the pH dependent anti-CD3 antibody moieties described herein, and a second binding moiety (such as a second antibody moiety) specifically recognizing a second antigen. In some embodiments, the multi-specific anti-CD3 molecule comprises an anti-CD3 antibody moiety and a second antibody moiety specifically recognizing a second antigen. In some embodiments, the second antigen is a tumor associated antigen. In some embodiments, the second antigen is a T cell surface molecule other than CD3 (such as CD28 and CD2).

In some embodiments, the multispecific anti-CD3 TMATE construct comprises a) an anti-CD3 antibody moiety according to any one of the pH dependent anti-CD3 antibody moieties described herein; b) a second binding moiety (such as a second antibody moiety) specifically recognizing a second antigen (such as a tumor associated antigen) and c) a third binding moiety (such as a third antibody moiety) specifically recognizing a third antigen (such as a T cell surface molecule other than CD3, e.g., CD28, CD27 or CD2).

In some embodiments, the pH dependent anti-CD3 antibody moiety, the second binding moiety, and/or the third binding moiety are fused with each other via a linker such as any of the linkers described herein with any operable form that allows the proper function of the binding moieties.

In some embodiments, the anti-CD3 TMATE construct comprises a multispecific anti-CD3 construct such as any one of the constructs illustrated in FIG. 1 through FIG. 3.

Figure 8:
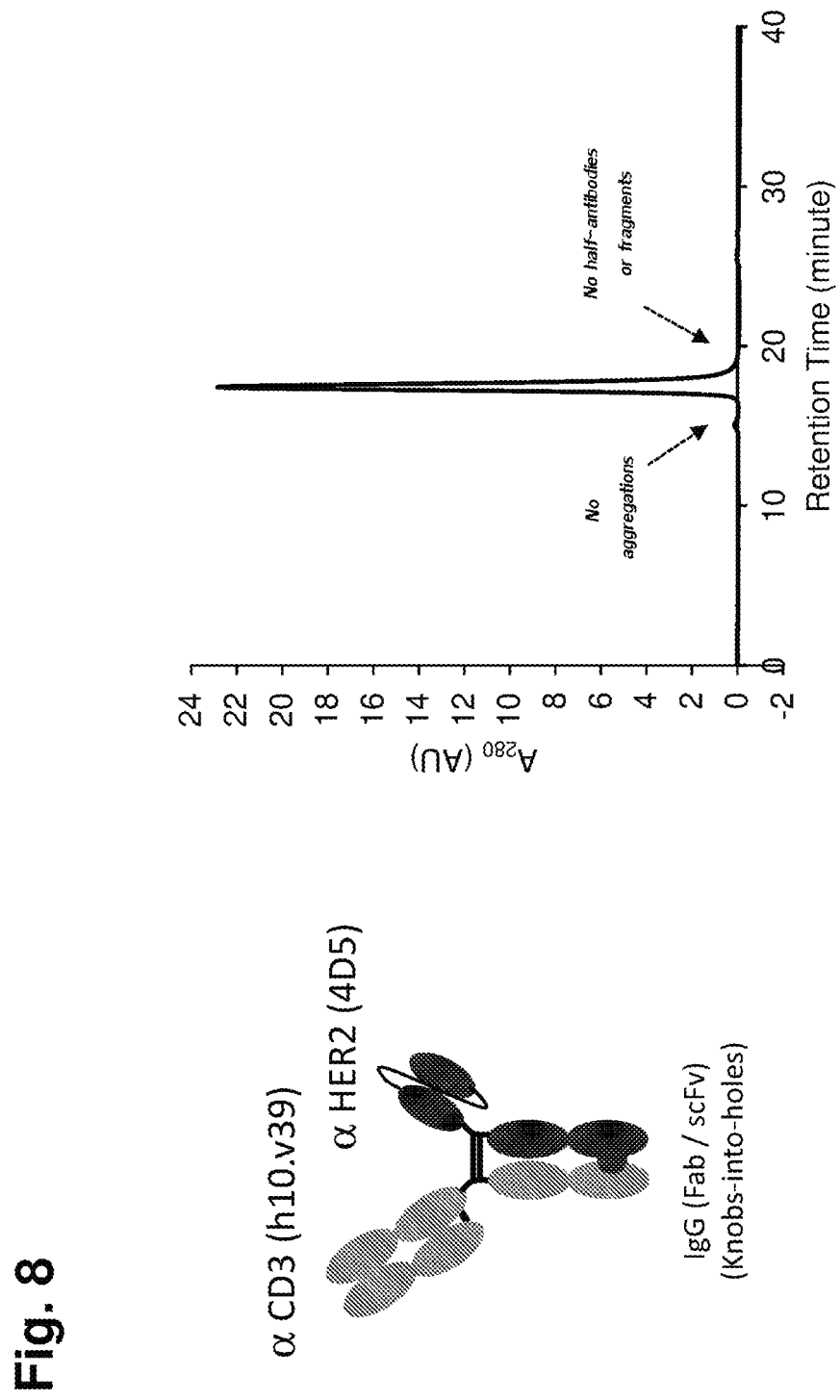
FIG. 8 shows the molecular configuration of a multispecific TMATE, CD3 (h10.v39)×HER2 (4D5) with a heterodimeric human IgG1-Fc (Knobs-into-Holes; "KiH") and an analytical high-performance liquid chromatography (HPLC) result indicating the ≥98% high purity of this TMATE that is recombinantly expressed in Expi293 cells and purified via chromatography.

In some embodiments, the anti-CD3 TMATE construct comprises an anti-TAA moiety (e.g., anti-HER2) and a pH selective anti-CD3 moiety. HER2 is an established marker and therapeutic target for breast, gastric and lung cancers. In some embodiments, the anti-HER2 moiety is a Fab or a scFv or a single domain antibody. In some embodiments, the anti-HER2 scFv or Fab is derived from the established antibody clone known as 4D5, which comprises the same or homologous HER2-binding CDRs as those of Trastuzumab. In some embodiments, the anti-HER2 scFv or Fab is derived from the established antibody clone known as 2C4, which comprises the same or homologous HER2-binding CDRs as those of Pertuzumab. In some embodiments, the anti-CD3 moiety of the HER2-targeting TMATE is a scFv or Fab derived from and corresponding to one of the pH-dependent anti-CD3 antibodies selected from a group consisting of h10.v23, h10.v26, h10.v27, h10.v32, h10.v34, h10.v38, h10.v39, h10.v48, and h10.v49. See Tables 3 and 4 and sequence table for CDR and VH/VL sequences of these antibodies. As shown in FIG. 8, one of such exemplary TMATE constructs, CD3 (h10.v39)×HER2 (4D5) in a hIgG1-Fc (KiH) format can be readily expressed from a CHO or HEK293 cell based mammalian cell system and purified via chromatography to achieve ≥98% purity, which is validated by an analytical HPLC chromatogram showing no aggregations or half antibodies or partial fragments of the said CD3 (h10.v39)×HER2 (4D5) TMATE.

In some embodiments, the anti-CD3 TMATE construct comprises an alternative anti-TAA moiety (e.g., anti-TROP-2) and a pH selective anti-CD3 moiety. TROP-2 (aka Trop2 or TACSTD2) is a well-established tumor associated antigen that is known to be upregulated in a variety of human cancers, regardless of the baseline TROP-2 expression in the patient-matched normal tissues. TROP-2-positive cancers include without limitation to breast cancer, colon cancer, urothelial cancer, non-small cell lung carcinoma, gastric cancer, pancreatic cancer, prostate cancer, ovarian cancers, head and neck cancers and squamous cell carcinomas among others. The highest prevalence of TROP-2 upregulation can be found in cervix and pancreas tumors, followed by stomach, colon, breast and prostate cancers and then ovary, lung and endometrium neoplasia. On the other hand, TROP-2 is widely expressed in a panel of normal tissues, particularly in the epithelial tissues, although the TROP-2 expression in health tissues is generally lower than that in tumors. In some embodiments, the anti-TROP-2 moiety is a Fab or a scFv or a single-domain antibody. In some embodiments, the anti-TROP-2 antibody moiety is derived from an established antibody clone represented by clone RS7-3G11 ("RS7") initially published by Stein et al (Cancer Research, v30.1330-1336, 1990) and in the US Pat. Docs. (US2004/0001825 A1; 2016/0264678 A1; U.S. Pat. No. 9,670, 286B2), clones K5-70, K5-107 and T6-16 published in the US Pat. Doc. (US2016/0053018 A1), clone 4F6 published in the US Pat. Doc. (US2012/0052076 A1), clone PR1E11 in the US Pat. Doc. (US2012/0237518), clone 2EF published in the US Pat. Doc. (US2018/0002437 A1), and clones 7E6 and 15E2 published in the US Pat. Doc. (US2013/0122020 A1).

In some embodiments, the anti-CD3 moiety of a TROP-2-targeting TMATE is a scFv or Fab derived from and corresponding to one of the pH-dependent anti-CD3 antibodies selected from a group consisting of h10.v23, h10.v26, h10.v27, h10.v32, h10.v34, h10.v38, h10.v39, h10.v48, and h10.v49. See Tables 3 and 4 and sequence table for CDR and VH/VL sequences of these antibodies. As shown in FIG. 9, one of such exemplary TMATE constructs, CD3 (h10.v38)×TROP-2 (RS7.v1) can be readily expressed from an Expi293 or 293F (FreeStyle) or CHO based mammalian expression system and purified via chromatography to achieve ≥98% purity, which is validated by an analytical HPLC chromatogram showing no aggregations or half antibodies or partial fragments of the said CD3 (h10.v38)× TROP-2 (RS7.v1) TMATE.

In some embodiments, the anti-CD3 multispecific TMATE construct comprises an anti-TAA moiety (e.g., anti-EpCAM) and a pH-sensitive anti-CD3 moiety. EpCAM (aka TACSTD1, TROP-1 or CD326) is an established marker and therapeutic target to treat malignant ascites in certain cancer patients. EpCAM is a well-known tumor associated antigen that is known to be overexpressed in many types of human cancers including without limitation to those originated from the tissues of liver, head and neck, lung, prostate, pancreas, breast, colon, uterus, ovary and stomach. EpCAM is frequently upregulated in carcinomas but is typically not expressed in cancers of non-epithelial origin. In cancer cells, EpCAM is expressed in a dispersed pattern across the cell membrane. On the other hand, EpCAM is widely expressed (albeit at a lower level than in tumor tissues) in many normal tissues/organs, particularly in the normal epithelial tissues. EpCAM is known to be expressed on the basolateral membrane of all simple (especially glandular), pseudo-stratified, and transitional epithelia.

Figure 10:
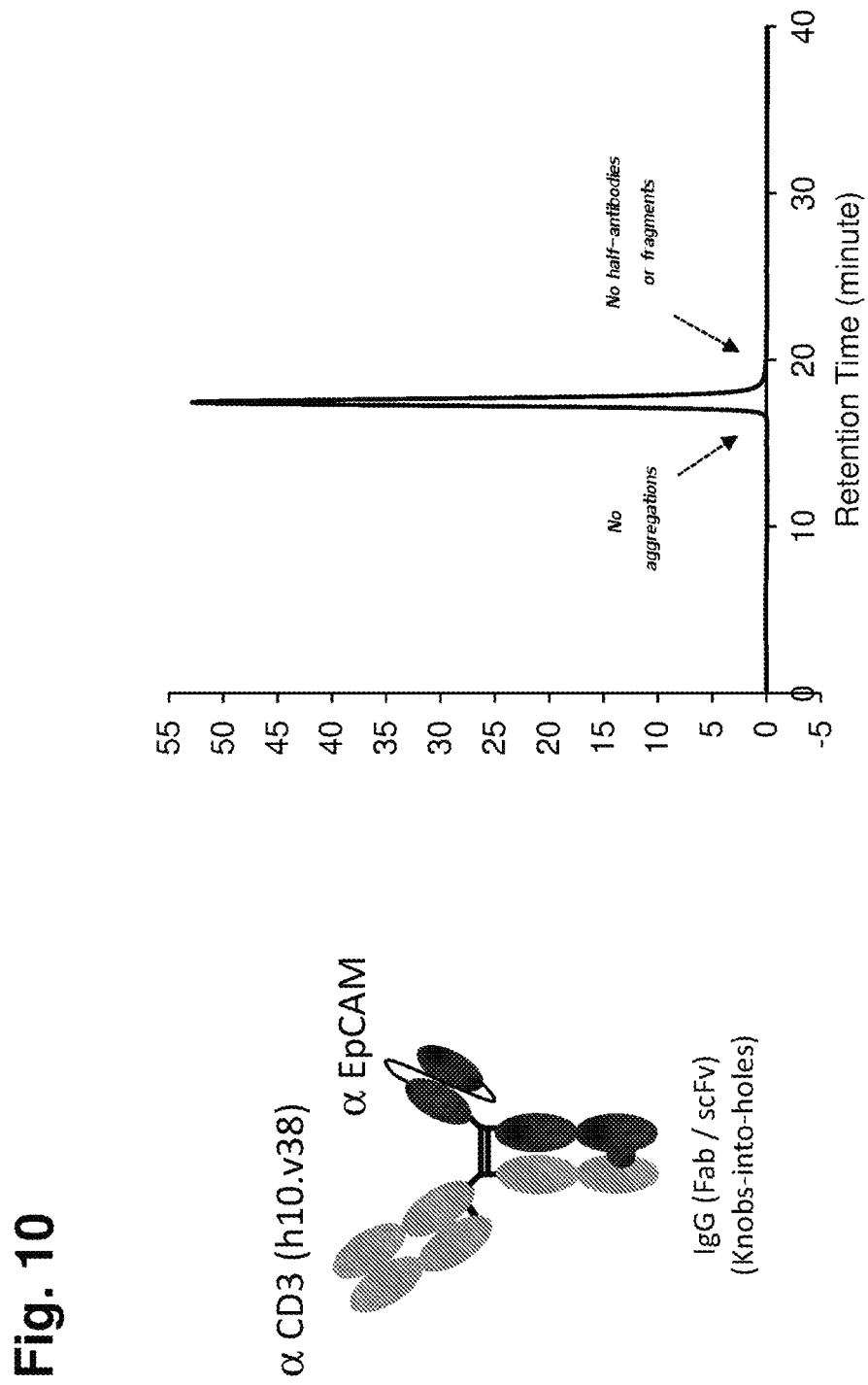
FIG. 10 shows the molecular configuration of a multispecific CD3 (h10.v38)×EpCAM (G8.8)) TMATE and an analytical HPLC chromatogram result indicating ≥98% high purity of the said TMATE that is recombinantly expressed in Expi293 cells and purified via chromatography.

In some embodiments, the anti-EpCAM moiety of an EpCAM-targeting TMATE construct is a Fab or a scFv or a single domain antibody. In some embodiments, the anti-EpCAM scFv or Fab or single domain antibody is derived from an exemplary clone comprising the same or homologous CDRs from Catumaxomab, Adecatumumab (MT201), Solitomab (MT110), ING-1, 3622W94, Edrecolomab, or EpAb2-6 among others. In some embodiments, the anti-CD3 moiety of the said EpCAM-targeting TMATE is a scFv or a Fab derived from and corresponding to one of the pH dependent anti-CD3 antibodies selected from a group consisting of h10.v23, h10.v26, h10.v27, h10.v32, h10.v34, h10.v38, h10.v39, h10.v48, and h10.v49. See Tables 3 and 4 and sequence table for CDR and VH/VL sequences of these antibodies. As shown in FIG. 10, one of such exemplary TMATE constructs, CD3 (h10.v38)×EpCAM (MuS110) can be readily expressed from an Expi293 or 293F or CHO cell based mammalian cell system and purified via chromatography to achieve ≥98% purity, which is validated by an analytical HPLC chromatogram showing no aggregations or half antibodies or partial fragments of the said CD3 (h10.v38)×EpCAM (MuS110) TMATE.

The functional properties of a T cell engager are generally multifaceted. In one aspect, one kind of TMA function is the ability of activating T cells (both CD4 and CD8 T cells), which can manifest as altered levels of cell surface markers (CD69, CD25, CD137, CD62L, PD-1, LAG3, among others). In another aspect, the function of a TMA can be indicated by the elevated release of certain cytokines including chemokines (e.g., IL-2, IFNγ, TNFα, IL-6, IL-10, IL-8, IL-10, MCP-1, CXCL10, IFNα) and by the induction of some apoptotic factors (e.g., death receptor ligands such as Fas ligands, which can directly contribute to target cell killing). The induced cytokines by TMAs are pharmacologically relevant to tumor treatment because the secreted cytokines can directly promote T cell expansion and indirectly effect proximal immune cells (i.e., "bystander effects") to enhance anti-disease responses, which together can help fight the intended target cells more efficiently. On the other hand, the induced cytokines may trigger harmful adverse effects such as cytokine release syndromes, vascular leakage, and neurotoxicity. In yet another aspect, TMA can elicit the cytotoxicity of T cells to directly engage and kill a target-specific cell which can be a non-disease cell, i.e., normal cells that express the said the target molecule can be subject to the TMA mediated direct killing by the engaged T cells (so called "on-target off-site" toxicity), leading to unfavorable clinical adverse events and patient intolerability. Thus, it has been a great challenge to discover and develop TMAs that can optimally engage T cells to kill or thwart disease target cells in a specific and potent manner, and meanwhile will only induce a favorable low-level of cytokine secretion to minimize potential adverse effects associated with cytokine "over secretion".

Figure 11:
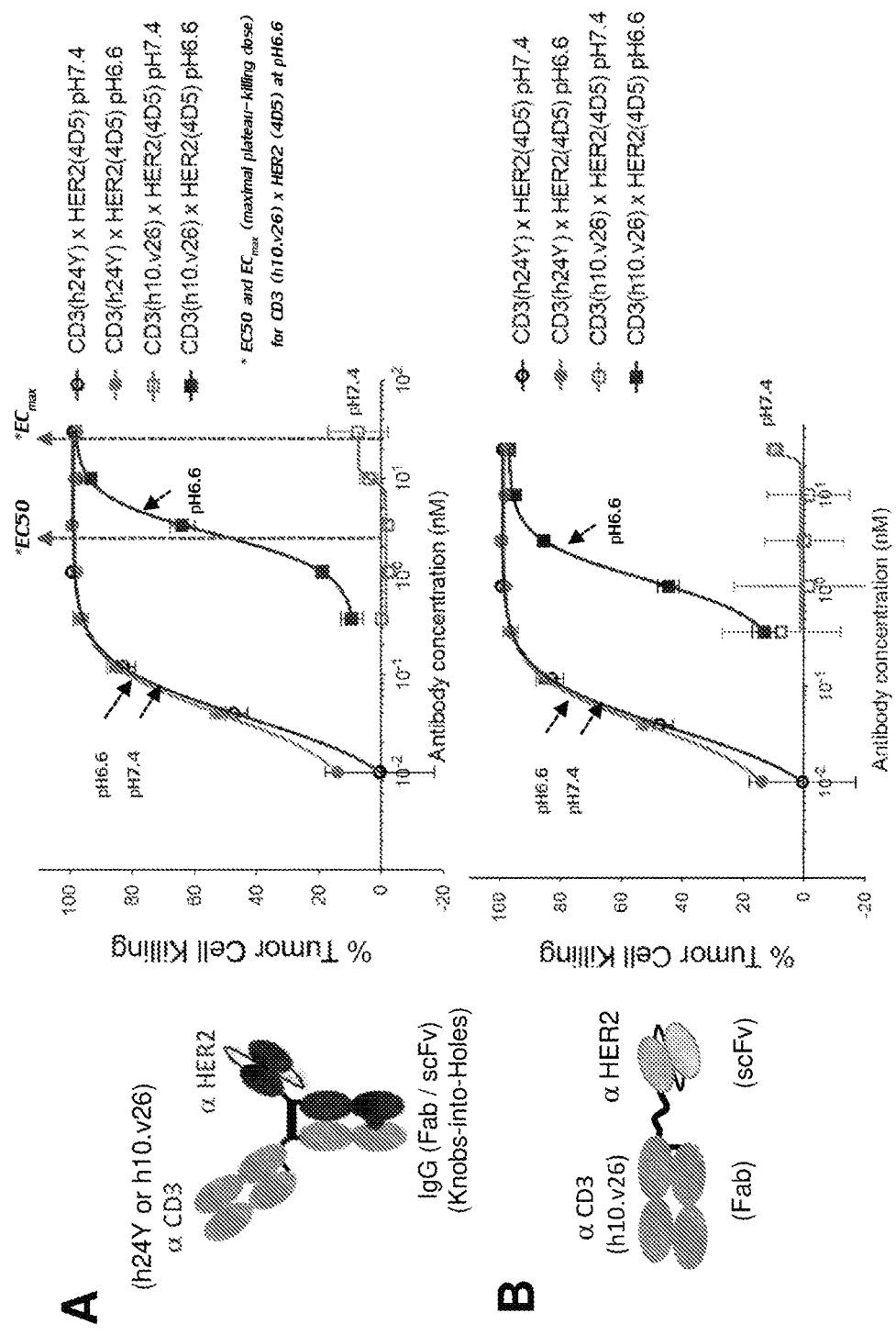
FIG. 11 (top panel A) demonstrates the molecular configurations of two multispecific TMATEs, CD3(h10.v26)× HER2(4D5) and a conventional control TMA, CD3(H24Y)× HER2(4D5), respectively, and their cell killing profiles under different pHs. Specifically, this T cell cytotoxicity assay shows the percentage of tumor cell killing after 48 hours of co-incubation of donor-derived human primary T cells and HER2-positive BT474 cells (Effector cell: Target cell (E:T) ratio≈11:1) in the presence of CD3(h10.v26)× HER2(4D5) or CD3(H24Y)×HER2(4D5) under specific pH media, respectively.

In some embodiments, shown in FIG. 11 are the killing assays for two closely related exemplary HER2-targeting TMATEs comprising anti-CD3 moiety h10.v26, namely the CD3 (h10.v26)×HER2 (4D5-scFv)-Fc (KiH) in a human IgG1-Fc (Knobs-in-Holes) bispecific format, and the CD3 (h10.v26)×HER2 (4D5) Fab-scFv with a flexible linker directly linking the VH of h10.v26 and 4D5 scFv instead of heterodimerization via a Fc. Both of these two TMATEs can engage human primary T cells (donor #81) to potently kill a HER2-positive breast cancer model line BT474 in a dose-dependent manner, given an effector (pan T)/target ratio of about 11:1 and an assay duration of about 72 hours in a DMEM-based culture medium of about pH 6.6. The EC50s for the killing activity are about 2 nM and 1.5 nM for these two TMATEs, respectively. In contrast, the killing activity of these same TMATEs are largely abolished (EC50 not definitive) under similar assay conditions except the culture medium pH being adjusted to about 7.4, representing an indefinite-fold reduction of the potency in comparison to that under pH 6.6 for both of the said TMATE constructs.

In some embodiments, upon contact with a plurality of T cells and a plurality of tumor cells that express the tumor-associated antigen, the anti-CD3 construct described herein promotes a significantly higher cytotoxicity of the plurality of the T cells against the tumor cells at a pH of about 6.7 than the counterpart cytotoxicity at a pH of about 7.4. For example, the EC50 at pH 7.4 is at least about 5-fold, 10-fold, 20-fold, 30-fold, 40-fold, 50-fold, 60-fold, or 70-fold than the EC50 at pH 6.7.

Figure 12:
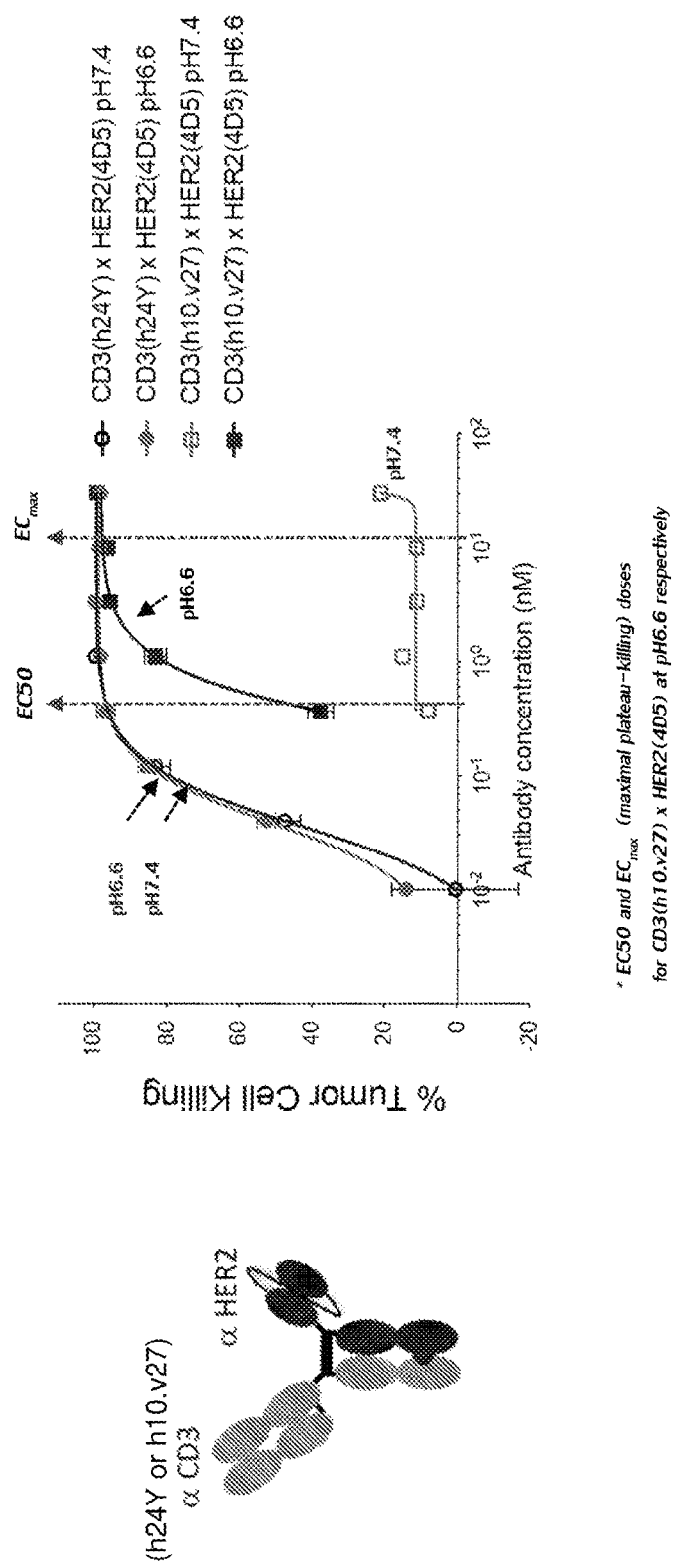
FIG. 12 illustrates the molecular format of a multispecific CD3(h10.v27)×HER2(4D5) TMATE and a conventional control TMA, CD3(H24Y)×HER2(4D5), and the percentage of tumor-cell killing after 48 hours of co-incubation of human primary T cells and HER2-positive BT474 cells (E:T ratio≈11:1) with one of the two said antibodies under specific pH media (pH 7.4 and pH 6.6) respectively.

In some embodiments, as shown in FIG. 12 (the same assay described in the foregoing paragraph as in FIG. 11), an alternative HER2-targeting TMATE, namely CD3 (h10.v27)×HER2(4D5-scFv)-Fc (KiH), showed a killing activity EC50 of about 0.5 nM under pH 6.6. However, the killing activity under pH 7.4 drops to a much lower level (~20% cell killing at the highest tested dose, 30 nM), leading to an indefinite-fold (or >60-fold) reduction of the cell-killing potency. Such pH dependent killing activity is similarly observed for the other two TMATEs comprising anti-CD3 (h10.v26). As a control, a conventional TMA, namely CD3(h24Y)×HER2(4D5-scFv)-Fc (KiH) comprising a conventional anti-CD3 moiety (clone H24Y) (FIG. 11 and FIG. 12), showed potent killing of BT474 cells but such killing remains potent at pH 7.4, which is typical to conventional TMAs (or TCEs). For CD3(h24Y)×HER2(4D5-scFv)-Fc (KiH), its EC50s for the HER2-positive BT474 cells differ very little (within 50% deviation) between assay conditions of about pH6.6 and about pH7.4.

While the EC50 dose is a common way to assess the potency of candidate therapeutic agents, the maximal plateau-killing dose ("ECmax") is an alternative way to examine and correlate with the maximally achievable percentage of target-cell killing. In some embodiments, as exemplified in FIG. 11 and FIG. 12, any one of the two CD3(h10.v26)×HER2(4D5-scFv) TMATEs and the CD3(h10.v27)×HER2 (4D5-scFv) TMATE can reach near 100% target-cell killing at their respective ECmax doses under the pH 6.6 condition. However, under the condition of pH 7.4, even given the same ECmax doses (about 12 to 25 nM) or the highest tested dose (30 nM), the maximal achieved killing activity is only about 8-20% target-cell killing, significantly and consistently lower than the foregoing near 100% by the same TMATEs under the otherwise pH 6.6 conditions.

As used herein and thereafter, the anti-CD3 or anti-TAA antibody is used in a Fab format unless otherwise specified (e.g., "4D5-scFv" specifies a scFv format of the anti-HER2 4D5 clone, so on and so forth). As used herein and thereafter, the anti-CD3 and anti-TAA half antibody are co-expressed and purified as a heterodimerized multispecific antibody through using the so-called Knobs-in-holes Fc domain derived from human IgG1, unless otherwise specified. Notwithstanding the foregoing sentences, the antigen-binding region of anti-CD3 and anti-TAA antibodies can include many other established or alternative formats without limitations to scFv and Fab; likewise, the heterodimeric Fc of a multispecific TMATE can be replaced by many alternative heterodimerization domains without limitation to a Fc with the Knobs-in-holes mutations.

Figure 14:
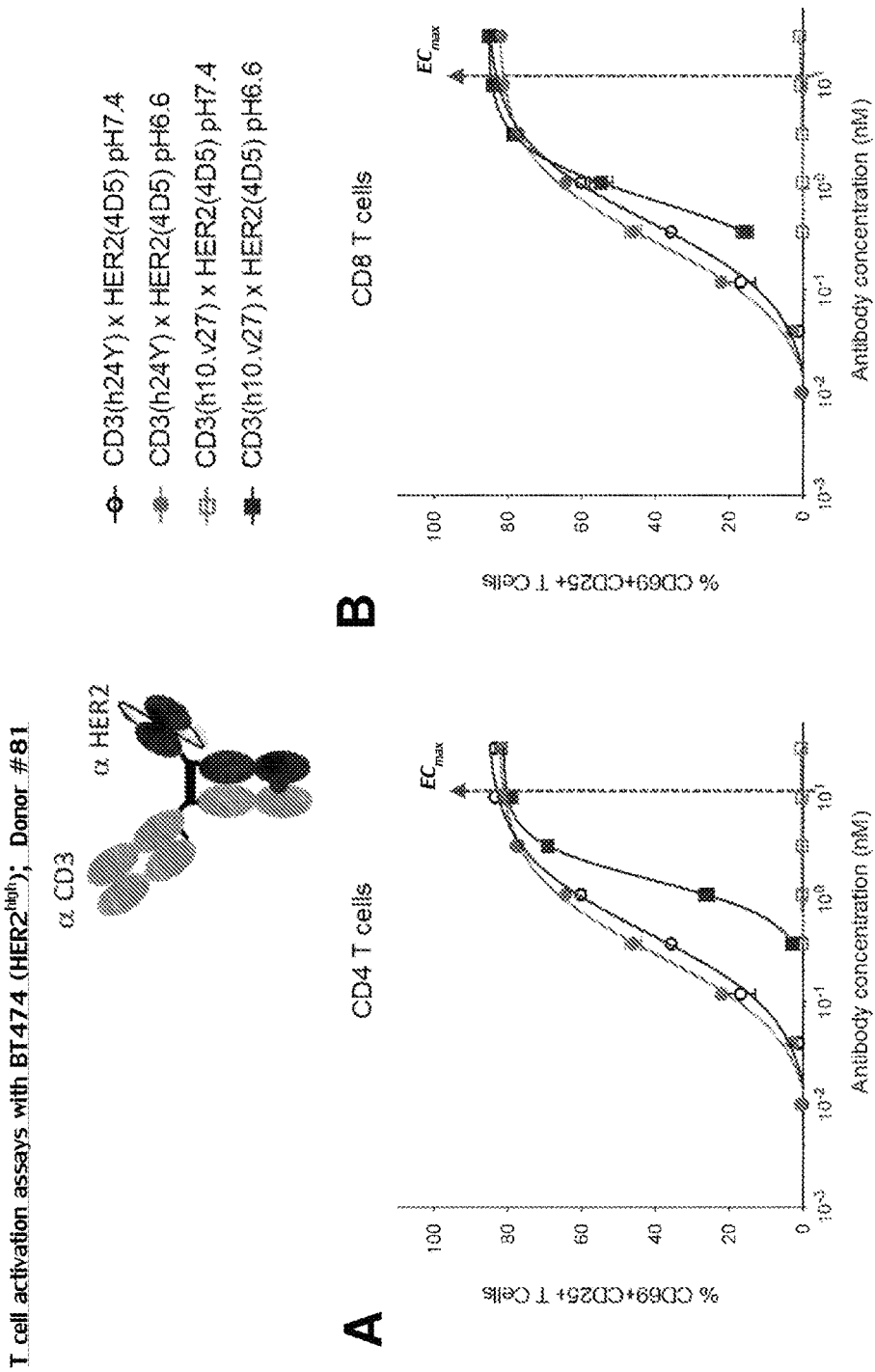
FIGS. 14A-B shows the percentage of T cell activation, as measured by CD69 and CD25 double positive cell surface expression with flow cytometry, after 48 hours of co-incubation of donor-derived human primary T cells, including CD4 T cells (FIG. 14A) and CD8 T cells (FIG. 14B), and HER2-positive BT474 cells in the presence of one of the two multispecific antibodies (CD3(h10.v27)×HER2(4D5) and CD3(H24Y)×HER2(4D5)) under specific pH media, respectively. This activation assay is based on samples from one and the same T cell cytotoxicity assay described in FIG. 12.

T cell mediated killing of an antigen-positive target cell involves exquisite steps leading to T cell full activation. As a common method known to a person with average skills, the T cell activation status can be analyzed using flow cytometry to examine a few T cell activation markers such as CD69 and CD25. In the similar assay as described in FIGS. 11 and 12, the three HER2×CD3 TMATEs display a pH-dependent CD4 and CD8 T cell activation profile (FIGS. 13 and 14), which is consistent with the pH-sensitive killing activity profile shown in FIGS. 11 and 12. In essence, under culture conditions of about pH 7.4, there is no evident activation of any CD4 or CD8 T cells at any tested TMATE doses up to about 30 nM, which is in direct contrast to the conditions of pH 6.6 wherein the T cell activation is increasingly more evident upon the TMATE dose escalation and can reach a plateau activation level up to about 70-85% of all T cells.

Figure 15:
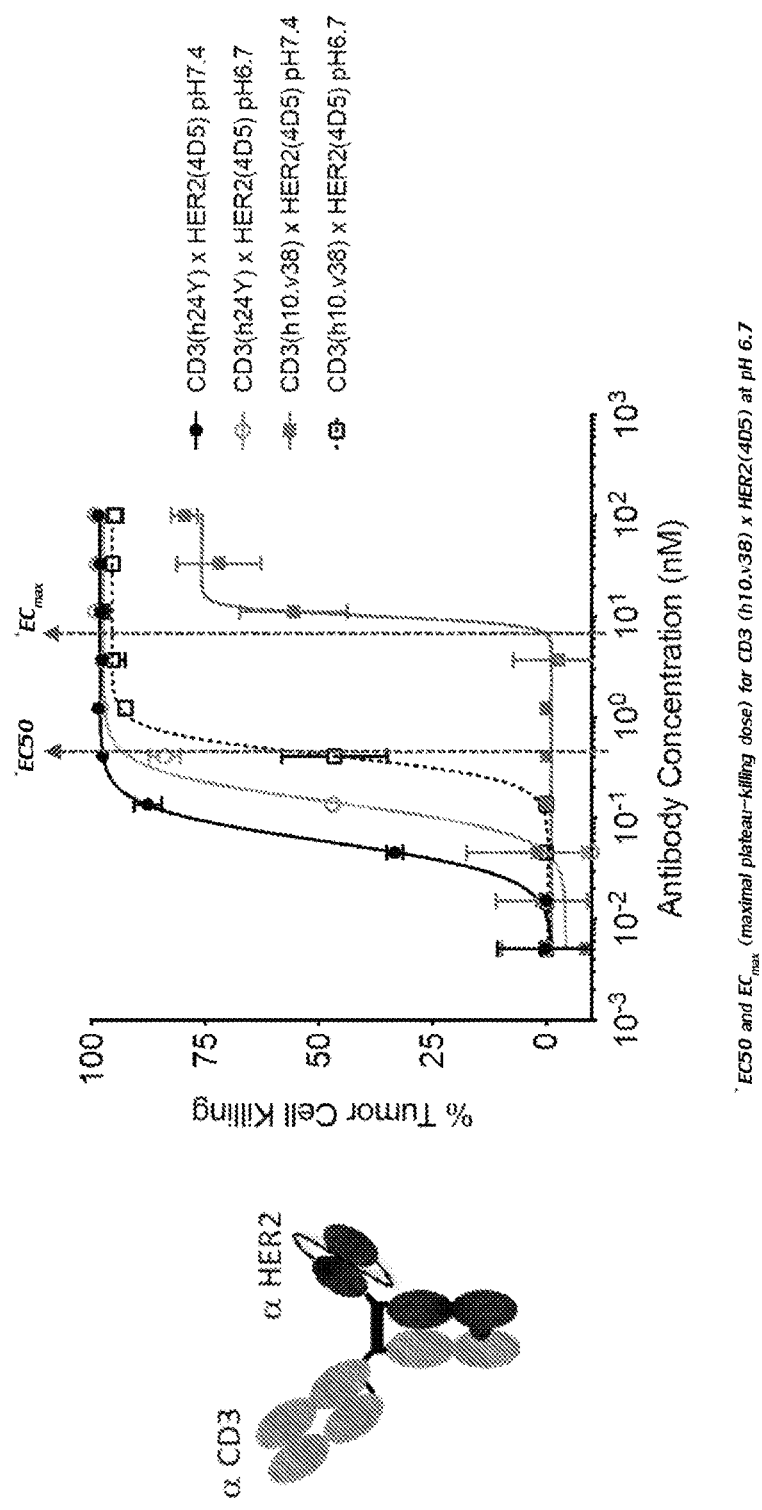
FIG. 15 shows the molecular format of an alternative multispecific TMATE, CD3(h10.v38)×HER2(4D5), and the conventional control TMA, CD3(h24Y)×HER2(4D5), and the percentage of tumor-cell killing after 72 hours of incubation duration with human primary T cells and HER2-positive BT474 cells (E:T ratio≈11:1), given one of the two antibodies under specific culture medium of pH 7.4 and pH6.7, respectively.

In some embodiments, the anti-CD3 multispecific TMATE construct can be based on alternative variants of a pH sensitive anti-CD3 antibody moiety. As indicated in FIG. 15, a HER2×CD3 TMATE comprising the anti-CD3 moiety h10.v38 (i.e., CD3 (h10.v38)×HER2 (4D5-scFv)) with a human IgG1-Fc (KIH), can engage human primary T cells (donor #78) to potently kill the HER2-positive BT474 cells in a dose-dependent manner, given an effector (pan T cell)/target (BT474) ratio of 11:1 and an assay duration of about 70 hours in a DMEM-based culture medium of about pH 6.7, leading to a cell-killing EC50 of about 0.42 nM and an ECmax of about 7 nM. However, under the same assay conditions except the medium pH being adjusted from about 6.7 to about 7.4, the same TMATE's EC50 increases to about 10 nM (i.e., 24-fold potency reduction). Even given the TMATE dose at 7 nM (corresponding to the pH 6.6-associated ECmax), the corresponding cell killing is still minimal (~3%) under the conditions of about pH 7.4. As a control, the cell killing activity of the conventional TMA, CD3(h24Y)×HER2 (4D5-scFv) is largely unaffected by the pH switch from about 6.7 to about 7.4.

In the same assays as described in the foregoing paragraph, the CD3(h10.v38)×HER2(4D5-scFv) TMATE display a pH-dependent T cell activation profile (see FIG. 16), which is consistent with the pH-sensitive killing activity profile shown in FIG. 15. Under the same culture conditions except adjusting pH to about 7.4, there is only minimal activation (<3%) of CD4 or CD8 T cells at the pH6.7-associated EC50 dose of the CD3(h10.v38)×HER2(4D5-scFv) TMATE. Nonetheless, at the pH6.7-associated ECmax dose (~7 nM), there is already evident strong activation (70-75%) for both CD4 and CD8 T cell subpopulations, unlike the low activation observed with TMATEs otherwise comprising the anti-CD3 clone h10.v26 or h10.27 at their respective pH6.6-associated ECmax doses.

In general, T cell receptor binding, T cell activation, T cell-mediated target killing and T cell cytokine induction are not necessarily coupled with one another. In other words, these four aspects of T cell signaling events require different thresholds of T cell signaling; as such, pH-dependent binding activity of an anti-CD3 antibody does not readily translate into pH-dependent T cell activation, or pH-dependent killing activity or pH-dependent cytokine induction activity of the said antibody. Thus, engineering or optimizing a pH-dependent killing activity for TMATEs generally involves different technical requirements from that for a pH-dependent CD3 binding clone.

In some embodiments, an anti-CD3 multispecific molecule with a pH-dependent binding activity may not show any pH-dependent killing activity, for instance, showing no significant difference under a pH 7.4 versus a pH 6.6 condition with substantially the same assay setup except the two pH values. In some embodiments, an anti-CD3 multispecific molecule with a pH-dependent binding activity shows only suboptimal pH-dependent killing activity, for instance, eliciting lower than 30% or 20% killing of a TAA-high tumor cell that can be otherwise efficiently killed by a favorable TMATE or a conventional TMA under substantially the same assay setup except using different anti-CD3 moieties in the T cell engagers. Additional relevant embodiments can be found in the Example section to illustrate the notion that engineering a pH-dependent killing activity of a TMATE involves unique technical requirements.

In general, it is preferred to achieve drastically reduced cell killing upon pH switch from an acidic tumor microenvironment-like condition (e.g., pH 6.6 or 6.7) to a physiologically relevant condition (e.g., pH 7.3 or pH 7.4), which can potentially improve the safety profile of a prospective therapeutic. Such safety improvement is presumably partly due to reduced "on-target off-site" killing of otherwise normal cells that typically resides in an interstitial extracellular environment of about 7.2 to 7.6 or more commonly of about pH 7.3 to about pH 7.5. In another aspect, toxic drug side effects may arise from the systemic increase of cytokines, the so-called cytokine release syndrome ("CRS").

The effect of released cytokines can be multifaceted. On one hand, cytokines can augment the immune response including promoting T cell activation, migration and/or memory formation to improve the immunity against a disease. Cytokines can also contribute to the activation and engagement of proximal immune cells to fight the disease condition ("bystander effect"). Thus, positive cytokine secretion is generally considered as a beneficial aspect of the T cell engagers' pharmacological activities. On the other hand, "too much" cytokine release can potentially lead to pathological outcomes, which can be a lethal event in a worst-case scenario. Moreover, a high level of cytokine secretion may unfavorably result in or accelerate the T cell exhaustion, potentially leading to reduced therapeutic efficacy. Unfortunately, conventional TMAs usually elicit high levels of cytokines without adequate discrimination of disease microenvironment from healthy tissue environment. These cytokines are commonly exemplified by IL-2, IFNγ and TNFα among others (e.g., IL-6, IL-10, IL-8, IL-1, IL-4).

It is therefore generally advantageous to have a reduced level of cytokine release upon T cell activation triggered by a TMA under a physiologically relevant condition as compared to a disease microenvironment. For instance, the preferred level of cytokine release triggered by an innovative "safer" TMA under a physiologically relevant condition shall be lower than about 50%, 40%, 30%, 25%, 20%, 15%, 10%, 5% of that triggered by one and the same TMA under a pathological condition (e.g., an acidic tumor microenvironment like condition).

Moreover, the preferred level of cytokine release triggered by an innovative TMA under a physiologically relevant condition shall be lower than about 50%, 40%, 30%, 25%, 20%, 15%, 10%, 5% of that triggered by a "benchmark" TMA of the same construct but otherwise comprising a conventional anti-CD3 antibody moiety, wherein the said benchmark TMA is similarly assayed except that it is under a pathologically relevant assay condition (e.g., an acidic condition that mimics a tumor microenvironment). Exemplary conventional anti-CD3 antibodies are exemplified by the OKT3, L2K, SP34, hu38E4 and hu40G5c clones that are well-known in the field.

Figure 16:
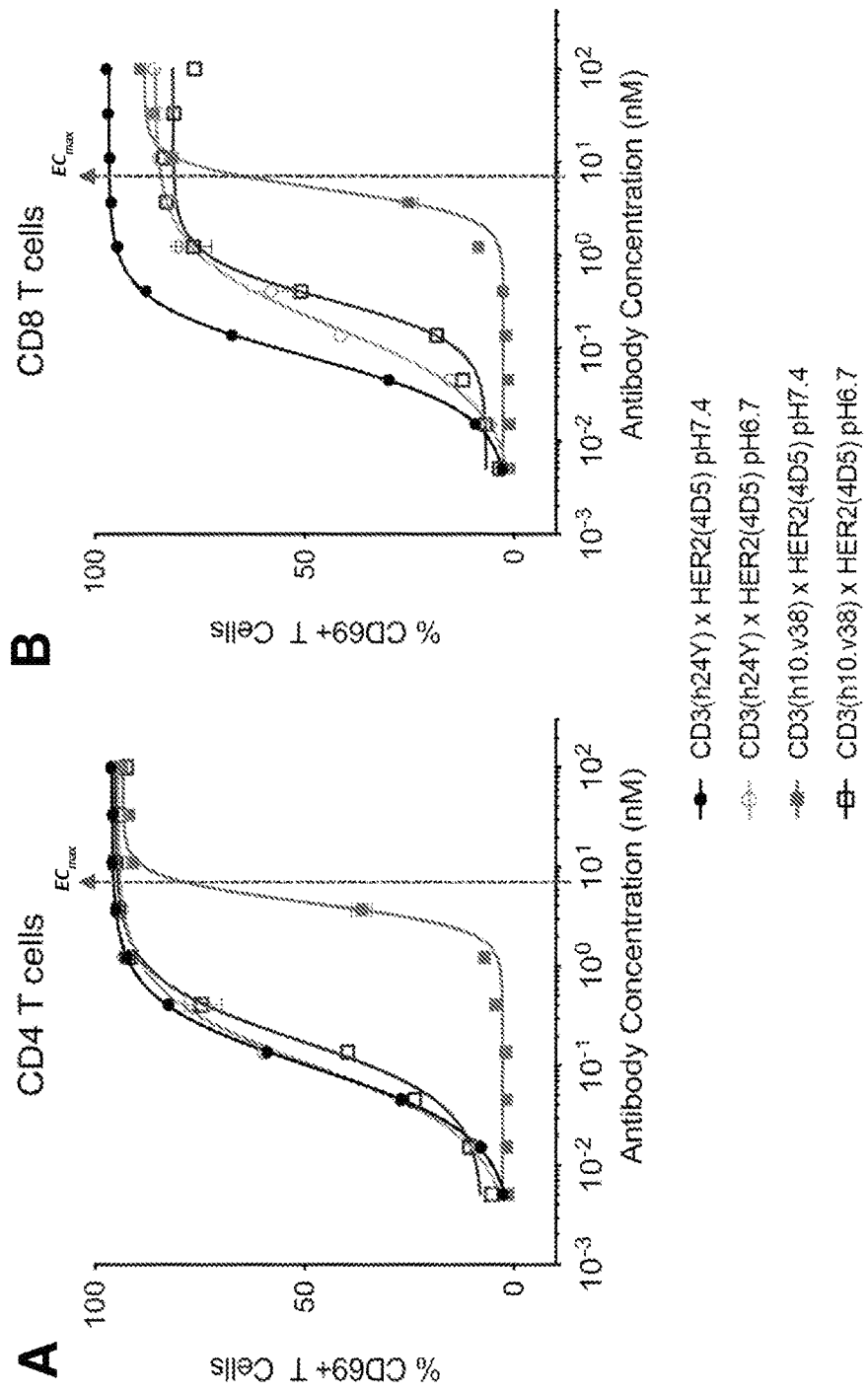
FIGS. 16A-B shows the percentage of CD4 (FIG. 16A) and CD8 (FIG. 16B) T cell activation, respectively, as measured by CD69 and CD25 double positive cell surface expression with flow cytometry, as part of one and the same killing assay described in FIG. 15.
Figure 17:
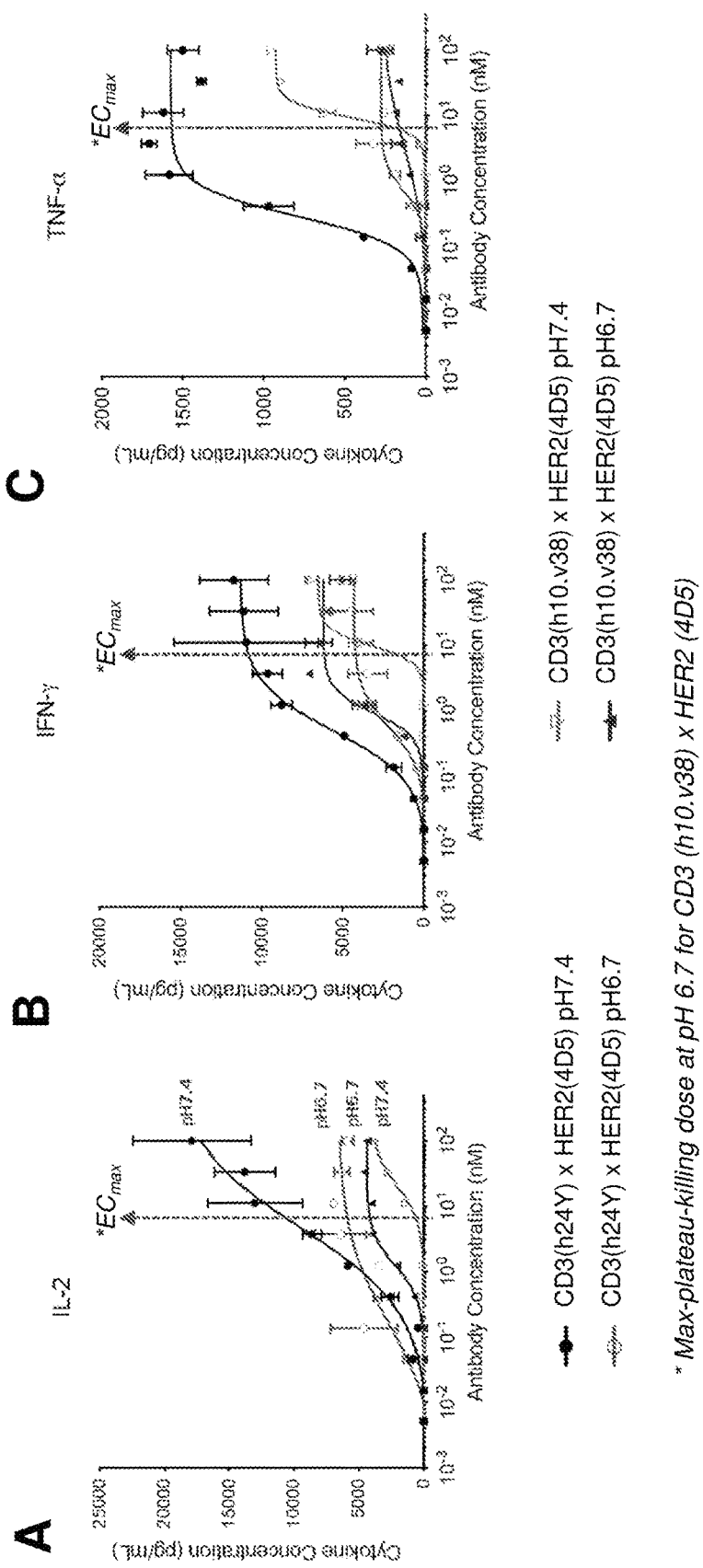
FIGS. 17A-C shows the cytokine release profiled by ELISAs for IL-2 (FIG. 17A), IFN-γ (i.e., IFNγ or IFN-gamma) (FIG. 17B), and TNFα (i.e., TNF-alpha) (FIG. 17C), respectively, using samples from one and the same T cell cytotoxicity assay described in FIG. 15.

In some embodiments, as exemplified in FIG. 17 which corresponds to the same assays as described for FIGS. 15 and 16, at the ECmax dose (the maximal plateau-killing dose at pH 6.7), the IL-2 release triggered by CD3(h10.v38)×HER2(4D5) TMATE under pH7.4 is reduced by about nine-fold as compared to that released under the TME-like acidic condition (pH6.7); Similarly, the IFNγ release is reduced by about six-fold whereas the TNFα secretion is barely changed at pH7.4 versus at pH6.7. In another aspect, the same IL-2, IFNγ and TNFα release triggered by CD3 (h10.v38)×HER2(4D5) TMATE under pH7.4 is reduced by about 12-fold, nine-fold and seven-fold respectively as compared to those same three cytokines triggered by a conventional TMA, CD3(h24Y)×HER2(4D5) comprising a non-pH selective anti-CD3 moiety (H24Y) under the same physiologically relevant assay condition of pH7.4, at a dose of about 1 nM, which is the ECmax of this CD3(h24Y)×HER2 (4D5) TMATE under the same condition of pH6.7 described in this same Figure (FIG. 17).

Figure 18:
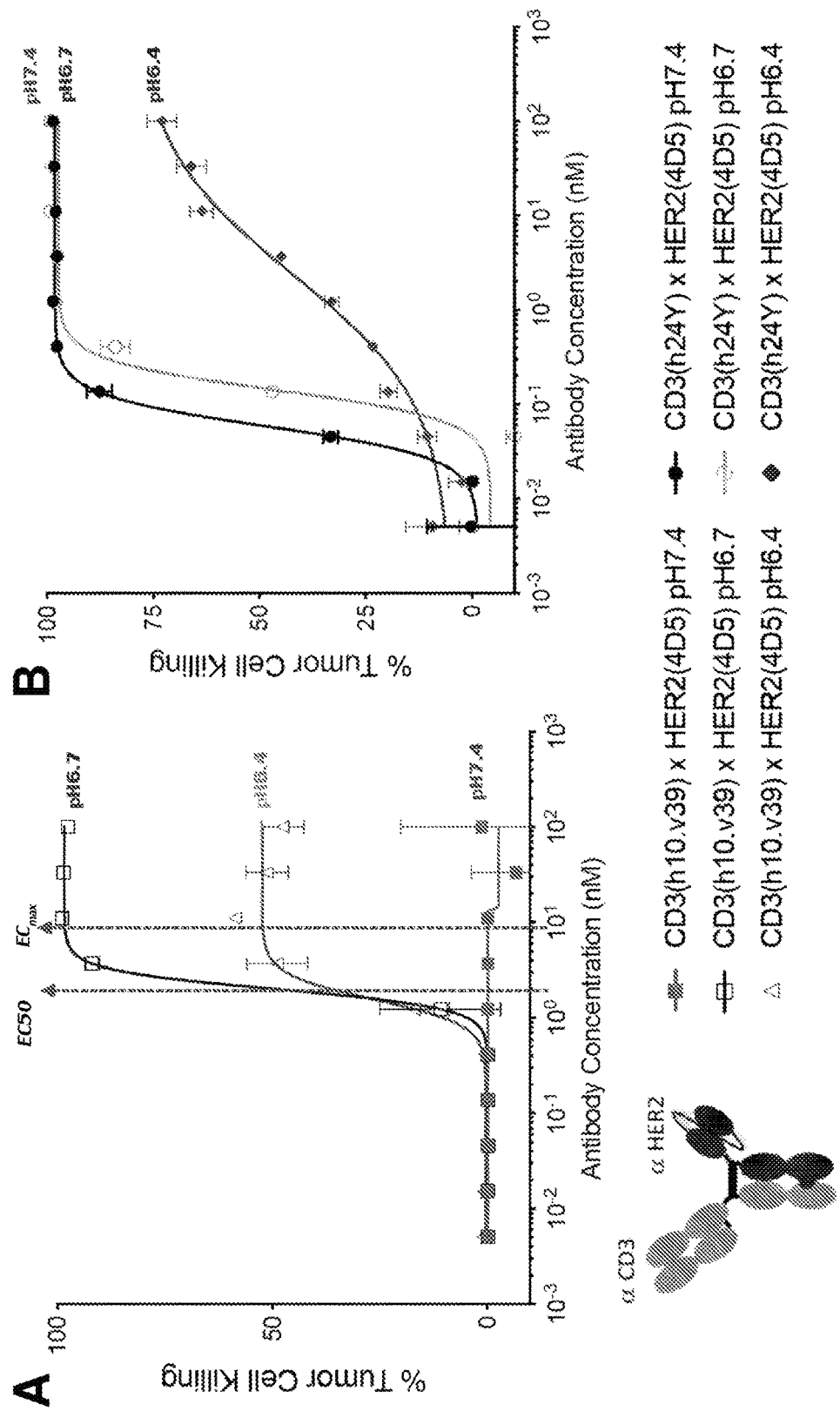
FIG. 18A shows the respective molecular format of an alternative multispecific TMATE comprising CD3 (h10.v39)×HER2(4D5), and its T cell cytotoxicity profile over a 72-hour assay with human primary T cells and HER2-positive BT474 (E:T ratio≈11:1) under specific culture medium of pH 7.4, pH 6.7 and pH 6.4, respectively.
FIG. 18B shows the T cell cytotoxicity profile of a conventional control TMA comprising CD3(h24Y)×HER2(4D5) under the same conditions.

In some embodiments, the anti-CD3 multispecific TMATE construct can be based on other variants of a pH sensitive anti-CD3 antibody moiety such as clone h10.v39. As illustrated in FIG. 18, the corresponding CD3(h10.v39)×HER2(4D5) TMATE with a human IgG1-Fc (KIH), can engage human primary T cells (donor #78) to potently kill the HER2-positive BT474 cells in a dose-dependent manner, given an effector (pan T cell)/target (BT474) ratio of 11:1 and an assay duration of about 70 hours in a DMEM-based culture medium of about pH 6.7, resulting in a cell-killing EC50 of about 1 nM and an ECmax of about 9 nM. However, under the same assay conditions except with the medium pH being adjusted from about 6.7 to 7.4, the same TMATE's EC50 becomes indefinite, as there is virtually no target-cell killing even at the highest TMATE treatment dose of 100 nM (i.e., indefinite-fold or >100-fold potency reduction). As a control, the cell killing activity of the conventional TMA, CD3(h24Y)×HER2(4D5) is largely unaffected by the pH switch from about 6.7 to about 7.4, showing less than three-fold difference.

It is noteworthy that, due to the intrinsic T cell property, both TMATEs and conventional TMAs will show significantly reduced activities under significantly acidified conditions of about pH 6.4, pH 6.3 or a lower pH, wherein the T cell receptor signaling and/or the downstream effector machinery will be presumably overwhelmed by such enhanced acidity.

Figure 19:
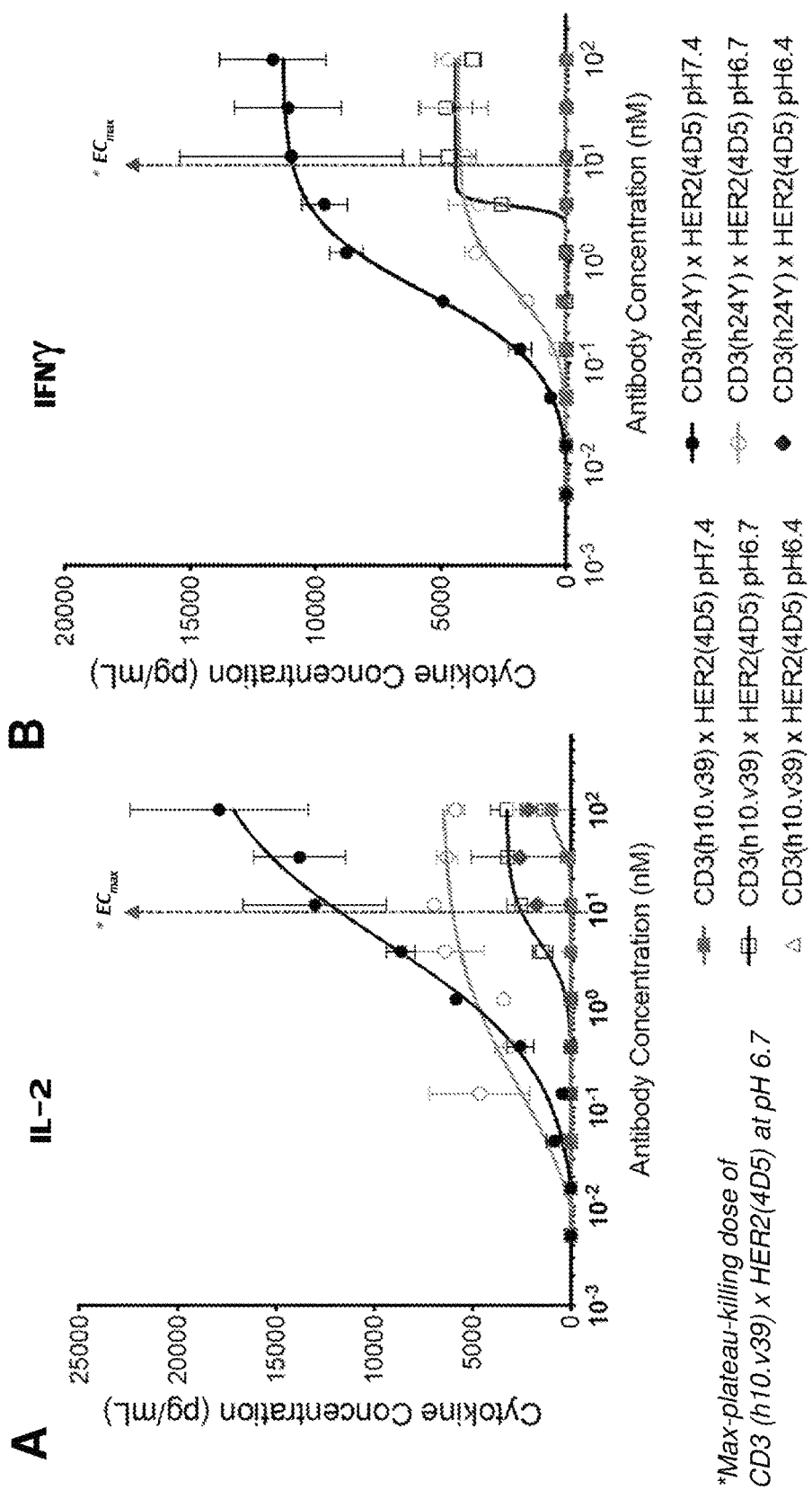
FIGS. 19A-B is an example of ELISA results showing the cytokine secretion profile for IL-2 (FIG. 19A) and IFN-γ (FIG. 19B) from T cells activated by CD3(h10.v39)×HER2 (4D5) and CD3(h24Y)×HER2(4D5). This ELISA is based on using the same culture medium samples from one and the same killing assay described in FIG. 18.
Figure 20:
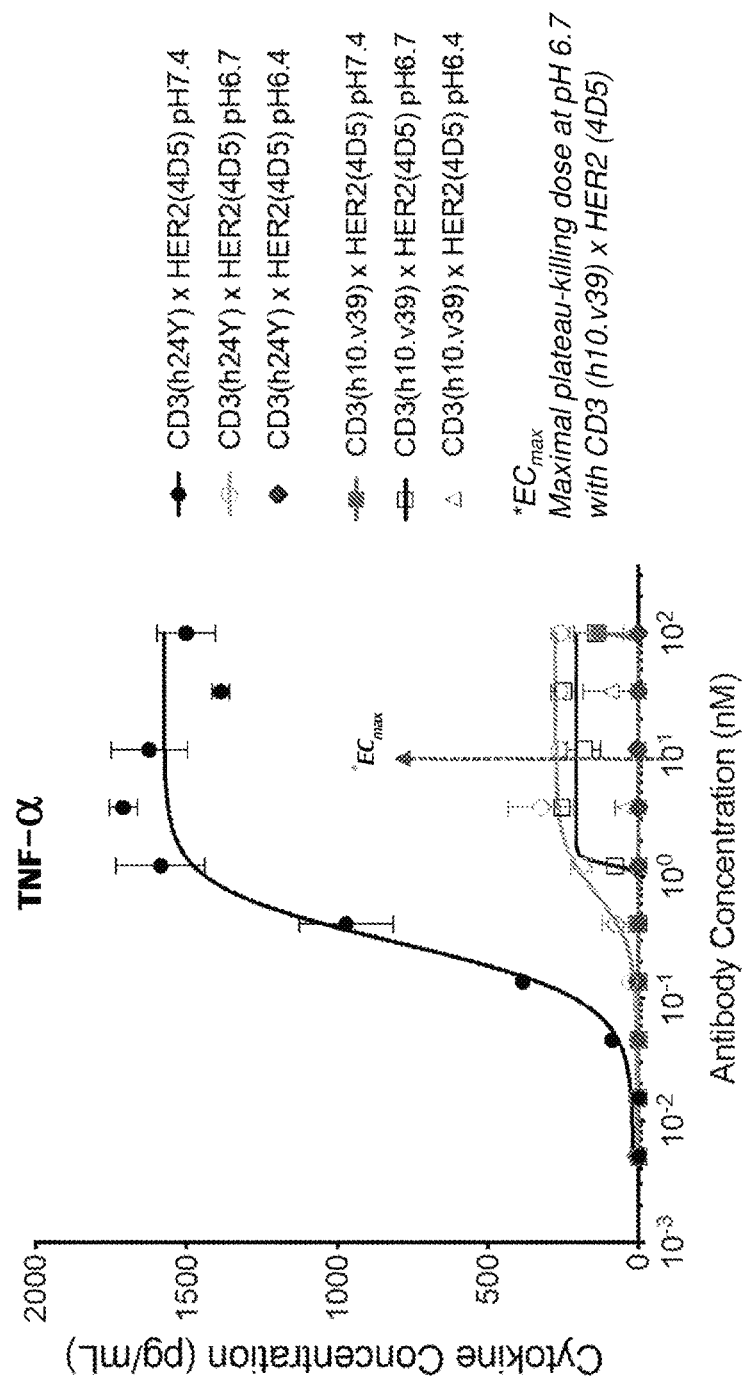
FIG. 20 is an example of ELISA results showing the cytokine secretion profile for TNFα. This ELISA is based on one and the same ELISA assay described in FIG. 19.

In some embodiments, as exemplified in FIG. 19 and FIG. 20 which correspond to the same assays as described for FIGS. 15 and 16, at the ECmax (the maximal plateau-killing dose at pH 6.7), the IL-2 release triggered by CD3 (h10.v39)×HER2 (4D5) TMATE under pH7.4 is reduced by about eight-fold as compared to that released under the TME-like acidic condition (pH6.7); Similarly, the IFNγ release is reduced by about 20-fold whereas the TNFα secretion is decreased by about ten-fold at pH7.4 as compared to that at pH6.7. Further, the release level of the same IL-2, IFNγ and TNFα triggered by CD3(h10.v39)×HER2 (4D5) TMATE under pH7.4 is reduced by about ten-fold, about 40-fold and about 60-fold respectively as compared to those same three cytokines triggered by the conventional TMA, CD3(h24Y)×HER2(4D5) under the same physiologically relevant assay condition of pH7.4, at a dose of about 1 nM, which is the ECmax of this CD3(h24Y)×HER2(4D5) TMATE under the otherwise TME-like acidic condition of about pH6.7.

Figure 21:
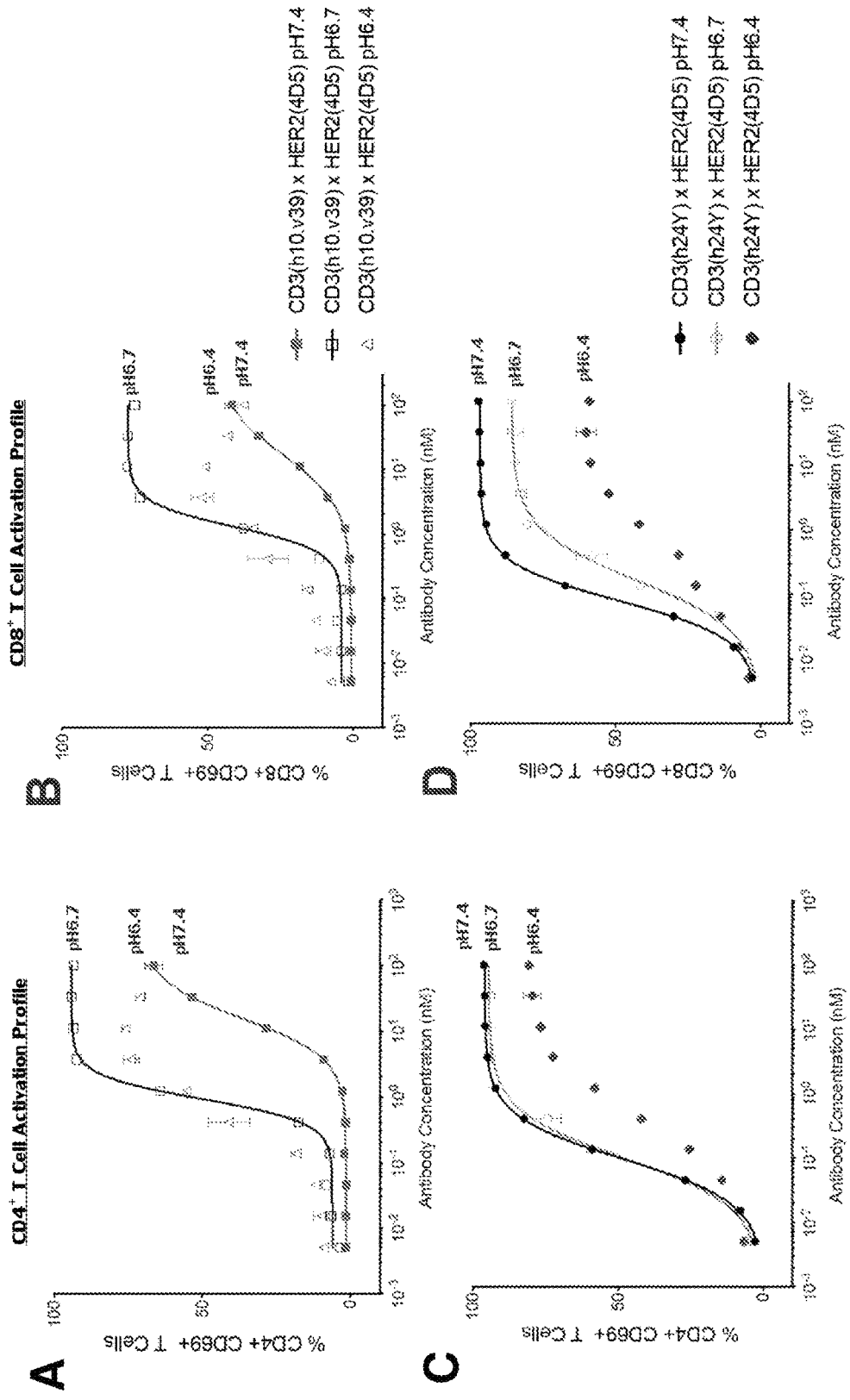
FIG. 21 provides the flow cytometric analysis results for the CD4 and CD8 T cell activation status as indicated by CD69 and CD25 double positive cell markers (A & B for CD3(h10.v39)×HER2(4D5); C & D for CD3(h24Y)×HER2 (4D5)). This analysis is based on using the same cell samples from one and the same killing assay described in FIG. 18.

In the same assays as described in the foregoing two paragraphs, the CD3 (h10.v39)×HER2(4D5) TMATE display a pH-dependent CD4 and CD8 T cell activation profile (FIG. 21), which is consistent with its pH-sensitive killing activity profile shown in FIG. 18 and with the functional property profiles of other TMATE variants. Under the same culture conditions except the pH being adjusted from about pH 6.7 to 7.4, there is little activation of CD4 or CD8 T cells at the pH6.7-associated EC50 dose of the TMATE. Nonetheless, at the pH6.7-associated ECmax dose (~9 nM), there is moderate activation (20-35%) of CD4 and CD8 T cell subpopulations, which is stronger than the little-to-no activation observed for TMATEs comprising h10.v26 or h10.v27, but weaker than the strong activation observed for TMATEs comprising h10.v38. Thus, whereas the thresholds for T cell activation appears to be somewhat heterogeneous among TMATE variants.

Figure 22:
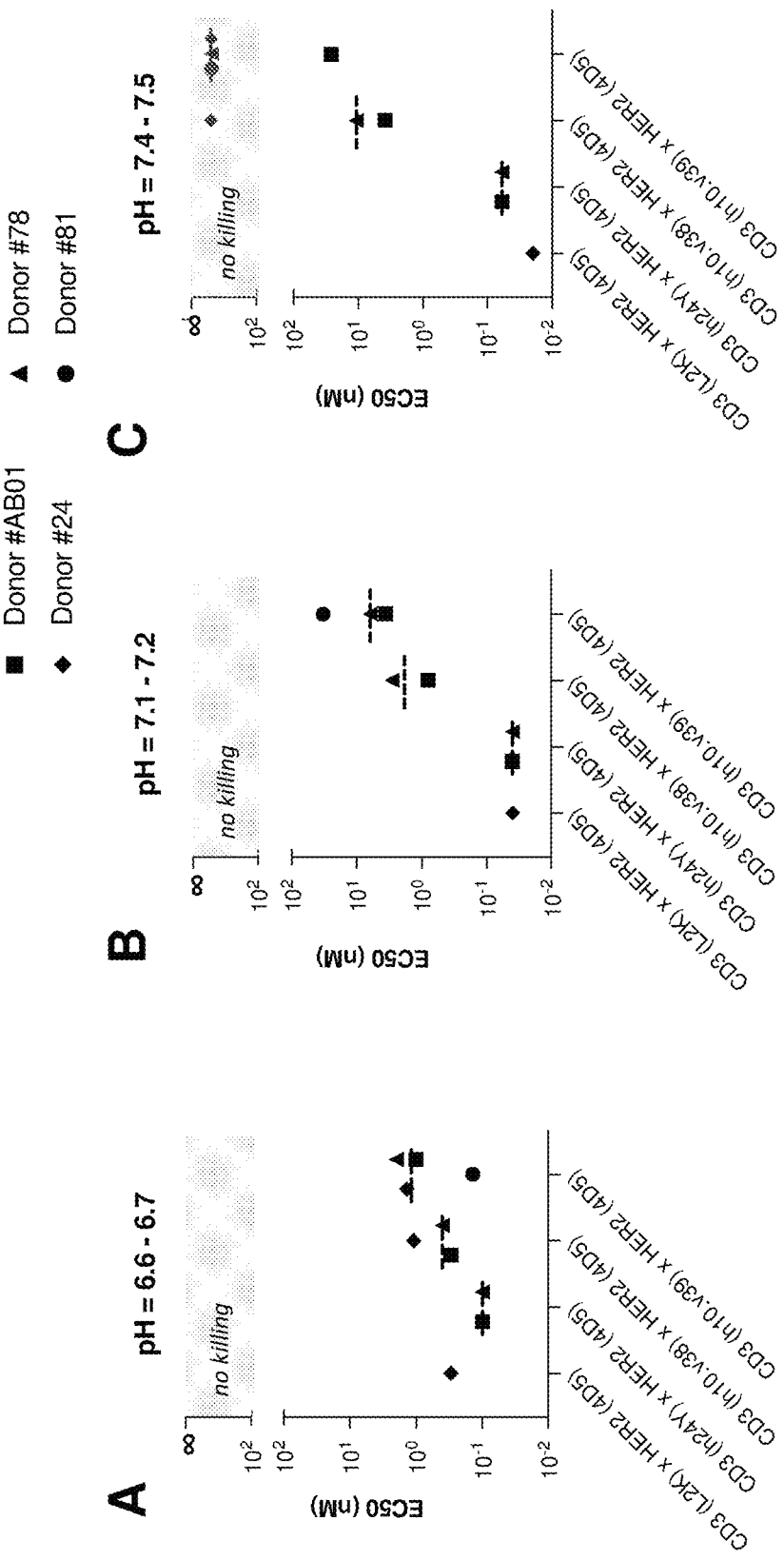
FIGS. 22A-C show three bar graphs that summarize the target-cell killing EC50 doses under culture conditions of about pH 6.6-6.7 (FIG. 22A), pH 7.1-7.2 (FIG. 22B), and pH 7.4-7.5 (FIG. 22C) for two TMATEs comprising a pH sensitive anti-CD3 clone (h10.v38 or h10.v39) and two control TMAs comprising a conventional anti-CD3 clone (L2K or h24Y), respectively. The EC50 values are derived from T cell cytotoxicity assays using human primary T cells from four different donors and target-positive BT474 over a duration of 72 hours with an E:T ration of about 11:1. In cases where no killing activity was observed under any tested doses (up to 400 nM), the EC50 data points will be assigned to the upper gray zone indicating indefinite EC50 (i.e., "no killing").

In some embodiments, additional human primary T cell samples from various donors are tested for two TMATEs' killing activity under various pH conditions (e.g. about pH 6.6 or pH 6.7, about pH7.1 or pH7.2, and about pH7.4 or pH7.5). In some embodiments, as summarized in FIG. 22, the potency of the two TMATEs comprising either CD3 (h10.v38)×HER2(4D5) or CD3(h10.v39)×HER2(4D5), as measured by respective EC50 values, are reduced by at least 15-fold and up to indefinite-fold with primary T cells from any one of the four donor under the pH 6.6-6.7 conditions versus the pH7.4-7.5 conditions.

In some embodiments, the anti-CD3 construct triggers a significantly higher level (e.g., at least about 10%, 20%, 30%, 40%, 50%, 60%, 70%, 80%, 90%, one-fold, 2.5-fold, five-fold, 7.5-fold, or ten-fold higher) of a cytokine secretion (e.g., IL-2, IFNγ, TNFα, IL-6 and IL-10) of an immune cell (e.g., a T cell) at a pH of about 6.0-6.9 (e.g., 6.7) than at a pH of about 7.2-7.6 (e.g., 7.4).

In some embodiments, the anti-CD3 construct does not trigger a significant level of a cytokine secretion (e.g., IL-2, IFNγ, TNFα, IL-6 and IL-10) of an immune cell (e.g., a T cell) at a pH of about 7.2-7.6 (e.g., 7.4). In some embodiments, the anti-CD3 construct triggers less than about 3000, 2000, 1000, 750, 500, 300, 200, or 100 µg/ml IL-2 or IFNγ with a treatment concentration of the anti-CD3 construct of about 1 nM to about 10 nM (e.g., 1 nM, e.g., 10 nM).

In general, the following advantageous features are shared among the TMATEs comprising a pH selective anti-CD3 moiety, in the context of engaging primary T cells and target-positive cells:

(1) pH dependent binding to CD3, wherein the binding is relatively strong at pH 6.0, relatively strong or moderate strong at about pH 6.6 and weak or largely abolished at about pH 7.4;
(2) pH dependent target-cell killing activity, wherein the activity is relatively potent at about pH 6.6, but significantly reduced or largely abolished at about pH 7.4;
(3) pH dependent cytokine-secretion profile, i.e., triggering a relatively low-to-moderate level of cytokine release at about pH 6.6, but only a minimal or very low level of cytokine release at about pH 7.4;
(4) triggering a much lower cytokine secretion as compared to that triggered by conventional benchmark TMAs under substantially the same pH 7.4 assay conditions.

It is generally preferred to avoid potential toxicity towards normal or non-target cells that may express a relatively low or medium-low level of a cell-surface target molecule, for example at a level that is about 50% lower, 60% lower, 70% lower, 80% lower, 90% lower or ≥95% lower than that of target-positive cells. In the case for HER2 as a model of tumor associated antigen, MCF7 (HER2$^{low}$) is often used as a surrogate of a "normal cell" for the activity assessment for candidate TMAs, as MCF7 expresses a comparable level of HER2 (10,000~15,000 cell-surface HER2 molecules per cell) as normal heart cardiomyocytes, versus the ≥200,000 cell surface HER2 molecules in many HER2-positive cancer cells such as SKBR3 and BT474.

Figure 23:
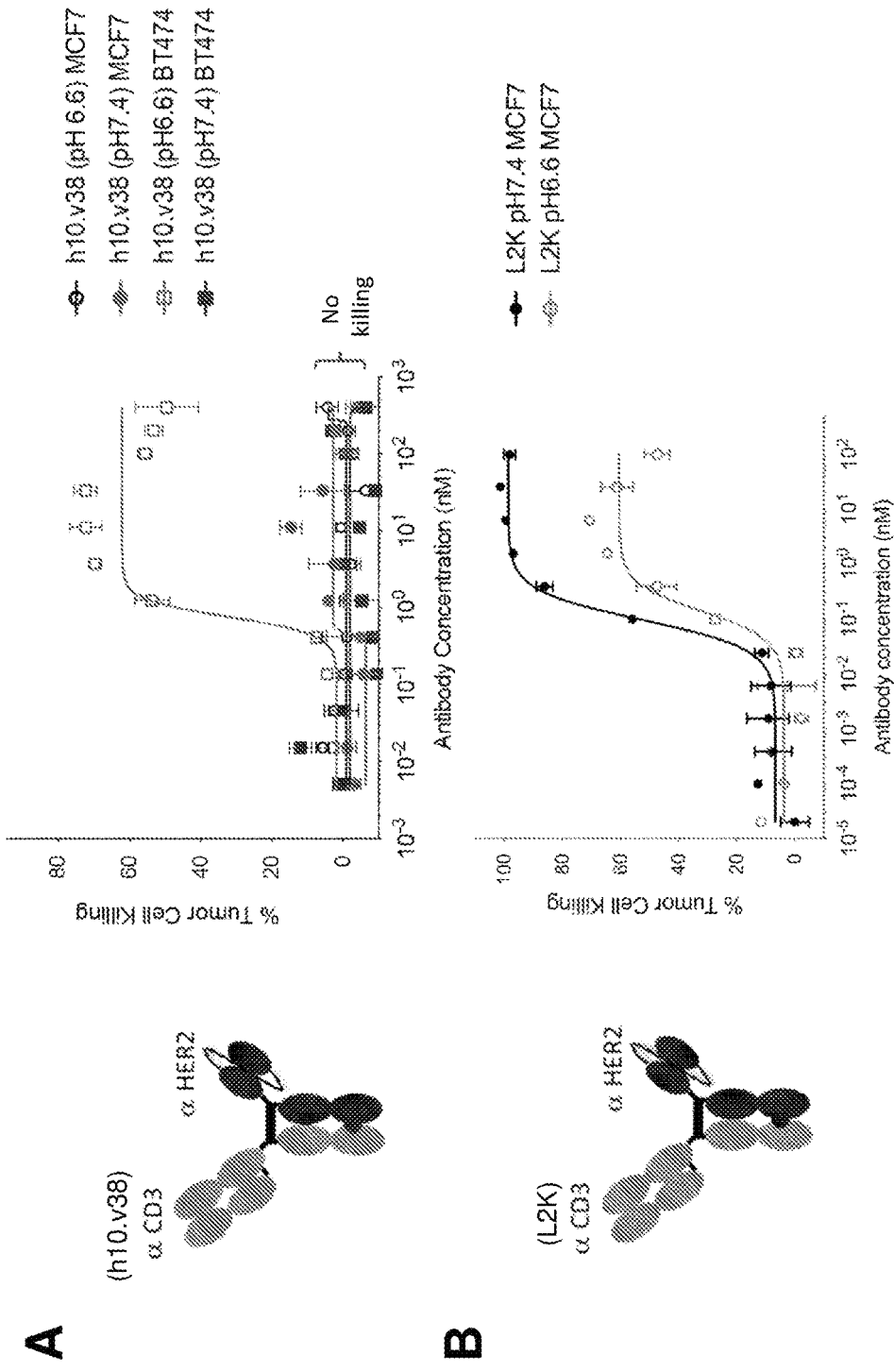
FIGS. 23A-B show the respective molecular format of a multispecific TMATE comprising CD3(h10.v38)×HER2 (4D5) (FIG. 23A) and a conventional control TMA comprising CD3(L2K)×HER2(4D5) (FIG. 23B) each with a human IgG1-Fc (KiH), and their dose-dependent T cell cytotoxicity profile with human primary T cells and HER2$^{low}$ (i.e., HER2-negative) cell line MCF7 (E:T ratio≈11:1; 72-hr duration) under specific culture medium of pH 7.4 and pH 6.6 respectively. The HER2-positive BT474 cell is also included as a control for positive killing in this assay.

In some embodiments, as exemplified in FIG. 23 top panel (A), a TMATE comprising CD3(h10.v38)×HER2 (4D5) in a KiH format with human IgG1-Fc shows virtually no killing activity towards MCF7 (HER2$^{low}$ or HER2-negative) given the primary T cells (donor #24) and various treatment doses of this TMATE (up to 400 nM) under either the pH 7.4 or pH 6.6 culture condition. As a positive control, the same TMATE showed potent killing of BT474 (HER2$^{high}$ or HER2-positive) at pH 6.6 and expectedly little-to-no killing at pH 7.4. In comparison, as shown in FIG. 23 bottom panel (B), a conventional TMA comprising CD3(L2K)×HER2 (4D5) results in potent killing of the same MCF7 at either pH 6.6 or pH 7.4 condition.

Figure 24:
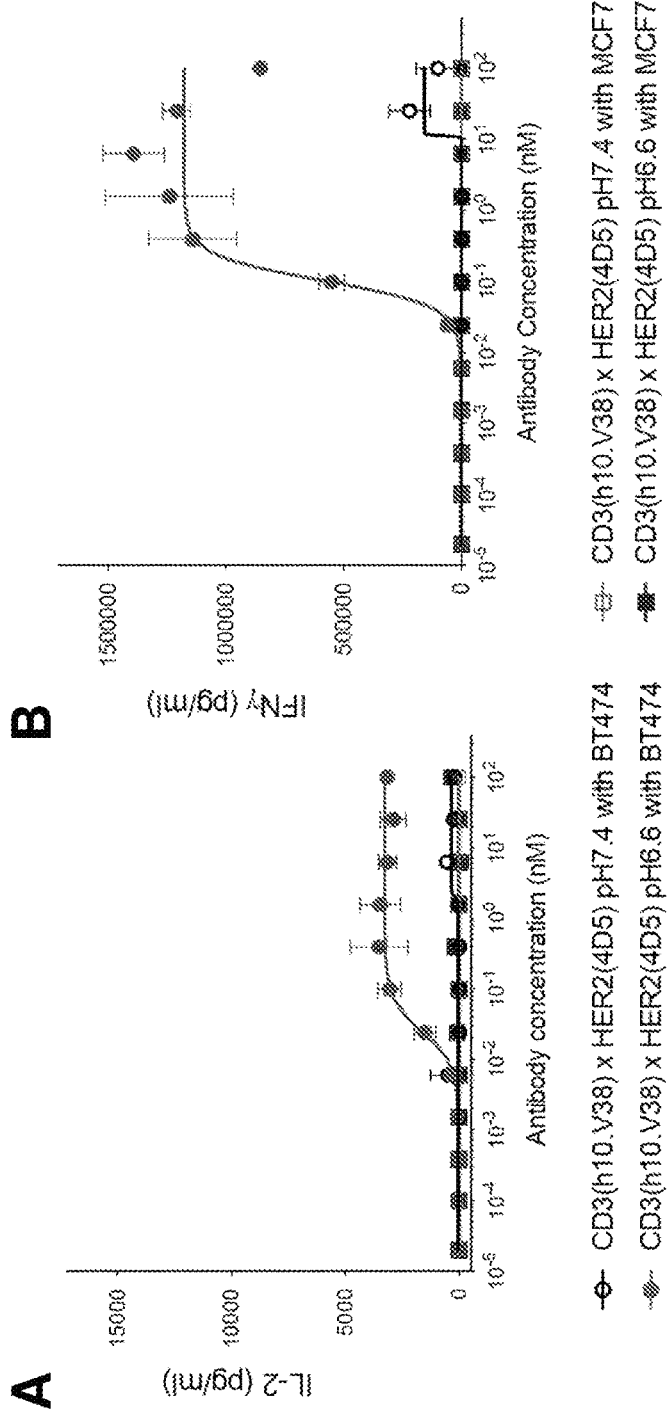
FIGS. 24A-B show the ELISA results to examine the cytokine secretion profile for IL-2 (FIG. 24A) and IFN-γ (FIG. 24B) with treating HER2$^{low}$ MCF7 cells and HER2$^{high}$ BT474 cells respectively in the presence of primary T cells (donor #24) and the TMATE comprising CD3(h10.v38)× HER2(4D5) under pH 7.4 and pH 6.6 conditions respectively.

Consistently, as shown in FIG. 24 (based on similar assay conditions as for FIG. 23), upon co-incubation of HER2$^{high}$ BT474 cells with the donor T cells, secreted cytokines (IL-2 and IFN-γ) triggered by CD3(h10.v38)×HER2(4D5) are virtually none or negligible, corresponding to at least 50-fold or indefinite-fold reduction as compared to that induced under the pH 6.6 culture condition using the EC$_{max}$ treatment dose.

Figure 25:
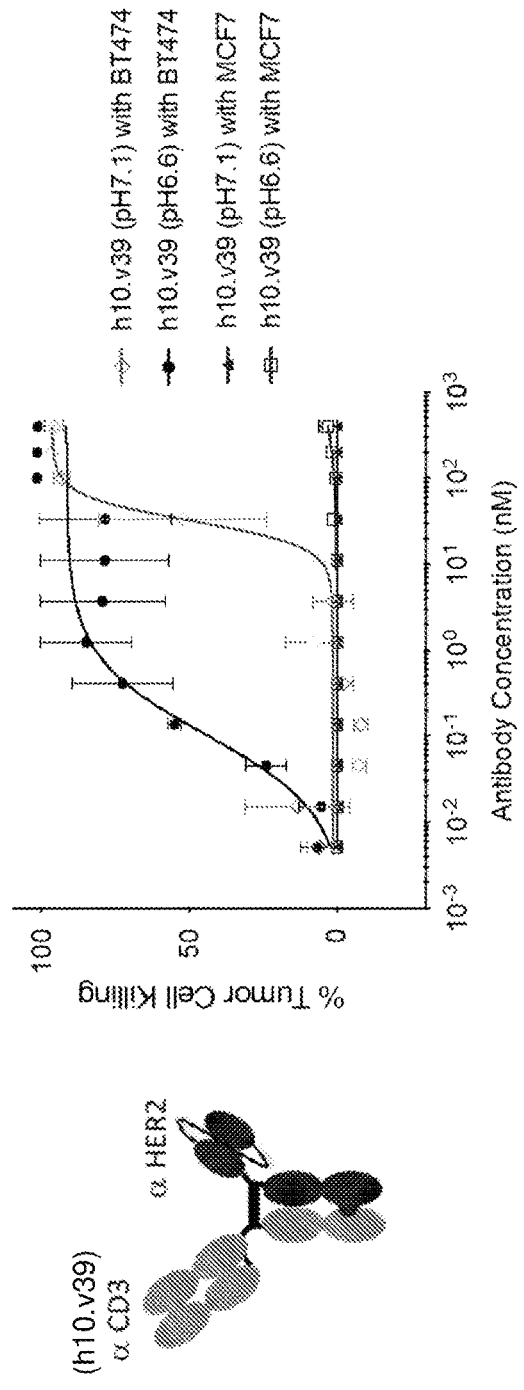
FIG. 25 shows the T cell cytotoxicity profile for an alternative TMATE comprising CD3(h10.v39)×HER2 (4D5) with human primary T cells and HER$^{low}$ cell line MCF7 at an E:T ratio of 11:1 over a 72-hr duration under specific culture medium of pH 7.1 and pH 6.6 respectively. Herein the HER2-positive BT474 cell is also included to serve as a control for positive T cell mediated killing triggered by this TMATE.
Figure 26:
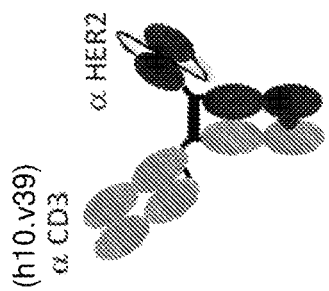
FIG. 26 illustrates the molecular configuration of a TMATE comprising CD3 (h10.v39)×HER2 (4D5) and a table that summarizes the killing activity (as % of target-cell killing) using a high TMATE dose of 400 nM for the HER2$^{low}$ MCF7 cells co-incubated with different donor T cells under the same culture conditions except having distinct pHs of about 6.6 or 6.7, about 7.1 or 7.2 and about 7.4 or 7.5, respectively.
Figure 27:
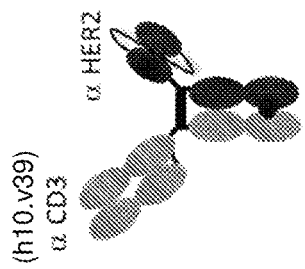
FIG. 27 summarizes the CD4 and CD8 T cell activation status for the TMATE comprising CD3 (h10.v39)×HER2 (4D5) in a table that matches the one in FIG. 26, wherein the T cell samples are from one and the same assays as described in FIG. 26.

Under certain circumstances, e.g., upon strenuous exercise, the heart tissues may generate an extracellular environment with reduced pH, which can be as low as about pH 7.1 instead of the commonly observed pH 7.4. Nonetheless, as exemplified in FIG. 25, even under the pH 7.1 condition, a TMATE comprising CD3 (h10.v39)×HER2 (4D5) elicits minimal killing effect on the heart cardiomyocyte surrogate, MCF7. As a control, the same TMATE retains potent killing towards BT474 cells at pH 7.1 albeit with a much higher EC50 than that under the pH 6.6 condition. To further validate TMATEs does not trigger any cytotoxic effect on MCF7, a variety of donor T cells were tested, and none leads to any MCF7 killing under conditions of pH 7.1 or 7.2, or pH 7.4 or pH7.5 (FIG. 26). Even under the pH 6.6 or pH6.7 condition where TMATE can bind to the CD3 potently, there is either no killing, or only a 20% killing at the maximum for a donor. In alignment with the killing activity, the T cell activation with the same CD3 (h10.v39)×HER2 (4D5) TMATE and the same donor T cells are with low or absent (summarized in FIG. 27).

Figure 28:
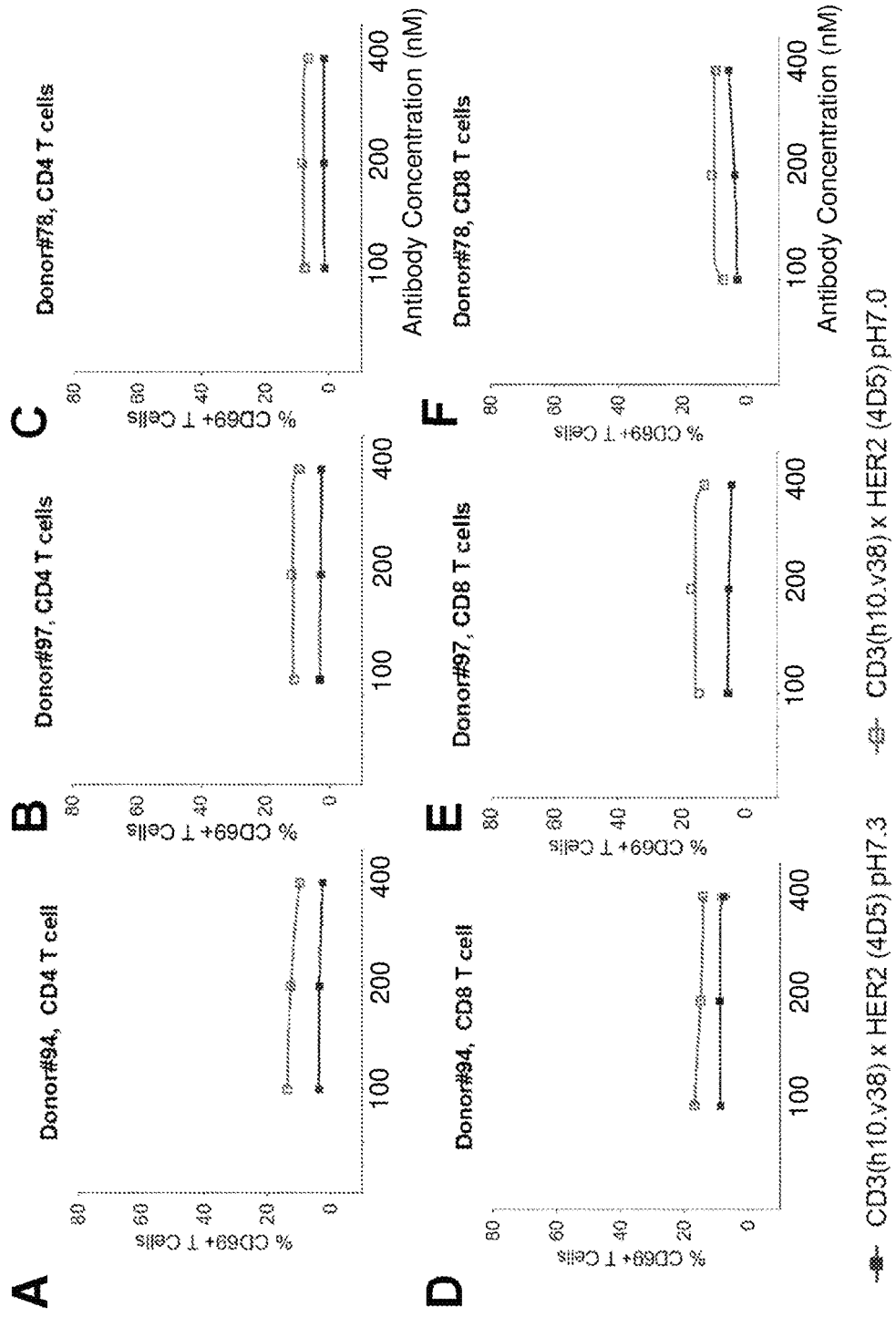
FIGS. 28A-F shows virtually no activation of T cells by the TMATE comprising CD3 (h10.v38)×HER2 (4D5) provided at any dose of 100, 200 or 400 nM, in the presence of the HER2$^{low}$ target cell MCF7 and various donor T cells (each with E:T=11:1), under the same culture conditions of about pH 7.0 and pH 7.3 respectively. Tested conditions include Donor #94 with CD4 T cells (FIG. 28A), Donor #97 with CD4 T cells (FIG. 28B), Donor #78 with CD4 T cells (FIG. 28C), Donor #94 with CD8 T cells (FIG. 28D), Donor #97 with CD8 T cells (FIG. 28E), and Donor #78 with CD8 T cells (FIG. 28F).
Figure 30:
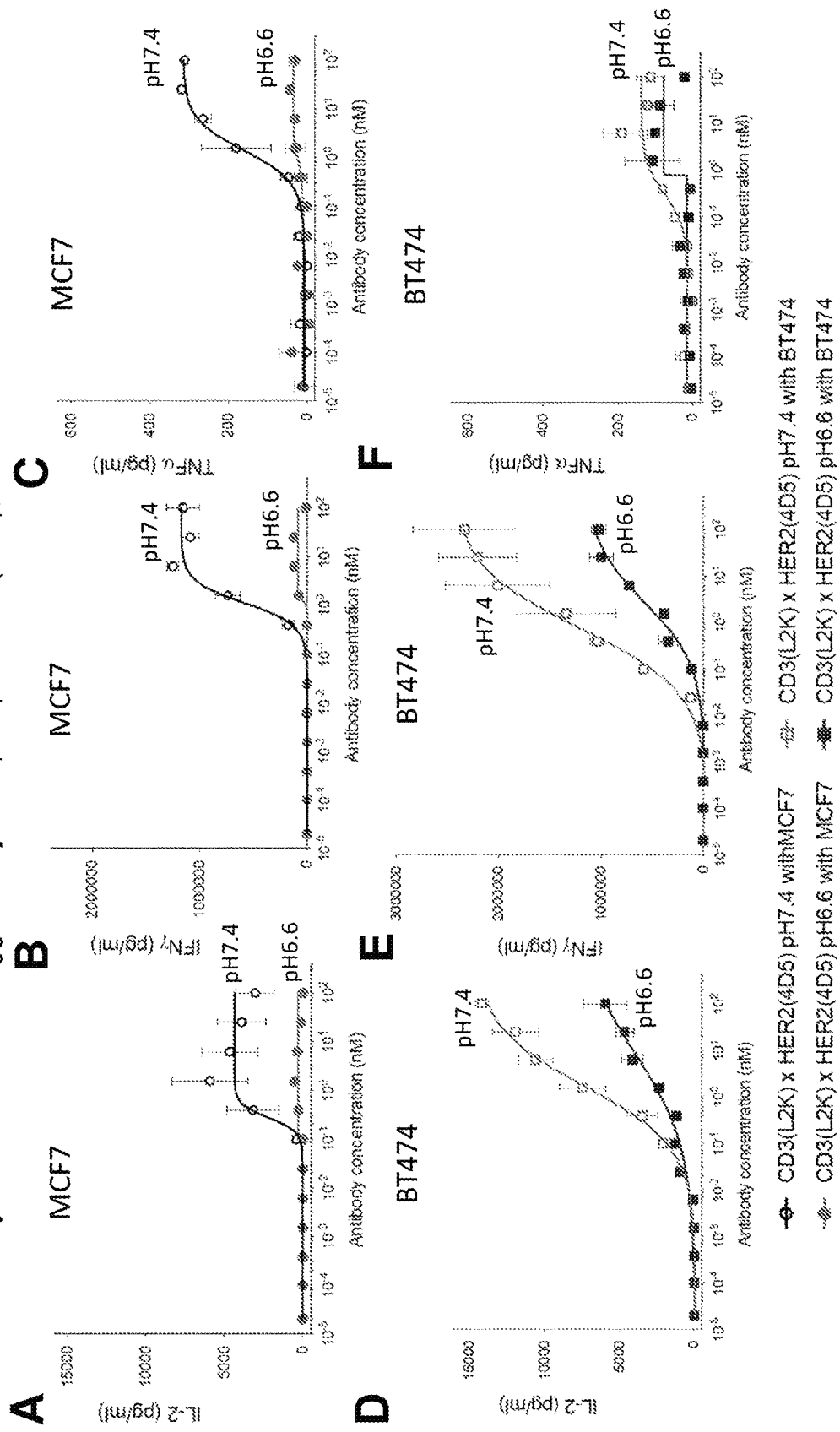
FIGS. 30A-F show robust cytokine release triggered by a conventional TMA comprising CD3(L2K)×HER2(4D5), either with HER2$^{low}$ MCF7 cells (IL-2 measured in FIG. 30A, IFNγ in FIG. 30B, and TNFα in FIG. 30C) or HER2$^{high}$ BT474 cells (IL-2 measured in FIG. 30D, IFNγ in FIG. 30E, and TNFα in FIG. 30F) under the pH 7.4 condition.

To further validate the "no-kill" property of TMATEs towards the normal-like HER2$^{low}$ surrogate cell MCF7, two additional pH conditions (about pH 7.0 and pH 7.3) for an alternative TMATE comprising CD3(h10.v38)×HER2 (4D5), which is generally more potent than CD3(h10.v39)× HER2(4D5), are tested using primary T cells from three different donors. The results further verified the lack of T cell activation (FIG. 28) at very high treatment doses of the CD3(h10.v38)×HER2(4D5) TMATE (up to 400 nM), leading to no killing of MCF7 either (data not shown). Consistent with the lack of T activation with either TMATE comprising h10.v38 or h10.v39, the level of cytokine secretion (IL-2, IFN-γ and TNF-α) remain at the baseline (i.e., no upregulation) under any of the tested pH conditions of about pH 6.6, about pH 7.1 and about pH 7.4 (FIG. 30). In contrast, MCF7 as well as the HER2-positive BT474 can still be effectively targeted by a benchmark conventional TMA, CD3(L2K)×HER2(4D5) that comprise the conventional anti-CD3 clone L2K-07 leading to significant cytokine release (FIG. 30), which is more evident under the pH 7.4 conditions than under pH 6.6.

In some embodiments, the CD3-dependent TMATE comprises an anti-disease-target moiety. In some embodiments, the disease-target is an TAA (tumor associated antigen). In some embodiments, the disease-target is non-TAA molecule on a non-tumorous cell that can contribute to a disease process. In some embodiments, the non-TAA molecule is a marker on myeloid derived suppressor cell, such as CD33. In some embodiments, the non-TAA molecule is a marker on Treg cells, such as CD25. In some embodiments, the non-TAA molecule is a virus derived peptide that is presented on infected cells.

In some embodiments, the disease-target molecule for TMATEs is a protein. In some embodiments, the disease-target molecule is a peptide in a complex with a peptide presenting receptor. In some embodiments, the disease-target molecule is a disease-specific sugar-containing molecule. In some embodiments, the disease-target molecule is a carbohydrate or glycolipid moiety. In some embodiments, the disease-target molecule is an RNA molecule that is presented on a target cell surface.

TMATEs can be used to target a variety of human diseases. In some embodiments, the disease is an abnormal cell proliferation disorder. In some embodiments, the abnormal cell proliferation disorder is a solid tumor or a liquid cancer such as myeloma, leukemia and lymphoma. In some embodiments, the disease is an auto-immunity condition. In some embodiments, the disease is a neurological degeneration disease. In some embodiments, the disease is an infectious disease. In some embodiments, the disease is an inflammatory disorder. In some embodiments, the disease is a graft versus host diseases (GvHD). In some embodiments, the disease is a transplant rejection condition.

In some embodiments, the CD3×HER2 TMATE comprises an anti-HER2 antibody moiety and a pH sensitive anti-CD3 moiety selected from the h10.v23, h10.v26, h10.v27, h10.v32, h10.v34, h10.v38, h10.v39, h10.v48, and h10.v49. See Tables 3 and 4 and sequence table for CDR and VH/VL sequences of these antibodies.

In some embodiments, the anti-HER2 TMATE comprises an alternative CD3×HER2 TMATE comprising a pH sensitive anti-CD3 moiety and an alternative anti-HER2 antibody moiety other than 4D5. In some embodiments, the alternative CD3×HER2 TMATE comprises a pH sensitive anti-CD3 moiety and two anti-HER2 antibody moieties. In some embodiments, the two anti-HER2 antibody moieties recognize one and the same epitope of two HER2 molecules. In some embodiments, the two anti-HER2 antibody moieties recognize two distinct epitopes of HER2. In some embodiments, the two anti-HER2 antibody moieties comprises the same set of CDRs. In some embodiments, the two anti-HER2 antibody moieties comprises two distinct sets of CDRs. In some embodiments, the CD3×HER2 TMATE comprises a pH sensitive anti-CD3 moiety and at least one pH-sensitive anti-HER2 antibody moieties.

In some embodiments, the anti-CD3 TMATE comprises an alternative CD3×TAA TMATE comprising a pH sensitive anti-CD3 moiety selected from h10.v23, h10.v26, h10.v27, h10.v32, h10.v34, h10.v38, h10.v39, h10.v48, and h10.v49, and an antibody moiety specific to a TAA other than HER2. In some embodiments, the alternative CD3×TAA TMATE comprises a pH sensitive anti-CD3 moiety and two anti-TAA antibody moieties. In some embodiments, the two anti-TAA antibody moieties recognize one and the same epitope of two TAA molecules. In some embodiments, the two anti-TAA antibody moieties recognize two distinct epitopes of TAA. In some embodiments, the two anti-TAA antibody moieties comprise the same set of CDRs. In some embodiments, the two anti-TAA antibody moieties comprise two distinct sets of CDRs. In some embodiments, the CD3×TAA TMATE comprises a pH sensitive anti-CD3 moiety and at least one pH-sensitive anti-TAA antibody moieties. The said TAAs are exemplified by EGFR, EGFRviii, CEA, CA-125, AFP, MAGE, PSA, PSMA, CD38, BCMA, CD19, CD20, CD22, CD30, CD123, CD276, CD39, CD70, GPC3, CEACAM5, Claudin 18.2, Mesothelin, MUC-1, MUC-16, CLEC12A, 5T4, GPC3, SSTR2, SSTR5, DLL1, DLL3, TROP-1 or EpCAM, TROP-2 or TACSTD2, Nectin-4, AXL, P-Cadherin, MerTK, HER3, CD25, CD38, ROR1, ROR2, PSCA, ADAM17, FOLRI, GD-2, CA-IX or CA9, EphA2, CD22, CD79b, GPNMB, CD56, CD52, CD74, RON, FAP, NY-ESO and any of its derivative peptides, gp100 and any of its derivative peptides, a KRAS variant and any of its derivative peptides, a NRAS mutant and any of its derivative peptides, and a WT1 mutant and any of its derivative peptides.

In some embodiments, the TMATE comprises an anti-TROP-2 antibody moiety. TROP-2 (aka TROP2 or TACSTD2) is a well-known tumor associated target molecule that is upregulated in a variety of human cancers, regardless of the baseline TROP-2 expression. TROP-2-positive (or TROP-2 high) tumors include breast cancer, colon cancer, urothelial cancer, non-small cell lung carcinoma, gastric cancer, pancreatic cancer, prostate cancer, ovarian cancers, and head and neck cancers among others. On the other hand, TROP-2 is broadly expressed in a variety of normal tissues, particularly in the epithelial tissues, albeit at a level that is lower than that in tumors. As illustrated in FIG. 31 are the cell surface TROP-2 copy number on some example cancer cell lines and human primary keratinocytes respectively.

In some embodiments, the anti-TROP-2 TMATE comprises an anti-TROP-2 antibody moiety (e.g., RS7.v1) and a pH sensitive anti-CD3 moiety selected from the h10.v23, h10.v26, h10.v27, h10.v32, h10.v34, h10.v38, h10.v39, h10.v48, and h10.v49. See Tables 3 and 4 and sequence table for CDR and VH/VL sequences of these antibodies.

In some embodiments, the present application provides an anti-CD3 multispecific construct comprising a) an anti-CD3 antibody moiety comprising a heavy variable region ($V_H$) and a light chain variable region ($V_L$), wherein the $V_L$ comprising the HC-CDR1 comprising the amino acid sequence of SEQ ID NO: 5, the HC-CDR2 comprising the amino acid sequence of SEQ ID NO: 2, and the HC-CDR3 comprising the amino acid sequence of SEQ ID NO: 12, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, and b) a second antibody moiety comprising a second heavy chain variable region ($V_{H-2}$) and a third light chain variable region ($V_{L-2}$), wherein the second antibody moiety specifically binds to a tumor-associated antigen. In some embodiments, the tumor-associated antigen is selected from the group consisting of Her2, Trop-2 and EpCAM. In some embodiments, the $V_{H-2}$ comprises an amino acid sequence of SEQ ID NO: 120, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 121, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises an amino acid sequence of SEQ ID NO: 122, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 123, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises an amino acid sequence of SEQ ID NO: 124, or a variant comprising an amino acid sequence having at least about 80% (such as at least about any one of 80%, 85%, 90%, 95%, 96%, 97%, 98%, or 99%) sequence identity; and the $V_L$.2 comprises an amino acid sequence of SEQ ID NO: 125, or a variant comprising an amino acid sequence having at least about 80% (such as at least about any one of 80%, 85%, 90%, 95%, 96%, 97%, 98%, or 99%) sequence identity.

In some embodiments, the present application provides an anti-CD3 multispecific construct comprising a) an anti-CD3 antibody moiety comprising a heavy variable region ($V_H$) and a light chain variable region ($V_L$), wherein the $V_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 12, and the $V_L$ comprises the LC-CDR1 comprising the amino acid sequence of SEQ ID NO: 26, the LC-CDR2 comprising the amino acid sequence of SEQ ID NO: 24, and the LC-CDR3 comprising the amino acid sequence of SEQ ID NO: 31, and b) a second antibody moiety comprising a second heavy chain variable region ($V_{H-2}$) and a third light chain variable region ($V_{L-2}$), wherein the second antibody moiety specifically binds to a tumor-associated antigen. In some embodiments, the tumor-associated antigen is selected from the group consisting of Her2, Trop-2 and EpCAM. In some embodiments, the $V_{H-2}$ comprises an amino acid sequence of SEQ ID NO: 120, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 121, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises an amino acid sequence of SEQ ID NO: 122, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 123, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises an amino acid sequence of SEQ ID NO: 124, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 125, or a variant comprising an amino acid sequence having at least about 80% (such as at least about any one of 80%, 85%, 90%, 95%, 96%, 97%, 98%, or 99%) sequence identity.

In some embodiments, the present application provides an anti-CD3 multispecific construct comprising a) an anti-CD3 antibody moiety comprising a heavy variable region ($V_H$) and a light chain variable region ($V_L$), wherein the $V_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 12, and the $V_L$ comprises the LC-CDR1 comprising the amino acid sequence of SEQ ID NO: 26, the LC-CDR2 comprising the amino acid sequence of SEQ ID NO: 28, and the LC-CDR3 comprising the amino acid sequence of SEQ ID NO: 31, and b) a second antibody moiety comprising a second heavy chain variable region ($V_{H-2}$) and a third light chain variable region ($V_{L-2}$), wherein the second antibody moiety specifically binds to a tumor-associated antigen. In some embodiments, the tumor-associated antigen is selected from the group consisting of Her2, Trop-2 and EpCAM. In some embodiments, the $V_{H-2}$ comprises an amino acid sequence of SEQ ID NO: 120, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 121, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises an amino acid sequence of SEQ ID NO: 122, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 123, or a variant comprising an amino acid sequence having at least about 80% (such as at least about any one of 80%, 85%, 90%, 95%, 96%, 97%, 98%, or 99%) sequence identity. In some embodiments, the VW-2 comprises an amino acid sequence of SEQ ID NO: 124, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 125, or a variant comprising an amino acid sequence having at least about 80% (such as at least about any one of 80%, 85%, 90%, 95%, 96%, 97%, 98%, or 99%) sequence identity.

In some embodiments, the present application provides an anti-CD3 multispecific construct comprising a) an anti-CD3 antibody moiety comprising a heavy variable region ($V_H$) and a light chain variable region ($V_L$), wherein the $V_H$ comprising the HC-CDR1 comprising the amino acid sequence of SEQ ID NO: 5, the HC-CDR2 comprising the amino acid sequence of SEQ ID NO: 2, and the HC-CDR3 comprising the amino acid sequence of SEQ ID NO: 12, and the $V_L$ comprises the LC-CDR1 comprising the amino acid sequence of SEQ ID NO: 26, the LC-CDR2 comprising the amino acid sequence of SEQ ID NO: 28, and the LC-CDR3 comprising the amino acid sequence of SEQ ID NO: 31, and b) a second antibody moiety comprising a second heavy chain variable region ($V_{H-2}$) and a third light chain variable region ($V_{L-2}$), wherein the second antibody moiety specifically binds to a tumor-associated antigen. In some embodiments, the tumor-associated antigen is selected from the group consisting of Her2, Trop-2 and EpCAM. In some embodiments, the $V_{H-2}$ comprises an amino acid sequence of SEQ ID NO: 120, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 121, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises an amino acid sequence of SEQ ID NO: 122, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 123, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises an amino acid sequence of SEQ ID NO: 124, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 125, or a variant comprising an amino acid sequence having at least about 80% (such as at least about any one of 80%, 85%, 90%, 95%, 96%, 97%, 98%, or 99%) sequence identity.

In some embodiments, the present application provides an anti-CD3 multispecific construct comprising a) an anti-CD3 antibody moiety comprising a heavy variable region ($V_H$) and a light chain variable region ($V_L$), wherein the $V_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 13, and the $V_L$ comprises the LC-CDR1 comprising the amino acid sequence of SEQ ID NO: 26, the LC-CDR2 comprising the amino acid sequence of SEQ ID NO: 28, and the LC-CDR3 comprising the amino acid sequence of SEQ ID NO: 31, and b) a second antibody moiety comprising a second heavy chain variable region ($V_{H-2}$) and a third light chain variable region ($V_{L-2}$), wherein the second antibody moiety specifically binds to a tumor-associated antigen. In some embodiments, the tumor-associated antigen is selected from the group consisting of Her2, Trop-2 and EpCAM. In some embodiments, the $V_{H-2}$ comprises an amino acid sequence of SEQ ID NO: 120, or a variant comprising an amino acid sequence having at least about any one of 80%, 85%, 90%, 95%, 96%, 97%, 98%, or 99%) sequence identity; and the $V_{L-2}$ comprises an amino acid sequence of SEQ ID NO: 121, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises an amino acid sequence of SEQ ID NO: 122, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 123, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises an amino acid sequence of SEQ ID NO: 124, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 125, or a variant comprising an amino acid sequence having at least about 80% (such as at least about any one of 80%, 85%, 90%, 95%, 96%, 97%, 98%, or 99%) sequence identity.

In some embodiments, the present application provides an anti-CD3 multispecific construct comprising a) an anti-CD3 antibody moiety comprising a heavy variable region ($V_H$) and a light chain variable region ($V_L$), wherein the $V_H$ comprising the HC-CDR1 comprising the amino acid sequence of SEQ ID NO: 6, the HC-CDR2 comprising the amino acid sequence of SEQ ID NO: 2, and the HC-CDR3 comprising the amino acid sequence of SEQ ID NO: 14, and the $V_L$ comprises the LC-CDR1 comprising the amino acid sequence of SEQ ID NO: 26, the LC-CDR2 comprising the amino acid sequence of SEQ ID NO: 28, and the LC-CDR3 comprising the amino acid sequence of SEQ ID NO: 31, and b) a second antibody moiety comprising a second heavy chain variable region ($V_{H-2}$) and a third light chain variable region ($V_{L-2}$), wherein the second antibody moiety specifically binds to a tumor-associated antigen. In some embodiments, the tumor-associated antigen is selected from the group consisting of Her2, Trop-2 and EpCAM. In some embodiments, the $V_{H-2}$ comprises an amino acid sequence of SEQ ID NO: 120, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 121, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises an amino acid sequence of SEQ ID NO: 122, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 123, or a variant comprising an amino acid sequence having at least about 80% (such as at least about any one of 80%, 85%, 90%, 95%, 96%, 97%, 98%, or 99%) sequence identity. In some embodiments, the $V_{H-2}$ comprises an amino acid sequence of SEQ ID NO: 124, or a variant comprising an amino acid sequence having at least about 80% (such as at least about any one of 80%, 85%, 90%, 95%, 96%, 97%, 98%, or 99%) sequence identity; and the $V_{L-2}$ comprises an amino acid sequence of SEQ ID NO: 125, or a variant comprising an amino acid sequence having at least about 80% (such as at least about any one of 80%, 85%, 90%, 95%, 96%, 97%, 98%, or 99%) sequence identity.

In some embodiments, the multispecific anti-CD3 construct comprises two heavy chains and two light chains, wherein the first heavy chain and the first light chain pair together and form the anti-CD3 antibody moiety, wherein the second heavy chain and the second light chain pair together and form the second antibody moiety which optionally specifically recognizes a tumor-associated antigen, and wherein the two heavy chains each comprises a Fc domain, and the two Fc domains form a Fc fragment which optionally is a Fc fragment from IgG.

In some embodiments, the multispecific anti-CD3 construct comprises i) a first polypeptide comprising a light chain, ii) a second polypeptide comprising a heavy chain comprising a first Fc domain, and iii) a third polypeptide comprising a single chain fragment (scFv) and a second Fc domain, wherein the first polypeptide and the second polypeptide pair together and form the anti-CD3 antibody moiety, wherein the scFv specifically recognizes the second antigen which is optionally a tumor-associated antigen, and wherein and the first and the second Fc domains form a Fc fragment which optionally is a Fc fragment from IgG.

In some embodiments, the multispecific anti-CD3 construct comprises i) a first polypeptide comprising a light chain, ii) a second polypeptide comprising a heavy chain comprising a first Fc domain, and iii) a third polypeptide comprising a single domain antibody (sdAb) and a second Fc domain, wherein the first polypeptide and the second polypeptide pair together and form the anti-CD3 antibody moiety, wherein the sdAb specifically recognizes the second antigen which is optionally a tumor-associated antigen, and wherein the first and the second Fc domains form a Fc fragment which optionally is a Fc fragment from IgG.

In some embodiments, the multispecific anti-CD3 construct comprises i) a first polypeptide comprising a light chain, ii) a second polypeptide comprising a heavy chain comprising a first Fc domain, and iii) a third polypeptide comprising a single chain fragment (scFv) and a second Fc domain, wherein the first polypeptide and the second polypeptide pair together and form the second antibody moiety that optionally recognizes a tumor-associated antigen, wherein the scFv comprises the anti-CD3 antibody domain, and wherein the first and the second Fc domains form a Fc fragment which optionally is a Fc fragment from IgG.

In some embodiments, the multispecific anti-CD3 construct comprises a first single chain fragment (scFv) comprising the anti-CD3 antibody moiety and a second scFv that specifically recognizes the second antigen which is optionally a tumor-associated antigen, and wherein optionally the first scFv and the second scFv are fused via a linker (such as any of the linkers described herein). In some embodiments, the first scFv is fused to the N-terminus of the second scFv. In some embodiments, the first scFv is fused to the C-terminus of the second scFv.

In some embodiments, the multispecific anti-CD3 construct comprises a single chain fragment (scFv) comprising the anti-CD3 antibody moiety and a single domain antibody (sdAb) that specifically recognizes the second antigen which is optionally a tumor-associated antigen, and wherein optionally the scFv and the sdAb are fused via a linker (such as any of the linkers described herein). In some embodiments, the sdAb is fused to the N-terminus of the scFv. In some embodiments, the sdAb is fused to the C-terminus of the scFv.

In some embodiments, the multispecific anti-CD3 construct comprises an antigen-binding domain (Fab) comprising the anti-CD3 antibody moiety and a single chain fragment (scFv) that specifically recognizes the second antigen which is optionally a tumor-associated antigen, and wherein optionally the Fab and the scFv are fused via a linker (such as any of the linkers described herein). In some embodiments, the Fab is fused to the N-terminus of the scFv. In some embodiments, the Fab is fused to the C-terminus of the scFv.

In some embodiments, the multispecific anti-CD3 construct comprises i) a single chain fragment (scFv) comprising the anti-CD3 antibody moiety, ii) a first single domain antibody (sdAb) that specifically recognizes the second antigen which is optionally a tumor-associated antigen, and iii) a second sdAb that specifically recognizes a third antigen which is optionally a second tumor-associated antigen or a human serum albumin, and optionally i) the scFv is fused to the N-terminus of the first sdAb via a first linker, and the first sdAb is fused to the N-terminus of the second sdAb via a second linker, or ii) the scFv is fused to the C-terminus of the first sdAb via a first linker and fused to the N-terminus of the second sdAb via a second linker. The first and/or the second linker can be any of the linkers described herein.

Figure 32:
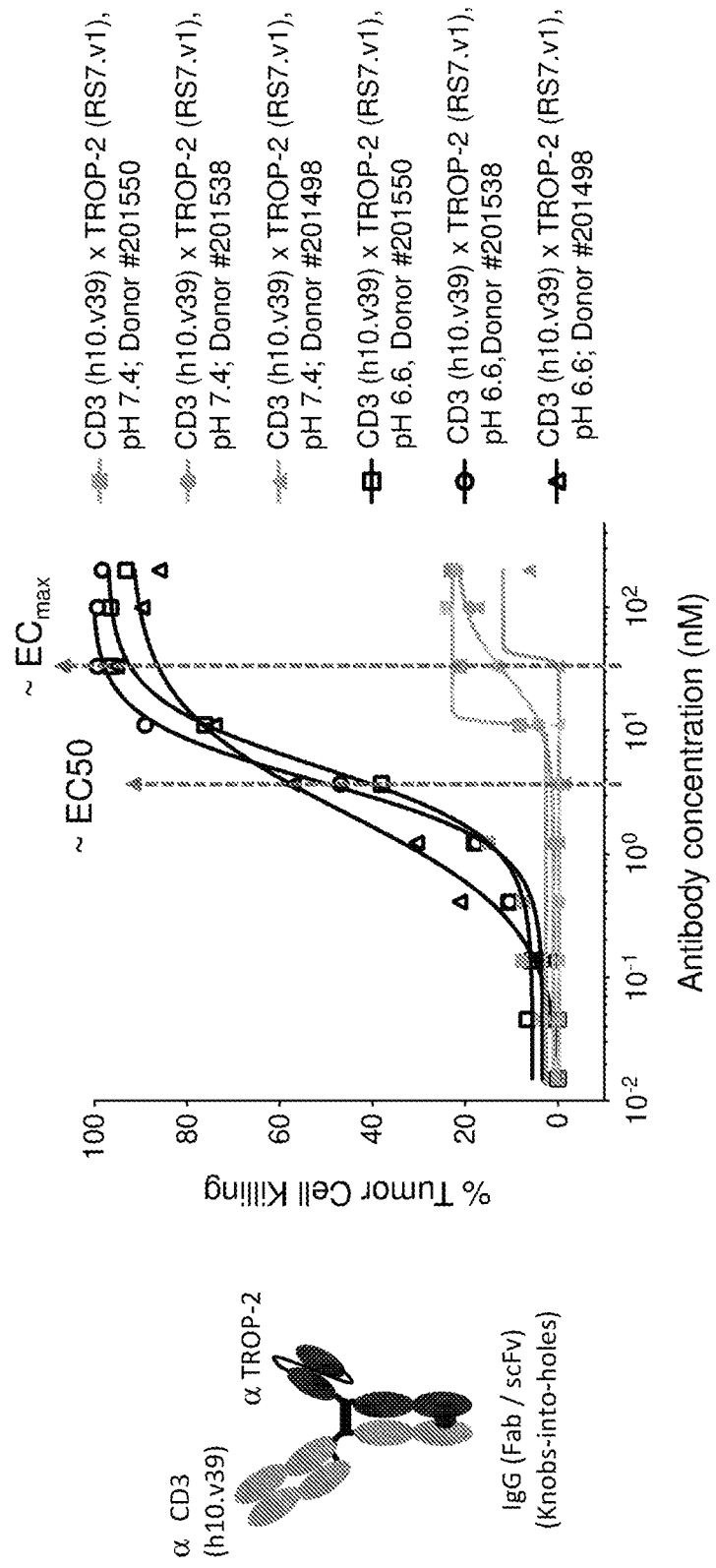
FIG. 32 shows the pH- and dose-dependent T cell cytotoxicity towards the TROP-2$^{high}$ MDA-MB-468 cancer cells elicited by a TMATE comprising CD3(h10.v39)×TROP-2 (RS7.v1) under the culture conditions of about pH 6.6 and pH 7.4 respectively. Human primary T cells from two different donors are used with an E:T ratio at 11:1 and a co-incubation period of about 70 hours.

As shown in FIG. 32, a TMATE comprising CD3 (h10.v39)×TROP-2(RS7.v1) assembled in a human IgG1-Fc (Knobs-in-Holes) demonstrated pH sensitive killing of MDA-MB-468, a TROP-2$^{high}$ (TROP-2-positive) triple negative breast cancer cell line. Potent cell killing (near 100% cell death) can be observed at the pH 6.6 culture condition using any of the multiple different donor T cell sources, which is nevertheless significantly weakened at the pH 7.4 condition. Specifically, at the otherwise ECmax dose specific to the pH 6.6 condition, the maximally achieved percentage of cell killing drops to about 16% (median level), which corresponds to about six-fold potency reduction at pH 7.4.

Figure 33:
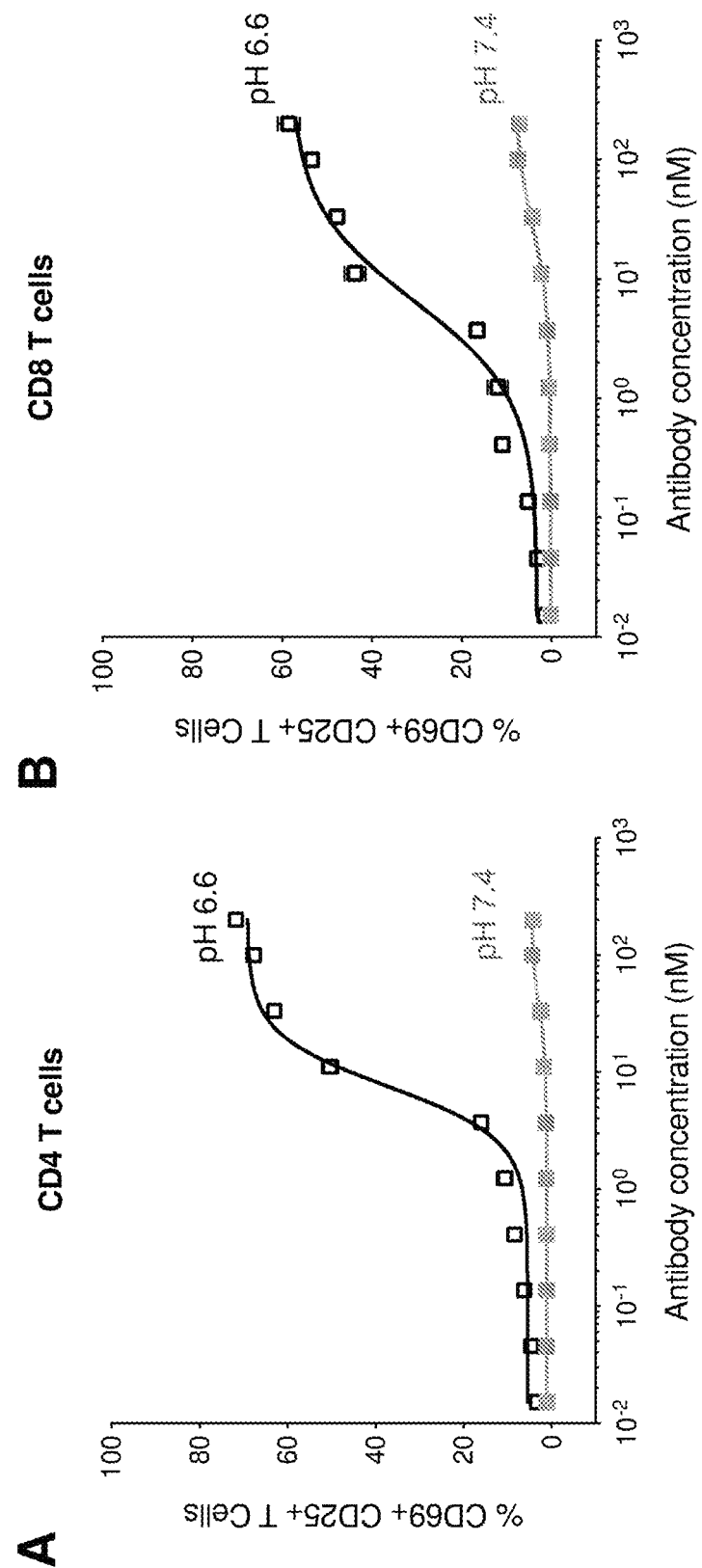
FIGS. 33A-B show the pH- and dose-dependent T cell activation profiles (using either CD4 T cells in FIG. 33A or CD8 T cells in FIG. 33B) towards the TROP-2$^{high}$ MDA-MB-468 cancer cells elicited by the same TMATE comprising CD3(h10.v39)×TROP-2(RS7.v1) using the cell samples from one and the same assay as described in FIG. 31.

Consistent with the results derived from using anti-HER2 TMATEs, the T cell activation of both CD4 and CD8 T cells, as indicated by CD69 and CD25 flow cytometry analysis, is also significantly hampered at pH 7.4 in comparison with that at pH 6.6 (FIG. 33). The reduced T cell activation profile is consistent with the cytokine secretion profile.

For TROP-2 as a model of tumor associated antigen, MDA-MB-231 (TROP-2$^{medium-low}$) can be used as a surrogate of normal cells for the activity assessment for candidate TMAs, as MDA-MB-231 expresses a comparable level of TROP-2 (~44,000 cell-surface TROP-2 molecules per cell) as human primary keratinocytes.

Figure 34:
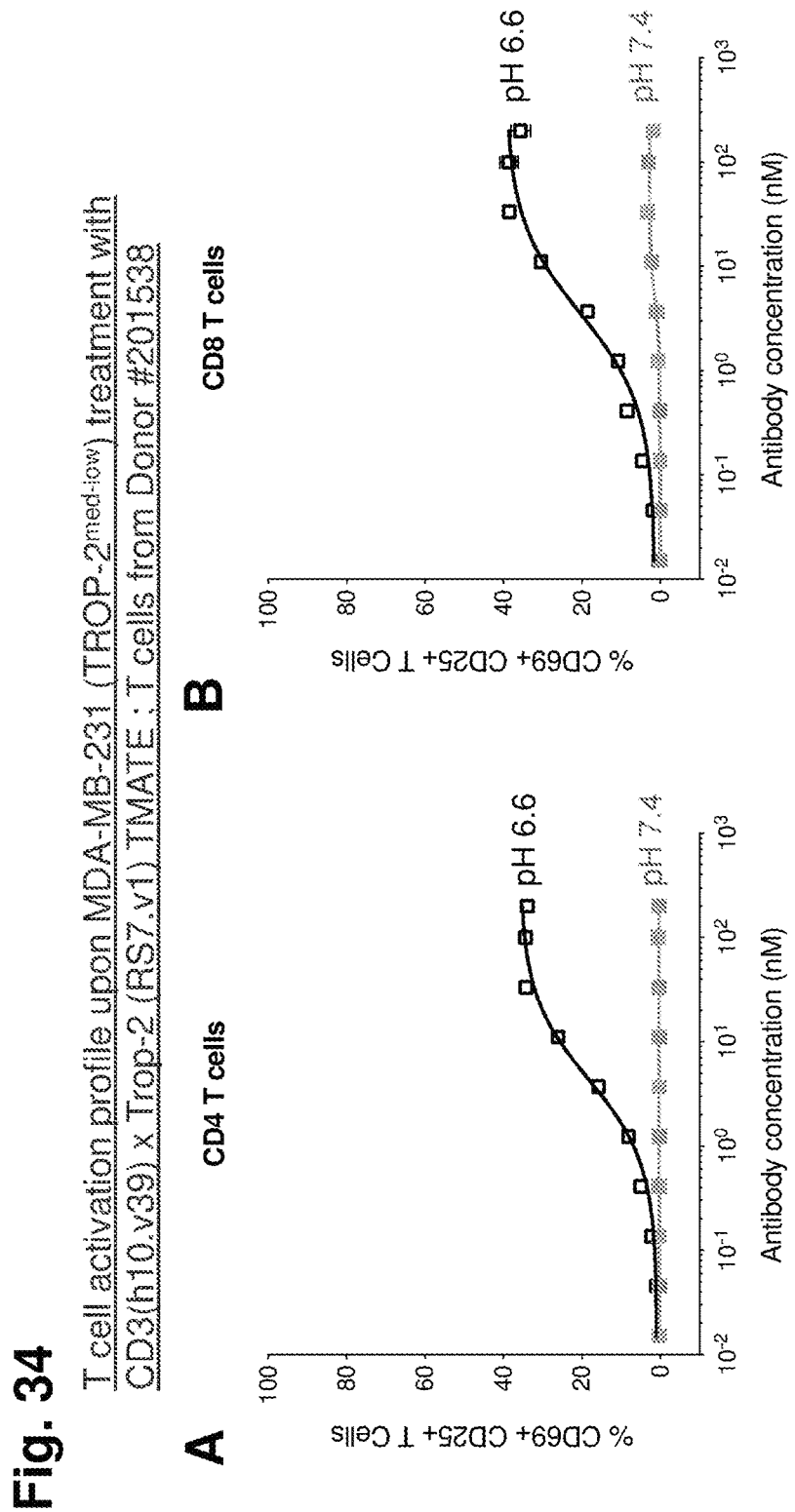
FIGS. 34A-B show the pH-dependent T cell activation status (of either CD4 T cells in FIG. 34A or CD8 T cells in FIG. 34B) triggered by the TMATE comprising CD3 (h10.v39)×TROP-2(RS7.v1) towards the TROP-2$^{med-low}$ MDA-MB-231 target cell under either pH 7.4 or pH 6.6 culture condition. The activation profile was based on flow cytometric analysis of CD69 and CD25 using samples from the one and same assay as described in FIG. 33.
Figure 35:
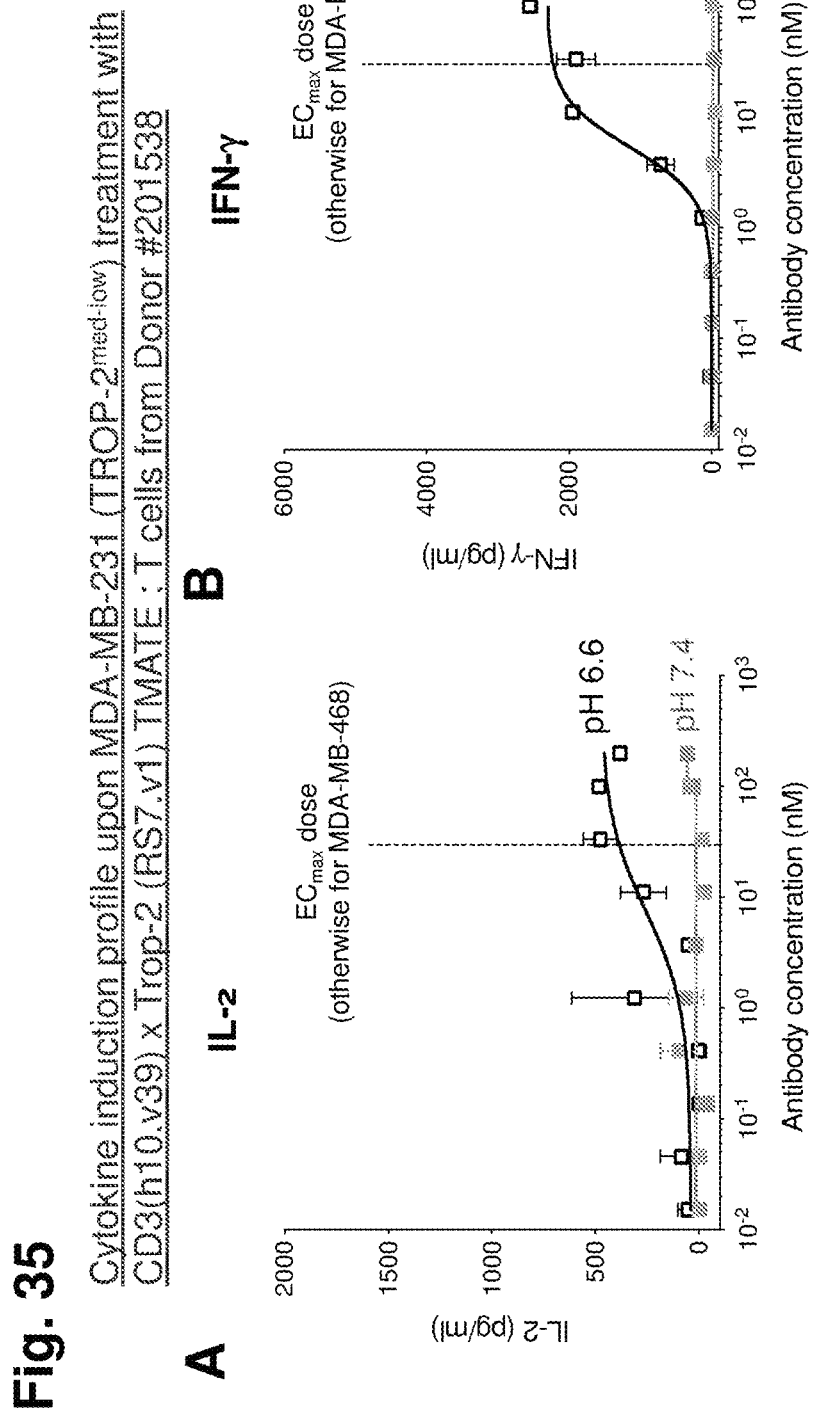
FIGS. 35A-B show the negative cytokine secretion profile triggered by CD3(h10.v39)×TROP-2(RS7.v1) TMATE towards the TROP-2$^{med-low}$ MDA-MB-231 under a pH 7.4 culture condition as compared to that of pH 6.6. The cytokine profile of IL-2 (FIG. 35A) and IFN-γ (FIG. 35B) was based on ELISA analysis using samples from one and the same assay as described in FIG. 33.

In some embodiments, one and the same anti-TROP-2 TMATE comprising CD3(h10.v39)×TROP-2 (RS7.v1) illustrated in FIG. 32 shows a very low killing activity towards MDA-MB-231 (TROP-2$^{medium-low}$) mediated by human primary T cells (donor #24) (data not shown). For instance, at the high dose of ~35 nM (corresponding to the max plateau killing dose for MDA-MB-468 at pH 6.6), there is virtually no killing of MDA-MB-231 under the culture condition of about pH 7.4. Consistently, in the same assays under either pH 6.6 or pH 7.4, the relevant CD4 and CD8 T cell activation induced by this CD3(h10.v39)×TROP-2 (RS7.v1) TMATE are almost negligible under the pH 7.4 culture condition, corresponding to at least 20-fold reduction as compared to that induced by the same TMATE while engaging MDA-MB-468 cells under an otherwise pH 6.6 culture condition (FIG. 34). Consistently, in the same assays under either pH 6.6 or pH 7.4, the relevant cytokine secretion (IL-2 and IFN-γ) triggered by the said CD3(h10.v39)× TROP-2 (RS7.v1) are virtually none or negligible under the pH 7.4 culture condition (FIG. 35), corresponding to at least 40-fold or indefinite-fold reduction as compared to that induced by the same TMATE while engaging MDA-MB-468 cells under a pH 6.6 culture condition.

Figure 36:
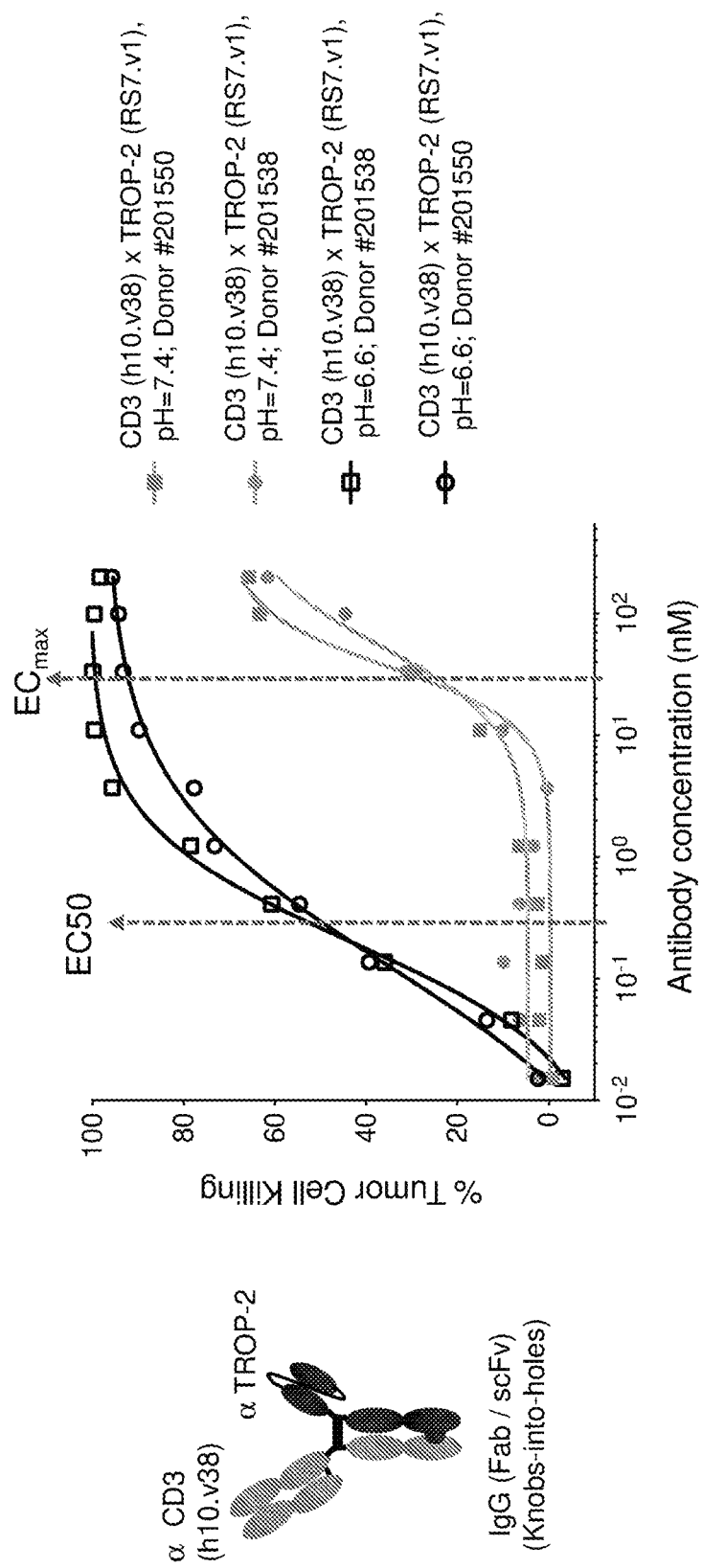
FIG. 36 shows the pH- and dose-dependent T cell cytotoxicity towards the TROP-2$^{high}$ MDA-MB-468 cancer cells elicited by an alternative TMATE comprising CD3 (h10.v38)×TROP-2(RS7.v1) under the culture conditions of about pH 6.6 and pH 7.4 respectively. Human primary T cells from two different donors are used with an E:T ratio at 11:1 and a co-incubation period of three days.

In some embodiments, the anti-TROP-2 TMATE comprises an alternative CD3×TROP-2 TMATE such as CD3 (h10.v38)×TROP-2(RS7.v1) comprising a pH sensitive anti-CD3 variant h10.v38. As shown in FIG. 36, this CD3 (h10.v38)×TROP-2(RS7.v1) TMATE can potently kill the TROP-2-positive tribble negative breast cancer line MDA-MB-468 cells, given any of the two different donor T cells under pH 6.6 culture condition over a duration of about 48 hours, leading to an EC50 of about 0.3 nM and ECmax (max plateau killing) of about 30 nM. With either one of these two doses but under a pH 7.4 condition, the T-cell mediated killing activity induced by the said TMATE decreases by at least about 70% or about 3.3-fold. Consistent with the killing-activity reduction, the T cell activation of CD4 and CD8 subpopulations is reduced by >20-fold and >three-fold respectively. (FIG. 37)

Figure 37:
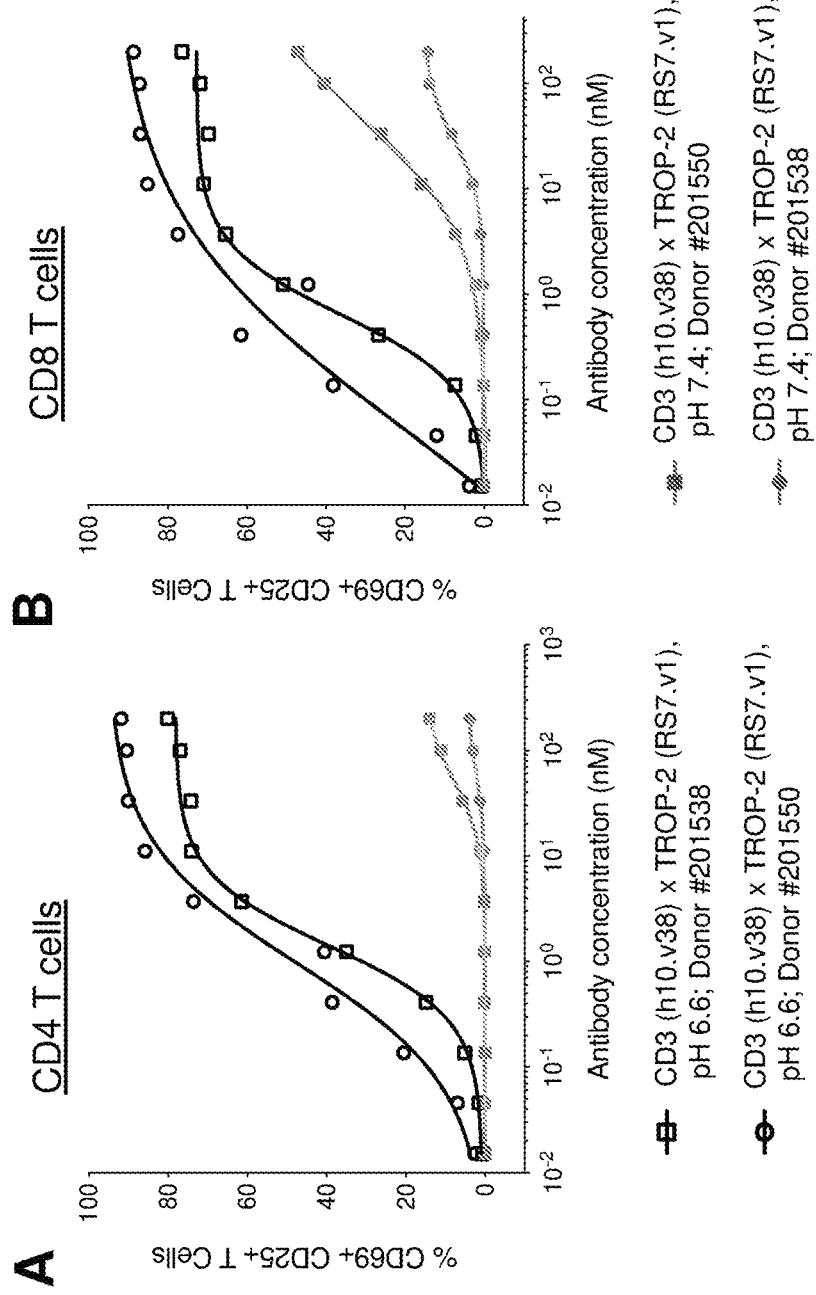
FIGS. 37A-B show the pH- and dose-dependent T cell activation profile towards the TROP-2$^{high}$ MDA-MB-468 cancer cells triggered by the CD3(h10.v38)×TROP-2 (RS7.v1) TMATE. T cell activation of either CD4 (FIG. 37A) or CD8 (FIG. 37B) T cells was examined by flow cytometry of CD69 and CD25 markers using the T cell samples from one and the same assay described in FIG. 36.
Figure 38:
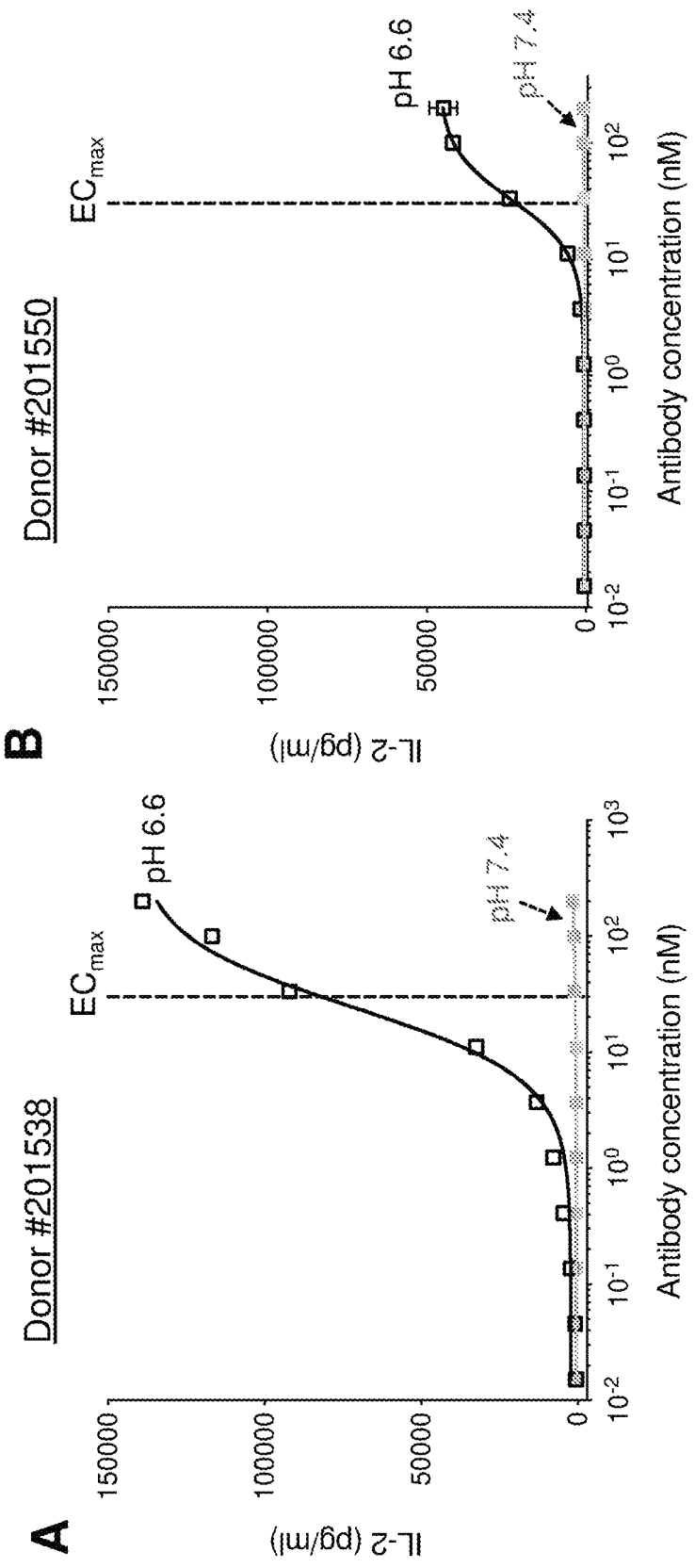
FIGS. 38A-B show the pH- and dose-dependent cytokine (IL-2) secretion profile towards the TROP-2$^{high}$ MDA-MB-468 cancer cells triggered by the CD3(h10.v38)×TROP-2 (RS7.v1) TMATE. IL-2 secretion level was measured by ELISA using the medium samples collected at the 48-hour incubation timepoint corresponding to one and the same assay described in FIG. 36. Tested donor cells were from Donor #201538 (FIG. 38A) and Donor #201550 (FIG. 38B).
Figure 39:
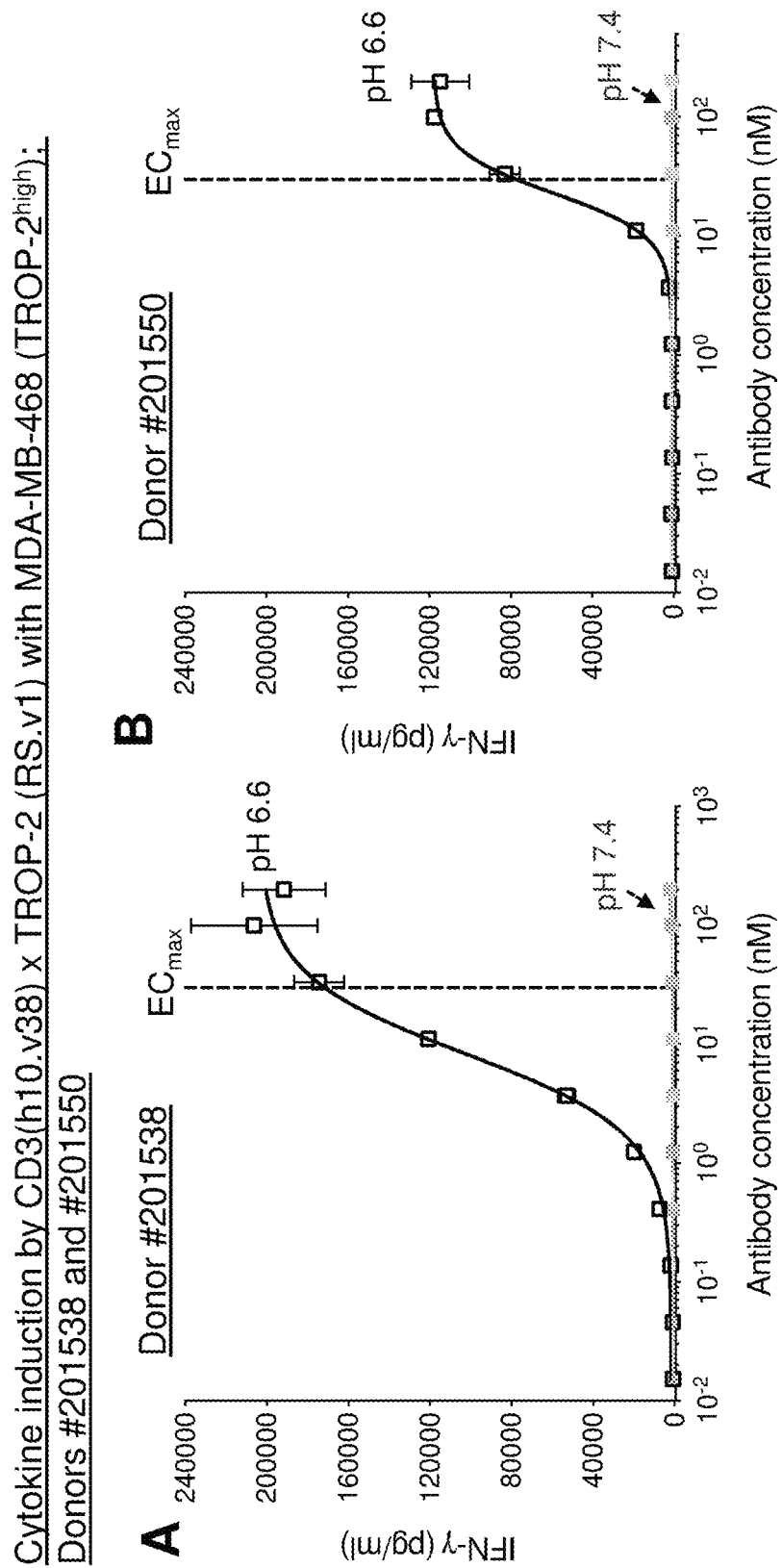
FIGS. 39A-B show the pH- and dose-dependent cytokine (IFN-γ) secretion profile towards the TROP-2$^{high}$ MDA-MB-468 cancer cells triggered by the CD3(h10.v38)× TROP-2(RS7.v1) TMATE. IFN-γ secretion level was measured by ELISA using the medium samples collected at the 48-hour incubation point corresponding to one and the same assay described in FIG. 36. Tested donor cells were from Donor #201538 (FIG. 39A) and Donor #201550 (FIG. 39B).
Figure 40:
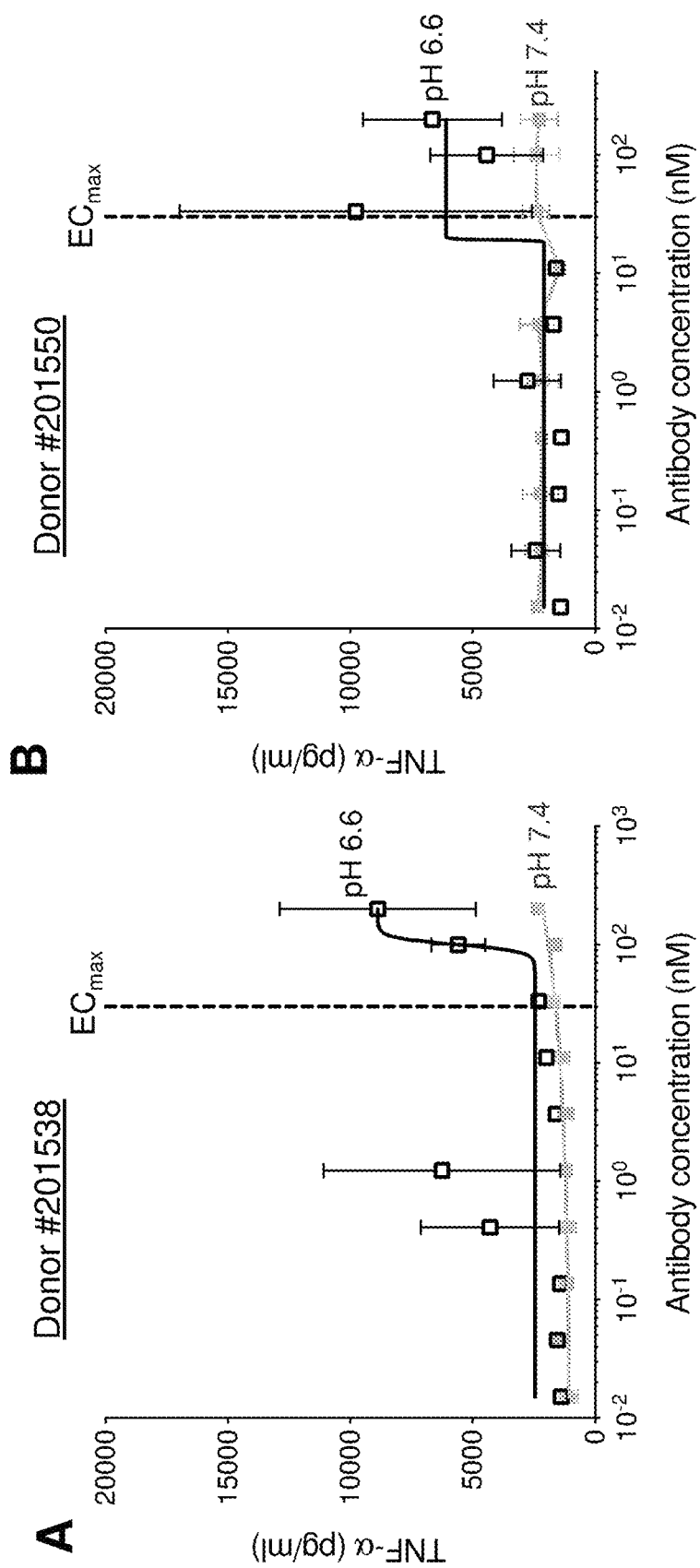
FIGS. 40A-B show the pH- and dose-dependent cytokine (TNF-α) secretion profile towards the TROP-2$^{high}$ MDA-MB-468 cancer cells triggered by the CD3(h10.v38)× TROP-2(RS7.v1) TMATE. TNF-α release level was measured by ELISA using the medium samples collected at the 48-hour incubation point corresponding to one and the same assay described in FIG. 36. Tested donor cells were from Donor #201538 (FIG. 40A) and Donor #201550 (FIG. 40B).
Figure 41:
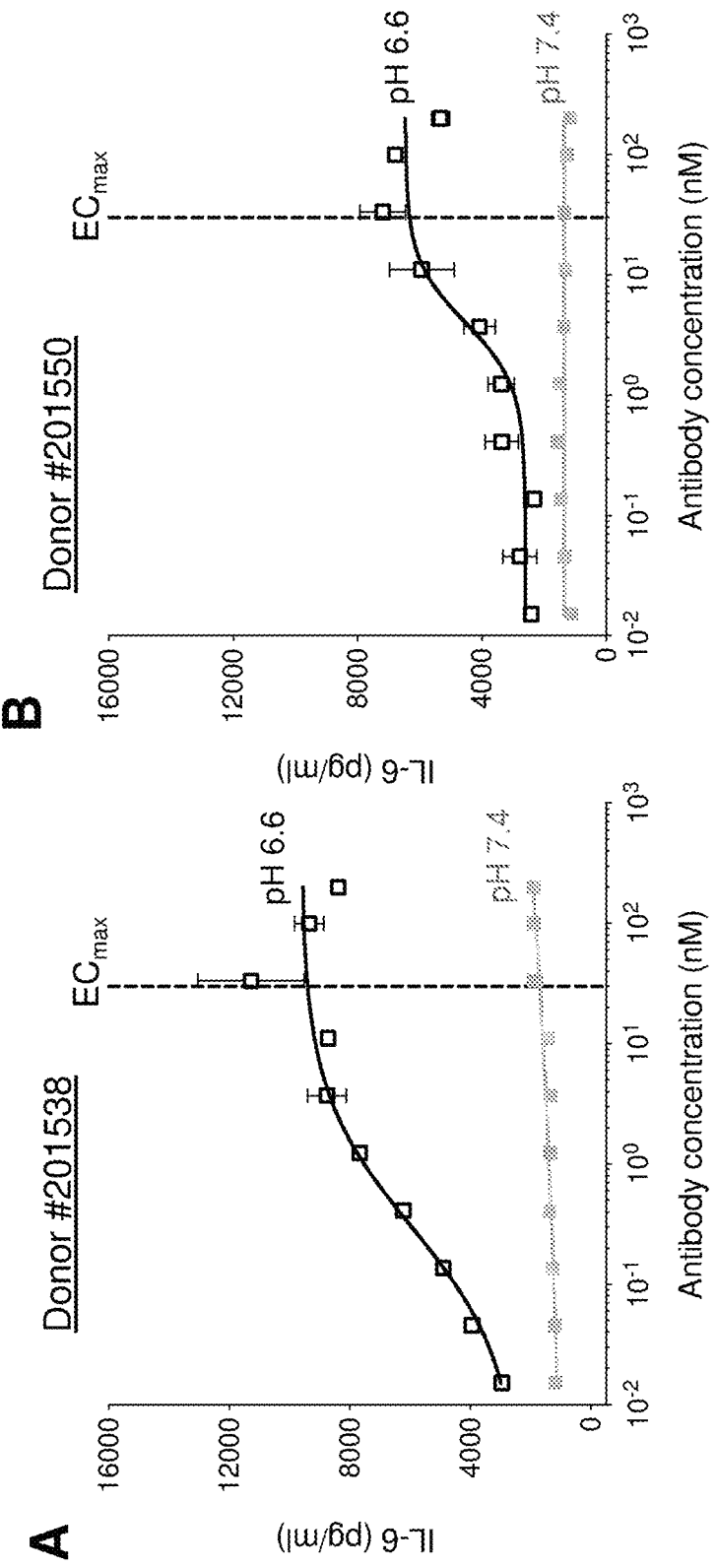
FIGS. 41A-B show the pH- and dose-dependent cytokine (IL-6) secretion profile towards the TROP-2$^{high}$ MDA-MB-468 cancer cells triggered by the CD3(h10.v38)×TROP-2 (RS7.v1) TMATE. IL-6 secretion level was measured by ELISA using the medium samples collected at the 48-hour incubation point corresponding to one and the same assay described in FIG. 36. Tested donor cells were from Donor #201538 (FIG. 41A) and Donor #201550 (FIG. 41B).
Figure 42:
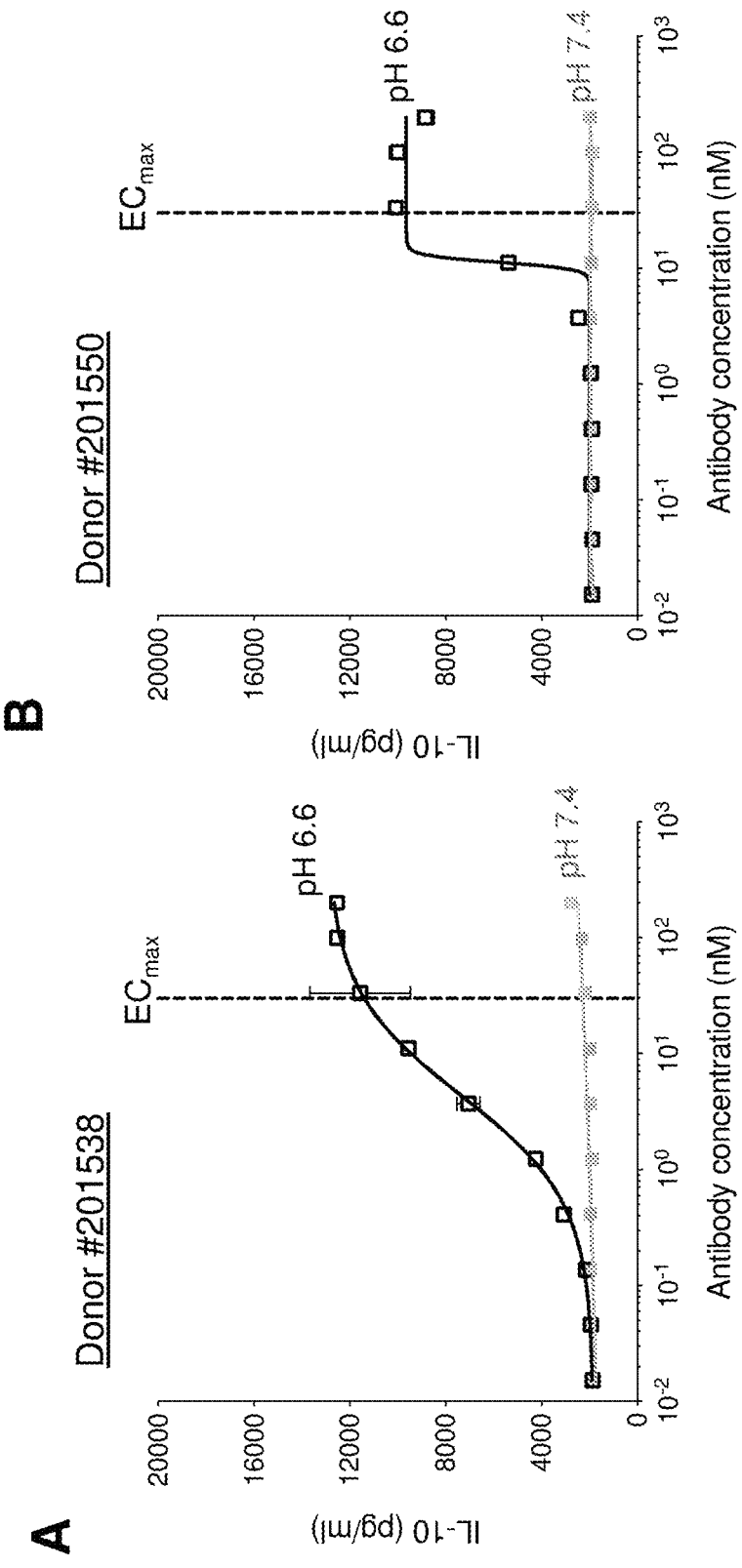
FIGS. 42A-B show the pH- and dose-dependent cytokine (IL-10) secretion profile towards the TROP-2$^{high}$ MDA-MB-468 cancer cells triggered by the CD3(h10.v38)× TROP-2(RS7.v1) TMATE. IL-10 release level was measured by ELISA using the medium samples collected at the 48-hour incubation point corresponding to one and the same assay described in FIG. 36. Tested donor cells were from Donor #201538 (FIG. 42A) and Donor #201550 (FIG. 42B).

Consistent with the observations illustrated in FIG. 36 and FIG. 37, the examination of a panel of cytokines (IL-2, IFN-γ, TNF-α, IL-10, IL-6) revealed near universal reduction of the cytokine secretion under the pH 7.4 assay condition as compared to the pH 6.6 assay condition performed in parallel. As exemplified in FIG. 38, the IL-2 secretion under the pH 7.4 killing-assay condition remains to be at the base lines, whereas the secretion is increasingly evident in a dose dependent manner under the pH 6.6 assay condition. As exemplified in FIG. 39, the IFN-γ secretion under the pH 7.4 killing-assay condition remains to be at the base lines, whereas the secretion is evident and dose-dependent under the pH 6.6 assay condition. As exemplified in FIG. 40, the TNF-α secretion under the pH 7.4 killing-assay condition is minimal, whereas the secretion is low at the lower end of the doses but increases sharply at the near max-plateau-killing dose under the pH 6.6 assay condition. As exemplified in FIG. 41, the IL-6 secretion under the pH 7.4 killing-assay condition remains to be at the base lines, whereas the secretion is increasingly evident in a dose dependent manner under the pH 6.6 assay condition. As exemplified in FIG. 42, the IL-10 secretion under the pH 7.4 killing-assay condition remains to be at the base lines, whereas the secretion is increasingly evident in a dose dependent manner under the pH 6.6 assay condition.

In some embodiments, the profile of low cytokine-release for a TMATE under near physiological pH condition is applicable to at least one of the five cytokines consisting of IL-2, IFN-γ, TNF-α, IL-10, and IL-6. In some embodiments, the profile of low cytokine-release for a TMATE under near physiological pH condition is applicable to at least two of the five cytokines consisting of IL-2, IFN-γ, TNF-α, IL-10, and IL-6. In some embodiments, the profile of low cytokine-release for a TMATE under near physiological pH condition is applicable to IL-2 and IFN-γ. In some embodiments, the profile of low cytokine-release for a TMATE under near physiological pH condition is not limited to the aforedescribed five cytokines but rather can be applied to other cytokines such as IL-8, IL-1p, IL-4, IL-13, IL-12, and MCP-1.

In some embodiments, an anti-CD3 TMATE construct (such as any of the TMATEs described above) does not trigger a significant level of at least one cytokine's secretion of an immune cell (such as a T cell, such as a CD4 or CD3 T cell). In some embodiments, the anti-CD3 TMATE construct does not trigger a significant level of a cytokine secretion of an immune cell when it triggers a lower cytokine secretion of an immune cell of at least one, two, three, four, or five cytokines as compared to a reference anti-CD3 antibody. Exemplary reference anti-CD3 antibody can be any conventional anti-CD3 antibody on market (such as OKT3, L2K, SP34, hu38E4, hu40G5c, SK7). In some embodiments, under pH 7.4 conditions, the anti-CD3 TMATE construct described herein triggers a cytokine secretion of an immune cell at a level that is at least about 10%, 20%, 30%, 40%, 50%, 60%, 70%, 80%, 90%, or 95% lower than the reference conventional anti-CD3 antibody. In some embodiments, the cytokine is selected from the group consisting of IL-2, IFNγ, TNFα, IL-6 and IL-10.

In general, significantly reduced cytokine release under the physiologically relevant pH conditions may lead to significantly slower exhaustion of activated T cells and hence more durable TMA efficacy. Reduced cytokines may also lead to fewer or weaker adverse effects in vivo, for instance, reduced risks for cytokine release syndrome (CRS). CRS is a clinical condition that is characterized by fever, fatigue, loss of appetite, muscle and joint pain, nausea, vomiting, diarrhea, rashes, fast breathing, rapid heartbeat, low blood pressure, seizures, headache, confusion, delirium, hallucinations, tremor, and loss of coordination, and may lead to death in very severe cases. Moreover, reduced cytokine secretion, particularly that of IL-2, can mitigate the risks for vascular leakage and neurotoxicity due to compromised blood brain barrier that is otherwise attributable to high cytokine secretion.

In some embodiments, cytokine secretion triggered by a conventional TMA or a TMATE in a disease site such as a tumor environment can promote immune response, leading to favorable therapeutic response or disease eradication. For instance, under an acidic tumor microenvironment, it is generally favored to induce a certain level of cytokines by the TMATE, which are an important part of the pharmacological mode of action of a TMATE (or a conventional TMA).

In some embodiments, a TMATE can induce positive cytokine release upon engaging T cells and target cells under a tumor microenvironment-relevant acidic condition of about pH 6.6 or 6.7 as illustrated in FIGS. 17, 19, 20, 29, 30, 35, and 38 through 42. In some embodiments, a TMATE can induce positive cytokine release upon engaging T cells and target cells under a tumor microenvironment like acidic condition of about pH 6.4 as illustrated in FIGS. 19 and 20. In some embodiments, a TMATE can induce positive cytokine release upon engaging T cells and target cells under a near neutral condition of about pH 7.0, albeit with reduced potency. In some embodiments, a TMATE can induce positive cytokine release upon engaging T cells and target cells under a tumor microenvironment-like acidic condition of about pH 6.4 to about pH 7.0. In some embodiments, the cytokine release level induced by TMATE is comparable to or within about two-fold difference from that induced by a conventional TMA under conditions of near pH 6.6 as illustrated in FIGS. 17, 19 and 20.

Figure 43:
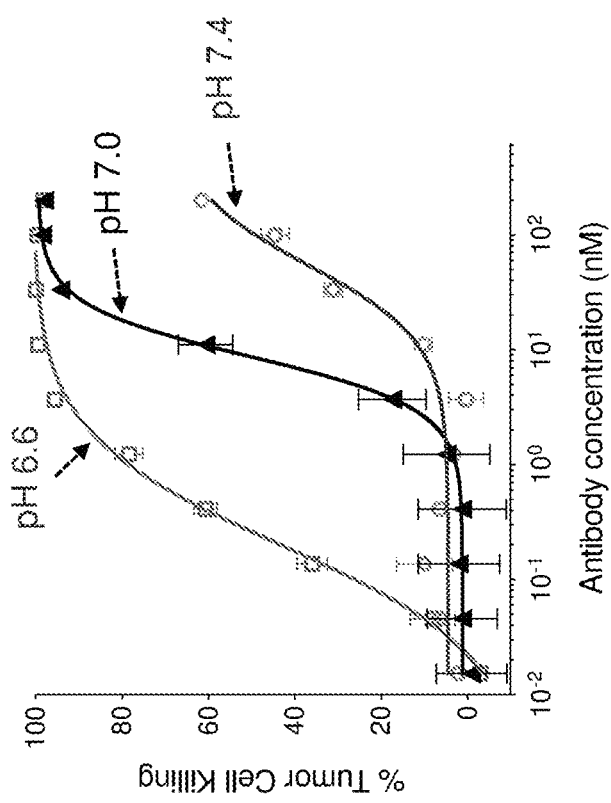
FIG. 43 shows the pH- and dose-dependent T cell cytotoxicity towards the TROP-2$^{high}$ MDA-MB-468 cancer cells elicited by the TMATE comprising CD3(h10.v38)×TROP-2(RS7.v1) under the culture conditions of about pH 6.6, pH 7.0 and pH 7.4 respectively. Human primary T cells are used with an E:T ratio at 11:1 with a three-day co-incubation period.

In some embodiments, as exemplified in FIG. 43, the T cell mediated killing activity induced by TMATE at a near neutral pH such as pH 7.0 can be observed in the presence of a TAA-high target cell, showing an EC50 of about 9 nM under the pH 7.0 condition, corresponding to a 32-fold potency reduction as compared to that under the pH 6.6 condition. In the cases with a TAA-low cell, the killing activity by TMATE at pH 7.0 would be typically negligible, as exemplified in FIG. 28.

Figure 44:
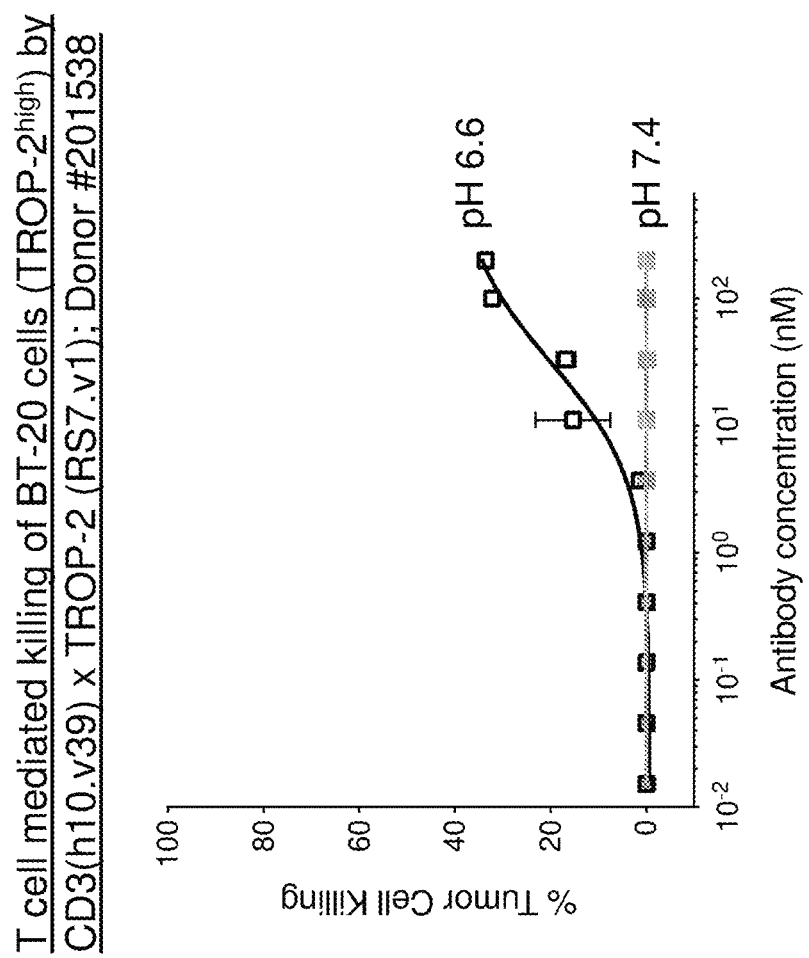
FIG. 44 shows the pH- and dose-dependent T cell cytotoxicity towards the TROP-2$^{high}$ BT-20 cancer cells elicited by the TMATE comprising CD3(h10.v39)×TROP-2 (RS7.v1) under the culture conditions of about pH 6.6 and pH 7.4 respectively. Human primary T cells are used with an E:T ratio at 11:1 with a three-day co-incubation assay duration.

In some embodiments, a TMATE can induce potent T cell dependent killing of a TAA-high target cell under an acidic tumor microenvironment like condition of about pH 6.6. In some embodiments, the killing effect induced by a TMATE can vary between different TAA-high cancer cells, presumably because cancer cells are heterogenous in many genetic and non-genetic biological aspects including their inherent heterogenous susceptibility to apoptotic factors such as death ligands, perforin and granzyme B that can be delivered from cytotoxic T cells upon full activation by a TMATE. As exemplified in FIG. 44, an anti-TROP-2 TMATE comprising CD3(h10.v39)×TROP-2(RS7.v1) can only trigger partial killing of a TROP-2$^{high}$ cell (BT-20), e.g. no more than 40% cell-killing even under a very high treatment dose of 200 nM over an assay period of about 72 hours with the same T cells (Donor #201538) that can be otherwise activated to potently kill another TROP-2$^{high}$ cell (MDA-MB-468) (FIGS. 32 and 36).

Figure 45:
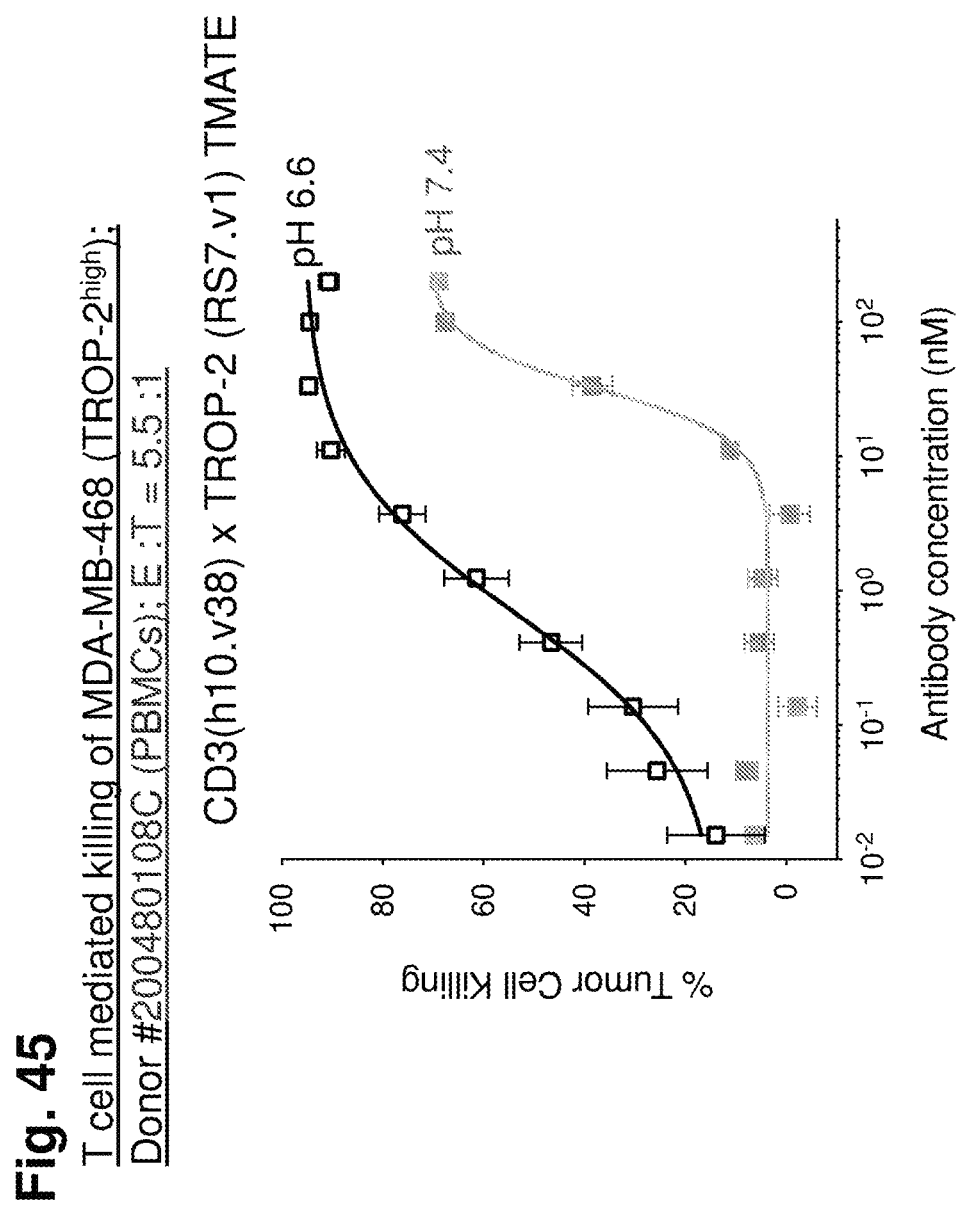
FIG. 45 shows the pH- and dose-dependent T cell cytotoxicity towards the TROP-2$^{high}$ MDA-MB-468 cancer cells elicited by the TMATE comprising CD3(h10.v39)×TROP-2(RS7.v1) under the culture conditions of about pH 6.6 and pH 7.4 respectively. Human peripheral blood mononuclear cells (PMBCs) are used with an E:T ratio of 5.5:1 in a three-day co-incubation assay duration.

In some embodiments, a TMATE can induce acidity-dependent potent target cell killing of a TAA-high target cell in the presence of human peripheral blood mononuclear cells((PBMCs). As exemplified in FIG. 45, the anti-TROP-2 TMATE comprising CD3(h10.v38)×TROP-2(RS7.v1) triggers potent killing of the TROP-2$^{high}$ cell (MDAMB-468) under a pH 6.6 assay condition provided an E:T ratio of about 5.5:1, in comparison to significantly lower potency under the pH 7.4 condition (near 80-fold potency reduction).

In some embodiments, the anti-TROP-2 TMATE comprises an alternative CD3×TROP-2 TMATE comprising a pH sensitive anti-CD3 moiety selected from h10.v23, h10.v26, h10.v27, h10.v32, h10.v34, h10.v38, h10.v39, h10.v48, and h10.v49 (See Tables 3 and 4 and sequence table for CDR and VH/VL sequences of these antibodies) and an alternative anti-TROP-2 antibody moiety other than RS7.v1. In some embodiments, the alternative CD3×TROP-2 TMATE comprises a pH sensitive anti-CD3 moiety and two anti-TROP-2 antibody moieties. In some embodiments, the two anti-TROP-2 antibody moieties recognize one and the same epitope of two TROP-2 molecules. In some embodiments, the two anti-TROP-2 antibody moieties recognize two distinct epitopes of TROP-2. In some embodiments, the two anti-TROP-2 antibody moieties comprises the same CDRs. In some embodiments, the two anti-TROP-2 antibody moieties comprises two distinct sets of CDRs. In some embodiments, the CD3×TROP-2 TMATE comprises a pH sensitive anti-CD3 moiety and at least one pH-sensitive anti-TROP-2 antibody moieties.

In some embodiments, CD3×HER2 TMATEs capable of killing HER2-positive cells in a pH selective manner can be used to treat HER2-positive tumors of human subjects. In some embodiments, HER2-positive tumors are HER2-high tumors that are characterized by a HER2 immunohistology staining score of 2+ or 3+. In some embodiments, HER2-positive tumors are HER2-low tumors that are characterized by a HER2 immunohistology staining score of 1+. In some embodiments, HER2-positive tumors are human breast cancer. In some embodiments, HER2-positive tumors are human gastric cancers. In some embodiments, a HER2-positive tumor is one of the following cancer types or subtypes: ovarian cancer, bladder cancer, salivary gland cancer, colon cancer, endometrial cancer, pancreatic cancer, and non-small-cell lung cancer (NSCLC).

In some embodiments, CD3×TROP-2 TMATEs capable of killing TROP-2-positive cells in a pH selective manner can be used to treat TROP-2-positive tumors of human subjects. In some embodiments, TROP-2-positive tumors are TROP-2-high tumors that are characterized by a TROP-2 immunohistology staining. In some embodiments, TROP-2-positive tumors are TROP-2-moderate-high tumors that are characterized by a TROP-2 immunohistology staining. In some embodiments, TROP-2-positive tumors are human breast cancers. In some embodiments, TROP-2-positive tumors are human colon or colorectal cancers. In some embodiments, a TROP-2-positive tumor is one of the following cancer types or subtypes: urothelial or bladder cancer, kidney cancer, colon or colorectal cancer, endometrial cancer, pancreatic cancer, prostate cancer, head and neck cancers, ovarian cancer, non-small-cell lung cancer (NSCLC), small cell lung cancer, squamous cell carcinoma, cervical cancer, neuroendocrine cancer, gastric cancer, melanoma, and medullary carcinoma.

Moreover, it is understood that the foregoing described pH sensitive anti-CD3 moieties as referenced in the h10.v23, h10.v26, h10.v27, h10.v32, h10.v34, h10.v38, h10.v39, h10.v48, and h10.v49 (See Tables 3 and 4 and sequence table for CDR and VH/VL sequences of these antibodies) can be integrated in alternative TMATEs to target a variety of human abnormal cell proliferation disorders such as cancer, for instance, by targeting a tumor associated antigen. As used herein, abnormal cell proliferation disorders generally refer to tumor, cancer, anaplasia, dysplasia, hyperplasia, hypertrophy, metaplasia. The term "cancer" as used herein refers to hematological and solid tissue cancers, which include but are not limited to, carcinoma, sarcoma, melanoma, lymphoma, and leukemia. Exemplary cancers are lung cancer, breast cancer, gastric cancer, pancreatic cancer, colon cancer, colorectal cancer, bladder cancer, cervical cancer, kidney cancer, gall bladder cancer, head and neck carcinomas, brain tumors, sarcoma, melanoma, liver cancer, renal cancer, prostate cancer, ovarian cancer, acute myeloid leukemia (AML), multiple myeloma (MM), acute lymphocytic leukemia (ALL), chronic lymphocytic leukemia (CLL), non-Hodgkin's lymphoma, and chronic myeloid leukemia (CML). As used herein, the term "cancer" can be used interchangeably with "tumor", particularly in conditions where the cancer is a solid tissue malignant tumor.

In some embodiments, the anti-CD3 constructs (e.g., anti-CD3 TMATEs) described in this disclosure are multi-specific antibodies that are expressed in vitro recombinantly and formulated as off-shelf protein therapeutics. In alternative embodiments, the anti-CD3 constructs (e.g., anti-CD3 TMATEs) described in this disclosure are expressed in vivo from engineered cells that are formulated as a cell therapeutic and directly administered into human subjects.

In general, it is expected that administered TMATEs in vivo can preferentially link T cells in an acidic environment to a cancer cell for direct killing. Moreover, the secreted cytokines from the activated T cells can presumably activate, promote, or mobilize proximal bystander immune cells to achieve enhanced immune response against the tumor cells. In some embodiments the bystander cells can be T cells such as tumor infiltrating T cells and tissue resident T cells. In some embodiments, the bystander cells can be innate immune cells such as dendritic cells, NK cells, neutrophils, basophils, eosinophils, monocytes, and macrophages. In some embodiments, the bystander cells can be adaptive immune cells such as B cells. On the other hand, in a healthy tissue, TMATEs will not or will only minimally engage T cells and therefore will not or will barely trigger any killing of or cytokine release towards normal cells that may express a target molecule.

Figure 46:
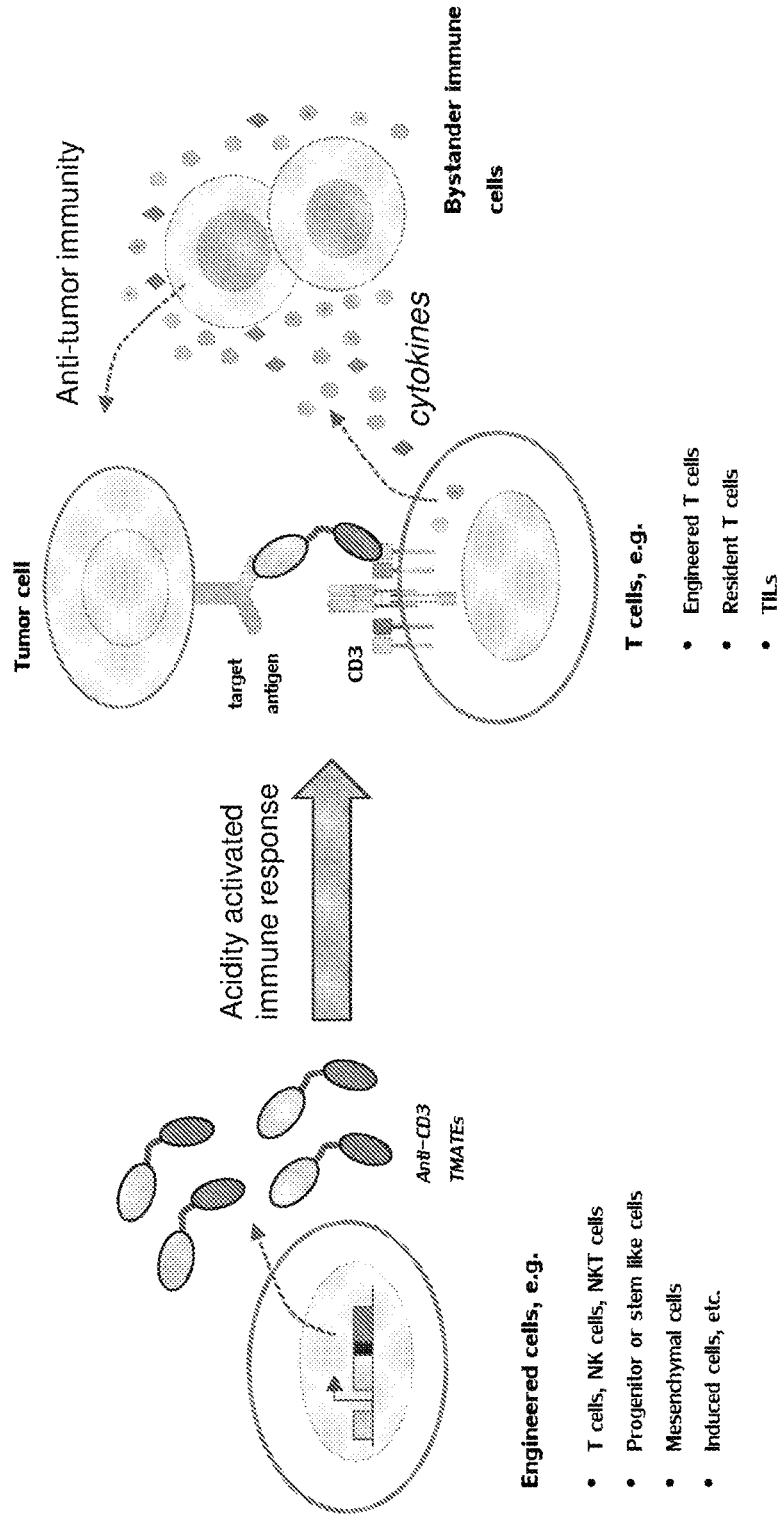
FIG. 46 is a schematic illustrating the use of an engineered human cell to express and secrete in vivo an anti-CD3 TMATE from a genetic sequence delivered into the engineered cell, wherein the TMATE is conditionally activated under an acidic tumor microenvironment. TMATE can also indirectly activate bystander immune cells in part through local cytokine signaling to promote or enhance anti-tumor immunity.

In some embodiments, the anti-CD3 constructs (e.g., anti-CD3 TMATEs) expressed from cell therapeutic are in a secreted form expressed and secreted from the said therapeutic cells in vivo. As exemplified in FIG. 46, the engineered human cells such as conventional T cells and NK cells will secrete TMATEs in vivo. Under physiological-like microenvironment with a pH of near 7.4, TMATEs presumably will not or will only minimally engage T cells and therefore are largely inactive, although they may or may not engage a target cell via its anti-target-molecule moiety. Under a tissue microenvironment with an acidic pH of about 6.4 to about 7.0 (e.g. a tumor microenvironment of about pH 6.5 to about pH 7.0) and the presence of target cells, TMATEs will engage and activate T cells for direct killing of target cells, whereas the killing can be further enhanced indirectly by bystander immune cells that are activated or mobilized by the said activated T cells. In some embodiments, the TMATE-expressing cell therapeutics can comprise an engineered, edited, or derivative form of a variety of human cell types including without limitation to T cells, NK cells, CAR-T cells, TCR-T cells, NKT cells, induced NKT cells, macrophages or macrophage progenitors or progenitor-like cells, stem or stem-like cells, mesenchymal cells, induced progenitor cells, induced pluripotent cells, iPSCs, lineage progenitor cells, tissue progenitor cells and hybrid cells.

In some embodiments, the said TMATEs as a secreted form can be expressed from one or more genetic elements that are integrated into the genome of TMATE-expressing therapeutic cells. In some embodiments, the genetic integration of a TMATE encoding sequence can be done by using a lentiviral vehicle or a retroviral vehicle that typically results in non-site-specific integration. In some embodiments, the genetic integration of a TMATE encoding sequence can be done by using a site-specific integration approach, for instance, a genomic landing-pad approach that is mediated by a recombinase or integrase such as CRISPR-Cas9 and the like, Bxb1 recombinase and the like, φC31 integrase and the like, Wβ integrase and the like, Zinc Finger Nuclease and the like, or mediated by a transposase (e.g., a Sleeping Beauty or PiggyBac transposase) based approach. In some embodiments, the said TMATEs as a secreted form can be expressed from one or more genetic elements that are introduced into TMATE-expressing therapeutic cells as a non-integrated genetic vehicle such as an episomal construct, exosomes, extracellular vesicles (EVs), or a circular nucleic acid molecule.

In some embodiments, the anti-CD3 TMATEs can be expressed in vivo from an RNA therapeutic comprising genetic sequences encoding the said TMATE, wherein such an RNA therapeutic is formulated for direct administering into human subjects, wherein the TMATE is expressed as a secreted form in the said subjects for therapeutic uses. In some embodiments, the said RNA is provided in a linear RNA format. In some embodiments, the said RNA is provided in a circular RNA format.

In some embodiments, the anti-CD3 TMATEs can be expressed in vivo from a gene therapeutic comprising genetic sequences encoding the said TMATE, wherein such a gene therapeutic is formulated for direct administering directly administered into human subjects, wherein the TMATE is expressed as a secreted form in the said subjects for therapeutic uses. In some embodiments, the gene therapeutic comprises a viral vehicle. In some embodiments, the viral vehicle is engineered or derived from a virus that is exemplified by an adenovirus and an adeno-associated virus (AAV) and/or lentivirus.

Figure 47:
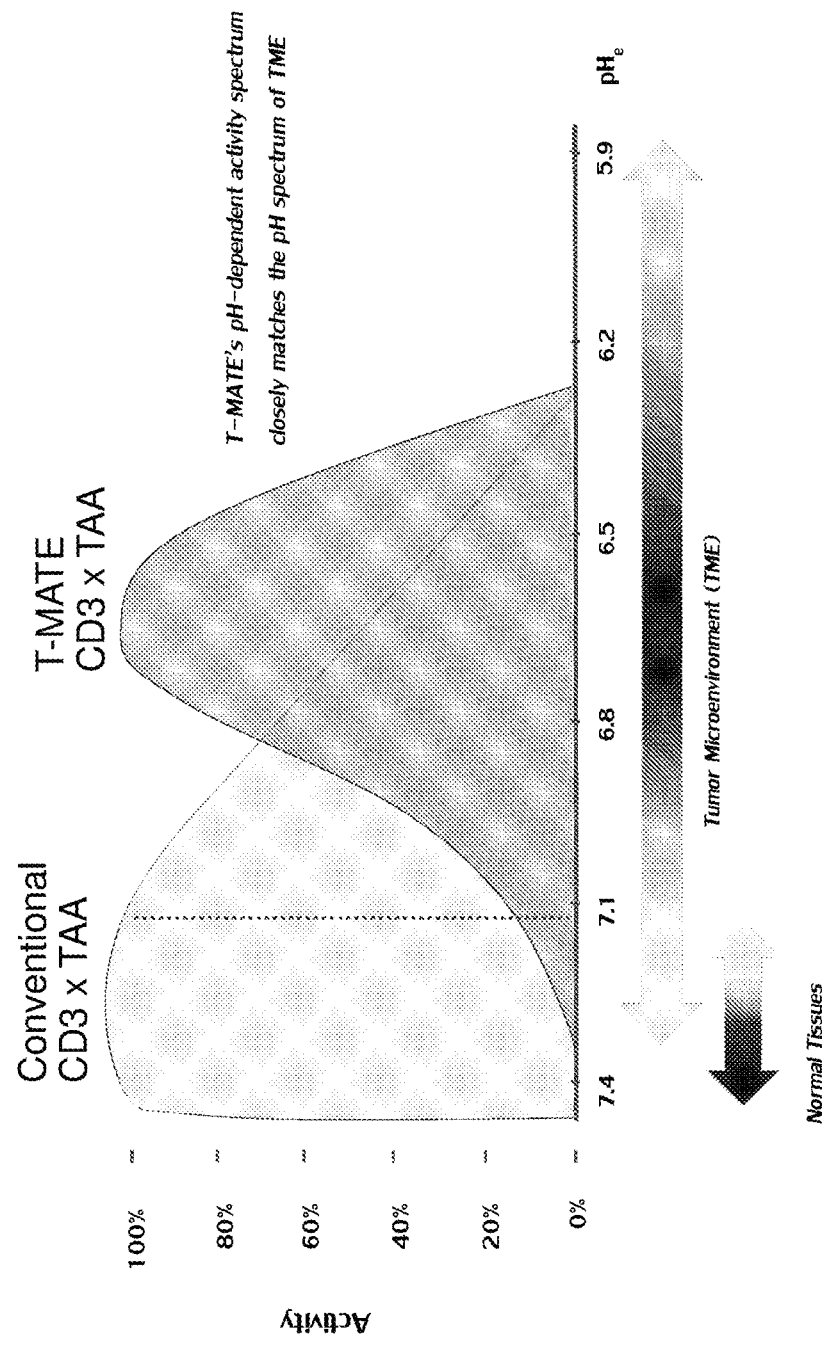
FIG. 47 illustrates the concept of fine-tuning the activity spectrum of TMATEs to match pH spectrum of tumor microenvironment to reduce the on-target off-site killing effect on healthy tissue cells, which are otherwise commonly observed with conventional TMAs that typically have an optimal activity under conditions of near pH 7.4.

In general, as illustrated in FIG. 47, a fine-tuned or optimized anti-CD3 TMATE will exhibit a pH-dependent killing activity spectrum, which closely mirrors the pH spectrum of common tumor microenvironment and have a peak activity under conditions of about pH 6.6 or 6.7. In comparison, the conventional TMAs typically are most potent under conditions of near pH 7.4 or near a neutral pH.

It is noteworthy that, because of the intrinsic T cell property, both TMATEs and conventional TMAs will show significantly reduced activities under further acidified conditions of about pH 6.4, about pH 6.3 or a lower pH, wherein the T cell receptor signaling and/or the relevant downstream effector machinery will be overwhelmed by such further low acidity.

In some embodiments, the tumor associated antigen is a molecule that is specifically or preferentially expressed on tumor cells. Exemplary TAAs include without limitation to EGFR and mutant KRAS-derived peptide/HLA complexes for some lung cancer subtypes, CEA for bowel cancer types, CA-125 for ovarian cancer, AFP for liver cancer, MAGE for malignant melanoma, PSMA for prostate cancer, TROP-2, 5T4, and EpCAM for breast and colon cancer, CD38 and BCMA for multiple myeloma, CD19, CD20 and CD123 for certain hematological cancers, GPC3, CEACAM5, Claudin 18.2, Mesothelin, TROP-2, and MUC-1 for breast cancers among others, CLEC12A in acute myelogenous leukemia and myelodysplastic syndrome.

In some embodiments, the anti-CD3 constructs (e.g., the anti-CD3 TMATE constructs) described herein comprise one or more linkers between two moieties (e.g., the anti-CD3 antibody moiety and the half-life extending moiety, the anti-CD3 scFv and the full-length antibody in the bispecific antibodies described above). The length, the degree of flexibility and/or other properties of the linker(s) used in the bispecific antibodies may have some influence on properties, including but not limited to the affinity, specificity or avidity for one or more particular antigens or epitopes. For example, longer linkers may be selected to ensure that two adjacent domains do not sterically interfere with one another. In some embodiment, a linker (such as peptide linker) comprises flexible residues (such as glycine and serine) so that the adjacent domains are free to move relative to each other. For example, a glycine-serine doublet can be a suitable peptide linker. In some embodiments, the linker is a non-peptide linker. In some embodiments, the linker is a peptide linker. In some embodiments, the linker is a non-cleavable linker. In some embodiments, the linker is a cleavable linker.

Other linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, modulation of antibody binding, the ability to be incorporated into a micelle or liposome, and the like.

Non-Peptide Linkers

Coupling of two moieties may be accomplished by any chemical reaction that will bind the two molecules so long as both components retain their respective activities, e.g., binding to CD3 and a second agent in a bispecific antibody, respectively. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents may be useful in coupling protein molecules in this context. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents (see Killen and Lindstrom, Jour. Immun. 133:1335-2549 (1984); Jansen et al., Immunological Reviews 62:185-216 (1982); and Vitetta et al., Science 238:1098 (1987)).

Linkers can be applied in the present application are described in the literature (see, for example, Ramakrishnan, S. et al., Cancer Res. 44:201-208 (1984) describing use of MBS (M-maleimidobenzoyl-N-hydroxysuccinimide ester). In some embodiments, non-peptide linkers used herein include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus may lead to bispecific antibodies with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form antibody fusion protein with increased stability. Disulfide linkages, are in general, less stable than other linkages because the disulfide linkage is cleaved in vitro, resulting in less antibody fusion protein available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Peptide Linkers

The peptide linker may have a naturally occurring sequence, or a non-naturally occurring sequence. For example, a sequence derived from the hinge region of heavy chain only antibodies may be used as the linker. See, for example, WO1996/34103.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 99 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acid to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

An essential technical feature of such peptide linker is that said peptide linker does not comprise any polymerization activity. The characteristics of a peptide linker, which comprise the absence of the promotion of secondary structures, are known in the art and described, e.g., in Dall'Acqua et al. (Biochem. (1998) 37, 9266-9273), Cheadle et al. (Mol Immunol (1992) 29, 21-30) and Raag and Whitlow (FASEB (1995) 9(1), 73-80). A particularly preferred amino acid in context of the "peptide linker" is Gly. Furthermore, peptide linkers that also do not promote any secondary structures are preferred. The linkage of the domains to each other can be provided by, e.g., genetic engineering. Methods for preparing fused and operatively linked bispecific single chain constructs and expressing them in mammalian cells or bacteria are well-known in the art (e.g. WO 99/54440, Ausubel, Current Protocols in Molecular Biology, Green Publishing Associates and Wiley Interscience, N. Y. 1989 and 1994 or Sambrook et al., Molecular Cloning: A Laboratory Manual, Cold Spring Harbor Laboratory Press, Cold Spring Harbor, N. Y., 2001).

The peptide linker can be a stable linker, which is not cleavable by proteases, especially by Matrix metalloproteinases (MMPs).

The linker can also be a flexible linker. Exemplary flexible linkers include glycine polymers $(G)_n$ (SEQ ID NO: 102), glycine-serine polymers (including, for example, $(GS)_n$ (SEQ ID NO: 103), $(GSGGS)_n$ (SEQ ID NO: 104), $(GGGGS)_n$ (SEQ ID NO: 105), and $(GGGS)_n$ (SEQ ID NO: 106), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11 173-142 (1992)). The ordinarily skilled artisan will recognize that design of an antibody fusion protein can include linkers that are all or partially flexible, such that the linker can include a flexible linker portion as well as one or more portions that confer less flexible structure to provide a desired antibody fusion protein structure.

In some embodiments, the anti-HER-2 scFv and the at least one of the anti-CD3 heavy chains or light chains are linked together by a linker of sufficient length to enable the anti-HER-2 scFv and anti-CD3 antigen binding domain to fold in such a way as to permit binding to HER-2 and CD3. Further to this embodiment, such a linker may comprise, for example, the amino acid sequence of such as $(GGGGS)_n$ (SEQ ID NO: 105), wherein n is an integer between 1 and 8, e.g. $(GGGGS)_3$ (SEQ ID NO: 107; hereinafter referred to as "(G4S)3" or "GS3"), or $(GGGGS)_6$ (SEQ ID NO: 108; hereinafter referred to as "(G4S)6" or "GS6"). In some embodiments, the peptide linker comprises the amino acid sequence of $(GSTSGSGKPGSGEGS)_n$ (SEQ ID NO: 109), wherein n is an integer between 1 and 3.

Anti-CD3 Fusion Proteins

The anti-CD3 constructs in some embodiments comprise an anti-CD3 antibody moiety and a half-life extending moiety. In some embodiments, the half-life extending moiety is an Fc fragment. In some embodiments, the half-life extending moiety is an albumin binding moiety (e.g., a human albumin binding antibody moiety). In some embodiments, the half-life extending moiety is a transferrin binding moiety (e.g., a human transferrin binding antibody moiety).

In some embodiments, the half-life extending moiety is an Fc fragment (such as any of the Fc fragments or variants thereof described herein). The term "Fc region," "Fc domain" or "Fc" refers to a C-terminal non-antigen binding region of an immunoglobulin heavy chain that contains at least a portion of the constant region. The term includes native Fc regions and variant Fc regions. In some embodiments, a human IgG heavy chain Fc region extends from Cys226 to the carboxyl-terminus of the heavy chain. However, the C-terminal lysine (Lys447) of the Fc region may or may not be present, without affecting the structure or stability of the Fc region. Unless otherwise specified herein, numbering of amino acid residues in the IgG or Fc region is according to the EU numbering system for antibodies, also called the EU index, as described in Kabat et al., Sequences of Proteins of Immunological Interest, 5th Ed. Public Health Service, National Institutes of Health, Bethesda, MD, 1991.

In some embodiments, the Fc fragment is selected from the group consisting of Fc fragments from IgG, IgA, IgD, IgE, IgM, and combinations and hybrids thereof. In some embodiments, the Fc fragment is selected from the group consisting of Fc fragments from IgG1, IgG2, IgG3, IgG4, and combinations and hybrids thereof.

In some embodiments, the Fc fragment has a reduced effector function as compared to corresponding wildtype Fc fragment (such as at least about 30%, 40%, 50%, 60%, 70%, 80%, 85%, 90%, or 95% reduced effector function as measured by the level of antibody-dependent cellular cytotoxicity (ADCC)).

In some embodiments, the Fc fragment is an IgG1 Fc fragment. In some embodiments, the IgG1 Fc fragment comprises a L234A mutation and/or a L235A mutation. In some embodiments, the Fc fragment is an IgG2 or IgG4 Fc fragment. In some embodiments, the Fc fragment is an IgG4 Fc fragment comprising a S228P, F234A, and/or a L235A mutation. In some embodiments, the Fc fragment comprises a N297A mutation. In some embodiments, the Fc fragment comprises a N297G mutation.

In some embodiments, the anti-CD3 antibody moiety and the half-life extending moiety is linked via a linker (such as any of the linkers described in the "Linkers" section).

In some embodiments, the anti-CD3 fusion protein further comprises a second agent. In some embodiments, the second agent binds to a tumor agent (such as any one of the tumor agents described herein).

Nucleic Acids

Nucleic acid molecules encoding the anti-CD3 constructs or anti-CD3 antibody moieties described herein are also contemplated. In some embodiments, there is provided a nucleic acid (or a set of nucleic acids) encoding a full-length anti-CD3 antibody. In some embodiments, there is provided a nucleic acid (or a set of nucleic acids) encoding an anti-CD3 scFv. In some embodiments, there is provided a nucleic acid (or a set of nucleic acids) encoding an anti-CD3 Fc fusion protein. In some embodiments, there is provided a nucleic acid (or a set of nucleic acids) encoding a multi-specific anti-CD3 molecule (e.g., a multi-specific anti-CD3 antibody or a bispecific anti-CD3 antibody), or polypeptide portion thereof. In some embodiments, the nucleic acid (or a set of nucleic acids) encoding the anti-CD3 construct described herein may further comprises a nucleic acid sequence encoding a peptide tag (such as protein purification tag, e.g., His-tag, HA tag).

Also contemplated here are isolated host cell comprising an anti-CD3 construct, an isolated nucleic acid encoding the polypeptide components of the anti-CD3 construct, or a vector comprising a nucleic acid encoding the polypeptide components of the anti-CD3 construct described herein.

The present application also includes variants to these nucleic acid sequences. For example, the variants include nucleotide sequences that hybridize to the nucleic acid sequences encoding the anti-CD3 constructs or anti-CD3 antibody moieties of the present application under at least moderately stringent hybridization conditions.

The present invention also provides vectors in which a nucleic acid of the present invention is inserted.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584, WO 01/29058; and U.S. Pat. No. 6,326,193).

III. Methods of Preparation

Isolation of pH Sensitive Antibodies

In some embodiments, there is provided a method of preparing an anti-CD3 construct (e.g., an anti-CD3 TMATE construct or a pH-sensitive antibody moiety) that specifically binds to CD3 and a composition such as polynucleotide, nucleic acid construct, vector, host cell, or culture medium that is produced during the preparation of the anti-CD3 construct or antibody moiety. The anti-CD3 construct or antibody moiety or composition described herein may be prepared by a number of processes as generally described in the section "Anti-CD3 Antibody Moieties" as well as below and more specifically in the Examples.

In some embodiments, the screening method comprises a phage display based antibody discovery approach which is a commonly known method to a person with average skills in the field, which has been used to isolate pH dependent monoclonal or bispecific antibodies previously (see U.S. Pat. Doc. US2013/0336963A1, now U.S. Pat. No. 9,890,377 B2; Nat. Biotechnol. (2010) 28:1203-1207). For instance, one may: (1) prepare a recombinant antigen or cell-based antigen; (2) optionally immunize a host species of choice (e.g. mouse, rat, rabbits, llama, alpaca); (3) generate a phage-displayed antibody library using $V_H$/VL sequences derived from antigen-immunized or naïve animals such as the wild-type and IgG-humanized mice; (4) screen the phage library by conventional phage panning using a recombinant antigen probe such as a purified recombinant CD3's extracellular domain with an initial binding condition of pH 6.0 and a subsequent washing condition of pH 7.4 to enrich for clones with biased binding under pH 6.0; (5) perform step (4) for one or more iterations; (6) recover the variable region sequences of the resulted clones with biased pH-dependent binding property via genetic sequencing. In some embodiments, one or more iterations of the afore-described steps (I) through (5) in this section can be performed to improve the probability of obtaining pH dependent clones.

In some embodiments, the screening method comprises a yeast display based antibody discovery approach, an alternative well-known method to an average artisan in the field. The yeast display method was initially described more than two decades ago (Nat. Biotechnol. (1997) 15: 553-557) and has been used for isolating pH sensitive antibodies in multiple cases (Biotechnol. J. (2014) 9: 1013-1022; MAbs (2015) 7: 138-151; Front. Immunol. (2019) 10: 1892). For instance, one may: (1) prepare a recombinant antigen or cell-based antigen; (2) optionally immunize a host species of choice (e.g. mouse, rat, rabbits, llama, alpaca); (3) generate a yeast-display antibody library using VH and/or VL sequences derived from antigen-immunized or naïve animals; (4) screen the yeast library in part by using fluorescence activated cell sorting (FACS) with a recombinant antigen probe such as a purified recombinant antigen with an initial binding condition of pH 6.0 and a subsequent washing condition of pH 7.4 to enrich for clones with biased binding under pH 6.0; (5) perform step (4) for one or more iterations; (6) recover the VH and/or VL sequences of the resulted clones with biased pH-dependent binding property via genetic sequencing.

In some embodiments, the screening method comprises a phage- or yeast-display based antibody discovery approach as similarly described in the foregoing two paragraphs, except that the antibody library is generated using synthetic or semi-synthetic variable sequences to increase the library's genetic diversity.

In some embodiments, the screening method comprises a single cell-based antibody discovery approach, which are an increasingly well-known method to common persons in the field. In general, the antibody-expressing cells can be plasma cells or antigen-activated B cells derived from antigen-immunized animals such as rodents and llamas. Single cell based platforms can be a FACS system available from multiple vendors such as BD Biosciences and Thermo Fisher, a Beacon system from Berkeley Light Inc, a microchamber based single-cell platform from Abcellera Inc and the like. The screening can be initially based on binding under a pH 6.0 condition and then switched to pH 7.4 to reduce false positive hits with one or iterations between pH 6.0 and pH 7.4 conditions, to ultimately isolate pH-dependent clones.

In some embodiments, the single cell based discovery approach comprises generating a plurality of droplets, wherein at least one of the droplets has one single plasma cell and one or more functional reporter cells. The droplets can be generated using a common droplet generation device and screened by using a single cell-cell interaction based discovery platform. See for example, Example 1 of the present application, US20180321130A1, WO2020/076730A and PCT/US2020/035340, all of which are hereby incorporated by reference in their entirety. In some embodiments, the method comprises incubating the droplets (e.g., to allow activation of reporter cell). In some embodiments, the method comprises soring droplets with an activating antibody (such as a single activating antibody) under a pH-tuned condition. In some embodiments, the method further comprises sequencing the activating antibodies.

In some embodiments, a pH dependent antibody can be generated using a focused library comprising pre-enriched antibodies against a select target, wherein the so-called histidine scan can be used to generate pH-dependent clones, i.e., histidine mutation can be introduced into one or more residues of one or more CDRs of any candidate antibodies to obtain a focused library via molecular biology methods. Such molecular biology methods are a common art known to average persons in the field. The resultant focused library can then be screened using a phage-display, a yeast-display, or a single cell based screening method to enrich for clones with biased binding under pH 6.0 conditions.

In some embodiments, a pH dependent antibody can be generated using a focused library comprising pre-enriched antibodies against a select target, wherein one or more negatively charged residues such as glutamic acid and aspartic acid can be used to replace one or more residues in any CDRs of candidate antibodies to obtain a focused library. In some embodiments, a pH dependent antibody can be generated using a focused library comprising pre-enriched antibodies against a select target, wherein one or more negatively charged residues (e.g. Asp and Glu) in any combinations with histidine can be used to replace one or more residues in any CDRs of candidate antibodies to obtain a focused library. In some embodiments, the genetic replacement can be achieved using site-specific mutagenesis, random mutations, other Polymerase Chain Reaction (PCR)— or DNA recombination-based molecular biology approaches that are generally known to skilled average persons.

In some embodiments, a first panel of antibody moieties comprising one or more pH-sensitive candidates that can bind to a first antigen can be "paired" with a second panel of antibody moieties comprising one or more candidates that can bind to a second antigen to ultimately generate a multispecific TMATE candidate pool (library). In some embodiments, a first panel of antibody moieties comprising one or more pH-sensitive candidates that can bind to a first antigen can be assembled with a second panel of antibody moieties comprising one or more candidates that can bind to a second antigen and a third panel of antibody moieties comprising one or more candidates that can bind to a third antigen or the same second antigen, to generate a TMATE candidate pool. In some embodiments, the TMATE candidate pool can be subject to iterative rounds of screening assays comprising a binding step under a pH 6.0 condition and a sequential washing step under a pH 7.4 condition to isolate initial pH sensitive hits (or clones). In some embodiments, the initial TMATE hits (e.g. their heavy and light chain-coding plasmids) can be co-transfected and expressed in CHO or 293 cells, and purified using routine protein chromatography methods. The purified TMATEs can be analyzed under buffer conditions of pH 7.4 and pH 6.0, or under any pH of about pH 5.8 to about pH 7.5, for the binding kinetics towards the intended antigen such as CD3. In some embodiments, the binding kinetic can be assessed using a bio-layer interferometry (e.g., Octet or Gator) or a surface plasma resonance approach (e.g. BiaCore) to derive the association constant ($K_{on}$), dissociation constant ($K_{off}$) and the equilibrium constant ($K_D$).

In some embodiments, given the availability of antigen-antibody structure information, a TMATE construct or a pH-sensitive antibody moiety can be engineered using a structure-aided rational design approach. In some embodiments, the goal of rational design is to widen the binding free energy gap of TMATE variants between an acidic and a physiological environment. This binding free energy gap should be as negative as possible and in the meantime the variants should maintain relative high affinity in the acidic environment in order to maintain optimal biological activity. In some embodiments, one or more select residues of critical structural importance including without limitations to glutamic acid, aspartic acid, histidine, arginine and lysine can be introduced to a candidate TMATE, which can be validated by "wet-lab" approaches; for example, such a candidate can be expressed, purified and tested for its pH dependence in terms of its antigen-binding, which can be based on an ELISA or a flow cytometric cell-binding assay, and optionally its functional activity, which can be based on a microtiter-plate based conventional reporter assay. In some embodiments, there will one or more iterations of rational design and then web-lab validation to obtain the optimal TMATEs with the best pH selectivity. In some embodiments, the rational design can be assisted by computational programs or informatic tools such as SCWRL, FoldX, Rosetta, Schrodinger, and ADAPT.

In some embodiments, one, two, three or more approaches or methods as described in this "Isolating pH sensitive antibodies" section can be adapted concurrently or in any combination with any orders of execution. For instance, a structure-aided design plus a phage display method have been used in combination to isolate pH-sensitive anti-VISTA and anti-HER2 antibodies respectively (Nature (2019) 574:565-570; MAbs (2020) 12:1682866).

Antibody Expression and Production

The antibodies (including anti-CD3 monoclonal antibodies, anti-CD3 bispecific antibodies, and anti-CD3 antibody moieties) described herein can be prepared using any known methods in the art, including those described below and in the Examples.

Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies. For example, the monoclonal antibodies may be made using the hybridoma method first described by Kohler et al., *Nature*, 256:495 (1975), or may be made by recombinant DNA methods (U.S. Pat. No. 4,816,567). In the hybridoma method, a mouse or other appropriate host animal, such as a hamster or a llama, is immunized as hereinabove described to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (*Goding, Monoclonal Antibodies: Principles and Practice*, pp. 59-103 (Academic Press, 1986). Also see Example 1 for immunization in Camels.

The immunizing agent will typically include the antigenic protein or a fusion variant thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130:151-188 (1992).

In a further embodiment, antibodies can be isolated from antibody phage libraries generated using the techniques described in McCafferty et al., *Nature,* 348:552-554 (1990). Clackson et al., *Nature.* 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nucl. Acids Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide. Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may be monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Nucleic Acid Molecules Encoding Antibody Moieties

In some embodiments, there is provided a polynucleotide encoding any one of the anti-CD3 constructs or antibody moieties described herein. In some embodiments, there is provided a polynucleotide prepared using any one of the methods as described herein. In some embodiments, a nucleic acid molecule comprises a polynucleotide that encodes a heavy chain or a light chain of an antibody moiety (e.g., anti-CD3 antibody moiety). In some embodiments, a nucleic acid molecule comprises both a polynucleotide that encodes a heavy chain and a polynucleotide that encodes a light chain, of an antibody moiety (e.g., anti-CD3 antibody moiety). In some embodiments, a first nucleic acid molecule comprises a first polynucleotide that encodes a heavy chain and a second nucleic acid molecule comprises a second polynucleotide that encodes a light chain. In some embodiments, a nucleic acid molecule encoding an scFv (e.g., anti-CD3 scFv) is provided.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an antibody moiety (e.g., anti-CD3 antibody moiety) comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

In some embodiments, the polynucleotide is a DNA. In some embodiments, the polynucleotide is an RNA. In some embodiments, the RNA is an mRNA.

Nucleic acid molecules may be constructed using recombinant DNA techniques conventional in the art. In some embodiments, a nucleic acid molecule is an expression vector that is suitable for expression in a selected host cell.

Nucleic Acid Constructs

In some embodiments, there is provided a nucleic acid construct comprising any one of the polynucleotides described herein. In some embodiments, there is provided a nucleic acid construct prepared using any method described herein.

In some embodiments, the nucleic acid construct further comprises a promoter operably linked to the polynucleotide. In some embodiments, the polynucleotide corresponds to a gene, wherein the promoter is a wild-type promoter for the gene.

Vectors

In some embodiments, there is provided a vector comprising any polynucleotides that encode the heavy chains and/or light chains of any one of the antibody moieties described herein (e.g., anti-CD3 antibody moieties) or nucleic acid construct described herein. In some embodiments, there is provided a vector prepared using any method described herein. Vectors comprising polynucleotides that encode any of anti-CD3 constructs such as antibodies, scFvs, fusion proteins or other forms of constructs described herein (e.g., anti-CD3 scFv) are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, e.g., in Running Deer et al., *Biotechnol. Prog.* 20:880-889 (2004).

Host Cells

In some embodiments, there is provided a host cell comprising any polypeptide, nucleic acid construct and/or vector described herein. In some embodiments, there is provided a host cell prepared using any method described herein. In some embodiments, the host cell is capable of producing any of antibody moieties described herein under a fermentation condition.

In some embodiments, the antibody moieties described herein (e.g., anti-CD3 antibody moieties) may be expressed in prokaryotic cells, such as bacterial cells, or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, the antibody moieties described herein (e.g., anti-CD3 antibody moieties) may be expressed in yeast. See, e.g., U.S. Publication No. US 2006/0270045 A1. In some embodiments, a particular eukaryotic host cell is selected based on its ability to make desired post-translational modifications to the heavy chains and/or light chains of the antibody moiety. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

The invention also provides host cells comprising any of the polynucleotides or vectors described herein. In some embodiments, the invention provides a host cell comprising an anti-CD3 antibody. Any host cells capable of overexpressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

In some embodiments, the antibody moiety is produced in a cell-free system. Non-limiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Culture Medium

In some embodiments, there is provided a culture medium comprising any antibody moiety, polynucleotide, nucleic acid construct, vector, and/or host cell described herein. In some embodiments, there is provided a culture medium prepared using any method described herein.

In some embodiments, the medium comprises hypoxanthine, aminopterin, and/or thymidine (e.g., HAT medium). In some embodiments, the medium does not comprise serum. In some embodiments, the medium comprises serum. In some embodiments, the medium is a D-MEM (aka DMEM), MEM, RPMI-1640 or Leibovitz's L-15 medium.

Purification of Antibody Moieties

The anti-CD3 constructs (e.g., anti-CD3 monoclonal antibodies or bispecific antibodies) may be purified by any suitable method. Such methods include, but are not limited to, the use of affinity matrices or hydrophobic interaction chromatography. Suitable affinity ligands include the ROR1 ECD and ligands that bind antibody constant regions. For example, a Protein A, Protein G, Protein A/G, or an antibody affinity column may be used to bind the constant region and to purify an anti-CD3 construct comprising an Fc fragment. Hydrophobic interactive chromatography, for example, a butyl or phenyl column, may also suitable for purifying some polypeptides such as antibodies. Ion exchange chromatography (e.g. anion exchange chromatography and/or cation exchange chromatography) may also suitable for purifying some polypeptides such as antibodies. Mixed-mode chromatography (e.g. reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

V. Methods of Treatments or Modulating an Immune Response in an Individual

Also provided here are methods of treating a disease or condition in an individual or modulating an immune response in an individual. The methods comprise administering the anti-CD3 construct described herein into individuals (e.g., mammals such as humans).

In some embodiments, there is provided a method of treating a disease or condition or modulating an immune response in an individual, comprising administering to the individual an effective amount of an anti-CD3 construct described herein.

In some embodiments, the anti-CD3 constructs described herein such as TMAs described herein are used to target a variety of human abnormal cell proliferation disorders such as cancer, for instance, by targeting a tumor associated antigen. As used herein, abnormal cell proliferation disorders generally refer to tumor, cancer, anaplasia, dysplasia, hyperplasia, hypertrophy, metaplasia. The term "cancer" as used herein refers to hematological and solid tissue cancers, which include but are not limited to, carcinoma, sarcoma, melanoma, lymphoma, and leukemia. Exemplary cancers are lung cancer, breast cancer, gastric cancer, pancreatic cancer, colon cancer, colorectal cancer, bladder cancer, cervical cancer, kidney cancer, gall bladder cancer, head and neck carcinomas, brain tumors, sarcoma, melanoma, liver cancer, renal cancer, prostate cancer, ovarian cancer, acute myeloid leukemia (AML), multiple myeloma (MM), acute lymphocytic leukemia (ALL), chronic lymphocytic leukemia (CLL), non-Hodgkin's lymphoma, and chronic myeloid leukemia (CML). As used herein, the term "cancer" can be used interchangeably with "tumor", particularly in conditions where the cancer is a solid tissue malignant tumor.

In some embodiments, the anti-CD3 constructs described herein can be used to treat autoimmune diseases, allergy, graft versus host diseases (GvHD), and transplant rejection conditions. In some embodiments, the said composition can preferentially activate regulatory T cells (Treg) or Treg-like immune cells that generally serve to suppress immune responses. Activating Treg or Treg-like cells can restore an abnormally active immune system or a subset of abnormally active immune cells to a normal state and therefore offer therapeutic benefits for relevant patients. The term "autoimmune disease", as used herein, is defined as a disorder that results from an autoimmune response. An autoimmune disease is generally the result of an inappropriate and excessive response to a self-antigen. Examples of autoimmune diseases include but are not limited to, Addision's disease, alopecia areata, ankylosing spondylitis, autoimmune hepatitis, autoimmune parotitis, Crohn's disease, Type I diabetes, dystrophic epidermolysis bullosa, epididymitis, glomerulonephritis, Graves' disease, Guillain-Barre syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual is diagnosed with or genetically prone to one or more of the diseases or disorders described herein (such as a cancer, an autoimmune disease). In some embodiments, the individual has one or more risk factors associated with one or more diseases or disorders described herein.

Dosing and Method of Administering the Anti-CD3 Construct (e.g., Anti-CD3 TMATE Construct)

The dose of the anti-CD3 construct (such as anti-CD3 TMATE monoclonal or multispecific antibodies) used for treating a disease or disorder as described herein administered into the individual may vary with the particular anti-CD3 construct (such as anti-CD3 TMATE monoclonal or multispecific antibodies), the mode of administration, and the type of disease or condition being treated. In some embodiments, the type of disease or condition is a cancer. In some embodiments, the effective amount of the anti-CD3 construct (such as anti-CD3 TMATE monoclonal or multi-specific antibodies) is an amount that is effective to result in an objective response (such as a partial response or a complete response). In some embodiments, the effective amount of the anti-CD3 construct (such as anti-CD3 TMATE monoclonal or multispecific antibodies) is an amount that is sufficient to result in a complete response in the individual. In some embodiments, the effective amount of the anti-CD3 construct (such as anti-CD3 TMATE monoclonal or multispecific antibodies) is an amount that is sufficient to result in a partial response in the individual. In some embodiments, the effective amount of anti-CD3 construct (such as anti-CD3 TMATE monoclonal or multispecific antibodies) is an amount that is sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the anti-CD3 construct (such as anti-CD3 TMATE monoclonal or multispecific antibodies). Responses of an individual to the treatment of the methods described herein can be determined, for example, based on Response Evaluation Criteria in Solid Tumors (RECIST) levels.

In some embodiments, the effective amount of the anti-CD3 construct (such as anti-CD3 TMATE monoclonal or multispecific antibodies) is an amount that is sufficient to prolong progress-free survival of the individual. In some embodiments, the effective amount of the anti-CD3 construct (such as anti-CD3 TMATE monoclonal or multispecific antibodies) is an amount that is sufficient to prolong overall survival of the individual. In some embodiments, the effective amount of the anti-CD3 construct (such as anti-CD3 TMATE monoclonal or multispecific antibodies) is an amount that is sufficient to produce clinical benefit of more than about any of 50%, 60%, 70%, or 77% among a population of individuals treated with the anti-CD3 construct (such as anti-CD3 TMATE monoclonal or multispecific antibodies).

In some embodiments, the effective amount of the anti-CD3 construct (such as anti-CD3 TMATE monoclonal or multispecific antibodies) alone or in combination with a second, third, and/or fourth agent, is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment (e.g., receiving a placebo treatment). Standard methods can be used to measure the magnitude of this effect, such as in vitro assays with purified enzyme, cell-based assays, animal models, or human testing.

In some embodiments, the effective amount of the anti-CD3 construct (such as anti-CD3 TMATE monoclonal or multispecific antibodies) is an amount that is below the level that induces a toxicological effect (i.e., an effect above a clinically acceptable level of toxicity) or is at a level where a potential side effect can be controlled or tolerated when the composition is administered to the individual.

In some embodiments, the effective amount of the anti-CD3 construct (such as anti-CD3 TMATE monoclonal or multispecific antibodies) is an amount that is close to a maximum tolerated dose (MTD) of the composition following the same dosing regimen. In some embodiments, the effective amount of the anti-CD3 construct (such as anti-CD3 TMATE monoclonal or multispecific antibodies) is no more than about any of 80%, 90%, 95%, or 98% of the MTD.

In some embodiments, the effective amount of the anti-CD3 construct (such as anti-CD3 TMATE monoclonal or multispecific antibodies) is an amount that slows or inhibits the progression of the disease or condition (for example, by at least about 5%, 10%, 15%, 20%, 30%, 40%, 50%) as compared to that of the individual not receiving the treatment. In some embodiments, the disease or condition is an autoimmune disease. In some embodiments, the disease or condition is an infection.

In some embodiments, the effective amount of the anti-CD3 construct (such as anti-CD3 TMATE monoclonal or multispecific antibodies) is an amount that reduces the side effects (auto-immune response) of a condition (e.g., transplantation) (for example, by at least about 5%, 10%, 15%, 20%, 30%, 40%, or 50%) as compared to that of the individual not receiving the treatment.

In some embodiments of any of the above aspects, the effective amount of an anti-CD3 construct (such as anti-CD3 TMATE monoclonal or multispecific antibodies) is in the range of about 0.1 µg/kg to about 100 mg/kg of total body weight, for example, about 1 µg/kg to about 30 mg/kg, about 10 µg/kg to about 10 mg/kg, or about 50 µg/kg to about 5 mg/kg.

In some embodiments of any of the above aspects, the effective amount of an anti-CD3 construct (such as anti-CD3 TMATE monoclonal or multispecific antibodies) is administered to a subject at a dose of at least about 1 mg/kg. In some embodiments, the effective amount of an anti-CD3 construct (such as anti-CD3 TMATE monoclonal or multispecific antibodies) is administered to a human at a dose equivalent to a dose of at least 1 mg/kg in mice. See Nair, A. B., & Jacob, S. (2016). A simple practice guide for dose conversion between animals and human. *Journal of basic and clinical pharmacy*, 7(2), 27.

In some embodiments, the treatment comprises more than one administration of the anti-CD3 constructs (such as about two, three, four, five, six, seven, eight, night, or ten administrations of anti-CD3 TMATE constructs). In some embodiments, two administrations are carried out within about a week. In some embodiments, a second administration is carried out at least about 1, 2, 3, 4, 5, 6, or 7 days after the completion of the first administration. In some embodiments, a second administration is carried out about 1-14 days, 1-10 days, 1-7 days, 2-6 days, or 3-5 days after the completion of the first administration. In some embodiments, the anti-CD3 TMATE construct is administered about 1-3 times a week (such as about once a week, about twice a week, or about three times a week).

The anti-CD3 construct (e.g., the anti-CD3 TMATE construct) can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, transdermal, or a local injection route such as intratumoral injection. In some embodiments, the anti-CD3 construct is included in a pharmaceutical composition while administered into the individual. In some embodiments, sustained continuous release formulation of the composition may be used. In some embodiments, the composition is administered intravenously. In some embodiments, the composition is administered intraperitoneally. In some embodiments, the composition is administered intravenously. In some embodiments, the composition is administered intraperitoneally. In some embodiments, the composition is administered intramuscularly. In some embodiments, the composition is administered subcutaneously. In some embodiments, the composition is administered intravenously. In some embodiments, the composition is administered orally.

Combination Therapies

This application also provides methods of administering an anti-CD3 construct into an individual for treating a disease or condition (such as cancer), wherein the method further comprises administering a second agent or therapy. In some embodiments, the second agent or therapy is a standard or commonly used agent or therapy for treating the disease or condition. In some embodiments, the second agent or therapy comprises a chemotherapeutic agent. In some embodiments, the second agent or therapy comprises a surgery. In some embodiments, the second agent or therapy comprises a radiation therapy. In some embodiments, the second agent or therapy comprises an immunotherapy. In some embodiments, the second agent or therapy comprises a hormonal therapy. In some embodiments, the second agent or therapy comprises an angiogenesis inhibitor. In some embodiments, the second agent or therapy comprises a tyrosine kinase inhibitor. In some embodiments, the second agent or therapy comprises an infectious agent. In some embodiments, the second agent or therapy comprises a vaccine.

In some embodiments, the anti-CD3 construct is administered simultaneously with the second agent or therapy. In some embodiments, the anti-CD3 construct is administered concurrently with the second agent or therapy. In some embodiments, the anti-CD3 construct is administered sequentially with the second agent or therapy. In some embodiments, the anti-CD3 construct is administered in the same unit dosage form as the second agent or therapy. In some embodiment, the anti-CD3 construct is administered in a different unit dosage form from the second agent or therapy.

In some embodiments, the anti-CD3 construct is administered simultaneously with a second agent or therapy that comprises an immune checkpoint inhibitor (IC). In some embodiments, the anti-CD3 construct is administered sequentially with an ICI. In some embodiments, the anti-CD3 construct is administered in a "mixed or alternate order" that involves both simultaneous and sequential administering of one or both of anti-CD3 and the ICI and may involve different doses or different administration routes of the same one or both respectively. In some embodiments, the combination therapy comprising anti-CD3 construct and an ICI comprises an anti-PD-1 antibody, an anti-PD-L1 antibody, an anti-CTLA-4 antibody, an anti-LAG3 antibody, an anti-TIM3 antibody, and anti-TIGIT antibody, or an anti-PD-L2 antibody. In some embodiments, the ICI used in the combination therapy with anti-CD3 construct (e.g., an anti-CD3 TMATE construct) comprises a bispecific antibody recognizing any one or two of the afore-described immune checkpoint molecules. In some embodiments, the anti-PD-1 antibody used in the combination therapy with TMATEs includes without limitation to nivolumab, pembrolizumab, cemiplimab, tislelizumab, toripalimab, sintilimab, serplulimab and retifanlimab. In some embodiments, the anti-PD-1 antibody used in the combination therapy with TMATEs includes without limitation to atezolizumab, durvalumab, avelumab, and envafolimab.

In some embodiments, the anti-CD3 is administered in a combination therapy with a second agent or therapy that comprises an anti-angiogenic agent such as Avastin. In some embodiments, the anti-CD3 is administered in a combination therapy with a second agent that comprises a tyrosine kinase inhibitor (TKI).

In some embodiments, the anti-CD3 construct (e.g., the anti-CD3 TMATE construct) is administered in a combination therapy with a second agent or therapy that comprises a chemotherapeutic agent.

In some embodiments, the anti-CD3 construct (e.g., the anti-CD3 TMATE construct) is administered in a combination therapy with a second agent or therapy that comprises a radiotherapy.

VI. Compositions, Kits and Articles of Manufacture

Also provided herein are compositions (such as formulations) comprising any one of the anti-CD3 constructs (e.g., any of the CD3 TMATE constructs or pH sensitive anti-CD3 antibody moieties described herein), nucleic acid encoding the antibody moieties, vector comprising the nucleic acid encoding the antibody moieties, or host cells comprising the nucleic acid or vector.

Suitable formulations of the anti-CD3 construct (e.g., anti-CD3 TMATE construct) described herein can be obtained by mixing the anti-CD3 construct or anti-CD3 antibody moiety having the desired degree of purity with optional pharmaceutically acceptable carriers, excipients or 'stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be imaged, diagnosed, or treated herein.

The formulations to be used for in vivo administration must be sterile. This is readily accomplished by, e.g., filtration through sterile filtration membranes.

Also provided are kits comprising any one of the anti-CD3 constructs (e.g., any of the anti-CD3 TMATE constructs or pH sensitive anti-CD3 antibody moieties) described herein. The kits may be useful for any of the methods of modulating cell composition or treatment described herein.

In some embodiments, there is provided a kit comprising an anti-CD3 construct (e.g., an anti-CD3 TMATE construct) specifically binding to CD3.

In some embodiments, the kit further comprises a device capable of delivering the anti-CD3 construct into an individual. One type of device, for applications such as parenteral delivery, is a syringe that is used to inject the composition into the body of a subject. Inhalation devices may also be used for certain applications.

In some embodiments, the kit further comprises a therapeutic agent for treating a disease or condition, e.g., cancer, infectious disease, autoimmune disease, inflammatory disorder or transplantation.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information.

The present application thus also provides articles of manufacture. The article of manufacture can comprise a container and a label or package insert on or associated with the container. Suitable containers include vials (such as sealed vials), bottles, jars, flexible packaging, and the like. Generally, the container holds a composition, and may have a sterile access port (for example the container may be an intravenous solution bag or a vial having a stopper pierceable by a hypodermic injection needle). The label or package insert indicates that the composition is used for imaging, diagnosing, or treating a particular condition in an individual. The label or package insert will further comprise instructions for administering the composition to the individual and for imaging the individual. The label may indicate directions for reconstitution and/or use. The container holding the composition may be a multi-use vial, which allows for repeat administrations (e.g. from 2-6 administrations) of the reconstituted formulation. Package insert refers to instructions customarily included in commercial packages of diagnostic products that contain information about the indications, usage, dosage, administration, contraindications and/or warnings concerning the use of such diagnostic products. Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the compositions and instructions for use, packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

The examples below are intended to be purely exemplary of the application and should therefore not be considered to limit the application in any way. The following examples and detailed description are offered by way of illustration and not by way of limitation.
Compositions and Method
Abbreviation of Units Throughout the disclosure, units and the abbreviations follow routine practices as exemplified in the following: picomolar (pM), nanomolar (nM), micromolar (pM), millimolar (mM), molar (M), nanogram (ng), microgram (µg), milligram (mg), gram (g), microliter (µl or µL), milliliter (ml or mL), liter (l or L), nanometer (nm), micrometer (µm), meter (m), minute (min), hour (h or hr), mean fluorescence intensity (MFI).

Reporter Cell Line

An ZsGreen expression cassette under the control of responsive elements for nuclear factor of activated T-cells (NFAT) and API was introduced into Jurkat cells, a human T cell line. One of the derived single cell clones (dubbed Jurkat-D1 or Jurkat reporter cell) with favorable fast kinetics of activation was amplified and used as a reporter cell for T cell activation by CD3 binding antibodies in studies that are connected with the current disclosure.

Example 1: Antibody Discovery, Expression and Purification

Plasma cells were isolated from CD3 antigen immunized mice, encapsulated with Jurkat-D1 reporter cells using a conventional droplet generation device to achieve one plasma cell and one or more Jurkat-D1 reporter cells per droplet in a plurality of droplets. The droplets were incubated in conventional $CO_2$ incubator at 37° C. for about 6 to 9 hours to allow T cell reporter activation. Droplets with a single activating antibody were sorted based on Jurkat-DI reporter ZsGreen fluorescence. Single plasma cells were individually lysed and the antibody sequences were individually amplified and retrieved using reverse transcription and then polymerase chain reaction (RT-PCR). See for example, US20180321130A1, WO2020/076730A1, PCT/US2020/035340 and U.S. 63/120,384, all of which are hereby incorporated herein by reference in their entirety. Antibody sequences were assembled into a human IgG1 expression vector as chimeric antibodies and expressed in the regular Expi293 or 293F or CHO suspension cells through routine transient DNA transfection. The antibody purification was in part performed using Protein A affinity chromatography followed by polishing steps with gel filtration chromatography (AKTApure FPLC system, GE Healthcare, Chicago, IL, USA). Optional QC and biophysical analysis of purified proteins and antibodies were in part performed using High Pressure Liquid Chromatography (HPLC) approaches (Agilent 1100 system, Santa Clara, CA, USA).

Various anti-CD3 antibodies were generated and sequenced. See Tables 3 and 4 below.

TABLE 3

$V_H$ CDRs of various antibodies and consensus sequences.

|  | CDRH1 | CDRH2 | CDRH3 |
| --- | --- | --- | --- |
| h10.v1 | SYYVH (SEQ ID NO: 1) | WIYPGDFNTKFNEKFKG (SEQ ID NO: 2) | DAYSYYYFDY (SEQ ID NO: 3) |
| h10.v7 | SYYVH (SEQ ID NO: 1) | WIYPGDFNTKFNEKFKG (SEQ ID NO: 2) | DHYSYYYFDY (SEQ ID NO: 9) |
| h10.v9 | SYYVH (SEQ ID NO: 1) | WIYPGDFNTKFNEKFKG (SEQ ID NO: 2) | DAYHYYYFDY (SEQ ID NO: 10) |
| h10.v16 | SYYVH (SEQ ID NO: 1) | WIYPGDFNTKFNEKFKG (SEQ ID NO: 2) | DHYHYYYFDY (SEQ ID NO: 11) |
| h10.v17 | SYYVH (SEQ ID NO: 1) | WIYPGDFNTHFNEKFKG (SEQ ID NO: 7) | DAYSYYYFDY (SEQ ID NO: 3) |
| h10.v18 | SYYVH (SEQ ID NO: 1) | WIYPGDFNTHFNEKFKG (SEQ ID NO: 7) | DAYSYYYFDY (SEQ ID NO: 3) |
| h10.v19 | SYYVH (SEQ ID NO: 1) | WIYPGDFNTKFNEKFKG (SEQ ID NO: 2) | DHYGYYYFDY (SEQ ID NO: 12) |

TABLE 3-continued

V_H CDRs of various antibodies and consensus sequences.

| | CDRH1 | CDRH2 | CDRH3 |
|---|---|---|---|
| h10.v20 | SYYVH (SEQ ID NO: 1) | WIYPGDFNTKFNEKFKG (SEQ ID NO: 2) | DHYGYYYFDY (SEQ ID NO: 12) |
| h10.v21 | SYYVH (SEQ ID NO: 1) | WIYPGDFNTKFNEKFKG (SEQ ID NO: 2) | DHYSYYYFDY (SEQ ID NO: 9) |
| h10.v22 | SYYVH (SEQ ID NO: 1) | WIYPGDFNTKFNEKFKG (SEQ ID NO: 2) | DHYGYYYFDY (SEQ ID NO: 12) |
| h10.v23 | SYYVH (SEQ ID NO: 1) | WIYPGDFNTKFNEKFKG (SEQ ID NO: 2) | DHYGYYYFDY (SEQ ID NO: 12) |
| h10.v24 | SYYVH (SEQ ID NO: 1) | WIYPGDFNTKFNEKFKG (SEQ ID NO: 2) | DHYGYYYFDY (SEQ ID NO: 12) |
| h10.v25 | SGYVH (SEQ ID NO: 4) | WIYPGDFNTKFNEKFKG (SEQ ID NO: 2) | DHYGYYYFDY (SEQ ID NO: 12) |
| h10.v26 | SYYTH (SEQ ID NO: 5) | WIYPGDFNTKFNEKFKG (SEQ ID NO: 2) | DHYGYYYFDY (SEQ ID NO: 12) |
| h10.v27 | SYYYH (SEQ ID NO: 6) | WIYPGDFNTKFNEKFKG (SEQ ID NO: 2) | DHYGYYYFDY (SEQ ID NO: 12) |
| h10.v28 | SYYVH (SEQ ID NO: 1) | WIGPGDFNTKFNEKFKG (SEQ ID NO: 8) | DHYGYYYFDY (SEQ ID NO: 12) |
| h10.v29 | SYYVH (SEQ ID NO: 1) | WIYPGDFNTKFNEKFKG (SEQ ID NO: 2) | DHYHYYYFDY (SEQ ID NO: 11) |
| h10.v30 | SYYVH (SEQ ID NO: 1) | WIYPGDFNTHFNEKFKG (SEQ ID NO: 7) | DHYGYYYFDY (SEQ ID NO: 12) |
| h10.v31 | SYYYH (SEQ ID NO: 6) | WIYPGDFNTHFNEKFKG (SEQ ID NO: 7) | DHYGYYYFDY (SEQ ID NO: 12) |
| h10.v32 | SYYYH (SEQ ID NO: 6) | WIYPGDFNTKFNEKFKG (SEQ ID NO: 2) | DHYHYYYFDY (SEQ ID NO: 11) |
| h10.v33 | SYYVH (SEQ ID NO: 1) | WIYPGDFNTKFNEKFKG (SEQ ID NO: 2) | DHYHYYYFDY (SEQ ID NO: 11) |
| h10.v34 | SYYYH (SEQ ID NO: 6) | WIYPGDFNTKFNEKFKG (SEQ ID NO: 2) | DHYHYYYFDY (SEQ ID NO: 11) |
| h10.v35 | SYYYH (SEQ ID NO: 6) | WIYPGDFNTKFNEKFKG (SEQ ID NO: 2) | DHYHYYYFDY (SEQ ID NO: 11) |
| h10.v36 | SYYYH (SEQ ID NO: 6) | WIYPGDFNTKFNEKFKG (SEQ ID NO: 2) | DHYHYYYFDY (SEQ ID NO: 11) |
| h10.v38 | SYYYH (SEQ ID NO: 6) | WIYPGDFNTKFNEKFKG (SEQ ID NO: 2) | DHYGYYYFDY (SEQ ID NO: 12) |
| h10.v39 | SYYTH (SEQ ID NO: 5) | WIYPGDFNTKFNEKFKG (SEQ ID NO: 2) | DHYGYYYFDY (SEQ ID NO: 12) |
| h10.v48 | SYYYH (SEQ ID NO: 6) | WIYPGDFNTKFNEKFKG (SEQ ID NO: 2) | DHYHHYYFDY (SEQ ID NO: 13) |
| h10.v49 | SYYYH (SEQ ID NO: 6) | WIYPGDFNTKFNEKFKG (SEQ ID NO: 2) | DHYHQYYFDY (SEQ ID NO: 14) |
| h10 consensus sequence | $SX_1YX_2H$ $X_1$ = G or Y, $X_2$ = V, Y, or T (SEQ ID NO: 15) | $WIX_1PGDFNTX_2FNEKFK$ G $X_1$ = G or Y, $X_2$ = H or K (SEQ ID NO: 16) | $DX_1YX_2X_3YYFDY$ $X_1$ = A or H, $X_2$ = S, H, or G, $X_3$ = H, Q, or Y (SEQ ID NO: 17) Or $DX_1YX_2X_3YYFDY$ $X_1$ = A or H, $X_2X_3$ = SY, HY, GY, HH, or HQ (SEQ ID NO: 18) |
| h24.v1 | DFYMN (SEQ ID NO: 19) | WIAPETGNTIYDPKFQG (SEQ ID NO: 20) | DSYGWYYFDY (SEQ ID NO: 21) |

TABLE 3-continued

V<sub>H</sub> CDRs of various antibodies and consensus sequences.

|  | CDRH1 | CDRH2 | CDRH3 |
|---|---|---|---|
| h24.v2 | DFYMN (SEQ ID NO: 19) | WIAPETGNTIYDPKFQG (SEQ ID NO: 20) | DSYGYYYFDY (SEQ ID NO: 22) |

TABLE 4

VL CDRs of various antibodies and consensus sequences.

|  | CDRL1 | CDRL2 | CDRL3 |
|---|---|---|---|
| h10.v1 | KSSQSLLNSRTRKNYLA (SEQ ID NO: 23) | WATTRDS (SEQ ID NO: 24) | IQSYTTRT (SEQ ID NO: 25) |
| h10.v7 | KSSQSLLNSRTRHNYLA (SEQ ID NO: 26) | WATTRDS (SEQ ID NO: 24) | IQSYTTRT (SEQ ID NO: 25) |
| h10.v9 | KSSQSLLNSRTRHNYLA (SEQ ID NO: 26) | WATTRDS (SEQ ID NO: 24) | IQSYTTRT (SEQ ID NO: 25) |
| h10.v16 | KSSQSLLNSRTRHNYLA (SEQ ID NO: 26) | WATTRDS (SEQ ID NO: 24) | IQSYTTRT (SEQ ID NO: 25) |
| h10.v17 | KSSQSLLNSRTRKNYLA (SEQ ID NO: 23) | WATTRDS (SEQ ID NO: 24) | IQSYTTRT (SEQ ID NO: 25) |
| h10.v18 | KSSQSLLNSRTRHNYLA (SEQ ID NO: 26) | WATTRDS (SEQ ID NO: 24) | IQSYTTRT (SEQ ID NO: 25) |
| h10.v19 | KSSQSLLNSRTRHNYLA (SEQ ID NO: 26) | WATTRDS (SEQ ID NO: 24) | IQSYTGRT (SEQ ID NO: 31) |
| h10.v20 | KSSQSLLNSRTRHNYLA (SEQ ID NO: 26) | WATTRDS (SEQ ID NO: 24) | IQSYTTRT (SEQ ID NO: 25) |
| h10.v21 | KSSQSLLNSRTRHNYLA (SEQ ID NO: 26) | WATTRDS (SEQ ID NO: 24) | IQSYTGRT (SEQ ID NO: 31) |
| h10.v22 | KSSQSLLNSRTGHNYLA (SEQ ID NO: 27) | WATTRDS (SEQ ID NO: 24) | IQSYTGRT (SEQ ID NO: 31) |
| h10.v23 | KSSQSLLNSRTRHNYLA (SEQ ID NO: 26) | WATTRAS (SEQ ID NO: 28) | IQSYTGRT (SEQ ID NO: 31) |
| h10.v24 | KSSQSLLNSRTRHNYLA (SEQ ID NO: 26) | WATTRDS (SEQ ID NO: 24) | AQSYTGRT (SEQ ID NO: 32) |
| h10.v25 | KSSQSLLNSRTRHNYLA (SEQ ID NO: 26) | WATTRDS (SEQ ID NO: 24) | IQSYTGRT (SEQ ID NO: 31) |
| h10.v26 | KSSQSLLNSRTRHNYLA (SEQ ID NO: 26) | WATTRDS (SEQ ID NO: 24) | IQSYTGRT (SEQ ID NO: 31) |
| h10.v27 | KSSQSLLNSRTRHNYLA (SEQ ID NO: 26) | WATTRDS (SEQ ID NO: 24) | IQSYTGRT (SEQ ID NO: 31) |
| h10.v28 | KSSQSLLNSRTRHNYLA (SEQ ID NO: 26) | WATTRDS (SEQ ID NO: 24) | IQSYTGRT (SEQ ID NO: 31) |
| h10.v29 | KSSQSLLNSRTRHNYLA (SEQ ID NO: 26) | WATTRDS (SEQ ID NO: 24) | IQSYTGRT (SEQ ID NO: 31) |
| h10.v30 | KSSQSLLNSRTRHNYLA (SEQ ID NO: 26) | WATTRDS (SEQ ID NO: 24) | IQSYTGRT (SEQ ID NO: 31) |
| h10.v31 | KSSQSLLNSRTRHNYLA (SEQ ID NO: 26) | WATTRDS (SEQ ID NO: 24) | IQSYTGRT (SEQ ID NO: 31) |
| h10.v32 | KSSQSLLNSRTRHNYLA (SEQ ID NO: 26) | WATTRDS (SEQ ID NO: 24) | IQSYTGRT (SEQ ID NO: 31) |
| h10.v33 | KSSQSLLNSRTRHNYLA (SEQ ID NO: 26) | WATTRAS (SEQ ID NO: 28) | IQSYTGRT (SEQ ID NO: 31) |

TABLE 4-continued

VL CDRs of various antibodies and consensus sequences.

| | CDRL1 | CDRL2 | CDRL3 |
|---|---|---|---|
| h10.v34 | KSSQSLLNSRTRHNYLA (SEQ ID NO: 26) | WATTRAS (SEQ ID NO: 28) | IQSYTGRT (SEQ ID NO: 31) |
| h10.v35 | KSSQSLLNSRTRHNYLA (SEQ ID NO: 26) | WASTRAS (SEQ ID NO: 29) | IQSHTGRT (SEQ ID NO: 33) |
| h10.v36 | KSSQSLLNSRTRHNYLA (SEQ ID NO: 26) | WASTRAS (SEQ ID NO: 29) | IQSHTLRT (SEQ ID NO: 34) |
| h10.v38 | KSSQSLLNSRTRHNYLA (SEQ ID NO: 26) | WATTRAS (SEQ ID NO: 28) | IQSYTGRT (SEQ ID NO: 31) |
| h10.v39 | KSSQSLLNSRTRHNYLA (SEQ ID NO: 26) | WATTRAS (SEQ ID NO: 28) | IQSYTGRT (SEQ ID NO: 31) |
| h10.v48 | KSSQSLLNSRTRHNYLA (SEQ ID NO: 26) | WATTRAS (SEQ ID NO: 28) | IQSYTGRT (SEQ ID NO: 31) |
| h10.v49 | KSSQSLLNSRTRHNYLA (SEQ ID NO: 26) | WATTRAS (SEQ ID NO: 28) | IQSYTGRT (SEQ ID NO: 31) |
| h10 consensus sequence | KSSQSLLNSRTX$_1$X$_2$NYLA<br>X$_1$ = R or G, X$_2$ = H or K<br>(SEQ ID NO: 36)<br>or<br>KSSQSLLNSRTX$_1$X$_2$NYLA<br>X$_1$X$_2$ = RK, RH, or GH<br>(SEQ ID NO: 37) | WAX$_1$TRX$_2$S<br>X$_1$ = S or T,<br>X$_2$ = A or D<br>(SEQ ID NO: 38) | X$_1$QSX$_2$TX$_3$RT<br>X$_1$ = I or A,<br>X$_2$ = Y or H,<br>X$_3$ = T, G, or L<br>(SEQ ID NO: 39) |
| h24.v1 | KSSQSLLNSRTRKNYLA (SEQ ID NO: 23) | WASTRES (SEQ ID NO: 30) | KQSYILRT (SEQ ID NO: 35) |
| h24.v2 | KSSQSLLNSRTRKNYLA (SEQ ID NO: 23) | WASTRES (SEQ ID NO: 30) | KQSYILRT (SEQ ID NO: 35) |
| h10 or h24 consensus sequence | KSSQSLLNSRTX$_1$X$_2$NYLA<br>X$_1$ = R or G, X$_2$ = H or K<br>(SEQ ID NO: 36)<br>or<br>KSSQSLLNSRTX$_1$X$_2$NYLA<br>X$_1$X$_2$ = RK, RH, or GH<br>(SEQ ID NO: 37) | WAX$_1$TRX$_2$S<br>X$_1$ = S or T,<br>X$_2$ = A, D, or E<br>(SEQ ID NO: 40) | X$_1$QSX$_2$TX$_3$RT<br>X$_1$ = I, K, or A,<br>X$_2$ = Y or H,<br>X$_3$ = T, G, or L<br>(SEQ ID NO: 41) |

Example 2: Antibody Characterization

A. CD3 ELISA Binding Assay

The CD3 binding ELISA assay was performed in 96-well Maxisorp ELISA plates (Thermo Fisher Scientific, MA, USA) coated with either human or cynomolgus monkey CD3& recombinant antigen at 2 μg/ml in 50 mM carbonate buffer (pH 9.6) at 4° C. for overnight. The plates were then blocked with 200 μL ELISA assay diluents with BSA after discarding the coating solution and washing three times with washing buffer (pH-adjusted 1×PBS+0.05% Tween). About 100 μL. of antibody-containing culture supernatant or diluted purified antibodies (e.g., monovalent Fabs, bivalent monoclonal antibodies and multispecific anti-CD3 TMATEs) were added and incubated for 1 hour at room temperature. The plates were washed three times with pH-adjusted 1×PBS buffer and incubated with horseradish peroxidase (HRP) conjugated with goat anti-human IgG Fc for about 30 minutes (min) to one hour. After washing three times, the bound HRP enzyme was detected by addition of 100 μL/well trimethylamine substrate (BioFX Laboratories, MD, USA) for about 1 to 5 min and then the detection of color was done based on 630 nm absorption. The pH-adjusted 1×PBS buffer of about pH 6.0, 6.1, 6.2, 6.3, 6.4, 6.5, 6.6, 6.7, 6.8, 6.9, 7.0, 7.1, 7.2, 7.3, 7.4, 7.5 or 7.6 can be based on a regular PBS buffer that is substantially the same as the well-known Cold Spring Harbor Lab's recipe which comprises 137 mM NaCl, 2.7 mM KCl, 10 mM Na$_2$HPO$_4$, 1.8 mM KH$_2$PO$_4$, and optionally 1 mM CaCl$_2$ and 0.5 mM MgCl$_2$, wherein the buffer's pH is adjusted using HCl or H$_3$PO$_4$. Alternatively, the pH-adjusted 1×PBS buffers can be based on a modified PBS recipe that comprises 118-146 mM NaCl, 2.7 mM KCl, 10 mM Na$_2$HPO$_4$, 1.8 mM KH$_2$PO$_4$, and optionally 1 mM CaCl$_2$) and 0.1-0.8 mM MgCl$_2$, iron (0-9 mM), sulfide (0.8-5 mM), and optionally further comprising one or more components selected from the following: 5-15 mM D-glucose, NaHCO$_3$ (5-20 mM), 0.1 mM NEAA (non-essential amino acids), 2-20 mM lactic acid and 0.1-0.5% BSA, wherein the buffer's pH is adjusted using HCl or H$_3$PO$_4$.

B. Binding Kinetics Analysis

Kinetics analysis was performed using a Bio-Layer Interferometry approach with a Gator™ system (ProbeLife, Palo alto, CA, USA) or Octet™ system (ForteBio, Fremont, CA, USA). Biotin labeled CD3 was immobilized onto a streptavidin probe, followed by association for 5 min with 3-fold serially diluted antibodies (e.g., monovalent Fabs, bivalent monoclonal antibodies and multispecific anti-CD3 TMATEs) from about 100 nM to about 3.7 nM, followed by dissociation for 10 min. The kinetics was measured with the system's software fitting program. The probe equilibration and kinetic association and dissociation steps were performed using respective pH-adjusted 1×PBS buffers. The pH-adjusted 1×PBS buffers of about pH 6.0, 6.2, 6.3, 6.4, 6.5, 6.6, 6.7, 6.8, 6.9, 7.0, 7.1, 7.2, 7.3, 7.4, 7.5 or 7.6 are substantially the same as described in the foregoing section A in this Example 2.

C. In Vitro Cell Binding Assays

For in vitro cell surface binding assays, cells were harvested by centrifugation, washed, and resuspended as single cell suspension, and the cell number were adjusted to a concentration of one to five million cells/ml in ice cold FACS buffer (1×PBS plus 0.5-1% BSA or 5-10% FBS). Cells were either stained in polystyrene round-bottom 12×75-mm BD Falcon tubes or regular Eppendorf tubes or 96-well round-bottom microtiter plates. About 100 μl of cell suspension was added to each tube and optionally blocked using 100 μl of a FcR blocking reagent (diluted in FACS buffer per manufacturer manual). Cells were incubated on ice for about 20 minutes (min), pelleted via centrifugation at 300×g for 5-10 min at 4° C., and the cell pellets were resuspended and added with 0.1-10 μg/ml of a diluted primary such as monovalent anti-CD3 Fabs, bivalent monoclonal antibodies and TMATEs. Resuspended cells were incubated with the respective primary antibodies for at least 30 min at room temperature or 4° C. in the dark. Next, the cells were washed for three times to remove unbound primary antibodies, e.g., by pelleting by centrifugation at 300×g for 5-10 min and resuspension in 200-1000 μl of ice cold FACS buffer. Next, the cells were resuspended for labeling with a fluorescently labeled secondary antibody in FACS buffer with the optimal dilution and incubation duration per manufacturer's instructions, at room temperature or 4° C. in the dark. Finally, cells were washed for one to three times by centrifugation at 300×g for 5-10 min and resuspended in 100-1000 μl of ice cold FACS buffer, followed by a regular flow cytometry analysis. For pH-dependent cell binding assays, the pH of the FACS buffer was adjusted with HCl or $H_3PO_4$ to reach the desired pHs (e.g., about pH 6.0, pH 6.3, pH 6.4, pH 6.5, pH 6.6, pH 6.7, pH 6.8, pH 6.9, pH 7.0, pH 7.1, pH7.2, pH 7.3, pH 7.4, pH 7.5 and/or pH 7.6).

D. In Vitro Human T Cell Activation and Cytotoxicity Assays

About 10,000 target cells (e.g., e.g., the $HER2^{high}$ tumor cell lines BT474 and SBKR3, $HER2^{low}$ cell line MCF7, TROP-$2^{high}$ cell lines MDA-MB-468 or BT-20, or TROP-$2^{low}$ MDA-MB-231 or keratinocytes) were plated in 96-well plates on day 0. Human pan T cells isolated from a donor's peripheral mononuclear cells (PBMCs) were co-cultured with tumor cells in T cell culture medium (RPMI-1640 with 10% fetal bovine serum (FBS), 1× penicillin-streptomycin, 4 mM L-Glutamine, 1 mM sodium pyruvate, 4.5 g/L D-Glucose, 0.1 mM NEAA, 50 μM β-mercaptoethanol, 10 μM HEPES) at an effector:tumor cell (E:T) ratio of about 12:1 to about 5:1 on a later day (e.g. day 1). As a control, pan T cells alone were also plated into 96-well plates in the absence of tumor cells. T cell-mediated multispecific antibodies such as anti-CD3 TMATEs and conventional TMAs were prepared in culture medium using serial dilutions, then added to achieve a final concentration ranging from about 1 μM to about 30 nM or up to about 400 nM on a need basis. About 48-72 hours post the co-incubation, T cells were collected for flow cytometry analysis, wherein the cells were stained with 7-AAD as well as with the desired primary antibodies such as anti-CD3, anti-CD4, anti-CD8, anti-CD69, anti-CD25, anti-PD1 and anti-CD137. T cell activation was measured by the percentage of cells positive for early activation markers (e.g. $CD69^+$, $CD25^+$ and/or $CD137^+$) for both $CD4^+$ T cells and $CD8^+$ T cells, after gating out the debris (using the FSC/SSC gating), gating the singlets (SSC-A/SSC-H) and gating the viable T Cells (7-AAD$^-$/CD3$^+$). As a control for nonspecific T cell activation not driven by the target-bound TMAs, the tubes/wells containing T cells only treated with the TMAs in the absence of target tumor cells were also analyzed. The percentages of T cell activation specifically mediated by the tumor cells and the TMAs were obtained by gating on the T-cell-only conditions without adding any TMA. The median fluorescence intensity corresponding to the human CD69 and/or CD25 staining was used to compare the T cell activation that is driven by the TMAs.

For the T cell cytotoxicity assay, tumor cell layer was gently washed with 1×PBS about 48-72 hours post the co-culturing. Cell viability reagent (Cell Counting Kit-8, Sigma, MO, USA) was added to the cells in fresh T cell culture medium at a 1:10 dilution or according to the manufacturer's instruction. Following an incubation period of about 3 hours, the absorbance was typically measured at the 450-nm wavelength with a BioTek reader (Tecan, Switzerland). The percentages of dead tumor cells were analyzed using the mock control wells (T cells+tumor cells) as baseline level.

E. Cytokine Release Assay

Purified pan-T-cells from a single human donor were incubated with or without target-positive cells (e.g., the $HER2^{high}$ cell lines BT474 and SBKR3, the $HER2^{low}$ cell line MCF7, the TROP-$2^{high}$ MDA-MB-468 or BT-20 cells, the TROP-$2^{med-low}$ cells MDA-MB-231 or keratinocytes) on a 96-well Maxisorp ELISA plates (Thermo Fisher Scientific, MA, USA) in the presence of varying concentrations of CD3×HER2 multispecific antibodies. Each multispecific antibody was tested in an eight-point, serial of typically about three-fold dilutions from about 10 nM to about 6 μM. Dilutions of T cells, tumor cells, and antibodies were performed in T cell culture (RPMI-1640 or D-MEM with 10% FBS, 1× Penicillin-Streptomycin, 4 mM L-Glu, 1 mM sodium pyruvate, 4.5 g/L D-Glucose, 0.1 mM NEAA, 50 μM β-mercaptoethanol, and 10 μM HEPES). Quantitation of cytokines (e.g., IL-2, IFNγ, TNFα, IL-10, IL-6, IL-8, CXCL10) from the culture supernatant was performed by ELISA according to the kit manufacturer's protocols using harvested supernatants diluted 1:2 to 1:200 in 1× assay diluent (BioLegend, San Diego, USA). Absorbance at 450 nm was read on a BioTek plate reader (Tecan, Switzerland). A custom standard curve was generated for each assay kit.

Example 3

Figure 48:
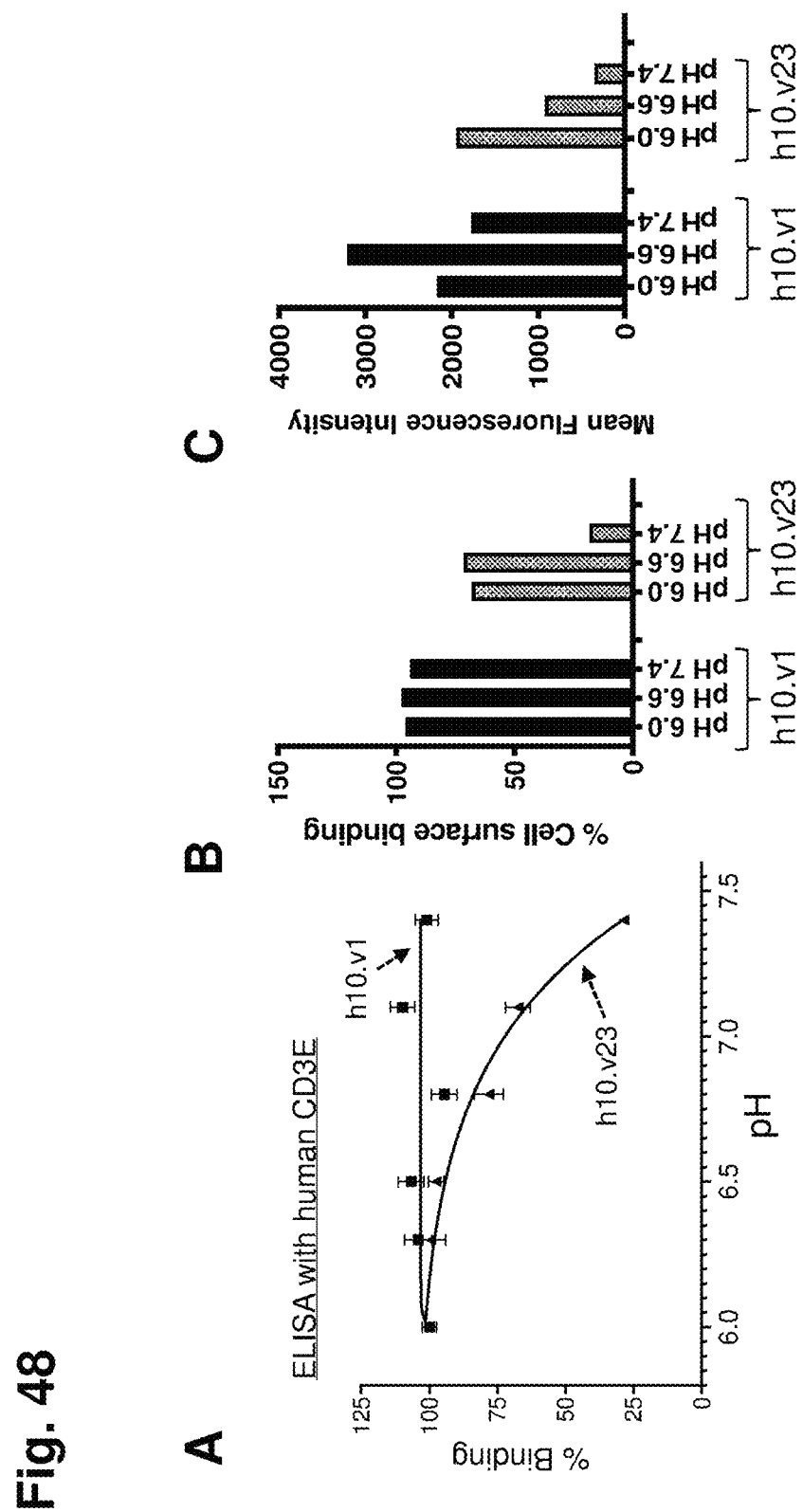
FIG. 48 (left, A) shows an ELISA based binding activity of anti-CD3 clone h10.v23 (Fab) with recombinant human CD3E (ECD) in a pH-dependent manner.

Characterization of a pH-dependent anti-CD3 clone comprising h10.v23. ELISA based binding assay was performed, showing preferred binding of h10.v23 (purified and used as a Fab) under low pHs of about 6.0-6.6 towards recombinant human CD3E (FIG. 48, left panel A), and towards human primary T cells (FIG. 48, middle and right panel B and C), wherein h10.v1 serves as a control (a conventional anti-CD3).

Figure 49:
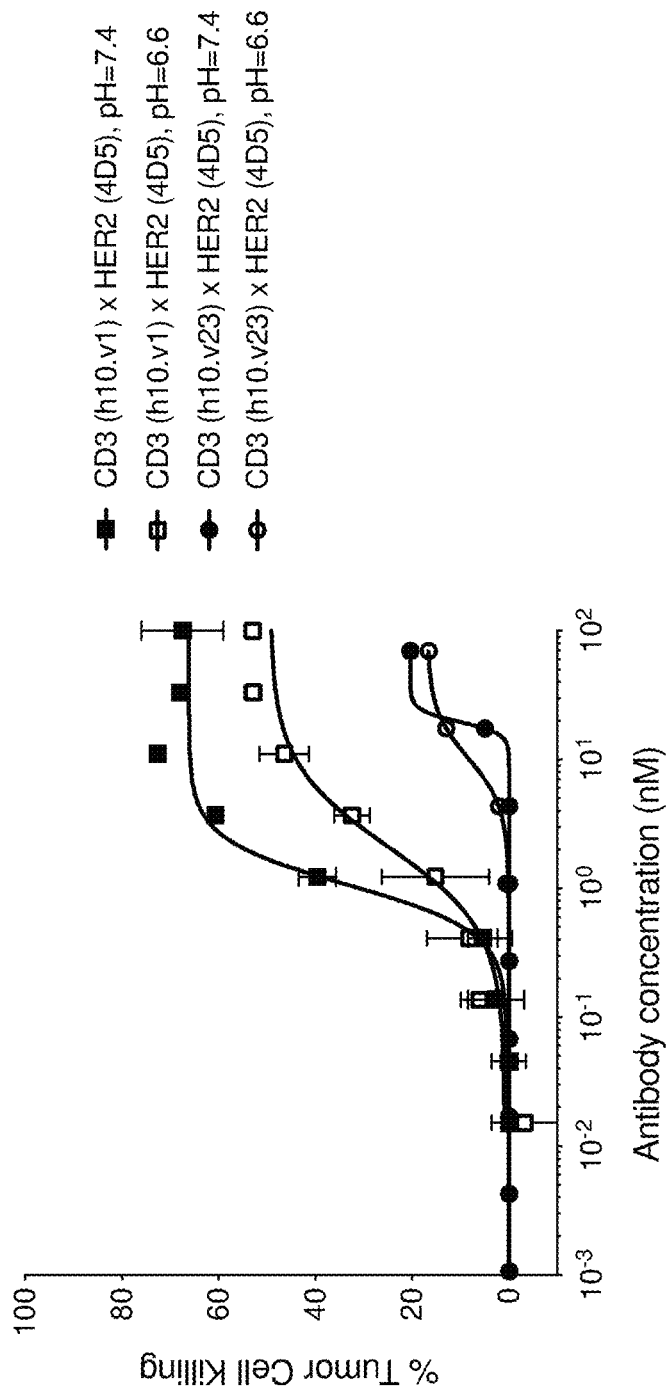
FIG. 49 shows T cell mediated tumor-cell killing assays for a CD3 (h10.v23)×HER2 (4D5) hIgG1-Fc (KiH) bispecific antibody over a dose range, showing that the killing activity is not dependent on the pH (i.e., no significant difference between about pH 6.6 and about pH 7.4; p>0.05, two-way ANOVA). Here CD3 (h10.v1)×HER2 (4D5) hIgG1-Fc (KiH) serves as a conventional control TMA showing robust killing activity under both pH 6.6 and pH 7.4 conditions.

Next, a multispecific antibody, CD3 (h10.v23)×HER2 (4D5) hIgG1-Fc (KiH) that comprises a h10.v23 Fab and a HER2 4D5 scFv was prepared for primary T cells mediated target cell killing assay, wherein the target tumor cell was BT474 (a $HER2^{high}$ cell line). As shown in FIG. 49, CD3 (h10.v23)×HER2 (4D5) hIgG1-Fc (KiH) did not induce pH-dependent differential killing activities under a pH 6.6 versus a pH 7.4 assay condition (p>0.05, two-way ANOVA analysis). In contrast, the control bispecific antibody comprising CD3 (h10.v1)×HER2 (4D5) hIgG1-Fc (KiH) showed potent killing activities under both pHs, wherein the killing activity was higher under the pH 7.4 condition than under pH 6.6 (p<0.05, two-way ANOVA analysis). These results clearly indicate that the positive pH-dependent binding activity of an anti-CD3 clone does not readily translate to pH-dependent killing activity, in part due to the exquisite biological nature of the T Cell Receptor signaling machinery that entails the substantial engineering and optimization of a TMATE to ultimately achieve the optimal pH-dependent killing activity.

Example 4

Characterization of an anti-CD3 antibody clone comprising h10.v32 or h10.v34. ELISA based binding assay was performed, showing preferred binding of h10.v32 and h10.v34 (purified and used as a Fab) under low pHs of about 6.0-6.6 and virtually no binding under about pH 7.4 towards the recombinant human CD3E (FIG. 50, top panel A), respectively, wherein h10.v1 served as a control (a conventional anti-CD3).

Next, a multispecific antibody with hIgG1-Fc (KiH) that comprises a h10.v32 (or h10.v34) Fab and an anti-HER2 4D5 scFv was prepared for primary T cells mediated target cell killing assay, wherein the target tumor cell was BT474 ($HER2^{high}$). As indicted in FIG. 50 bottom panel B, none of the two multispecific antibodies induced any significant killing activity under either pH 6.6 or pH 7.4 even at a very high dose (as high as 200 nM). In contrast, the control antibody as described in Example 3, comprising CD3 (h10.v1)×HER2 (4D5) hIgG1-Fc (KiH), showed potent killing activities under both pH 6.6 or 7.4, particularly at a treatment dose of 1 nM or higher. These results further strengthen the notion that the positive pH-dependent binding activity of anti-CD3 antibodies cannot be readily converted to a favorable or evident pH-dependent killing activity, in part due to the exquisite nature of the T Cell Receptor signaling machinery that entails extensive engineering efforts to ultimately achieve the optimal pH-dependent killing activity for relevant therapeutic uses.

Example 5

A bispecific antibody that comprises an anti-CD3 Fab derived from any one of the disclosed pH selective CD3 antibodies, and an anti-TROP-2 scFv, was assembled, prepared, and formulated as a pharmaceutical composition to treat human subjects with bladder cancer, breast cancer, ovarian cancer, head and neck cancer, colon cancer, and/or NSCLC.

Example 6

An asymmetric bispecific molecule that comprises an anti-CD3 scFv derived from any one of the disclosed pH selective CD3 antibodies, and an anti-GPC3 Fab, is prepared and formulated as a pharmaceutical composition to treat human subjects with GPC3-high cancer such as liver cancer.

Example 7

An asymmetric bispecific molecule that comprises an anti-CD3 Fab derived from any one of the disclosed pH sensitive CD3 antibodies, and an anti-CEA Fab, is prepared and formulated as a pharmaceutical composition to treat human subjects with metastatic non-small cell lung carcinoma.

Example 8

An asymmetric bispecific molecule that comprises any one of the disclosed pH sensitive CD3 antibodies, and an anti-HER2 single domain antibody (e.g., llama $V_HH$-only antibody), is prepared and formulated as a pharmaceutical composition to treat human subjects with advanced breast cancer or metastatic gastric cancer.

Example 9

An asymmetric trispecific molecule that comprises any one of the disclosed pH sensitive CD3 antibodies, an anti-CD28 scFv (e.g., clone 5.11 A1), and an anti-HER2 scFv, is prepared and formulated as a pharmaceutical composition to treat human subjects with advanced breast cancer or metastatic gastric cancer.

Example 10

An asymmetric trispecific molecule that comprises any one of the disclosed pH sensitive CD3 antibodies, a CD80 extracellular domain (ECD), and an anti-gpA33 scFv, is prepared and formulated as a pharmaceutical composition to treat human subjects with relapsed or refractory colorectal cancer.

Example 11

An asymmetric bispecific molecule that comprises any one of the disclosed pH sensitive CD3 antibodies, and a scFv that binds to a NY-ESO-1 peptide restricted by HLA-A2, is prepared and formulated as a pharmaceutical composition to treat human subjects with a variety of cancer types that are positive with NY-ESO-1 tumor neoantigen.

Example 12

An asymmetric bispecific molecule that comprises any one of the disclosed pH sensitive CD3 antibodies, and two or more copies of a lectin domain that binds to certain tumor-associated carbohydrate antigens such as the beta-1,6 glycan and Tn glyan, is prepared and formulated as a pharmaceutical composition to treat human subjects with a variety of cancer types that overexpress such tumor-associated glycans.

Example 13

An asymmetric trispecific molecule that comprises any one of the disclosed pH sensitive CD3 antibodies, an agonistic anti-CD137 scFv, and anti-TAA Fab or scFv, is prepared and formulated as a pharmaceutical composition to treat human subjects with a variety of cancer types that overexpress such TAA.

Example 14

An asymmetric trispecific molecule that comprises any one of the disclosed pH sensitive CD3 antibodies, an anti-CD276 antibody domain, and an anti-CD33 scFv or single domain antibody, is prepared and formulated as a pharmaceutical composition to treat human subjects with acute myeloid leukemia.

Example 15A

A common light chain antibody that comprises an anti-CD3 Fab derived from any one of the disclosed pH selective CD3 antibodies, and an anti-EpCAM moiety (such as a scFv or a Fab or a $V_H$-only), is assembled, prepared, and formulated as a pharmaceutical composition to treat human subjects with bladder cancer, breast cancer, ovarian cancer, head and neck cancer, colon cancer, and/or NSCLC.

Example 15B

A multispecific TMATE comprising CD3 (h10.v39)×HER2 (4D5) hIgG1-Fc (KiH) was formulated in either a PBS buffer of pH 7.4 or an alternative histidine acerate buffer of pH 5.5. This TMATE formulated in either of the two buffering conditions showed potent target cell (BT474) killing activity under culture condition of pH 6.6 or 6.7 (data not shown), with comparable potency as those described in FIGS. 18 and 20, indicating that the TMATE's activity can be reversed from an initial buffering condition of about physiological pH (pH 7.4), that it is not affected by further acidified storage condition or formulations of pH 5.5 either.

Example 16

A multispecific TMATE comprising CD3 (h10.v38)×TROP-2 (RS7.v1) hIgG1-Fc (KiH) was formulated in a histidine acerate buffer of pH 5.5 or a PBS buffer of pH 7.4. This TMATE was used to treat a prostate cancer model cell line, DU-145 expressing a medium-low TROP-2 level (TROP-2$^{med-low}$) in the presence of human primary T cells isolated from donor #201538 blood specimen.

Figure 51:
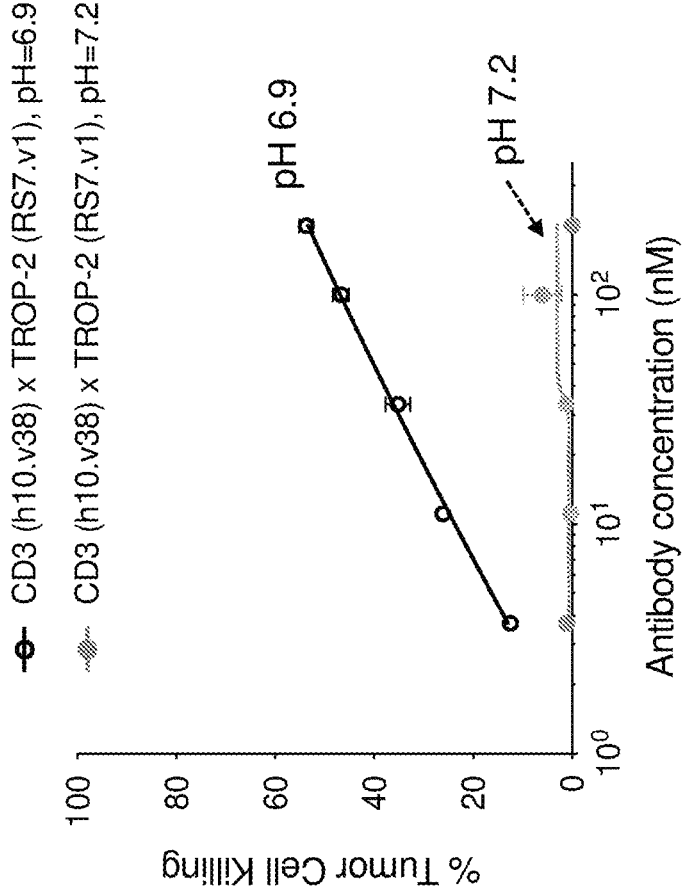
FIG. 51 shows a pH-dependent tumor cell killing assay of prostate cancer cell line DU-145 with CD3 (h10.v38)×TROP-2(RS7) bispecific T-MATE, wherein Pan T cells from the donor were used at an E:T ratio of 11:1 over the course of 3 days.

As shown in FIG. 51, DU-145 cells were potently killed by CD3 (h10.v38)×TROP-2 (RS7.v1) hIgG1-Fc (KiH) mediated by T cells, in a dose and pH dependent manner, showing a EC50 killing activity of about 144 nM under the pH 6.9 condition, whereas the killing activity under pH 7.2 condition was almost completely abolished.

Figure 52:
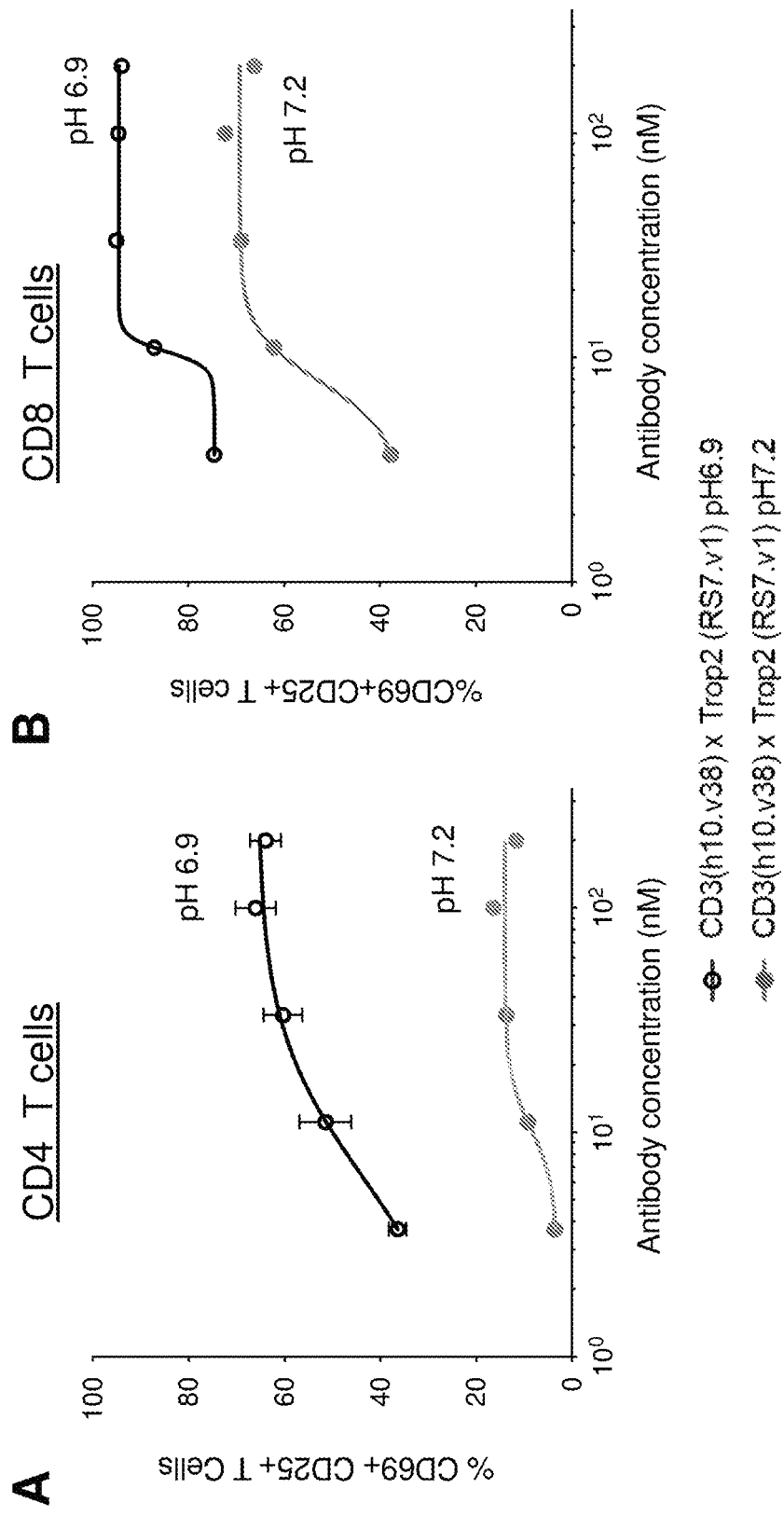
FIGS. 52A-B show T cell activation profile in a pH-dependent tumor cell killing assay (described in FIG. 51) of prostate cancer cell line DU-145 with CD3 (h10.v38)×TROP-2 (RS7.v1) bispecific T-MATE, wherein Pan T cells from the donor (either CD4 T cells in FIG. 52A or CD8 T cells in FIG. 52B) were used at an E:T ratio of 11:1 over the course of 3 days.

Next, as shown in FIG. 52, T cell activation by this TMATE under acidic pH (pH 6.9) was robust, particularly for CD8 T cells.

Figure 53:
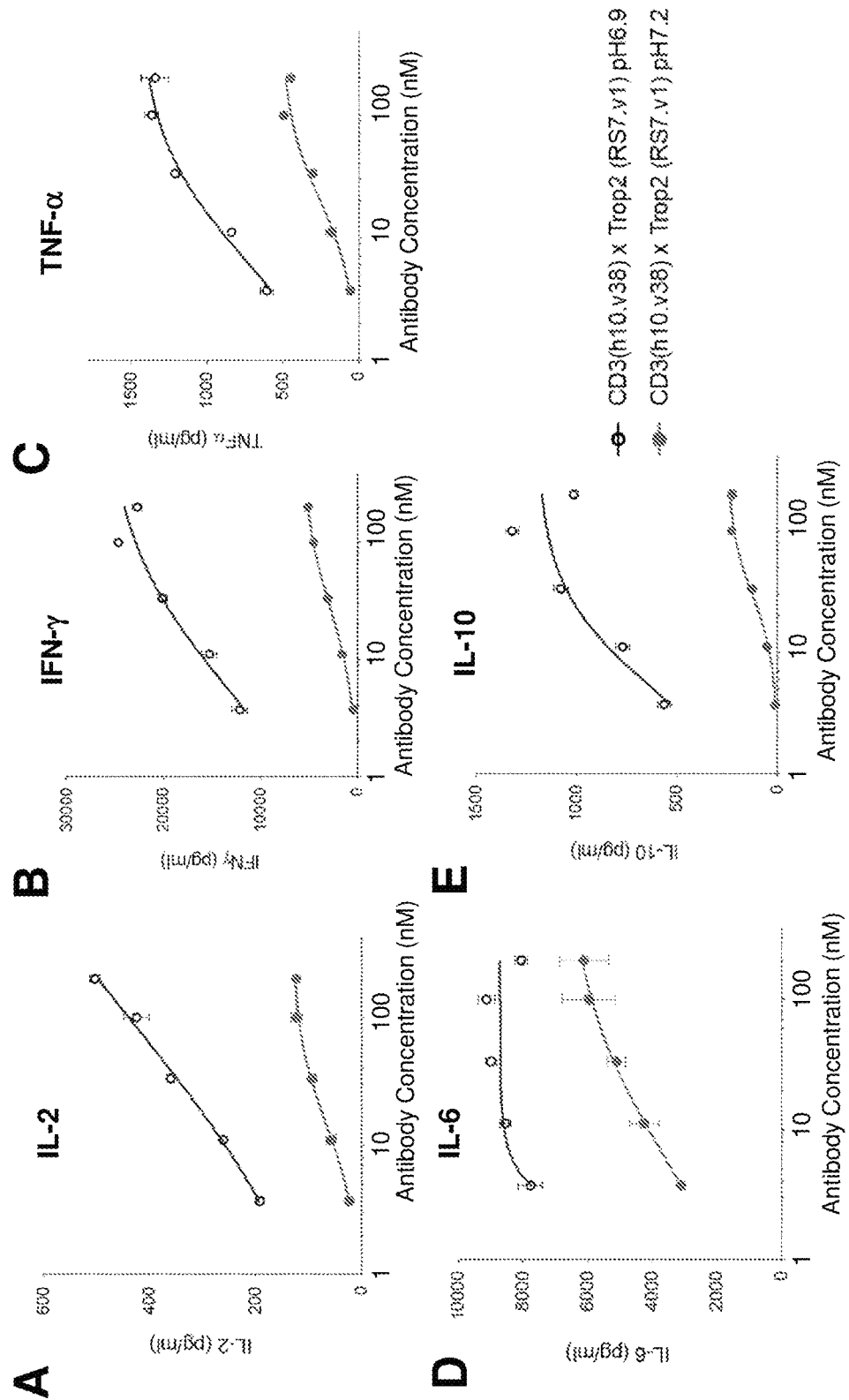
FIGS. 53A-E show cytokine release profile in a pH-dependent tumor cell killing assay (described in FIG. 52) of prostate cancer cell line DU-145 with CD3 (h10.v38)×TROP-2 (RS7.v1) bispecific T-MATE, wherein Pan T cells from the donor were used at an E:T ratio of 11:1 over the course of 3 days. Tested cytokines include IL-2 (FIG. 53A), IFNγ (FIG. 53B), TNFα (FIG. 53C), IL-6 (FIG. 53D), and IL-10 (FIG. 53E).

Lastly, as shown in FIG. 53, cytokine induction (IL-2, IFN-γ, TNF-α, IL-6 and IL-10) by this TMATE was also significantly lower under the pH 7.2 conditions than pH 6.9 for each of these five tested cytokines ($p<0.05$ for each; two-way ANOVA).

Example 17

In vivo anti-tumor efficacy study. Two multispecific TMATEs comprising CD3 (h10.v38)×HER2 (4D5) hIgG1-Fc (KiH) and CD3 (h10.v39)×HER2 (4D5) hIgG1-Fc (KiH) were tested respectively. BT474 cells, a HER2 high expressing breast cancer line, were implanted into NCG (NOD-Prkd$^{cem26Cd52}$Il2rg$^{em26}$/Nju) mice. Human PBMCs were then engrafted into these mice once tumors reached a size of about 80-100 mm$^3$, followed by intravenous administration of the indicated doses of test articles or vehicle control biweekly for 4 weeks. Tumor volumes were measured biweekly (n=8 mice per group).

Figure 54:
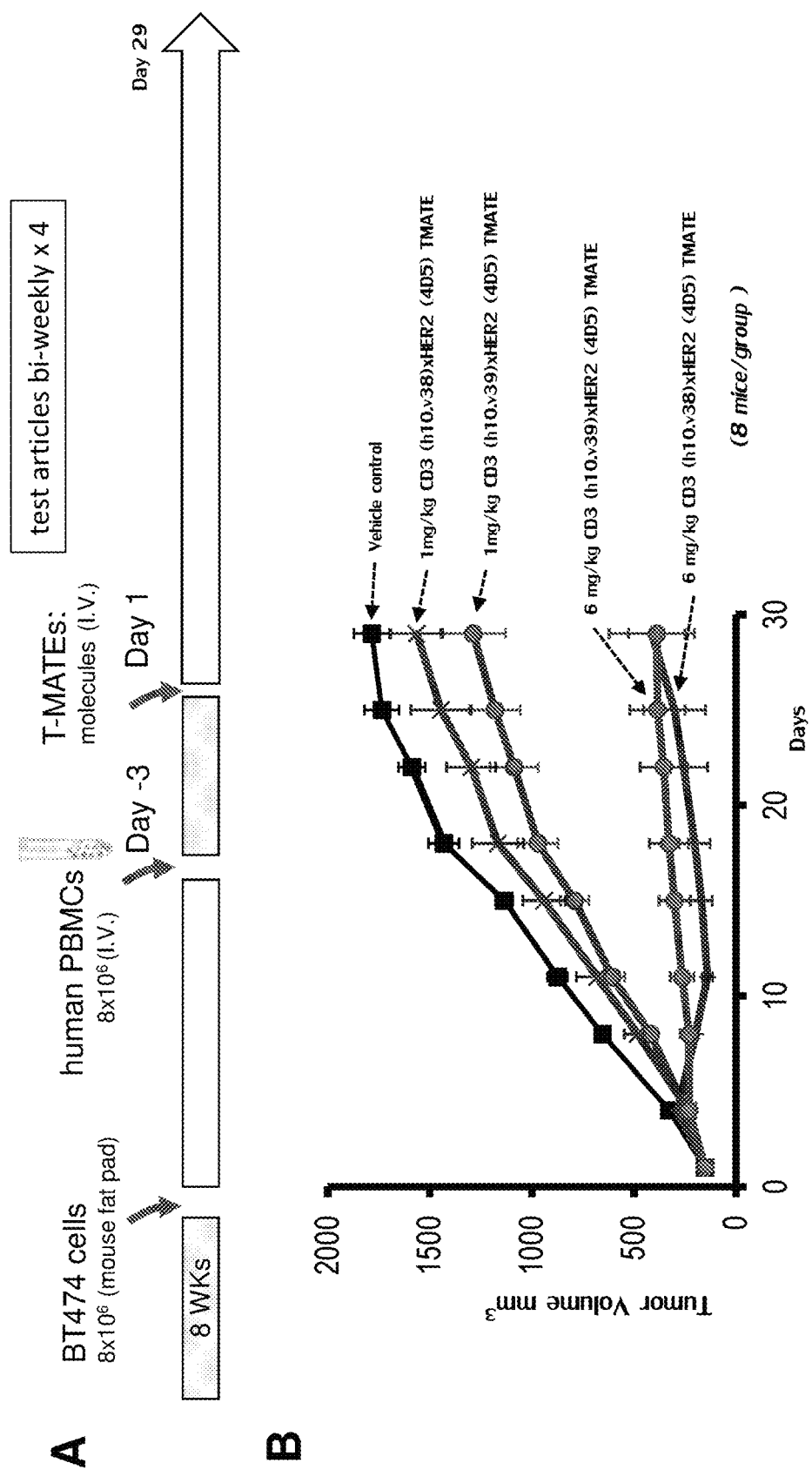
FIG. 54A shows the experimental schedule for the BT474 tumor and human PBMCs transplantations as well as the administration of the two TMATEs at indicated doses.
FIG. 54B shows the anti-tumor activity exhibited by the two TMATEs.
Figure 55:
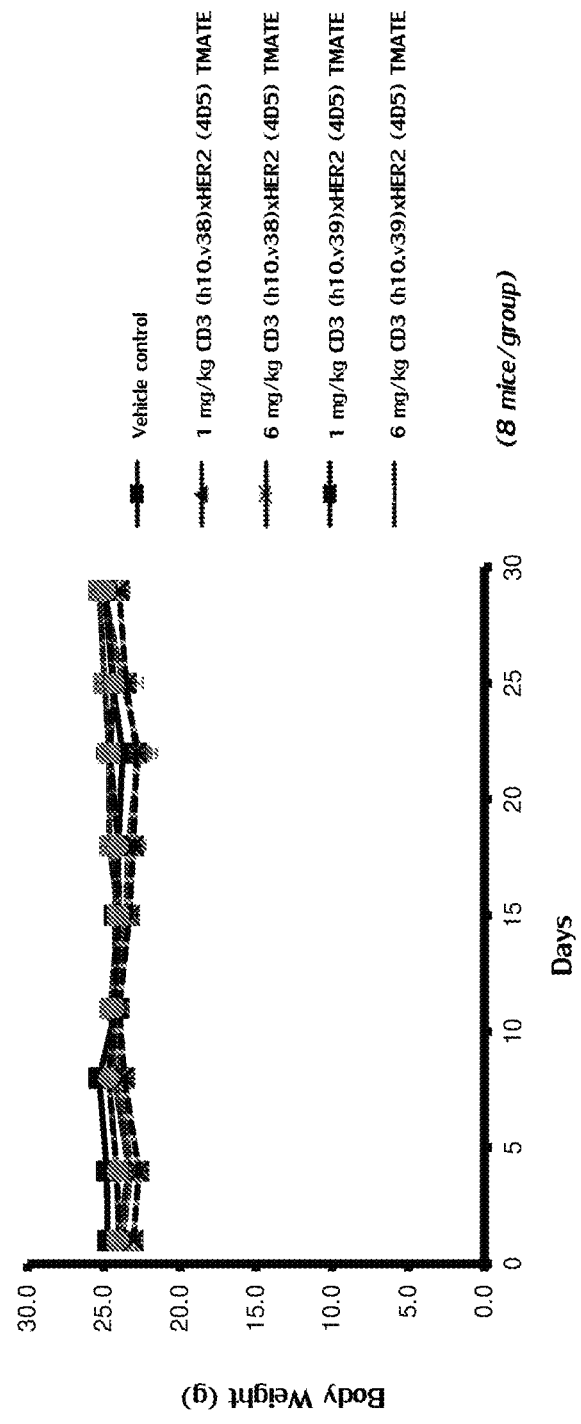
FIG. 55 shows the mice body weight-change over the in vivo study duration, with the highest doses at 6 mg/kg for each of the two test articles.

The experimental schedule for the tumor and human PBMCs transplantations as well as the administration of the two TMATEs is illustrated in FIG. 54 (top panel A). As shown in FIG. 54 (bottom panel B), the two TMATEs exhibited strong anti-tumor activity. Specifically, at the dose of 6 mg/kg, mice treated with either of the tested TMATEs achieved durable complete response. These treatments did not incur significant toxicity to the treated mice as evidenced by the minimum body weight-change over the in vivo study duration. See FIG. 55.

Example 18

In vivo anti-tumor efficacy study. Two multispecific TMATEs comprising CD3 (h10.v38)×TROP-2 (RS7.v1) hIgG1-Fc (KiH) and CD3 (h10.v39)×TROP-2 (RS7.v1) hIgG1-Fc (KiH) were tested respectively. MDA-MB-468 cells, a triple negative (HER2$^-$/ER$^-$/PR$^-$) breast cancer line expressing a moderate level of TROP-2, were implanted into NCG (NOD-Prkd$^{cem26Cd52}$Il2rg$^{em26}$/Nju) mice. Human PBMCs were then engrafted into these mice once tumors reached a size of about 180 mm$^3$, followed by intravenous administration of the indicated doses of test articles or vehicle control biweekly for 3 weeks. Tumor volumes were measured biweekly (n=8 mice per group). See FIG. 56.

Figure 56:
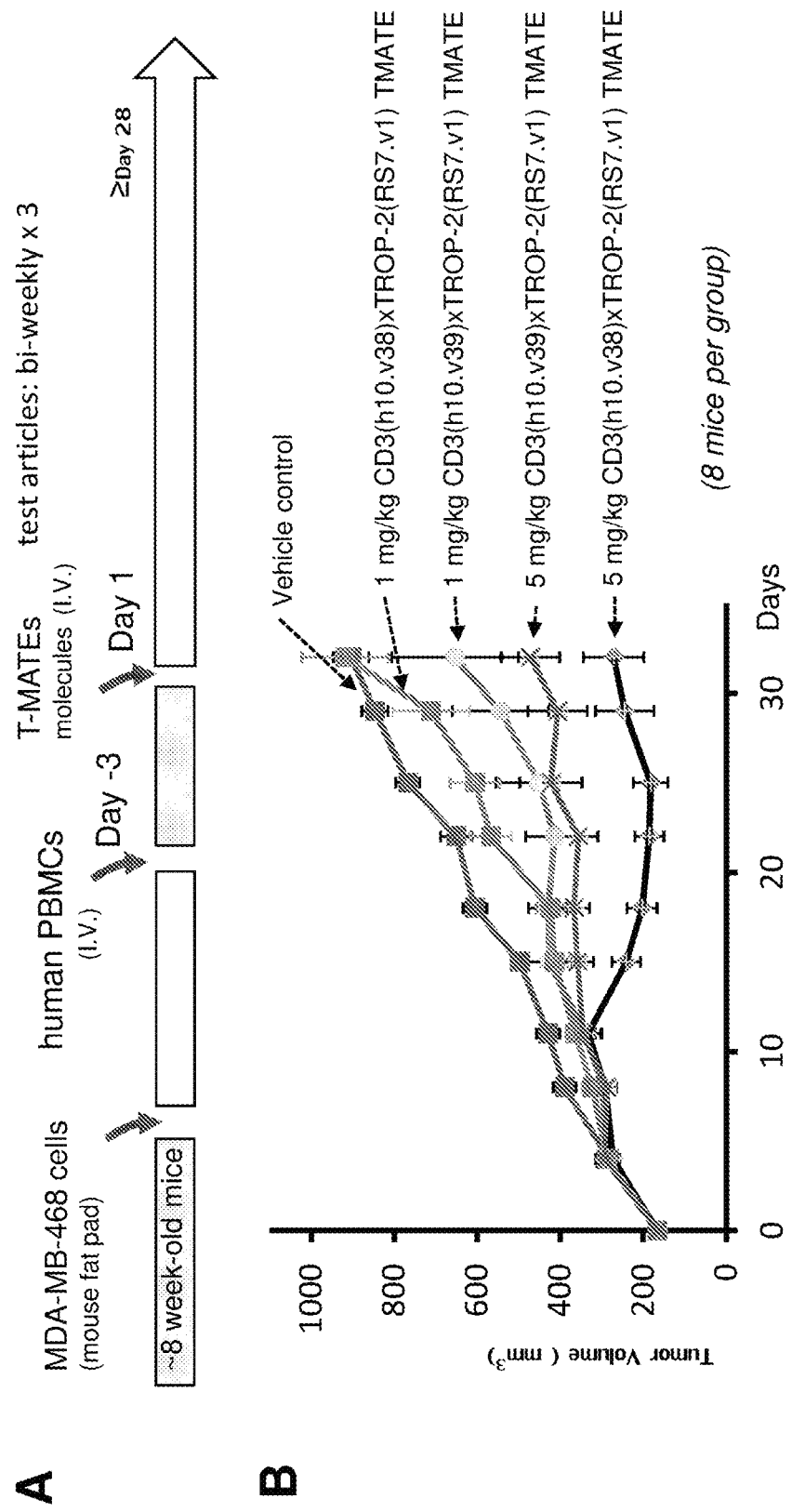
FIG. 56A shows the experimental schedule for the MDA-MB-468 tumor and human PBMCs transplantations as well as the administration of the two TMATE molecules at indicated doses.
FIG. 56B shows the in vivo anti-tumor activity exhibited by the two TMATEs, CD3 (h10.v38)×TROP2 (RS7.v1), and CD3 (h10.v39)×TROP2 (RS7.v1).

The experimental schedule for the tumor and human PBMCs transplantations as well as the administration of the two TMATEs is illustrated in FIG. 56 (top panel A). As shown in FIG. 56 (bottom panel B), the two TMATEs exhibited strong anti-tumor activity. Specifically, at the dose of 5 mg/kg, mice treated with either of the tested TMATEs achieved significant tumor regression.

Example 19

A pH-sensitive, T cell mediated cytotoxicity assay. Two multispecific TMATEs comprising CD3 (h10.v48)×HER2 (4D5) hIgG1-Fc (KiH) and CD3 (h10.v49)×HER2 (4D5) hIgG1-Fc (KiH) respectively were used to treat a breast cancer model cell line, BT474 in the presence of human primary T cells isolated from a human donor (ID #201538) with an effector-to-tumor ratio of about 10:1 over an incubation duration of about 48 hours.

Figure 57:
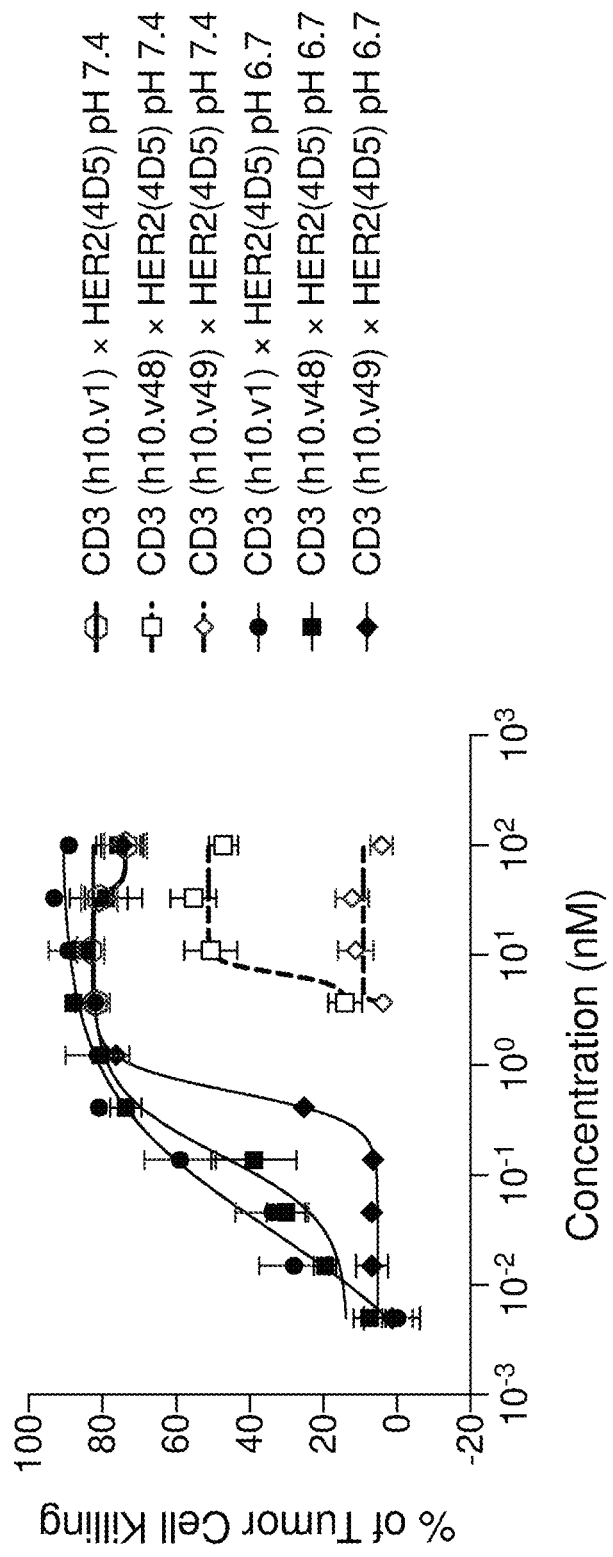
FIG. 57 shows pH-sensitive, T-cell-mediated killing of breast cancer cell line BT474 by two bispecific TMATEs, i.e., CD3 (h10.v48)×HER2 (4D5) and CD3 (h10.v49)×HER2 (4D5), wherein primary pan T cells isolated from a human donor were used. A non-pH-dependent T cell engager, CD3 (h10.v1)×HER2 (4D5), was used as a control.

As shown in FIG. 57, BT474 cells were potently killed by CD3 (h10.v48)×HER2 (4D5) and CD3 (h10.v49)×HER2 (4D5) mediated by T cells, in a dose- and pH-dependent manner, showing a EC50 killing activity of about 0.15 nM under the pH 6.7 condition, whereas the killing activity under pH 7.4 condition was largely abolished for CD3 (h10.v49)×HER2 (4D5), and significantly reduced for CD3 (h10.v48)×HER2 (4D5) with a EC50 of about 15 nM. Here a non pH-sensitive molecule, CD3 (h10.v1)×HER2 (4D5) bispecific antibody was used as a control. See FIG. 57.

SEQUENCE TABLE

| SEQ ID NO | Description | Amino acid sequence |
|---|---|---|
| | Exemplary anti-CD3 CDR sequences | |
| 1 | h10.v1 CDRH1 | SYYVH |
| 2 | h10.v1 CDRH2 | WIYPGDFNTKFNEKFKG |
| 3 | h10.v1 CDRH3 | DAYSYYYFDY |
| 4 | h10.v25 CDRH1 | SGYVH |
| 5 | h10.v26 CDRH1 | SYYTH |
| 6 | h10.v27 CDRH1 | SYYYH |
| 7 | h10.v17 CDRH2 | WIYPGDFNTHFNEKFKG |
| 8 | h10.v28 CDRH2 | WIGPGDFNTKFNEKFKG |
| 9 | h10.v7 CDRH3 | DHYSYYYFDY |
| 10 | h10.v9 CDRH3 | DAYHYYYFDY |
| 11 | h10.v16 CDRH3 | DHYHYYYFDY |
| 12 | h10.v19 CDRH3 | DHYGYYYFDY |
| 13 | h10.v48 CDRH3 | DHYHHYYFDY |
| 14 | h10.v49 CDRH3 | DHYHQYYFDY |
| 15 | h10 consensus sequence CDRH1 | $SX_1YX_2H$<br>$X_1$ = G or Y, $X_2$ = V, Y, or T |
| 16 | h10 consensus sequence CDRH2 | $WIX_1PGDFNTX_2FNEKFKG$<br>$X_1$ = G or Y, $X_2$ = H or K |
| 17 | h10 consensus sequence CDRH3 | $DX_1YX_2X_3YYFDY$<br>$X_1$ = A or H, $X_2$ = S, H, or G, $X_3$ = H, Q, or Y |
| 18 | h10 consensus sequence CDRH3 | $DX_1YX_2X_3YYFDY$<br>$X_1$ = A or H, $X_2X_3$ = SY, HY, GY, HH, or HQ |
| 19 | H24.v1 CDRH1 | DFYMN |
| 20 | H24.v1 CDRH2 | WIAPETGNTIYDPKFQG |
| 21 | H24.v1 CDRH3 | DSYGWYYFDY |
| 22 | H24.v2 CDRH3 | DSYGYYYFDY |
| 23 | H10.v1 CDRL1 | KSSQSLLNSRTRKNYLA |
| 24 | H10.v1 CDRL2 | WATTRDS |
| 25 | H10.v1 CDRL3 | IQSYTTRT |
| 26 | H10.v7 CDRL1 | KSSQSLLNSRTRHNYLA |
| 27 | h10.v22 CDRL1 | KSSQSLLNSRTGHNYLA |
| 28 | h10.v23 CDRL2 | WATTRAS |
| 29 | h10.v35 CDRL2 | WASTRAS |
| 30 | h24.v1 CDRL2 | WASTRES |
| 31 | h10.v19 CDRL3 | IQSYTGRT |
| 32 | h10.v24 CDRL3 | AQSYTGRT |
| 33 | h10.v35 CDRL3 | IQSHTGRT |

SEQUENCE TABLE

| SEQ ID NO | Description | Amino acid sequence |
|---|---|---|
| 34 | h10.v36 CDRL3 | IQSHTLRT |
| 35 | h24.v1 CDRL3 | KQSYILRT |
| 36 | h10 consensus sequence CDRL1 | KSSQSLLNSRTX$_1$X$_2$NYLA<br>X$_1$ = R or G, X$_2$ = H or K |
| 37 | h10 consensus sequence CDRL1 | KSSQSLLNSRTX$_1$X$_2$NYLA<br>X$_1$X$_2$ = RK, RH, or GH |
| 38 | h10 consensus sequence CDRL2 | WAX$_1$TRX$_2$S<br>X$_1$ = S or T, X$_2$ = A or D |
| 39 | h10 consensus sequence CDRL3 | X$_1$QSX$_2$TX$_3$RT<br>X$_1$ = I or A, X$_2$ = Y or H, X$_3$ = T, G, or L |
| 40 | h10 or h24 consensus sequence CDRL2 | WAX$_1$TRX$_2$S<br>X$_1$ = S or T, X$_2$ = A, D, or E |
| 41 | h10 or h24 consensus sequence CDRL3 | X$_1$QSX$_2$TX$_3$RT<br>X$_1$ = I, K, or A, X$_2$ = Y or H, X$_3$ = T, G, or L |
| Exemplary anti-CD3 VH/VL sequences | | |
| 42 | h10.v1 VH | EVQLVQSGAEVKKPGASVKVSCKASGYTFTSYYVHWVRQAPGQGLEWIGWIYPGDENTKFNEKFKGRVTLTADTSASTAYMELSSLRSEDTAVYYCARDAYSYYYFDYWGQGTLVTVSS |
| 43 | h10.v7 VH | EVQLVQSGAEVKKPGASVKVSCKASGYTFTSYYVHWVRQAPGQGLEWIGWIYPGDENTKFNEKFKGRVTLTADTSASTAYMELSSLRSEDTAVYYCARDHYSYYYFDYWGQGTLVTVSS |
| 44 | h10.v9 VH | EVQLVQSGAEVKKPGASVKVSCKASGYTFTSYYVHWVRQAPGQGLEWIGWIYPGDENTKFNEKFKGRVTLTADTSASTAYMELSSLRSEDTAVYYCARDAYHYYYFDYWGQGTLVTVSS |
| 45 | h10.v16 VH | EVQLVQSGAEVKKPGASVKVSCKASGYTFTSYYVHWVRQAPGQGLEWIGWIYPGDENTKFNEKFKGRVTLTADTSASTAYMELSSLRSEDTAVYYCARDHYHYYYFDYWGQGTLVTVSS |
| 46 | h10.v17 VH | EVQLVQSGAEVKKPGASVKVSCKASGYTFTSYYVHWVRQAPGQGLEWIGWIYPGDFNTHFNEKFKGRVTLTADTSASTAYMELSSLRSEDTAVYYCARDAYSYYYFDYWGQGTLVTVSS |
| 47 | h10.v18 VH | EVQLVQSGAEVKKPGASVKVSCKASGYTFTSYYVHWVRQAPGQGLEWIGWIYPGDFNTHFNEKFKGRVTLTADTSASTAYMELSSLRSEDTAVYYCARDAYSYYYFDYWGQGTLVTVSS |
| 48 | h10.v19 VH | EVQLVQSGAEVKKPGASVKVSCKASGYTFTSYYVHWVRQAPGQGLEWIGWIYPGDFNTKFNEKFKGRVTLTADTSASTAYMELSSLRSEDTAVYYCARDHYGYYYFDYWGQGTLVTVSS |
| 49 | h10.v20 VH | EVQLVQSGAEVKKPGASVKVSCKASGYTFTSYYVHWVRQAPGQGLEWIGWIYPGDENTKFNEKFKGRVTLTADTSASTAYMELSSLRSEDTAVYYCARDHYGYYYFDYWGQGTLVTVSS |
| 50 | h10.v21 VH | EVQLVQSGAEVKKPGASVKVSCKASGYTFTSYYVHWVRQAPGQGLEWIGWIYPGDFNTKFNEKFKGRVTLTADTSAS |

-continued

| SEQ ID NO | Description | Amino acid sequence |
|---|---|---|
| | | TAYMELSSLRSEDTAVYYCARDHYSYYYFDYWGQGTLV TVSS |
| 51 | h10.v22 VH | EVQLVQSGAEVKKPGASVKVSCKASGYTFTSYYVHWVR QAPGQGLEWIGWIYPGDFNTKFNEKFKGRVTLTADTSAS TAYMELSSLRSEDTAVYYCARDHYGYYYFDYWGQGTL VTVSS |
| 52 | h10.v23 VH | EVQLVQSGAEVKKPGASVKVSCKASGYTFTSYYVHWVR QAPGQGLEWIGWIYPGDFNTKFNEKFKGRVTLTADTSAS TAYMELSSLRSEDTAVYYCARDHYGYYYFDYWGQGTL VTVSS |
| 53 | h10.v24 VH | EVQLVQSGAEVKKPGASVKVSCKASGYTFTSYYVHWVR QAPGQGLEWIGWIYPGDFNTKFNEKFKGRVTLTADTSAS TAYMELSSLRSEDTAVYYCARDHYGYYYFDYWGQGTL VTVSS |
| 54 | h10.v25 VH | EVQLVQSGAEVKKPGASVKVSCKASGYTFTSGYVHWVR QAPGQGLEWIGWIYPGDFNTKFNEKFKGRVTLTADTSAS TAYMELSSLRSEDTAVYYCARDHYGYYYFDYWGQGTL VTVSS |
| 55 | h10.v26 VH | EVQLVQSGAEVKKPGASVKVSCKASGYTFTSYYTHWVR QAPGQGLEWIGWIYPGDFNTKFNEKFKGRVTLTADTSAS TAYMELSSLRSEDTAVYYCARDHYGYYYFDYWGQGTL VTVSS |
| 56 | h10.v27 VH | EVQLVQSGAEVKKPGASVKVSCKASGYTFTSYYYHWVR QAPGQGLEWIGWIYPGDENTKFNEKFKGRVTLTADTSAS TAYMELSSLRSEDTAVYYCARDHYGYYYFDYWGQGTL VTVSS |
| 57 | h10.v28 VH | EVQLVQSGAEVKKPGASVKVSCKASGYTFTSYYVHWVR QAPGQGLEWIGWIGPGDFNTKFNEKFKGRVTLTADTSAS TAYMELSSLRSEDTAVYYCARDHYGYYYFDYWGQGTL VTVSS |
| 58 | h10.v29 VH | EVQLVQSGAEVKKPGASVKVSCKASGYTFTSYYVHWVR QAPGQGLEWIGWIYPGDENTKFNEKFKGRVTLTADTSAS TAYMELSSLRSEDTAVYYCARDHYHYYYFDYWGQGTL VTVSS |
| 59 | h10.v30 VH | EVQLVQSGAEVKKPGASVKVSCKASGYTFTSYYVHWVR QAPGQGLEWIGWIYPGDFNTHFNEKFKGRVTLTADTSAS TAYMELSSLRSEDTAVYYCARDHYGYYYFDYWGQGTL VTVSS |
| 60 | h10.v31 VH | EVQLVQSGAEVKKPGASVKVSCKASGYTFTSYYYHWVR QAPGQGLEWIGWIYPGDFNTHFNEKFKGRVTLTADTSAS TAYMELSSLRSEDTAVYYCARDHYGYYYFDYWGQGTL VTVSS |
| 61 | h10.v32 VH | EVQLVQSGAEVKKPGASVKVSCKASGYTFTSYYYHWVR QAPGQGLEWIGWIYPGDENTKFNEKFKGRVTLTADTSAS TAYMELSSLRSEDTAVYYCARDHYHYYYFDYWGQGTL VTVSS |
| 62 | h10.v33 VH | EVQLVQSGAEVKKPGASVKVSCKASGYTFTSYYVHWVR QAPGQGLEWIGWIYPGDENTKFNEKFKGRVTLTADTSAS TAYMELSSLRSEDTAVYYCARDHYHYYYFDYWGQGTL VTVSS |
| 63 | h10.v34 VH | EVQLVQSGAEVKKPGASVKVSCKASGYTFTSYYYHWVR QAPGQGLEWIGWIYPGDFNTKFNEKFKGRVTLTADTSAS TAYMELSSLRSEDTAVYYCARDHYGYYYFDYWGQGTL VTVSS |
| 64 | h10.v35 VH | EVQLVQSGAEVKKPGASVKVSCKASGYTFTSYYYHWVR QAPGQGLEWIGWIYPGDFNTKFNEKFKGRVTLTADTSAS TAYMELSSLRSEDTAVYYCARDHYHYYYFDYWGQGTL VTVSS |

-continued

| SEQ ID NO | Description | Amino acid sequence |
|---|---|---|
| 65 | h10.v36 VH | EVQLVQSGAEVKKPGASVKVSCKASGYTFTSYYYHWVR QAPGQGLEWIGWIYPGDENTKFNEKFKGRVTLTADTSAS TAYMELSSLRSEDTAVYYCARDHYHYYYFDYWGQGTL VTVSS |
| 66 | h10.v38 VH | EVQLVQSGAEVKKPGASVKVSCKASGYTFTSYYYHWVR QAPGQGLEWIGWIYPGDFNTKFNEKFKGRVTLTADTSAS TAYMELSSLRSEDTAVYYCARDHYGYYYFDYWGQGTL VTVSS |
| 67 | h10.v39 VH | EVQLVQSGAEVKKPGASVKVSCKASGYTFTSYYTHWVR QAPGQGLEWIGWIYPGDFNTKFNEKFKGRVTLTADTSAS TAYMELSSLRSEDTAVYYCARDHYGYYYFDYWGQGTL VTVSS |
| 68 | h10.v48 VH | EVQLVQSGAEVKKPGASVKVSCKASGYTFTSYYYHWVR QAPGQGLEWIGWIYPGDENTKFNEKFKGRVTLTADTSAS TAYMELSSLRSEDTAVYYCARDHYHHYYFDYWGQGTL VTVSS |
| 69 | h10.v49 VH | EVQLVQSGAEVKKPGASVKVSCKASGYTFTSYYYHWVR QAPGQGLEWIGWIYPGDFNTKFNEKFKGRVTLTADTSAS TAYMELSSLRSEDTAVYYCARDHYHQYYFDYWGQGTL VTVSS |
| 70 | h24.v1 VH | EVQLVQSGAEVKKPGASVKVSCKASGFNIKDFYMHWVR QAPGQGLEWIGWIAPETGNTIYDPKFQGRATVTSDTSINT AYMELSRLRSDDTAVYYCARDSYGWYYFDYWGQGTLV TVSS |
| 71 | h24.v2 VH | EVQLVQSGAEVKKPGASVKVSCKASGFNIKDFYMHWVR QAPGQGLEWIGWIAPETGNTIYDPKFQGRATVTSDTSINT AYMELSRLRSDDTAVYYCARDSYGYYYFDYWGQGTLV TVSS |
| 72 | h10.v1 VL | DIVMTQSPDSLAVSLGERATINCKSSQSLLNSRTRKNYLA WYQQKPGQPPKLLIYWATTRDSGVPDRFSGSGSGTDFTL TISSLQAEDVAVYYCIQSYTTRTFGGGTKVEIK |
| 73 | h10.v7 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTTRTFGGGTKVEIK |
| 74 | h10.v9 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTTRTFGGGTKVEIK |
| 75 | h10.v16 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTTRTFGGGTKVEIK |
| 76 | h10.v17 VL | DIVMTQSPDSLAVSLGERATINCKSSQSLLNSRTRKNYLA WYQQKPGQPPKLLIYWATTRDSGVPDRFSGSGSGTDFTL TISSLQAEDVAVYYCIQSYTTRTFGGGTKVEIK |
| 77 | h10.v18 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTTRTFGGGTKVEIK |
| 78 | h10.v19 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTGRTFGGGTKVEIK |
| 79 | h10.v20 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTTRTFGGGTKVEIK |
| 80 | h10.v21 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTGRTFGGGTKVEIK |

SEQUENCE TABLE

| SEQ ID NO | Description | Amino acid sequence |
|---|---|---|
| 81 | h10.v22 VL | DIVMTQSPDSLAVSLGERATINCKSSQSLLNSRTGHNYLA WYQQKPGQPPKLLIYWATTRDSGVPDRESGSGSGTDFTL TISSLQAEDVAVYYCIQSYTGRTFGGGTKVEIK |
| 82 | h10.v23 VL | DIVMTQSPDSLAVSLGERATINCKSSQSLLNSRTRHNYLA WYQQKPGQPPKLLIYWATTRASGVPDRFSGSGSGTDFTL TISSLQAEDVAVYYCIQSYTGRTFGGGTKVEIK |
| 83 | h10.v24 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCAQSYTGRTFGGGTKVEIK |
| 84 | h10.v25 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTGRTFGGGTKVEIK |
| 85 | h10.v26 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTGRTFGGGTKVEIK |
| 86 | h10.v27 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTGRTFGGGTKVEIK |
| 87 | h10.v28 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTGRTFGGGTKVEIK |
| 88 | h10.v29 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTGRTFGGGTKVEIK |
| 89 | h10.v30 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTGRTFGGGTKVEIK |
| 90 | h10.v31 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTGRTFGGGTKVEIK |
| 91 | h10.v32 VL | DIVMTQSPDSLAVSLGERATINCKSSQSLLNSRTRHNYLA WYQQKPGQPPKLLIYWATTRDSGVPDRFSGSGSGTDFTL TISSLQAEDVAVYYCIQSYTGRTFGGGTKVEIK |
| 92 | h10.v33 VL | DIVMTQSPDSLAVSLGERATINCKSSQSLLNSRTRHNYLA WYQQKPGQPPKLLIYWATTRASGVPDRFSGSGSGTDFTL TISSLQAEDVAVYYCIQSYTGRTFGGGTKVEIK |
| 93 | h10.v34 VL | DIVMTQSPDSLAVSLGERATINCKSSQSLLNSRTRHNYLA WYQQKPGQPPKLLIYWATTRASGVPDRFSGSGSGTDFTL TISSLQAEDVAVYYCIQSYTGRTFGGGTKVEIK |
| 94 | h10.v35 VL | DIVMTQSPDSLAVSLGERATINCKSSQSLLNSRTRHNYLA WYQQKPGQPPKLLIYWASTRASGVPDRFSGSGSGTDFTL TISSLQAEDVAVYYCIQSHTGRTFGGGTKVEIK |
| 95 | h10.v36 VL | DIVMTQSPDSLAVSLGERATINCKSSQSLLNSRTRHNYLA WYQQKPGQPPKLLIYWASTRASGVPDRFSGSGSGTDFTL TISSLQAEDVAVYYCIQSHTLRTFGGGTKVEIK |
| 96 | h10.v38 VL | DIVMTQSPDSLAVSLGERATINCKSSQSLLNSRTRHNYLA WYQQKPGQPPKLLIYWATTRASGVPDRFSGSGSGTDFTL TISSLQAEDVAVYYCIQSYTGRTFGGGTKVEIK |
| 97 | h10.v39 VL | DIVMTQSPDSLAVSLGERATINCKSSQSLLNSRTRHNYLA WYQQKPGQPPKLLIYWATTRASGVPDRFSGSGSGTDFTL TISSLQAEDVAVYYCIQSYTGRTFGGGTKVEIK |
| 98 | h10.v48 VL | DIVMTQSPDSLAVSLGERATINCKSSQSLLNSRTRHNYLA WYQQKPGQPPKLLIYWATTRASGVPDRFSGSGSGTDFTL TISSLQAEDVAVYYCIQSYTGRTFGGGTKVEIK |

-continued

SEQUENCE TABLE

| SEQ ID NO | Description | Amino acid sequence |
|---|---|---|
| 99 | h10.v49 VL | DIVMTQSPDSLAVSLGERATINCKSSQSLLNSRTRHNYLA WYQQKPGQPPKLLIYWATTRASGVPDRFSGSGSGTDFTL TISSLQAEDVAVYYCIQSYTGRTFGGGTKVEIK |
| 100 | h24.v1 VL | DIVMTQSPDSLAVSLGERATINCKSSQSLLNSRTRKNYLA WYQQKPGQPPKLLIYWASTRESGVPDRFSGSGSGTDFTL TISSLQAEDVAVYYCKQSYILRTFGGGTKVEIK |
| 101 | h24.v2 VL | DIVMTQSPDSLAVSLGERATINCKSSQSLLNSRTRKNYLA WYQQKPGQPPKLLIYWASTRESGVPDRFSGSGSGTDFTL TISSLQAEDVAVYYCKQSYILRTFGGGTKVEIK |

Exemplary linker sequences

| | | |
|---|---|---|
| 102 | Linker | $(G)_n$, n> = 1 |
| 103 | Linker | $(GS)_n$, 8> = n> = 1 |
| 104 | Linker | $(GSGGS)_n$, 8> = n> = 1 |
| 105 | Linker | $(GGGGS)_n$, 8> = n> = 1 |
| 106 | Linker | $(GGGS)_n$, 8> = n> = 1 |
| 107 | Linker | $(GGGGS)3$ |
| 108 | Linker | $(GGGGS)6$ |
| 109 | Linker | $(GSTSGSGKPGSGEGS)_n$ 3> = n> = 1 |

Other exemplary antibody sequences

| | | |
|---|---|---|
| 110 | OKT3 (CD3) VH | QVQLQQSGAELARPGASVKMSCKASGYTFTRYTMHWV KQRPGQGLEWIGYINPSRGYTNYNQKFKDKATLTTDKSS STAYMQLSSLTSEDSAVYYCARYYDDHYCLDYWGQGTT LTVSS |
| 111 | OKT3 (CD3) VL | QIVLTQSPAIMSASPGEKVTMTCSASSSVSYMNWYQQKS GTSPKRWIYDTSKLASGVPAHFRGSGSGTSYSLTISGMEA EDAATYYCQQWSSNPFTFGSGTKLEIN |
| 112 | L2K (CD3) VH | DIKLQQSGAELARPGASVKMSCKTSGYTFTRYTMHWVK QRPGQGLEWIGYINPSRGYTNYNQKFKDKATLTTDKSSS TAYMQLSSLTSEDSAVYYCARYYDDHYCLDYWGQGTTL TVSS |
| 113 | L2K (CD3) VL | DIQLTQSPAIMSASPGEKVTMTCRASSSVSYMNWYQQKS GTSPKRWIYDTSKVASGVPYRFSGSGSGTSYSLTISSMEA EDAATYYCQQWSSNPLTFGAGTKLELK |
| 114 | hu40G5c (CD3) VH | EVQLVQSGAEVKKPGASVKVSCKASGYTFTNYYIHWVR QAPGQGLEWIGWIYPGDGNTKYNEKFKGRATLTADTSTS TAYLELSSLRSEDTAVYYCARDSYSNYYFDYWGQGTLV TVSS |
| 115 | hu40G5c (CD3) VL | DIVMTQSPDSLAVSLGERATINCKSSQSLLNSRTKNYLA WYQQKPGQPPKLLIYWASTRESGVPDRFSGSGSGTDFTL TISSLQAEDVAVYYCTQSFILRTFGQGTKVEIK |
| 116 | hu38E4 (CD3) VH | EVQLVQSGAEVKKPGASVKVSCKASGFTFTSYYIHWVRQ APGQGLEWIGWIYPENDNTKYNEKFKDRVTITADTSTST AYLELSSLRSEDTAVYYCARDGYSRYYFDYWGQGTLVT VSS |
| 117 | hu38E4 (CD3) VL | DIVMTQSPDSLAVSLGERATINCKSSQSLLNSRTRKNYLA WYQQKPGQSPKLLIYWTSTRKSGVPDRFSGSGSGTDFTL TISSLQAEDVAVYYCKQSFILRTFGQGTKVEIK |
| 118 | SP34 (CD3) VH | EVQLVESGGGLVQPKGSLKLSCAASGFTFNTYAMNWVR QAPGKGLEWVARIRSKYNNYATYYADSVKDRFTISRDDS QSILYLQMNNLKTEDTAMYYCVRHGNFGNSYVSWFAY WGQGTLVTVSS |

SEQUENCE TABLE

| SEQ ID NO | Description | Amino acid sequence |
|---|---|---|
| 119 | SP34 (CD3) VL | QAVVTQESALTTSPGETVTLTCRSSTGAVTTSNYANWVQ EKPDHLFTGLIGGTNKRAPGVPARFSGSLIGDKAALTITG AQTEDEAIYFCALWYSNLWVFGGGTKLTVL |
| 120 | MuS110 (EpCAM) VH | EVQLAESGGGLVQPGRSMKLSCAASGFTFSNFPMAWVR QAPTKGLEWVATISTSGGSTYYRDSVKGRFTISRDNAKST LYLQMNSLRSEDTATYYCTRTLYILRVFYFDYWGQGVM VTVSS |
| 121 | MuS110 (EpCAM) VL | DIQMTQSPASLSASLGETVSIECLASEGISNDLAWYQQKS GKSPQLLIYATSRLQDGVPSRFSGSGSGTRYSLKISGMQPE DEADYFCQQSYKYPWTFGGGTKLELK |
| 122 | MT110 (EpCAM) VH | EVQLEQSGAELVRPGTSVKISCKASGYAFTNYWLGWVK QRPGHGLEWIGDIFPGSGNIHYNEKFKGKATLTADKSSST AYMQLSSLTFEDSAVYFCARLRNWDEPMDYWGQGTTVT VSS |
| 123 | MT110 (EpCAM) VL | ELVMTQSPSSLTVTAGEKVTMSCKSSQSLLNSGNQKNYL TWYQQKPGQPPKLLIYWASTRESGVPDRFTGSGSGTDFT LTISSVQAEDLAVYYCQNDYSYPLTFGAGTKLEIK |
| 124 | RS7.v1 (Trop-2) VH | EVQLQQSGSELKKPGASVKVSCKASGYTFTNYGMNWVK QAPGQGLKWMGWINTYTGEPTYTDDFKGRFAFSLDTSV STAYLQISSLKADDTAVYFCARGGFGSSYWYFDVWGQG SLVTVSS |
| 125 | RS7.v1 (Trop-2) VL | DIQLTQSPSSLSASVGDRVSITCKASQDVSIAVAWYQQKP GKAPKLLIYSASYRYTGVPDRFSGSGSGTDFTLTISSLQPE DFAVYYCQQHYITPLTFGAGTKVEIK |
| 126 | 4D5 (Her2) VH | EVQLVESGGGLVQPGGSLRLSCAASGFNIKDTYIHWVRQ APGKGLEWVARIYPTNGYTRYADSVKGRFTISADTSKNT AYLQMNSLRAEDTAVYYCSRWGGDGFYAMDYWGQGT LVTVSS |
| 127 | 4D5 (Her2) VL | DIQMTQSPSSLSASVGDRVTITCRASQDVNTAVAWYQQK PGKAPKLLIYSASFLYSGVPSRFSGSRSGTDFTLTISSLQPE DFATYYCQQHYTTPPTFGQGTKVEIK |

The invention claimed is:

1. A method of treating a cancer in an individual in need thereof, comprising administering into the individual an anti-CD3 construct, wherein the anti-CD3 construct is a multi-specific construct that comprises 1) an antibody moiety that specifically binds to CD3 ("anti-CD3 antibody moiety"), wherein the anti-CD3 antibody moiety comprises a heavy chain variable ($V_H$) domain and a light chain variable ($V_L$) domain, and 2) a second antibody moiety that specifically recognizes a tumor-associated antigen: wherein:

(a) the $V_H$ domain comprises (1) a CDR-H1 comprising SYYTH (SEQ ID NO: 5); (2) a CDR-H2 comprising WIYPGDFNTKFNEKFKG (SEQ ID NO: 2); and (3) a CDR-H3 comprising DHYGYYYFDY (SEQ ID NO:12); and the $V_L$ domain comprises (1) a CDR-L1 comprising KSSQSLLNSRTRHNYLA (SEQ ID NO: 26); (2) a CDR-L2 comprising WATTRDS (SEQ ID NO: 24); and (3) a CDR-L3 comprising IQSYTGRT (SEQ ID NO: 31), (b) the $V_H$ domain comprises (1) a CDR-H1 comprising SYYYH (SEQ ID NO: 6); (2) a CDR-H2 comprising WIYPGDFNTKFNEKFKG (SEQ ID NO: 2); and (3) a CDR-H3 comprising DHYGYYYFDY (SEQ ID NO:12); and the $V_L$ domain comprises (1) a CDR-L1 comprising KSSQSLLNSRTRHNYLA (SEQ ID NO: 26); (2) a CDR-L2 comprising WATTRDS (SEQ ID NO: 24); and (3) a CDR-L3 comprising IQSYTGRT (SEQ ID NO: 31), (c) the $V_H$ domain comprises (1) a CDR-H1 comprising SYYYH (SEQ ID NO: 6); (2) a CDR-H2 comprising WIYPGDFNTKFNEKFKG (SEQ ID NO: 2); and (3) a CDR-H3 comprising DHYGYYYFDY (SEQ ID NO:12); and the $V_L$ domain comprises (1) a CDR-L1 comprising KSSQSLLNSRTRHNYLA (SEQ ID NO: 26); (2) a CDR-L2 comprising WATTRAS (SEQ ID NO: 28); and (3) a CDR-L3 comprising IQSYTGRT (SEQ ID NO: 31), (d) the $V_H$ domain comprises (1) a CDR-H1 comprising SYYTH (SEQ ID NO: 5); (2) a CDR-H2 comprising WIYPGDFNTKFNEKFKG (SEQ ID NO: 2); and (3) a CDR-H3 comprising DHYGYYYFDY (SEQ ID NO:12); and the $V_L$ domain comprises (1) a CDR-L1 comprising KSSQSLLNSRTRHNYLA (SEQ ID NO: 26); (2) a CDR-L2 comprising WATTRDS (SEQ ID NO: 24) or WATTRAS (SEQ ID NO: 28); and (3) a CDR-L3 comprising IQSYTGRT (SEQ ID NO: 31);

(e) the $V_H$ domain comprises (1) a CDR-H1 comprising SYYYH (SEQ ID NO: 6); (2) a CDR-H2 comprising WIYPGDFNTKFNEKFKG (SEQ ID NO: 2); and (3) a CDR-H3 comprising DHYHQYYFDY (SEQ ID NO:13); and the $V_L$ domain comprises (1) a CDR-L1 comprising KSSQSLLNSRTRHNYLA (SEQ ID NO: 26); (2) a CDR-L2 comprising WATTRAS (SEQ ID NO: 28); and (3) a CDR-L3 comprising IQSYTGRT (SEQ ID NO: 31); or (f) the $V_H$ domain comprises (1) a CDR-H1 comprising SYYYH (SEQ ID NO: 6); (2) a CDR-H2 comprising WIYPGDFNTKFNEKFKG (SEQ ID NO: 2); and (3) a CDR-H3 comprising DHYHQYYFDY (SEQ ID NO: 14); and the $V_L$ domain comprises (1) a CDR-L1 comprising KSSQSLLNSRTRHNYLA (SEQ ID NO: 26); (2) a CDR-L2 comprising WATTRAS (SEQ ID NO: 28); and (3) a CDR-L3 comprising IQSYTGRT (SEQ ID NO: 31).

2. The method of claim 1, wherein:

a) the $V_H$ comprises an amino acid sequence that has at least 80% identity to SEQ ID NO: 55; and the $V_L$ comprises an amino acid sequence that has at least 80% identity to SEQ ID NO: 85,
b) the $V_H$ comprises an amino acid sequence that has at least 80% identity to SEQ ID NO: 56; and the $V_L$ comprises an amino acid sequence that has at least 80% identity to SEQ ID NO: 86,
c) the $V_H$ comprises an amino acid sequence that has at least 80% identity to SEQ ID NO: 66; and the $V_L$ comprises an amino acid sequence that has at least 800% identity to SEQ ID NO: 96,
d) the $V_H$ comprises an amino acid sequence that has at least 80% identity to SEQ ID NO: 67; and the $V_L$ comprises an amino acid sequence that has at least 80% identity to SEQ ID NO: 97,
e) the $V_H$ comprises an amino acid sequence that has at least 80% identity to SEQ ID NO: 68; and the $V_L$ comprises an amino acid sequence that has at least 80% identity to SEQ ID NO: 99,
f) the $V_H$ comprises an amino acid sequence that has at least 80% identity to SEQ ID NO: 69; and the $V_L$ comprises an amino acid sequence that has at least 80% identity to SEQ ID NO: 99.

3. The method of claim 2, wherein the $V_H$ comprises an amino acid sequence of SEQ ID NO: 56; and the $V_L$ comprises an amino acid sequence of SEQ ID NO: 86.

4. The method of claim 2, wherein the $V_H$ comprises an amino acid sequence of SEQ ID NO: 66; and the $V_L$ comprises an amino acid sequence of SEQ ID NO: 96.

5. The method of claim 2, wherein the $V_H$ comprises an amino acid sequence of SEQ ID NO: 67; and the $V_L$ comprises an amino acid sequence of SEQ ID NO: 97.

6. The method of claim 2, wherein the $V_H$ comprises an amino acid sequence of SEQ ID NO: 68; and the $V_L$ comprises an amino acid sequence of SEQ ID NO: 98.

7. The method of claim 2, wherein the $V_H$ comprises an amino acid sequence of SEQ ID NO: 69; and the $V_L$ comprises an amino acid sequence of SEQ ID NO: 99.

8. The method of claim 2, wherein the anti-CD3 antibody moiety is an antibody or antigen-binding fragment thereof selected from the group consisting of a full-length antibody, a bispecific antibody, a single-chain Fv (scFv) fragment, a Fab fragment, a Fab' fragment, a F(ab')2, an Fv fragment, a disulfide stabilized Fv fragment (dsFv), a (dsFv)$_2$, a Fv-Fc fusion, a scFv-Fc fusion, a scFv-Fv fusion, a diabody, a tribody, and a tetrabody.

9. The method of claim 8, wherein the anti-CD3 antibody moiety is a full-length antibody comprising a Fc fragment.

10. The method of claim 9, wherein the Fc fragment is selected from the group consisting of Fc fragments from IgG1, IgG2, IgG3, IgG4, and combinations and hybrids thereof.

11. The method of claim 4 wherein the tumor-associated antigen is selected from the group consisting of HER2, Trop-2 and EpCAM.

12. The method of claim 1, wherein the cancer is a solid tumor.

13. An anti-CD3 construct comprising an antibody moiety that specifically binds to CD3 ("anti-CD3 antibody moiety"), comprising:
(a) a heavy chain variable ($V_H$) domain that comprises either:
(I): (1) a CDR-H1 comprising SYYTH (SEQ ID NO: 5); (2) a CDR-H2 comprising WIYPGDFNTKFNEKFKG (SEQ ID NO: 2); and (3) a CDR-H3 comprising DHYGYYYFDY (SEQ ID NO: 12); or (II): (1) a CDR-H1 comprising SYYYTH (SEQ ID NO: 6), (2) a CDR-H2 comprising WIYPGDFNTKFNEKFKG (SEQ ID NO: 2); and (3) a CDR-H$_3$ comprising an amino acid sequence selected from the group consisting of DHYGYYYFDY (SEQ ID NO:12), DHYHHYYFDY (SEQ ID NO:13), and DHYHQYYFDY (SEQ ID NO:14) and
(b) a light chain variable ($V_L$) domain that comprises (1) a CDR-L1 comprising KSSQSLLNSRTRHNYLA (SEQ ID NO: 26); (2) a CDR-L2 comprising WATTRDS (SEQ ID NO: 24) or WATTRAS (SEQ ID NO: 28); and (3) a CDR-L3 comprising IQSYTGRT (SEQ ID NO: 31).

14. A pharmaceutical composition comprising the anti-CD3 construct of claim 13, and a pharmaceutical acceptable carrier.

15. The method of claim 1, wherein a $V_H$ of the second antibody moiety comprises an amino acid sequence that has at least 80% identity to SEQ ID NO: 126 and comprises CDR1, CDR2, and CDR3 of SEQ ID NO: 126; and a $V_L$ of the second antibody moiety comprises an amino acid sequence that has at least 80% identity to SEQ ID NO: 127 and comprises CDR1, CDR2, and CDR3 of SEQ ID NO: 127.

16. The method of claim 1, wherein a $V_H$ of the second antibody moiety comprises an amino acid sequence that has at least 80% identity to SEQ ID NO: 124 and comprises CDR1, CDR2, and CDR3 of SEQ ID NO: 124; and a $V_L$ of the second antibody moiety comprises an amino acid sequence that has at least 80% identity to SEQ ID NO: 125 and comprises CDR1, CDR2, and CDR3 of SEQ ID NO: 125.

17. The method of claim 1, wherein a $V_H$ of the second antibody moiety comprises an amino acid sequence that has at least 80% identity to SEQ ID NO: 122 and comprises CDR1, CDR2, and CDR3 of SEQ ID NO: 122; and a $V_L$ of the second antibody moiety comprises an amino acid sequence that has at least 80% identity to SEQ ID NO: 123 and comprises CDR1, CDR2, and CDR3 of SEQ ID NO: 123.

18. The anti-CD3 construct of claim 13, wherein:
a) the $V_H$ comprises an amino acid sequence that has at least 80% identity to SEQ ID NO: 55; and the $V_L$ comprises an amino acid sequence that has at least 80% identity to SEQ ID NO: 85,
b) the $V_H$ comprises an amino acid sequence that has at least 80% identity to SEQ ID NO: 56; and the $V_L$ comprises an amino acid sequence that has at least 80% identity to SEQ ID NO: 86,
c) the $V_H$ comprises an amino acid sequence that has at least 80% identity to SEQ ID NO: 66; and the $V_L$ comprises an amino acid sequence that has at least 80% identity to SEQ ID NO: 96,
d) the $V_H$ comprises an amino acid sequence that has at least 80% identity to SEQ ID NO: 67; and the $V_L$ comprises an amino acid sequence that has at least 80% identity to SEQ ID NO: 97,
e) the $V_H$ comprises an amino acid sequence that has at least 80% identity to SEQ ID NO: 68; and the $V_L$ comprises an amino acid sequence that has at least 80% identity to SEQ ID NO: 98, or
f) the $V_H$ comprises an amino acid sequence that has at least 80% identity to SEQ ID NO: 69; and the $V_L$ comprises an amino acid sequence that has at least 80% identity to SEQ ID NO: 99.

19. The anti-CD3 construct of claim 18, wherein:
a) the $V_H$ comprises an amino acid sequence of SEQ ID NO: 56; and the $V_L$ Comprises an amino acid sequence of SEQ ID NO: 86;
b) the $V_H$ comprises an amino acid sequence of SEQ ID NO: 66; and the $V_L$ comprises an amino acid sequence of SEQ ID NO: 96;
c) the $V_H$ comprises an amino acid sequence of SEQ ID NO: 67; and the $V_L$ comprises an amino acid sequence of SEQ ID NO: 97;
d) the $V_H$ comprises an amino acid sequence of SEQ ID NO: 68; and the $V_L$ comprises an amino acid sequence of SEQ ID NO: 98; or
e) the $V_H$ comprises an amino acid sequence of SEQ ID NO: 69; and the $V_L$ comprises an amino acid sequence of SEQ ID NO: 99.

* * * * *

SEQUENCE LISTING

```
<160> NUMBER OF SEQ ID NOS: 140

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Ser Tyr Tyr Val His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Trp Ile Tyr Pro Gly Asp Phe Asn Thr Lys Phe Asn Glu Lys Phe Lys
1               5                   10                  15
```

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Asp Ala Tyr Ser Tyr Tyr Tyr Phe Asp Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Ser Gly Tyr Val His
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Ser Tyr Tyr Thr His
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Ser Tyr Tyr Tyr His
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic Construct

<400> SEQUENCE: 7

Trp Ile Tyr Pro Gly Asp Phe Asn Thr His Phe Asn Glu Lys Phe Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

```
Trp Ile Gly Pro Gly Asp Phe Asn Thr Lys Phe Asn Glu Lys Phe Lys
1               5                   10                  15
Gly

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Asp His Tyr Ser Tyr Tyr Tyr Phe Asp Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

Asp Ala Tyr His Tyr Tyr Tyr Phe Asp Tyr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Asp His Tyr His Tyr Tyr Tyr Phe Asp Tyr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Asp His Tyr Gly Tyr Tyr Tyr Phe Asp Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Asp His Tyr His His Tyr Tyr Phe Asp Tyr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14
```

```
Asp His Tyr His Gln Tyr Tyr Phe Asp Tyr
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Gly or Tyr
<220> FEATURE:
<221> NAME/KEY: VARIANT
<222> LOCATION: 4
<223> OTHER INFORMATION: Xaa = Val, Tyr, or Thr

<400> SEQUENCE: 15

Ser Xaa Tyr Xaa His
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Gly or Tyr
<220> FEATURE:
<221> NAME/KEY: VARIANT
<222> LOCATION: 10
<223> OTHER INFORMATION: Xaa = His or Lys

<400> SEQUENCE: 16

Trp Ile Xaa Pro Gly Asp Phe Asn Thr Xaa Phe Asn Glu Lys Phe Lys
1               5                   10                  15

Gly

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Ala or His
<220> FEATURE:
<221> NAME/KEY: VARIANT
<222> LOCATION: 4
<223> OTHER INFORMATION: Xaa = Ser, His, or Gly
<220> FEATURE:
<221> NAME/KEY: VARIANT
<222> LOCATION: 5
<223> OTHER INFORMATION: Xaa = His, Gln, or Tyr

<400> SEQUENCE: 17

Asp Xaa Tyr Xaa Xaa Tyr Tyr Phe Asp Tyr
1               5                   10

<210> SEQ ID NO 18
<211> LENGTH: 10
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: VARIANT
<222> LOCATION: 2
<223> OTHER INFORMATION: Xaa = Ala or His
<220> FEATURE:
<221> NAME/KEY: VARIANT
<222> LOCATION: (4)..(5)
<223> OTHER INFORMATION: Xaa = Ser Tyr, His Tyr, Gly Tyr, His His, or
      His Gln

<400> SEQUENCE: 18

Asp Xaa Tyr Xaa Xaa Tyr Tyr Phe Asp Tyr
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Asp Phe Tyr Met Asn
1               5

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Trp Ile Ala Pro Glu Thr Gly Asn Thr Ile Tyr Asp Pro Lys Phe Gln
1               5                   10                  15

Gly

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Asp Ser Tyr Gly Trp Tyr Tyr Phe Asp Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic Construct

<400> SEQUENCE: 22

Asp Ser Tyr Gly Tyr Tyr Tyr Phe Asp Tyr
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Synthetic Construct

<400> SEQUENCE: 23
```

```
Lys Ser Ser Gln Ser Leu Leu Asn Ser Arg Thr Arg Lys Asn Tyr Leu
1               5                   10                  15
Ala

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Trp Ala Thr Thr Arg Asp Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Ile Gln Ser Tyr Thr Thr Arg Thr
1               5

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Lys Ser Ser Gln Ser Leu Leu Asn Ser Arg Thr Arg His Asn Tyr Leu
1               5                   10                  15
Ala

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

Lys Ser Ser Gln Ser Leu Leu Asn Ser Arg Thr Gly His Asn Tyr Leu
1               5                   10                  15
Ala

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Trp Ala Thr Thr Arg Ala Ser
1               5

<210> SEQ ID NO 29
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 29

Trp Ala Ser Thr Arg Ala Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Trp Ala Ser Thr Arg Glu Ser
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct

<400> SEQUENCE: 31

Ile Gln Ser Tyr Thr Gly Arg Thr
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct

<400> SEQUENCE: 32

Ala Gln Ser Tyr Thr Gly Arg Thr
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct

<400> SEQUENCE: 33

Ile Gln Ser His Thr Gly Arg Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

Ile Gln Ser His Thr Leu Arg Thr
1               5

<210> SEQ ID NO 35
<211> LENGTH: 8
<212> TYPE: PRT
<213> ORGANISM: Artificial Sequence
```

```
<220> FEATURE:
<223> OTHER INFORMATION: Synthetic Construct

<400> SEQUENCE: 35

Lys Gln Ser Tyr Ile Leu Arg Thr
1               5

<210> SEQ ID NO 36
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 12
<223> OTHER INFORMATION: Xaa = Arg or Gly
<220> FEATURE:
<221> NAME/KEY: VARIANT
<222> LOCATION: 13
<223> OTHER INFORMATION: Xaa = His or Lys

<400> SEQUENCE: 36

Lys Ser Ser Gln Ser Leu Leu Asn Ser Arg Thr Xaa Xaa Asn Tyr Leu
1               5                   10                  15
Ala

<210> SEQ ID NO 37
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (12)..(13)
<223> OTHER INFORMATION: Xaa = Arg Lys, Arg His, or Gly His

<400> SEQUENCE: 37

Lys Ser Ser Gln Ser Leu Leu Asn Ser Arg Thr Xaa Xaa Asn Tyr Leu
1               5                   10                  15
Ala

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ser or Thr
<220> FEATURE:
<221> NAME/KEY: VARIANT
<222> LOCATION: 6
<223> OTHER INFORMATION: Xaa = Ala or Asp

<400> SEQUENCE: 38

Trp Ala Xaa Thr Arg Xaa Ser
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: VARIANT
<222> LOCATION: 1
<223> OTHER INFORMATION: Xaa = Ile or Ala
<220> FEATURE:
<221> NAME/KEY: VARIANT
<222> LOCATION: 4
<223> OTHER INFORMATION: Xaa = Tyr or His
<220> FEATURE:
<221> NAME/KEY: VARIANT
<222> LOCATION: 6
<223> OTHER INFORMATION: Xaa = Thr, Gly, or Leu

<400> SEQUENCE: 39

Xaa Gln Ser Xaa Thr Xaa Arg Thr
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ser or Thr
<220> FEATURE:
<221> NAME/KEY: VARIANT
<222> LOCATION: 6
<223> OTHER INFORMATION: Xaa = Ala, Asp, or Glu

<400> SEQUENCE: 40

Trp Ala Xaa Thr Arg Xaa Ser
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ile, Lys, or Ala
<220> FEATURE:
<221> NAME/KEY: VARIANT
<222> LOCATION: 4
<223> OTHER INFORMATION: Xaa = Tyr or His
<220> FEATURE:
<221> NAME/KEY: VARIANT
<222> LOCATION: 6
<223> OTHER INFORMATION: Xaa = Thr, Gly, or Leu

<400> SEQUENCE: 41

Xaa Gln Ser Xaa Thr Xaa Arg Thr
1               5

<210> SEQ ID NO 42
<211> LENGTH: 119
<212> TYPE: PRT
<213> ORGANISM: Artificial Sequence
<220> FEATURE:
<223> OTHER INFORMATION: Synthetic Construct

<400> SEQUENCE: 42

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

Tyr Val His Trp Val Arg Gln Ala Pro Gly Gln Gly Leu Glu Trp Ile
            35                  40                  45

Gly Trp Ile Tyr Pro Gly Asp Phe Asn Thr Lys Phe Asn Glu Lys Phe
 50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Tyr Ser Tyr Tyr Tyr Phe Asp Tyr Trp Gly Gln Gly
            100                 105                 110

Thr Leu Val Thr Val Ser Ser
        115

<210> SEQ ID NO 43
<211> LENGTH: 119
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Ile
            35                  40                  45

Gly Trp Ile Tyr Pro Gly Asp Phe Asn Thr Lys Phe Asn Glu Lys Phe
 50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr Ser Tyr Tyr Tyr Phe Asp Tyr Trp Gly Gln Gly
            100                 105                 110

Thr Leu Val Thr Val Ser Ser
        115

<210> SEQ ID NO 44
<211> LENGTH: 119
<212> TYPE: PRT
<213> ORGANISM: Artificial Sequence
<220> FEATURE:
<223> OTHER INFORMATION: Synthetic Construct

<400> SEQUENCE: 44

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Ile
            35                  40                  45

Gly Trp Ile Tyr Pro Gly Asp Phe Asn Thr Lys Phe Asn Glu Lys Phe
 50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Asp Ala Tyr His Tyr Tyr Phe Asp Tyr Trp Gly Gln Gly
            100                 105                 110

Thr Leu Val Thr Val Ser Ser
        115
```

<210> SEQ ID NO 45
<211> LENGTH: 119
<212> TYPE: PRT
<213> ORGANISM: Artificial Sequence
<220> FEATURE:
<223> OTHER INFORMATION: Synthetic Construct

<400> SEQUENCE: 45

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr His Tyr Tyr Phe Asp Tyr Trp Gly Gln Gly
            100                 105                 110

Thr Leu Val Thr Val Ser Ser
        115
```

<210> SEQ ID NO 46
<211> LENGTH: 119
<212> TYPE: PRT
<213> ORGANISM: Artificial Sequence
<220> FEATURE:
<223> OTHER INFORMATION: Synthetic Construct

<400> SEQUENCE: 46

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asp Phe Asn Thr His Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Tyr Ser Tyr Tyr Phe Asp Tyr Trp Gly Gln Gly
            100                 105                 110

Thr Leu Val Thr Val Ser Ser
        115
```

<210> SEQ ID NO 47
<211> LENGTH: 119
<212> TYPE: PRT

<213> ORGANISM: Artificial Sequence
<220> FEATURE:
<223> OTHER INFORMATION: Synthetic Construct

<400> SEQUENCE: 47

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asp Phe Asn Thr His Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Tyr Ser Tyr Tyr Phe Asp Tyr Trp Gly Gln Gly
                100                 105                 110

Thr Leu Val Thr Val Ser Ser
        115

<210> SEQ ID NO 48
<211> LENGTH: 119
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr Gly Tyr Tyr Phe Asp Tyr Trp Gly Gln Gly
                100                 105                 110

Thr Leu Val Thr Val Ser Ser
        115

<210> SEQ ID NO 49
<211> LENGTH: 119
<212> TYPE: PRT
<213> ORGANISM: Artificial Sequence
<220> FEATURE:
<223> OTHER INFORMATION: Synthetic Construct

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

```
Tyr Val His Trp Val Arg Gln Ala Pro Gly Gln Gly Leu Glu Trp Ile
            35                  40                  45

Gly Trp Ile Tyr Pro Gly Asp Phe Asn Thr Lys Phe Asn Glu Lys Phe
        50                  55                  60

Lys Gly Arg Val Thr Leu Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp His Tyr Gly Tyr Tyr Tyr Phe Asp Tyr Trp Gly Gln Gly
            100                 105                 110

Thr Leu Val Thr Val Ser Ser
            115

<210> SEQ ID NO 50
<211> LENGTH: 119
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Ile
            35                  40                  45

Gly Trp Ile Tyr Pro Gly Asp Phe Asn Thr Lys Phe Asn Glu Lys Phe
        50                  55                  60

Lys Gly Arg Val Thr Leu Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp His Tyr Ser Tyr Tyr Tyr Phe Asp Tyr Trp Gly Gln Gly
            100                 105                 110

Thr Leu Val Thr Val Ser Ser
            115

<210> SEQ ID NO 51
<211> LENGTH: 119
<212> TYPE: PRT
<213> ORGANISM: Artificial Sequence
<220> FEATURE:
<223> OTHER INFORMATION: Synthetic Construct

<400> SEQUENCE: 51

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Ile
            35                  40                  45

Gly Trp Ile Tyr Pro Gly Asp Phe Asn Thr Lys Phe Asn Glu Lys Phe
        50                  55                  60

Lys Gly Arg Val Thr Leu Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
```

```
                    85                  90                  95
Ala Arg Asp His Tyr Gly Tyr Tyr Phe Asp Tyr Trp Gly Gln Gly
                100                 105                 110

Thr Leu Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Val His Trp Val Arg Gln Ala Pro Gly Gln Gly Leu Glu Trp Ile
            35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr Gly Tyr Tyr Phe Asp Tyr Trp Gly Gln Gly
                100                 105                 110

Thr Leu Val Thr Val Ser Ser
        115

<210> SEQ ID NO 53
<211> LENGTH: 119
<212> TYPE: PRT
<213> ORGANISM: Artificial Sequence
<220> FEATURE:
<223> OTHER INFORMATION: Synthetic Construct

<400> SEQUENCE: 53

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Val His Trp Val Arg Gln Ala Pro Gly Gln Gly Leu Glu Trp Ile
            35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr Gly Tyr Tyr Phe Asp Tyr Trp Gly Gln Gly
                100                 105                 110

Thr Leu Val Thr Val Ser Ser
        115

<210> SEQ ID NO 54
<211> LENGTH: 119
```

```
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Gly
            20                  25                  30

Tyr Val His Trp Val Arg Gln Ala Pro Gly Gln Gly Leu Glu Trp Ile
        35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr Gly Tyr Tyr Phe Asp Tyr Trp Gly Gln Gly
            100                 105                 110

Thr Leu Val Thr Val Ser Ser
        115

<210> SEQ ID NO 55
<211> LENGTH: 119
<212> TYPE: PRT
<213> ORGANISM: Artificial Sequence
<220> FEATURE:
<223> OTHER INFORMATION: Synthetic Construct

<400> SEQUENCE: 55

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Thr His Trp Val Arg Gln Ala Pro Gly Gln Gly Leu Glu Trp Ile
        35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr Gly Tyr Tyr Phe Asp Tyr Trp Gly Gln Gly
            100                 105                 110

Thr Leu Val Thr Val Ser Ser
        115

<210> SEQ ID NO 56
<211> LENGTH: 119
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
            20                  25                  30
Tyr Tyr His Trp Val Arg Gln Ala Pro Gly Gln Gly Leu Glu Trp Ile
        35                  40                  45
Gly Trp Ile Tyr Pro Gly Asp Phe Asn Thr Lys Phe Asn Glu Lys Phe
    50                  55                  60
Lys Gly Arg Val Thr Leu Thr Ala Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp His Tyr Gly Tyr Tyr Tyr Phe Asp Tyr Trp Gly Gln Gly
            100                 105                 110
Thr Leu Val Thr Val Ser Ser
        115

<210> SEQ ID NO 57
<211> LENGTH: 119
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Val His Trp Val Arg Gln Ala Pro Gly Gln Gly Leu Glu Trp Ile
        35                  40                  45
Gly Trp Ile Gly Pro Gly Asp Phe Asn Thr Lys Phe Asn Glu Lys Phe
    50                  55                  60
Lys Gly Arg Val Thr Leu Thr Ala Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp His Tyr Gly Tyr Tyr Tyr Phe Asp Tyr Trp Gly Gln Gly
            100                 105                 110
Thr Leu Val Thr Val Ser Ser
        115

<210> SEQ ID NO 58
<211> LENGTH: 119
<212> TYPE: PRT
<213> ORGANISM: Artificial Sequence
<220> FEATURE:
<223> OTHER INFORMATION: Synthetic Construct

<400> SEQUENCE: 58

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Val His Trp Val Arg Gln Ala Pro Gly Gln Gly Leu Glu Trp Ile
        35                  40                  45
Gly Trp Ile Tyr Pro Gly Asp Phe Asn Thr Lys Phe Asn Glu Lys Phe
    50                  55                  60
Lys Gly Arg Val Thr Leu Thr Ala Asp Thr Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Asp His Tyr His Tyr Tyr Phe Asp Tyr Trp Gly Gln Gly
            100                 105                 110

Thr Leu Val Thr Val Ser Ser
        115

<210> SEQ ID NO 59
<211> LENGTH: 119
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asp Phe Asn Thr His Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr Gly Tyr Tyr Phe Asp Tyr Trp Gly Gln Gly
            100                 105                 110

Thr Leu Val Thr Val Ser Ser
        115

<210> SEQ ID NO 60
<211> LENGTH: 119
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Tyr His Trp Val Arg Gln Ala Pro Gly Gln Gly Leu Glu Trp Ile
        35                  40                  45

Gly Trp Ile Tyr Pro Gly Asp Phe Asn Thr His Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr Gly Tyr Tyr Phe Asp Tyr Trp Gly Gln Gly
            100                 105                 110

Thr Leu Val Thr Val Ser Ser
        115

<210> SEQ ID NO 61
```

<211> LENGTH: 119
<212> TYPE: PRT
<213> ORGANISM: Artificial Sequence
<220> FEATURE:
<223> OTHER INFORMATION: Synthetic Construct

<400> SEQUENCE: 61

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Tyr His Trp Val Arg Gln Ala Pro Gly Gln Gly Leu Glu Trp Ile
        35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr His Tyr Tyr Phe Asp Tyr Trp Gly Gln Gly
            100                 105                 110

Thr Leu Val Thr Val Ser Ser
        115

<210> SEQ ID NO 62
<211> LENGTH: 119
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr His Tyr Tyr Phe Asp Tyr Trp Gly Gln Gly
            100                 105                 110

Thr Leu Val Thr Val Ser Ser
        115

<210> SEQ ID NO 63
<211> LENGTH: 119
<212> TYPE: PRT
<213> ORGANISM: Artificial Sequence
<220> FEATURE:
<223> OTHER INFORMATION: Synthetic Construct

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Tyr His Trp Val Arg Gln Ala Pro Gly Gln Gly Leu Glu Trp Ile
            35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr His Tyr Tyr Tyr Phe Asp Tyr Trp Gly Gln Gly
                100                 105                 110

Thr Leu Val Thr Val Ser Ser
            115

<210> SEQ ID NO 64
<211> LENGTH: 119
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Tyr His Trp Val Arg Gln Ala Pro Gly Gln Gly Leu Glu Trp Ile
            35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr His Tyr Tyr Tyr Phe Asp Tyr Trp Gly Gln Gly
                100                 105                 110

Thr Leu Val Thr Val Ser Ser
            115

<210> SEQ ID NO 65
<211> LENGTH: 119
<212> TYPE: PRT
<213> ORGANISM: Artificial Sequence
<220> FEATURE:
<223> OTHER INFORMATION: Synthetic Construct

<400> SEQUENCE: 65

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Tyr His Trp Val Arg Gln Ala Pro Gly Gln Gly Leu Glu Trp Ile
            35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr His Tyr Tyr Phe Asp Tyr Trp Gly Gln Gly
            100                 105                 110

Thr Leu Val Thr Val Ser Ser
        115

<210> SEQ ID NO 66
<211> LENGTH: 119
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Tyr His Trp Val Arg Gln Ala Pro Gly Gln Gly Leu Glu Trp Ile
        35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr Gly Tyr Tyr Phe Asp Tyr Trp Gly Gln Gly
            100                 105                 110

Thr Leu Val Thr Val Ser Ser
        115

<210> SEQ ID NO 67
<211> LENGTH: 119
<212> TYPE: PRT
<213> ORGANISM: Artificial Sequence
<220> FEATURE:
<223> OTHER INFORMATION: Synthetic Construct

<400> SEQUENCE: 67

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Thr His Trp Val Arg Gln Ala Pro Gly Gln Gly Leu Glu Trp Ile
        35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr Gly Tyr Tyr Phe Asp Tyr Trp Gly Gln Gly
            100                 105                 110

Thr Leu Val Thr Val Ser Ser
        115

```
<210> SEQ ID NO 68
<211> LENGTH: 119
<212> TYPE: PRT
<213> ORGANISM: Artificial Sequence
<220> FEATURE:
<223> OTHER INFORMATION: Synthetic Construct

<400> SEQUENCE: 68
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Tyr His Trp Val Arg Gln Ala Pro Gly Gln Gly Leu Glu Trp Ile
        35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr His His Tyr Tyr Phe Asp Tyr Trp Gly Gln Gly
            100                 105                 110

Thr Leu Val Thr Val Ser Ser
        115

```
<210> SEQ ID NO 69
<211> LENGTH: 119
<212> TYPE: PRT
<213> ORGANISM: Artificial Sequence
<220> FEATURE:
<223> OTHER INFORMATION: Synthetic Construct

<400> SEQUENCE: 69
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Tyr His Trp Val Arg Gln Ala Pro Gly Gln Gly Leu Glu Trp Ile
        35                  40                  45

Gly Trp Ile Tyr Pro Gly Asp Phe Asn Thr Lys Phe Asn Glu Lys Phe
    50                  55                  60

Lys Gly Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Tyr His Gln Tyr Tyr Phe Asp Tyr Trp Gly Gln Gly
            100                 105                 110

Thr Leu Val Thr Val Ser Ser
        115

```
<210> SEQ ID NO 70
<211> LENGTH: 119
<212> TYPE: PRT
<213> ORGANISM: Artificial Sequence
<220> FEATURE:
<223> OTHER INFORMATION: Synthetic Construct

<400> SEQUENCE: 70
```

Glu Val Gln Leu Val Gln Ser Gly Ala Glu Val Lys Lys Pro Gly Ala
1               5                   10                  15

```
Ser Val Lys Val Ser Cys Lys Ala Ser Gly Phe Asn Ile Lys Asp Phe
            20                  25                  30

Tyr Met His Trp Val Arg Gln Ala Pro Gly Gln Gly Leu Glu Trp Ile
            35                  40                  45

Gly Trp Ile Ala Pro Glu Thr Gly Asn Thr Ile Tyr Asp Pro Lys Phe
 50                  55                  60

Gln Gly Arg Ala Thr Val Thr Ser Asp Thr Ser Ile Asn Thr Ala Tyr
 65                  70                  75                  80

Met Glu Leu Ser Arg Leu Arg Ser Asp Thr Ala Val Tyr Tyr Cys
                85                  90                  95

Ala Arg Asp Ser Tyr Gly Trp Tyr Tyr Phe Asp Tyr Trp Gly Gln Gly
            100                 105                 110

Thr Leu Val Thr Val Ser Ser
            115

<210> SEQ ID NO 71
<211> LENGTH: 119
<212> TYPE: PRT
<213> ORGANISM: Artificial Sequence
<220> FEATURE:
<223> OTHER INFORMATION: Synthetic Construct

<400> SEQUENCE: 71

Glu Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Phe
            20                  25                  30

Tyr Met His Trp Val Arg Gln Ala Pro Gly Gln Gly Leu Glu Trp Ile
            35                  40                  45

Gly Trp Ile Ala Pro Glu Thr Gly Asn Thr Ile Tyr Asp Pro Lys Phe
 50                  55                  60

Gln Gly Arg Ala Thr Val Thr Ser Asp Thr Ser Ile Asn Thr Ala Tyr
 65                  70                  75                  80

Met Glu Leu Ser Arg Leu Arg Ser Asp Asp Thr Ala Val Tyr Tyr Cys
                85                  90                  95

Ala Arg Asp Ser Tyr Gly Tyr Tyr Tyr Phe Asp Tyr Trp Gly Gln Gly
            100                 105                 110

Thr Leu Val Thr Val Ser Ser
            115

<210> SEQ ID NO 72
<211> LENGTH: 112
<212> TYPE: PRT
<213> ORGANISM: Artificial Sequence
<220> FEATURE:
<223> OTHER INFORMATION: Synthetic Construct

<400> SEQUENCE: 72

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Thr Thr Arg Asp Ser Gly Val
 50                  55                  60

Pro Asp Arg Phe Ser Gly Ser Gly Ser Gly Thr Asp Phe Thr Leu Thr
```

```
                65                  70                  75                  80
Ile Ser Ser Leu Gln Ala Glu Asp Val Ala Val Tyr Tyr Cys Ile Gln
                    85                  90                  95
Ser Tyr Thr Thr Arg Thr Phe Gly Gly Gly Thr Lys Val Glu Ile Lys
                100                 105                 110
```

<210> SEQ ID NO 73
<211> LENGTH: 112
<212> TYPE: PRT
<213> ORGANISM: Artificial Sequence
<220> FEATURE:
<223> OTHER INFORMATION: Synthetic Construct

<400> SEQUENCE: 73

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Leu Asn Ser
                20                  25                  30
Arg Thr Arg His Asn Tyr Leu Ala Trp Tyr Gln Gln Lys Pro Gly Gln
            35                  40                  45
Pro Pro Lys Leu Leu Ile Tyr Trp Ala Thr Thr Arg Asp Ser Gly Val
        50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Ile Gln
                    85                  90                  95
Ser Tyr Thr Thr Arg Thr Phe Gly Gly Gly Thr Lys Val Glu Ile Lys
                100                 105                 110
```

<210> SEQ ID NO 74
<211> LENGTH: 112
<212> TYPE: PRT
<213> ORGANISM: Artificial Sequence
<220> FEATURE:
<223> OTHER INFORMATION: Synthetic Construct

<400> SEQUENCE: 74

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Leu Asn Ser
                20                  25                  30
Arg Thr Arg His Asn Tyr Leu Ala Trp Tyr Gln Gln Lys Pro Gly Gln
            35                  40                  45
Pro Pro Lys Leu Leu Ile Tyr Trp Ala Thr Thr Arg Asp Ser Gly Val
        50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Ile Gln
                    85                  90                  95
Ser Tyr Thr Thr Arg Thr Phe Gly Gly Gly Thr Lys Val Glu Ile Lys
                100                 105                 110
```

<210> SEQ ID NO 75
<211> LENGTH: 112
<212> TYPE: PRT
<213> ORGANISM: Artificial Sequence
<220> FEATURE:
<223> OTHER INFORMATION: Synthetic Construct

<400> SEQUENCE: 75

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65              70                  75                  80

Ile Ser Ser Leu Gln Ala Glu Asp Val Ala Val Tyr Tyr Cys Ile Gln
                85                  90                  95

Ser Tyr Thr Thr Arg Thr Phe Gly Gly Gly Thr Lys Val Glu Ile Lys
            100                 105                 110
```

<210> SEQ ID NO 76
<211> LENGTH: 112
<212> TYPE: PRT
<213> ORGANISM: Artificial Sequence
<220> FEATURE:
<223> OTHER INFORMATION: Synthetic Construct

<400> SEQUENCE: 76

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65              70                  75                  80

Ile Ser Ser Leu Gln Ala Glu Asp Val Ala Val Tyr Tyr Cys Ile Gln
                85                  90                  95

Ser Tyr Thr Thr Arg Thr Phe Gly Gly Gly Thr Lys Val Glu Ile Lys
            100                 105                 110
```

<210> SEQ ID NO 77
<211> LENGTH: 112
<212> TYPE: PRT
<213> ORGANISM: Artificial Sequence
<220> FEATURE:
<223> OTHER INFORMATION: Synthetic Construct

<400> SEQUENCE: 77

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65              70                  75                  80

Ile Ser Ser Leu Gln Ala Glu Asp Val Ala Val Tyr Tyr Cys Ile Gln
```

```
                        85                  90                  95

Ser Tyr Thr Thr Arg Thr Phe Gly Gly Gly Thr Lys Val Glu Ile Lys
                100                 105                 110

<210> SEQ ID NO 78
<211> LENGTH: 112
<212> TYPE: PRT
<213> ORGANISM: Artificial Sequence
<220> FEATURE:
<223> OTHER INFORMATION: Synthetic Construct

<400> SEQUENCE: 78

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
                100                 105                 110

<210> SEQ ID NO 79
<211> LENGTH: 112
<212> TYPE: PRT
<213> ORGANISM: Artificial Sequence
<220> FEATURE:
<223> OTHER INFORMATION: Synthetic Construct

<400> SEQUENCE: 79

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Thr Arg Thr Phe Gly Gly Gly Thr Lys Val Glu Ile Lys
                100                 105                 110

<210> SEQ ID NO 80
<211> LENGTH: 112
<212> TYPE: PRT
<213> ORGANISM: Artificial Sequence
<220> FEATURE:
<223> OTHER INFORMATION: Synthetic Construct

<400> SEQUENCE: 80

Asp Ile Val Met Thr Gln Ser Pro Asp Ser Leu Ala Val Ser Leu Gly
1               5                   10                  15
```

```
Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110

<210> SEQ ID NO 81
<211> LENGTH: 112
<212> TYPE: PRT
<213> ORGANISM: Artificial Sequence
<220> FEATURE:
<223> OTHER INFORMATION: Synthetic Construct

<400> SEQUENCE: 81

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Gly His Asn Tyr Leu Ala Trp Tyr Gln Gln Lys Pro Gly Gln
        35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110

<210> SEQ ID NO 82
<211> LENGTH: 112
<212> TYPE: PRT
<213> ORGANISM: Artificial Sequence
<220> FEATURE:
<223> OTHER INFORMATION: Synthetic Construct

<400> SEQUENCE: 82

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
```

<210> SEQ ID NO 83
<211> LENGTH: 112
<212> TYPE: PRT
<213> ORGANISM: Artificial Sequence
<220> FEATURE:
<223> OTHER INFORMATION: Synthetic Construct

<400> SEQUENCE: 83

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ala Gln
                85                  90                  95

Ser Tyr Thr Gly Arg Thr Phe Gly Gly Gly Thr Lys Val Glu Ile Lys
            100                 105                 110

<210> SEQ ID NO 84
<211> LENGTH: 112
<212> TYPE: PRT
<213> ORGANISM: Artificial Sequence
<220> FEATURE:
<223> OTHER INFORMATION: Synthetic Construct

<400> SEQUENCE: 84

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110

<210> SEQ ID NO 85
<211> LENGTH: 112
<212> TYPE: PRT
<213> ORGANISM: Artificial Sequence
<220> FEATURE:
<223> OTHER INFORMATION: Synthetic Construct

<400> SEQUENCE: 85

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
            35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110

<210> SEQ ID NO 86
<211> LENGTH: 112
<212> TYPE: PRT
<213> ORGANISM: Artificial Sequence
<220> FEATURE:
<223> OTHER INFORMATION: Synthetic Construct

<400> SEQUENCE: 86

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
            35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110

<210> SEQ ID NO 87
<211> LENGTH: 112
<212> TYPE: PRT
<213> ORGANISM: Artificial Sequence
<220> FEATURE:
<223> OTHER INFORMATION: Synthetic Construct

<400> SEQUENCE: 87

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
            35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110

```
<210> SEQ ID NO 88
<211> LENGTH: 112
<212> TYPE: PRT
<213> ORGANISM: Artificial Sequence
<220> FEATURE:
<223> OTHER INFORMATION: Synthetic Construct

<400> SEQUENCE: 88

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110

<210> SEQ ID NO 89
<211> LENGTH: 112
<212> TYPE: PRT
<213> ORGANISM: Artificial Sequence
<220> FEATURE:
<223> OTHER INFORMATION: Synthetic Construct

<400> SEQUENCE: 89

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110

<210> SEQ ID NO 90
<211> LENGTH: 112
<212> TYPE: PRT
<213> ORGANISM: Artificial Sequence
<220> FEATURE:
<223> OTHER INFORMATION: Synthetic Construct

<400> SEQUENCE: 90

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45
```

```
Pro Pro Lys Leu Leu Ile Tyr Trp Ala Thr Thr Arg Asp Ser Gly Val
            50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110
```

<210> SEQ ID NO 91
<211> LENGTH: 112
<212> TYPE: PRT
<213> ORGANISM: Artificial Sequence
<220> FEATURE:
<223> OTHER INFORMATION: Synthetic Construct

<400> SEQUENCE: 91

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
                20                  25                  30

Arg Thr Arg His Asn Tyr Leu Ala Trp Tyr Gln Gln Lys Pro Gly Gln
            35                  40                  45

Pro Pro Lys Leu Leu Ile Tyr Trp Ala Thr Thr Arg Asp Ser Gly Val
            50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110
```

<210> SEQ ID NO 92
<211> LENGTH: 112
<212> TYPE: PRT
<213> ORGANISM: Artificial Sequence
<220> FEATURE:
<223> OTHER INFORMATION: Synthetic Construct

<400> SEQUENCE: 92

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
                20                  25                  30

Arg Thr Arg His Asn Tyr Leu Ala Trp Tyr Gln Gln Lys Pro Gly Gln
            35                  40                  45

Pro Pro Lys Leu Leu Ile Tyr Trp Ala Thr Thr Arg Ala Ser Gly Val
            50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110
```

<210> SEQ ID NO 93
<211> LENGTH: 112
<212> TYPE: PRT

<213> ORGANISM: Artificial Sequence
<220> FEATURE:
<223> OTHER INFORMATION: Synthetic Construct

<400> SEQUENCE: 93

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110
```

<210> SEQ ID NO 94
<211> LENGTH: 112
<212> TYPE: PRT
<213> ORGANISM: Artificial Sequence
<220> FEATURE:
<223> OTHER INFORMATION: Synthetic Construct

<400> SEQUENCE: 94

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser His Thr Gly Arg Thr Phe Gly Gly Gly Thr Lys Val Glu Ile Lys
            100                 105                 110
```

<210> SEQ ID NO 95
<211> LENGTH: 112
<212> TYPE: PRT
<213> ORGANISM: Artificial Sequence
<220> FEATURE:
<223> OTHER INFORMATION: Synthetic Construct

<400> SEQUENCE: 95

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Ser Thr Arg Ala Ser Gly Val
    50                  55                  60
```

-continued

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Ile Gln
                 85                  90                  95

Ser His Thr Leu Arg Thr Phe Gly Gly Gly Thr Lys Val Glu Ile Lys
            100                 105                 110
```

<210> SEQ ID NO 96
<211> LENGTH: 112
<212> TYPE: PRT
<213> ORGANISM: Artificial Sequence
<220> FEATURE:
<223> OTHER INFORMATION: Synthetic Construct

<400> SEQUENCE: 96

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
                 20                  25                  30

Arg Thr Arg His Asn Tyr Leu Ala Trp Tyr Gln Gln Lys Pro Gly Gln
            35                  40                  45

Pro Pro Lys Leu Leu Ile Tyr Trp Ala Thr Thr Arg Ala Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Ile Gln
                 85                  90                  95

Ser Tyr Thr Gly Arg Thr Phe Gly Gly Gly Thr Lys Val Glu Ile Lys
            100                 105                 110
```

<210> SEQ ID NO 97
<211> LENGTH: 112
<212> TYPE: PRT
<213> ORGANISM: Artificial Sequence
<220> FEATURE:
<223> OTHER INFORMATION: Synthetic Construct

<400> SEQUENCE: 97

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
                 20                  25                  30

Arg Thr Arg His Asn Tyr Leu Ala Trp Tyr Gln Gln Lys Pro Gly Gln
            35                  40                  45

Pro Pro Lys Leu Leu Ile Tyr Trp Ala Thr Thr Arg Ala Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Ile Gln
                 85                  90                  95

Ser Tyr Thr Gly Arg Thr Phe Gly Gly Gly Thr Lys Val Glu Ile Lys
            100                 105                 110
```

<210> SEQ ID NO 98
<211> LENGTH: 112
<212> TYPE: PRT
<213> ORGANISM: Artificial Sequence
<220> FEATURE:
<223> OTHER INFORMATION: Synthetic Construct

<400> SEQUENCE: 98

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110

<210> SEQ ID NO 99
<211> LENGTH: 112
<212> TYPE: PRT
<213> ORGANISM: Artificial Sequence
<220> FEATURE:
<223> OTHER INFORMATION: Synthetic Construct

<400> SEQUENCE: 99

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg His Asn Tyr Leu Ala Trp Tyr Gln Gln Lys Pro Gly Gln
        35                  40                  45

Pro Pro Lys Leu Leu Ile Tyr Trp Ala Thr Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Ile Gln
                85                  90                  95

Ser Tyr Thr Gly Arg Thr Phe Gly Gly Gly Thr Lys Val Glu Ile Lys
            100                 105                 110

<210> SEQ ID NO 100
<211> LENGTH: 112
<212> TYPE: PRT
<213> ORGANISM: Artificial Sequence
<220> FEATURE:
<223> OTHER INFORMATION: Synthetic Construct

<400> SEQUENCE: 100

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

```
Ile Ser Ser Leu Gln Ala Glu Asp Val Ala Val Tyr Tyr Cys Lys Gln
                85                  90                  95

Ser Tyr Ile Leu Arg Thr Phe Gly Gly Gly Thr Lys Val Glu Ile Lys
            100                 105                 110

<210> SEQ ID NO 101
<211> LENGTH: 112
<212> TYPE: PRT
<213> ORGANISM: Artificial Sequence
<220> FEATURE:
<223> OTHER INFORMATION: Synthetic Construct

<400> SEQUENCE: 101

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ile Leu Arg Thr Phe Gly Gly Gly Thr Lys Val Glu Ile Lys
            100                 105                 110

<210> SEQ ID NO 102
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Can be present in repeats of any integer

<400> SEQUENCE: 102

Gly
1

<210> SEQ ID NO 103
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3)..(16)
<223> OTHER INFORMATION: Can be absent
<220> FEATURE:
<221> NAME/KEY: VARIANT
<222> LOCATION: (5)..(16)
<223> OTHER INFORMATION: Can be absent
<220> FEATURE:
<221> NAME/KEY: VARIANT
<222> LOCATION: (7)..(16)
<223> OTHER INFORMATION: Can be absent
<220> FEATURE:
<221> NAME/KEY: VARIANT
<222> LOCATION: (9)..(16)
<223> OTHER INFORMATION: Can be absent
<220> FEATURE:
```

```
<221> NAME/KEY: VARIANT
<222> LOCATION: (11)..(16)
<223> OTHER INFORMATION: Can be absent
<220> FEATURE:
<221> NAME/KEY: VARIANT
<222> LOCATION: (13)..(16)
<223> OTHER INFORMATION: Can be absent
<220> FEATURE:
<221> NAME/KEY: VARIANT
<222> LOCATION: (15)..(16)
<223> OTHER INFORMATION: Can be absent

<400> SEQUENCE: 103

Gly Ser Gly Ser Gly Ser Gly Ser Gly Ser Gly Ser Gly Ser Gly Ser
1               5                   10                  15

<210> SEQ ID NO 104
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (6)..(40)
<223> OTHER INFORMATION: Can be absent
<220> FEATURE:
<221> NAME/KEY: VARIANT
<222> LOCATION: (11)..(40)
<223> OTHER INFORMATION: Can be absent
<220> FEATURE:
<221> NAME/KEY: VARIANT
<222> LOCATION: (16)..(40)
<223> OTHER INFORMATION: Can be absent
<220> FEATURE:
<221> NAME/KEY: VARIANT
<222> LOCATION: (21)..(40)
<223> OTHER INFORMATION: Can be absent
<220> FEATURE:
<221> NAME/KEY: VARIANT
<222> LOCATION: (26)..(40)
<223> OTHER INFORMATION: Can be absent
<220> FEATURE:
<221> NAME/KEY: VARIANT
<222> LOCATION: (31)..(40)
<223> OTHER INFORMATION: Can be absent
<220> FEATURE:
<221> NAME/KEY: VARIANT
<222> LOCATION: (36)..(40)
<223> OTHER INFORMATION: Can be absent

<400> SEQUENCE: 104

Gly Ser Gly Gly Ser Gly Ser Gly Ser Gly Ser Gly Ser Gly Ser Gly
1               5                   10                  15

Ser Gly Gly Ser Gly Ser Gly Ser Gly Ser Gly Ser Gly Ser Gly Ser
            20                  25                  30

Gly Gly Ser Gly Ser Gly Gly Ser
        35                  40

<210> SEQ ID NO 105
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (6)..(40)
<223> OTHER INFORMATION: Can be absent
<220> FEATURE:
<221> NAME/KEY: VARIANT
<222> LOCATION: (11)..(40)
<223> OTHER INFORMATION: Can be absent
```

```
<220> FEATURE:
<221> NAME/KEY: VARIANT
<222> LOCATION: (16)..(40)
<223> OTHER INFORMATION: Can be absent
<220> FEATURE:
<221> NAME/KEY: VARIANT
<222> LOCATION: (21)..(40)
<223> OTHER INFORMATION: Can be absent
<220> FEATURE:
<221> NAME/KEY: VARIANT
<222> LOCATION: (26)..(40)
<223> OTHER INFORMATION: Can be absent
<220> FEATURE:
<221> NAME/KEY: VARIANT
<222> LOCATION: (31)..(40)
<223> OTHER INFORMATION: Can be absent
<220> FEATURE:
<221> NAME/KEY: VARIANT
<222> LOCATION: (36)..(40)
<223> OTHER INFORMATION: Can be absent

<400> SEQUENCE: 105

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 106
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (5)..(32)
<223> OTHER INFORMATION: Can be absent
<220> FEATURE:
<221> NAME/KEY: VARIANT
<222> LOCATION: (9)..(32)
<223> OTHER INFORMATION: Can be absent
<220> FEATURE:
<221> NAME/KEY: VARIANT
<222> LOCATION: (13)..(32)
<223> OTHER INFORMATION: Can be absent
<220> FEATURE:
<221> NAME/KEY: VARIANT
<222> LOCATION: (17)..(32)
<223> OTHER INFORMATION: Can be absent
<220> FEATURE:
<221> NAME/KEY: VARIANT
<222> LOCATION: (21)..(32)
<223> OTHER INFORMATION: Can be absent
<220> FEATURE:
<221> NAME/KEY: VARIANT
<222> LOCATION: (25)..(32)
<223> OTHER INFORMATION: Can be absent
<220> FEATURE:
<221> NAME/KEY: VARIANT
<222> LOCATION: (29)..(32)
<223> OTHER INFORMATION: Can be absent

<400> SEQUENCE: 106

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

<210> SEQ ID NO 107
<211> LENGTH: 15
```

```
<212> TYPE: PRT
<213> ORGANISM: Artificial Sequence
<220> FEATURE:
<223> OTHER INFORMATION: Synthetic Construct

<400> SEQUENCE: 107

Gly Gly Gly Gly Ser Gly Gly Gly Gly Ser Gly Gly Gly Gly Ser
1               5                   10                  15

<210> SEQ ID NO 108
<211> LENGTH: 30
<212> TYPE: PRT
<213> ORGANISM: Artificial Sequence
<220> FEATURE:
<223> OTHER INFORMATION: Synthetic Construct

<400> SEQUENCE: 108

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 109
<211> LENGTH: 45
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (16)..(45)
<223> OTHER INFORMATION: Can be absent
<220> FEATURE:
<221> NAME/KEY: VARIANT
<222> LOCATION: (31)..(45)
<223> OTHER INFORMATION: Can be absent

<400> SEQUENCE: 109

Gly Ser Thr Ser Gly Ser Gly Lys Pro Gly Ser Gly Glu Gly Ser
1               5                   10                  15

Gly Ser Thr Ser Gly Ser Gly Lys Pro Gly Ser Gly Glu Gly Ser Gly Ser
            20                  25                  30

Thr Ser Gly Ser Gly Lys Pro Gly Ser Gly Glu Gly Ser
            35                  40                  45

<210> SEQ ID NO 110
<211> LENGTH: 119
<212> TYPE: PRT
<213> ORGANISM: Artificial Sequence
<220> FEATURE:
<223> OTHER INFORMATION: Synthetic Construct

<400> SEQUENCE: 110

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
```

```
                    85                  90                  95

Ala Arg Tyr Tyr Asp Asp His Tyr Cys Leu Asp Tyr Trp Gly Gln Gly
                100                 105                 110

Thr Thr Leu Thr Val Ser Ser
        115

<210> SEQ ID NO 111
<211> LENGTH: 106
<212> TYPE: PRT
<213> ORGANISM: Artificial Sequence
<220> FEATURE:
<223> OTHER INFORMATION: Synthetic Construct

<400> SEQUENCE: 111

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
                100                 105

<210> SEQ ID NO 112
<211> LENGTH: 119
<212> TYPE: PRT
<213> ORGANISM: Artificial Sequence
<220> FEATURE:
<223> OTHER INFORMATION: Synthetic Construct

<400> SEQUENCE: 112

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser
        115

<210> SEQ ID NO 113
<211> LENGTH: 106
<212> TYPE: PRT
<213> ORGANISM: Artificial Sequence
<220> FEATURE:
```

<223> OTHER INFORMATION: Synthetic Construct

<400> SEQUENCE: 113

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105
```

<210> SEQ ID NO 114
<211> LENGTH: 119
<212> TYPE: PRT
<213> ORGANISM: Artificial Sequence
<220> FEATURE:
<223> OTHER INFORMATION: Synthetic Construct

<400> SEQUENCE: 114

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
            35                  40                  45

Gly Trp Ile Tyr Pro Gly Asp Gly Asn Thr Lys Tyr Asn Glu Lys Phe
        50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115
```

<210> SEQ ID NO 115
<211> LENGTH: 112
<212> TYPE: PRT
<213> ORGANISM: Artificial Sequence
<220> FEATURE:
<223> OTHER INFORMATION: Synthetic Construct

<400> SEQUENCE: 115

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
```

```
                  50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Thr Gln
                     85                  90                  95

Ser Phe Ile Leu Arg Thr Phe Gly Gln Gly Thr Lys Val Glu Ile Lys
                100                 105                 110

<210> SEQ ID NO 116
<211> LENGTH: 119
<212> TYPE: PRT
<213> ORGANISM: Artificial Sequence
<220> FEATURE:
<223> OTHER INFORMATION: Synthetic Construct

<400> SEQUENCE: 116

Glu Val Gln Leu Val Gln Ser Gly Ala Glu Val Lys Lys Pro Gly Ala
  1               5                  10                  15

Ser Val Lys Val Ser Cys Lys Ala Ser Gly Phe Thr Phe Thr Ser Tyr
                 20                  25                  30

Tyr Ile His Trp Val Arg Gln Ala Pro Gly Gln Gly Leu Glu Trp Ile
             35                  40                  45

Gly Trp Ile Tyr Pro Glu Asn Asp Asn Thr Lys Tyr Asn Glu Lys Phe
 50                  55                  60

Lys Asp Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Gly Tyr Ser Arg Tyr Tyr Phe Asp Tyr Trp Gly Gln Gly
                100                 105                 110

Thr Leu Val Thr Val Ser Ser
            115

<210> SEQ ID NO 117
<211> LENGTH: 112
<212> TYPE: PRT
<213> ORGANISM: Artificial Sequence
<220> FEATURE:
<223> OTHER INFORMATION: Synthetic Construct

<400> SEQUENCE: 117

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Asn Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Thr Ser Thr Arg Lys Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Phe Ile Leu Arg Thr Phe Gly Gln Gly Thr Lys Val Glu Ile Lys
                100                 105                 110

<210> SEQ ID NO 118
<211> LENGTH: 125
```

```
<212> TYPE: PRT
<213> ORGANISM: Artificial Sequence
<220> FEATURE:
<223> OTHER INFORMATION: Synthetic Construct

<400> SEQUENCE: 118

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 119
<211> LENGTH: 109
<212> TYPE: PRT
<213> ORGANISM: Artificial Sequence
<220> FEATURE:
<223> OTHER INFORMATION: Synthetic Construct

<400> SEQUENCE: 119

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 120
<211> LENGTH: 121
<212> TYPE: PRT
<213> ORGANISM: Artificial Sequence
<220> FEATURE:
<223> OTHER INFORMATION: Synthetic Construct

<400> SEQUENCE: 120

Glu Val Gln Leu Ala Glu Ser Gly Gly Gly Leu Val Gln Pro Gly Arg
1               5                   10                  15

Ser Met Lys Leu Ser Cys Ala Ala Ser Gly Phe Thr Phe Ser Asn Phe
            20                  25                  30

Pro Met Ala Trp Val Arg Gln Ala Pro Thr Lys Gly Leu Glu Trp Val
```

```
                35                  40                  45
Ala Thr Ile Ser Thr Ser Gly Gly Ser Thr Tyr Tyr Arg Asp Ser Val
            50                  55                  60
Lys Gly Arg Phe Thr Ile Ser Arg Asp Asn Ala Lys Ser Thr Leu Tyr
 65                  70                  75                  80
Leu Gln Met Asn Ser Leu Arg Ser Glu Asp Thr Ala Thr Tyr Tyr Cys
                85                  90                  95
Thr Arg Thr Leu Tyr Ile Leu Arg Val Phe Tyr Phe Asp Tyr Trp Gly
            100                 105                 110
Gln Gly Val Met Val Thr Val Ser Ser
        115                 120

<210> SEQ ID NO 121
<211> LENGTH: 107
<212> TYPE: PRT
<213> ORGANISM: Artificial Sequence
<220> FEATURE:
<223> OTHER INFORMATION: Synthetic Construct

<400> SEQUENCE: 121

Asp Ile Gln Met Thr Gln Ser Pro Ala Ser Leu Ser Ala Ser Leu Gly
  1               5                  10                  15
Glu Thr Val Ser Ile Glu Cys Leu Ala Ser Glu Gly Ile Ser Asn Asp
                20                  25                  30
Leu Ala Trp Tyr Gln Gln Lys Ser Gly Lys Ser Pro Gln Leu Leu Ile
            35                  40                  45
Tyr Ala Thr Ser Arg Leu Gln Asp Gly Val Pro Ser Arg Phe Ser Gly
 50                  55                  60
Ser Gly Ser Gly Thr Arg Tyr Ser Leu Lys Ile Ser Gly Met Gln Pro
 65                  70                  75                  80
Glu Asp Glu Ala Asp Tyr Phe Cys Gln Gln Ser Tyr Lys Tyr Pro Trp
                85                  90                  95
Thr Phe Gly Gly Gly Thr Lys Leu Glu Leu Lys
            100                 105

<210> SEQ ID NO 122
<211> LENGTH: 119
<212> TYPE: PRT
<213> ORGANISM: Artificial Sequence
<220> FEATURE:
<223> OTHER INFORMATION: Synthetic Construct

<400> SEQUENCE: 122

Glu Val Gln Leu Glu Gln Ser Gly Ala Glu Leu Val Arg Pro Gly Thr
  1               5                  10                  15
Ser Val Lys Ile Ser Cys Lys Ala Ser Gly Tyr Ala Phe Thr Asn Tyr
                20                  25                  30
Trp Leu Gly Trp Val Lys Gln Arg Pro Gly His Gly Leu Glu Trp Ile
            35                  40                  45
Gly Asp Ile Phe Pro Gly Ser Gly Asn Ile His Tyr Asn Glu Lys Phe
 50                  55                  60
Lys Gly Lys Ala Thr Leu Thr Ala Asp Lys Ser Ser Ser Thr Ala Tyr
 65                  70                  75                  80
Met Gln Leu Ser Ser Leu Thr Phe Glu Asp Ser Ala Val Tyr Phe Cys
                85                  90                  95
Ala Arg Leu Arg Asn Trp Asp Glu Pro Met Asp Tyr Trp Gly Gln Gly
            100                 105                 110
```

Thr Thr Val Thr Val Ser Ser
        115

<210> SEQ ID NO 123
<211> LENGTH: 113
<212> TYPE: PRT
<213> ORGANISM: Artificial Sequence
<220> FEATURE:
<223> OTHER INFORMATION: Synthetic Construct

<400> SEQUENCE: 123

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys

<210> SEQ ID NO 124
<211> LENGTH: 121
<212> TYPE: PRT
<213> ORGANISM: Artificial Sequence
<220> FEATURE:
<223> OTHER INFORMATION: Synthetic Construct

<400> SEQUENCE: 124

Glu Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser
        115                 120

<210> SEQ ID NO 125
<211> LENGTH: 107
<212> TYPE: PRT
<213> ORGANISM: Artificial Sequence
<220> FEATURE:
<223> OTHER INFORMATION: Synthetic Construct

<400> SEQUENCE: 125

```
Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys
            100                 105
```

<210> SEQ ID NO 126
<211> LENGTH: 120
<212> TYPE: PRT
<213> ORGANISM: Artificial Sequence
<220> FEATURE:
<223> OTHER INFORMATION: Synthetic Construct

<400> SEQUENCE: 126

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 127
<211> LENGTH: 107
<212> TYPE: PRT
<213> ORGANISM: Artificial Sequence
<220> FEATURE:
<223> OTHER INFORMATION: Synthetic Construct

<400> SEQUENCE: 127

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln His Tyr Thr Thr Pro Pro
                    85                  90                  95
Thr Phe Gly Gln Gly Thr Lys Val Glu Ile Lys
            100                 105

<210> SEQ ID NO 128
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3)..(20)
<223> OTHER INFORMATION: Can be absent
<220> FEATURE:
<221> NAME/KEY: VARIANT
<222> LOCATION: (5)..(20)
<223> OTHER INFORMATION: Can be absent
<220> FEATURE:
<221> NAME/KEY: VARIANT
<222> LOCATION: (7)..(20)
<223> OTHER INFORMATION: Can be absent
<220> FEATURE:
<221> NAME/KEY: VARIANT
<222> LOCATION: (9)..(20)
<223> OTHER INFORMATION: Can be absent
<220> FEATURE:
<221> NAME/KEY: VARIANT
<222> LOCATION: (11)..(20)
<223> OTHER INFORMATION: Can be absent
<220> FEATURE:
<221> NAME/KEY: VARIANT
<222> LOCATION: (13)..(20)
<223> OTHER INFORMATION: Can be absent
<220> FEATURE:
<221> NAME/KEY: VARIANT
<222> LOCATION: (15)..(20)
<223> OTHER INFORMATION: Can be absent
<220> FEATURE:
<221> NAME/KEY: VARIANT
<222> LOCATION: (17)..(20)
<223> OTHER INFORMATION: Can be absent
<220> FEATURE:
<221> NAME/KEY: VARIANT
<222> LOCATION: (19)..(20)
<223> OTHER INFORMATION: Can be absent

<400> SEQUENCE: 128

Gly Ser Gly Ser Gly Ser Gly Ser Gly Ser Gly Ser Gly Ser Gly Ser
1               5                   10                  15

Gly Ser Gly Ser
            20

<210> SEQ ID NO 129
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (4)..(30)
<223> OTHER INFORMATION: Can be absent
<220> FEATURE:
<221> NAME/KEY: VARIANT
<222> LOCATION: (7)..(30)
<223> OTHER INFORMATION: Can be absent
<220> FEATURE:
<221> NAME/KEY: VARIANT
<222> LOCATION: (10)..(30)
<223> OTHER INFORMATION: Can be absent
```

```
<220> FEATURE:
<221> NAME/KEY: VARIANT
<222> LOCATION: (13)..(30)
<223> OTHER INFORMATION: Can be absent
<220> FEATURE:
<221> NAME/KEY: VARIANT
<222> LOCATION: (16)..(30)
<223> OTHER INFORMATION: Can be absent
<220> FEATURE:
<221> NAME/KEY: VARIANT
<222> LOCATION: (19)..(30)
<223> OTHER INFORMATION: Can be absent
<220> FEATURE:
<221> NAME/KEY: VARIANT
<222> LOCATION: (22)..(30)
<223> OTHER INFORMATION: Can be absent
<220> FEATURE:
<221> NAME/KEY: VARIANT
<222> LOCATION: (25)..(30)
<223> OTHER INFORMATION: Can be absent
<220> FEATURE:
<221> NAME/KEY: VARIANT
<222> LOCATION: (28)..(30)
<223> OTHER INFORMATION: Can be absent

<400> SEQUENCE: 129

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 130
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (5)..(40)
<223> OTHER INFORMATION: Can be absent
<220> FEATURE:
<221> NAME/KEY: VARIANT
<222> LOCATION: (9)..(40)
<223> OTHER INFORMATION: Can be absent
<220> FEATURE:
<221> NAME/KEY: VARIANT
<222> LOCATION: (13)..(40)
<223> OTHER INFORMATION: Can be absent
<220> FEATURE:
<221> NAME/KEY: VARIANT
<222> LOCATION: (17)..(40)
<223> OTHER INFORMATION: Can be absent
<220> FEATURE:
<221> NAME/KEY: VARIANT
<222> LOCATION: (21)..(40)
<223> OTHER INFORMATION: Can be absent
<220> FEATURE:
<221> NAME/KEY: VARIANT
<222> LOCATION: (25)..(40)
<223> OTHER INFORMATION: Can be absent
<220> FEATURE:
<221> NAME/KEY: VARIANT
<222> LOCATION: (29)..(40)
<223> OTHER INFORMATION: Can be absent
<220> FEATURE:
<221> NAME/KEY: VARIANT
<222> LOCATION: (33)..(40)
<223> OTHER INFORMATION: Can be absent
<220> FEATURE:
<221> NAME/KEY: VARIANT
<222> LOCATION: (37)..(40)
<223> OTHER INFORMATION: Can be absent

<400> SEQUENCE: 130
```

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30

Gly Gly Gly Ser Gly Gly Gly Ser
        35                  40

<210> SEQ ID NO 131
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (5)..(40)
<223> OTHER INFORMATION: Can be absent
<220> FEATURE:
<221> NAME/KEY: VARIANT
<222> LOCATION: (9)..(40)
<223> OTHER INFORMATION: Can be absent
<220> FEATURE:
<221> NAME/KEY: VARIANT
<222> LOCATION: (13)..(40)
<223> OTHER INFORMATION: Can be absent
<220> FEATURE:
<221> NAME/KEY: VARIANT
<222> LOCATION: (17)..(40)
<223> OTHER INFORMATION: Can be absent
<220> FEATURE:
<221> NAME/KEY: VARIANT
<222> LOCATION: (21)..(40)
<223> OTHER INFORMATION: Can be absent
<220> FEATURE:
<221> NAME/KEY: VARIANT
<222> LOCATION: (25)..(40)
<223> OTHER INFORMATION: Can be absent
<220> FEATURE:
<221> NAME/KEY: VARIANT
<222> LOCATION: (29)..(40)
<223> OTHER INFORMATION: Can be absent
<220> FEATURE:
<221> NAME/KEY: VARIANT
<222> LOCATION: (33)..(40)
<223> OTHER INFORMATION: Can be absent
<220> FEATURE:
<221> NAME/KEY: VARIANT
<222> LOCATION: (37)..(40)
<223> OTHER INFORMATION: Can be absent

<400> SEQUENCE: 131

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
                20                  25                  30

Gly Gly Ser Gly Gly Gly Ser Gly
        35                  40

<210> SEQ ID NO 132
<211> LENGTH: 50
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (6)..(50)
<223> OTHER INFORMATION: Can be absent
<220> FEATURE:
<221> NAME/KEY: VARIANT
<222> LOCATION: (11)..(50)
<223> OTHER INFORMATION: Can be absent

```
<220> FEATURE:
<221> NAME/KEY: VARIANT
<222> LOCATION: (16)..(50)
<223> OTHER INFORMATION: Can be absent
<220> FEATURE:
<221> NAME/KEY: VARIANT
<222> LOCATION: (21)..(50)
<223> OTHER INFORMATION: Can be absent
<220> FEATURE:
<221> NAME/KEY: VARIANT
<222> LOCATION: (26)..(50)
<223> OTHER INFORMATION: Can be absent
<220> FEATURE:
<221> NAME/KEY: VARIANT
<222> LOCATION: (31)..(50)
<223> OTHER INFORMATION: Can be absent
<220> FEATURE:
<221> NAME/KEY: VARIANT
<222> LOCATION: (36)..(50)
<223> OTHER INFORMATION: Can be absent
<220> FEATURE:
<221> NAME/KEY: VARIANT
<222> LOCATION: (41)..(50)
<223> OTHER INFORMATION: Can be absent
<220> FEATURE:
<221> NAME/KEY: VARIANT
<222> LOCATION: (46)..(50)
<223> OTHER INFORMATION: Can be absent

<400> SEQUENCE: 132

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 133
<211> LENGTH: 50
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (6)..(50)
<223> OTHER INFORMATION: Can be absent
<220> FEATURE:
<221> NAME/KEY: VARIANT
<222> LOCATION: (11)..(50)
<223> OTHER INFORMATION: Can be absent
<220> FEATURE:
<221> NAME/KEY: VARIANT
<222> LOCATION: (16)..(50)
<223> OTHER INFORMATION: Can be absent
<220> FEATURE:
<221> NAME/KEY: VARIANT
<222> LOCATION: (21)..(50)
<223> OTHER INFORMATION: Can be absent
<220> FEATURE:
<221> NAME/KEY: VARIANT
<222> LOCATION: (26)..(50)
<223> OTHER INFORMATION: Can be absent
<220> FEATURE:
<221> NAME/KEY: VARIANT
<222> LOCATION: (31)..(50)
<223> OTHER INFORMATION: Can be absent
<220> FEATURE:
<221> NAME/KEY: VARIANT
<222> LOCATION: (36)..(50)
<223> OTHER INFORMATION: Can be absent
<220> FEATURE:
```

```
<221> NAME/KEY: VARIANT
<222> LOCATION: (41)..(50)
<223> OTHER INFORMATION: Can be absent
<220> FEATURE:
<221> NAME/KEY: VARIANT
<222> LOCATION: (46)..(50)
<223> OTHER INFORMATION: Can be absent

<400> SEQUENCE: 133

Gly Gly Ser Gly Gly Gly Ser Gly Gly Gly Ser Gly Gly Gly Ser Gly Gly
1               5                   10                  15

Gly Ser Gly Gly Gly Ser Gly Gly Gly Ser Gly Gly Gly Ser Gly Gly Gly
                20                  25                  30

Ser Gly Gly Gly Ser Gly Gly Gly Ser Gly Gly Gly Ser
        35                  40                  45

Gly Gly
    50

<210> SEQ ID NO 134
<211> LENGTH: 47
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (7)..(46)
<223> OTHER INFORMATION: Can be absent
<220> FEATURE:
<221> NAME/KEY: VARIANT
<222> LOCATION: (12)..(46)
<223> OTHER INFORMATION: Can be absent
<220> FEATURE:
<221> NAME/KEY: VARIANT
<222> LOCATION: (17)..(46)
<223> OTHER INFORMATION: Can be absent
<220> FEATURE:
<221> NAME/KEY: VARIANT
<222> LOCATION: (22)..(46)
<223> OTHER INFORMATION: Can be absent
<220> FEATURE:
<221> NAME/KEY: VARIANT
<222> LOCATION: (27)..(46)
<223> OTHER INFORMATION: Can be absent
<220> FEATURE:
<221> NAME/KEY: VARIANT
<222> LOCATION: (32)..(46)
<223> OTHER INFORMATION: Can be absent
<220> FEATURE:
<221> NAME/KEY: VARIANT
<222> LOCATION: (37)..(46)
<223> OTHER INFORMATION: Can be absent
<220> FEATURE:
<221> NAME/KEY: VARIANT
<222> LOCATION: (42)..(46)
<223> OTHER INFORMATION: Can be absent

<400> SEQUENCE: 134

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Glu Ala Ala Ala Lys Glu
                20                  25                  30

Ala Ala Ala Lys Glu Ala Ala Ala Lys Glu Ala Ala Ala Lys Ala
        35                  40                  45

<210> SEQ ID NO 135
<211> LENGTH: 49
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: VARIANT
<222> LOCATION: (7)..(46)
<223> OTHER INFORMATION: Can be absent
<220> FEATURE:
<221> NAME/KEY: VARIANT
<222> LOCATION: (12)..(46)
<223> OTHER INFORMATION: Can be absent
<220> FEATURE:
<221> NAME/KEY: VARIANT
<222> LOCATION: (17)..(46)
<223> OTHER INFORMATION: Can be absent
<220> FEATURE:
<221> NAME/KEY: VARIANT
<222> LOCATION: (22)..(46)
<223> OTHER INFORMATION: Can be absent
<220> FEATURE:
<221> NAME/KEY: VARIANT
<222> LOCATION: (27)..(46)
<223> OTHER INFORMATION: Can be absent
<220> FEATURE:
<221> NAME/KEY: VARIANT
<222> LOCATION: (32)..(46)
<223> OTHER INFORMATION: Can be absent
<220> FEATURE:
<221> NAME/KEY: VARIANT
<222> LOCATION: (37)..(46)
<223> OTHER INFORMATION: Can be absent
<220> FEATURE:
<221> NAME/KEY: VARIANT
<222> LOCATION: (42)..(46)
<223> OTHER INFORMATION: Can be absent

<400> SEQUENCE: 135

Thr Ala Ala Ala Ala Thr Ala Ala Ala Ala Thr Ala Ala Ala Ala Thr
1               5                   10                  15

Ala Ala Ala Ala Thr Ala Ala Ala Ala Thr Ala Ala Ala Ala Thr Ala
                20                  25                  30

Ala Ala Ala Thr Ala Ala Ala Ala Thr Ala Ala Ala Ala Thr Ala Ala
            35                  40                  45

Ala

<210> SEQ ID NO 136
<211> LENGTH: 6
<212> TYPE: PRT
<213> ORGANISM: Artificial Sequence
<220> FEATURE:
<223> OTHER INFORMATION: Synthetic Construct

<400> SEQUENCE: 136

Phe Asn Arg Gly Glu Cys
1               5

<210> SEQ ID NO 137
<211> LENGTH: 5
<212> TYPE: PRT
<213> ORGANISM: Artificial Sequence
<220> FEATURE:
<223> OTHER INFORMATION: Synthetic Construct

<400> SEQUENCE: 137

Glu Pro Ser Gly Pro
1               5

<210> SEQ ID NO 138
<211> LENGTH: 4
<212> TYPE: PRT
<213> ORGANISM: Artificial Sequence
<220> FEATURE:
```

```
<223> OTHER INFORMATION: Synthetic Construct

<400> SEQUENCE: 138

Leu Gly Gly Cys
1

<210> SEQ ID NO 139
<211> LENGTH: 6
<212> TYPE: PRT
<213> ORGANISM: Artificial Sequence
<220> FEATURE:
<223> OTHER INFORMATION: Synthetic Construct

<400> SEQUENCE: 139

Val Glu Pro Lys Glu Cys
1               5

<210> SEQ ID NO 140
<211> LENGTH: 20
<212> TYPE: PRT
<213> ORGANISM: Artificial Sequence
<220> FEATURE:
<223> OTHER INFORMATION: Synthetic Construct

<400> SEQUENCE: 140

Pro Ser Gly Gln Ala Gly Ala Ala Ala Ser Glu Ser Leu Phe Val Ser
1               5                   10                  15

Asn His Ala Tyr
            20
```